(12) United States Patent
Barrat et al.

(10) Patent No.: US 9,476,053 B2
(45) Date of Patent: *Oct. 25, 2016

(54) METHODS AND COMPOSITIONS FOR INHIBITION OF IMMUNE RESPONSES AND AUTOIMMUNITY

(71) Applicant: Dynavax Technologies Corporation, Berkeley, CA (US)

(72) Inventors: Franck Barrat, New York, NY (US); Robert L. Coffman, Portola Valley, CA (US); Tracy Matray, Snohomish, WA (US); Cristiana Guiducci, Albany, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/613,280

(22) Filed: Feb. 3, 2015

(65) Prior Publication Data

US 2015/0275216 A1    Oct. 1, 2015

Related U.S. Application Data

(63) Continuation of application No. 12/767,692, filed on Apr. 26, 2010, now Pat. No. 8,962,579, which is a continuation of application No. PCT/US2008/012220, filed on Oct. 27, 2008.

(60) Provisional application No. 60/983,073, filed on Oct. 26, 2007.

(51) Int. Cl.
| | |
|---|---|
| *C12N 15/117* | (2010.01) |
| *A61K 31/711* | (2006.01) |
| *A61K 31/7115* | (2006.01) |
| *A61K 31/7125* | (2006.01) |
| *A61K 31/712* | (2006.01) |
| *A61K 31/713* | (2006.01) |
| *A61K 45/06* | (2006.01) |

(52) U.S. Cl.
CPC .......... *C12N 15/117* (2013.01); *A61K 31/711* (2013.01); *A61K 31/712* (2013.01); *A61K 31/713* (2013.01); *A61K 31/7115* (2013.01); *A61K 31/7125* (2013.01); *A61K 45/06* (2013.01); *C12N 2310/17* (2013.01); *C12N 2310/314* (2013.01); *C12N 2310/315* (2013.01); *C12N 2310/321* (2013.01); *C12N 2310/3231* (2013.01); *C12N 2310/331* (2013.01); *C12N 2310/336* (2013.01); *C12N 2310/3341* (2013.01); *C12N 2310/345* (2013.01)

(58) Field of Classification Search
None
See application file for complete search history.

(56) References Cited

U.S. PATENT DOCUMENTS

| | | | |
|---|---|---|---|
| 4,458,066 | A | 7/1984 | Caruthers et al. |
| 4,587,329 | A | 5/1986 | Tomalia et al. |
| 4,650,675 | A | 3/1987 | Borel et al. |
| 4,849,513 | A | 7/1989 | Smith et al. |
| 4,910,300 | A | 3/1990 | Urdea et al. |
| 4,948,882 | A | 8/1990 | Ruth |
| 5,015,733 | A | 5/1991 | Smith et al. |
| 5,093,232 | A | 3/1992 | Urdea et al. |
| 5,118,800 | A | 6/1992 | Smith et al. |
| 5,118,802 | A | 6/1992 | Smith et al. |
| 5,124,246 | A | 6/1992 | Urdea et al. |
| 5,171,264 | A | 12/1992 | Merrill |
| 5,338,532 | A | 8/1994 | Tomalia et al. |
| 5,391,723 | A | 2/1995 | Priest |
| 5,453,496 | A | 9/1995 | Caruthers et al. |
| 5,460,831 | A | 10/1995 | Kossovsky et al. |
| 5,552,391 | A | 9/1996 | Coutts et al. |
| 6,080,580 | A | 6/2000 | Baker et al. |
| 6,096,722 | A | 8/2000 | Bennett et al. |
| 6,117,657 | A | 9/2000 | Usman et al. |
| 6,177,414 | B1 | 1/2001 | Tomalia et al. |
| 6,225,292 | B1 | 5/2001 | Raz et al. |
| 8,759,305 | B2 | 6/2014 | Barrat et al. |
| 8,940,310 | B2 | 1/2015 | Barrat et al. |
| 8,962,579 | B2 | 2/2015 | Barrat et al. |
| 2001/0006945 | A1 | 7/2001 | Agrawal |
| 2003/0087848 | A1 | 5/2003 | Bratzler et al. |
| 2004/0009949 | A1 | 1/2004 | Krieg |
| 2004/0053880 | A1 | 3/2004 | Krieg |
| 2005/0239733 | A1 | 10/2005 | Jurk et al. |

(Continued)

FOREIGN PATENT DOCUMENTS

| | | |
|---|---|---|
| EP | 0 313 219 A2 | 4/1989 |
| EP | 0 313 219 A3 | 4/1989 |

(Continued)

OTHER PUBLICATIONS

Agrawal et al. (1986). "Efficient Methods for Attaching Non-Radioactive Labels to the 5' Ends of Synthetic Oligodeoxyribonucleotides," *Nucleic Acids Res.* 14:6227-6245.

(Continued)

*Primary Examiner* — Oluwatosin Ogunbiyi
(74) *Attorney, Agent, or Firm* — Morrison & Foerster LLP

(57) ABSTRACT

The application relates to the use of immunoregulatory polynucleotides and/or immunoregulatory compounds in combination with other therapeutic agents. The application further relates to immunoregulatory polynucleotides and/or immunoregulatory compounds comprising a modified immunoregulatory sequence. It also relates to the administration of the immunoregulatory polynucleotides and/or immunoregulatory compounds comprising a modified immunoregulatory sequence to regulate an immune response.

37 Claims, 41 Drawing Sheets

(56) References Cited

U.S. PATENT DOCUMENTS

| | | | |
|---|---|---|---|
| 2006/0193821 | A1 | 8/2006 | Diener et al. |
| 2006/0193869 | A1 | 8/2006 | Barrat et al. |
| 2007/0009899 | A1 | 1/2007 | Mounts et al. |
| 2011/0123561 | A1 | 5/2011 | Barrat et al. |
| 2013/0156814 | A1 | 6/2013 | Barrat et al. |
| 2015/0050296 | A1 | 2/2015 | Barrat et al. |

FOREIGN PATENT DOCUMENTS

| | | |
|---|---|---|
| EP | 0 313 219 B1 | 4/1989 |
| WO | WO-89/02439 A1 | 3/1989 |
| WO | WO-95/07073 A1 | 3/1995 |
| WO | WO-96/40197 A1 | 12/1996 |
| WO | WO-97/46251 A1 | 12/1997 |
| WO | WO-98/16247 A1 | 4/1998 |
| WO | WO-98/55495 A2 | 12/1998 |
| WO | WO-98/55495 A3 | 12/1998 |
| WO | WO-98/55495 B1 | 12/1998 |
| WO | WO-00/34231 A1 | 6/2000 |
| WO | WO-00/61151 A2 | 10/2000 |
| WO | WO-00/61151 A3 | 10/2000 |
| WO | WO-00/75105 A1 | 12/2000 |
| WO | WO-01/22972 A2 | 4/2001 |
| WO | WO-01/22972 A3 | 4/2001 |
| WO | WO-01/68697 A2 | 9/2001 |
| WO | WO-01/68697 A3 | 9/2001 |
| WO | WO-02/10438 A2 | 2/2002 |
| WO | WO-02/10438 A3 | 2/2002 |
| WO | WO-02/095010 A2 | 11/2002 |
| WO | WO-02/095010 A3 | 11/2002 |
| WO | WO-03/085110 A2 | 10/2003 |
| WO | WO-03/085110 A3 | 10/2003 |
| WO | WO-03/103586 A2 | 12/2003 |
| WO | WO-03/103586 A3 | 12/2003 |
| WO | WO-03/103708 A1 | 12/2003 |
| WO | WO-2004/014322 A2 | 2/2004 |
| WO | WO-2004/014322 A3 | 2/2004 |
| WO | WO-2004/047734 A2 | 6/2004 |
| WO | WO-2004/047734 A3 | 6/2004 |
| WO | WO-2004/058179 A2 | 7/2004 |
| WO | WO-2004/058179 A3 | 7/2004 |
| WO | WO-2005/115479 A2 | 8/2005 |
| WO | WO-2005/086835 A2 | 9/2005 |
| WO | WO-2005/086835 A3 | 9/2005 |
| WO | WO-2006/028742 A2 | 3/2006 |
| WO | WO-2006/028742 A3 | 3/2006 |
| WO | WO-2006/066003 A2 | 6/2006 |
| WO | WO-2006/066003 A3 | 6/2006 |
| WO | WO-2007/075626 A2 | 7/2007 |
| WO | WO-2007/075626 A3 | 7/2007 |
| WO | WO-2007/095387 A2 | 8/2007 |
| WO | WO-2007/095387 A3 | 8/2007 |
| WO | WO-2007/117686 A2 | 10/2007 |
| WO | WO-2007/117686 A3 | 10/2007 |
| WO | WO-2008/009693 A1 | 1/2008 |
| WO | WO-2009/055076 A2 | 4/2009 |
| WO | WO-2009/055076 A3 | 4/2009 |

OTHER PUBLICATIONS

Akira et al. (2003). "Recognition of Pathogen-Associated Molecular Patterns by TLR Family," *Immunol. Lett.* 85:85-95.
Alexopoulou et al. (2001). "Recognition of Double-Stranded RNA and Activation of NF-κB by Toll-Like Receptor 3," *Nature* 413:732-738.
Altmann et al. (1995). "NMR Studies of DNA Duplexes Singly Cross-Linked by Different Synthetic Linkers," *Nucleic Acids Res.* 23:4827-4835.
Ashman et al. (2005). "Sequence Requirements for Oligodeoxyribonucleotide Inhibitory Activity," *Int. Immunol.* 17:411-420.
Atherton et al. (1981). "Synthesis of a 21-Residue Fragment of Human Proinsulin by the Polyamide Solid Phase Method," *Hoppe Seylers Z. Physiol. Chem.* 362:833-839.
Barrat et al. (2005). "Nucleic Acids of Mammalian Origin can act as Endogenous Ligands for Toll-like Receptors and may Promote Systemic Lupus Erythematosus," *J. Exp. Med.* 202:1131-1139.
Barrat et al. (2008). "Development of TLR Inhibitors for the Treatment of Autoimmune Diseases," *Immunol. Rev.* 223:271-283.
Bartley et al. (1997). "Solution Conformation of an Intramolecular DNA Triplex Containing a Nonnucleotide Linker: Comparison with the DNA Duplex," *Biochemistry* 36:14502-14511.
Bauer et al. (2001). "Human TLR9 Confers Responsiveness to Bacterial DNA via Species-specific CpG Motif Recognition," *Proc. Natl. Acad. Sci. USA* 98:9237-9242.
Beaucage (1993). "Oligodeoxyribonucleotide Synthesis," Chapter 3 In *Protocols for Oligonucleotides and Analogs: Synthesis and Properties*, vol. 20, Agrawal, S. ed.,.Humana Press: Totowa, NJ, pp. 33-61.
Benoit et al. (1987). "Peptides: Strategies for Antibody Production and Radioimmunoassays," in *Neuromethods*, vol. 6, Boulton, A.A. et al. eds., Humana Press: Clifton, NJ, pp. 43-72.
Bischoff et al. (1987). "Introduction of 5'-Terminal Functional Groups into Synthetic Oligonucleotides for Selective Immobilization," *Anal. Biochem.* 164:336-344.
Blanks et al. (1988). "An Oligodeoxynucleotide Affinity Column For the Isolation of Sequence Specific DNA Binding Proteins," *Nucleic Acids Res.* 16:10283-10299.
Borel et al. (1990). "A Novel Technique to Link Either Proteins or Peptides to Gammaglobulin to Construct Tolerogens," *J. Immunol. Methods* 126:159-168.
Borel et al. (1995). "Food Allergens Transformed into Tolerogens," *Int. Arch. Allergy Immunol.* 107:264-267.
Borel et al. (1996). "Parenteral and Oral Administration of Tolerogens: Protein-IgG Conjugates," *Ann. N.Y. Acad. Sci.* 778:80-87.
Boujrad et al. (1993). "Inhibition of Hormone-Stimulated Steroidogenesis in Cultured Leydig Tumor Cells by a Cholesterol-Linked Phosphorothioate Oligodeoxynucleotide Antisense to Diazepam-Binding Inhibitor," *Proc. Natl. Acad. Sci. USA* 90:5728-5731.
Bousquet et al. (1999). "Molecular Mechanism of the Adsorption of a Model Protein (Human Serum Albumin) on Poly(Methylidene Malonate 2.1.2) Nanoparticles," *Pharm. Res.* 16:141-147.
Bowie et al. (1990). "Deciphering the Message in Protein Sequences: Tolerance to Amino Acid Substitutions," *Science* 247:1306-1310.
Chaturvedi et al. (1996). "Stabilization of Triple-Stranded Oligonucleotide Complexes: use of Probes Containing Alternating Phosphodiester and Stereo-Uniform Cationic Phosphoramidate Linkages," *Nucleic Acids Res.* 24:2318-2323.
Chavany et al. (1992). "Polyalkylcyanoacrylate Nanoparticles as Polymeric Carriers for Antisense Oligonucleotides," *Pharm. Res.* 9:441-449.
Chavany et al. (1994). "Adsorption of Oligonucleotides onto Polyisohexylcyanoacrylate Nanoparticles Protects Them Against Nucleases and Increases Their Cellular Uptake," *Pharm. Res.* 11:1370-1378.
Cload et al. (1991). "Polyether Tethered Oligonucleotide Probes," *J. Am. Chem. Soc.* 113:6324-6326.
Connolly (1985). "Chemical Synthesis of Oligonucleotides Containing a Free Sulphydryl Group and Subsequent Attachment of Thiol Specific Probes," *Nucleic Acids Res.* 13:4485-4502.
Connolly (1987). "The Synthesis of Oligonucleotides Containing a Primary Amino Group at the 5'-terminus," *Nucleic Acids Res.* 15:3131-3139.
Cook (1999). "Making Drugs Out of Oligonucleotides: A Brief Review and Perspective," *Nucleosides & Nucleotides* 18:1141-1162.
Corey et al. (1987). "Generation of a Hybrid Sequence-Specific Single-Stranded Deoxyribonuclease," *Science* 238:1401-1403.
Cowdery et al. (1996). "Bacterial DNA Induces NK Cells to Produce IFN-γ In Vivo and Increases the Toxicity of Lipopolysaccharides," *J. Immunol.* 156:4570-4575.
Dagneaux et al. (1996). "Parallel and Antiparallel A-A-T Intramolecular Triple Helices," *Nucleic Acids Res.* 24:4506-4512.
Datta et al. (2003). "The Therapeutic Potential of Antigen-Oligonucleotide Conjugates," *Ann. N.Y. Acad. Sci.* 1002:105-111.

(56) References Cited

OTHER PUBLICATIONS

Deng et al. (Jun. 1999). "Intra-Articularly Localized Bacterial DNA Containing CpG Motifs Induces Arthritis," *Nature Med.* 5:702-705.
Diebold et al. (Mar. 5, 2004). "Innate Antiviral Responses by Means of TLR7-mediated Recognition of Single-stranded RNA," *Science* 303:1529-1531.
Douglas et al. (1987). "Nanoparticles in Drug Delivery," *Crit. Rev. Ther. Drug. Carrier Syst.* 3:233-261.
Dumas et al. (1995). "Induction of Tolerance by Administration of Hapten-Immunoglobulin Conjugates is Associated with Decreased IL-2 and IL-4 Production," *Arch. Dematol. Res.* 287:123-128.
Duramad et al. (2003). "IL-10 Regulates Plasmacytoid Dendritic Cell Response to CpG-containing Immunostimulatory Sequences," *Blood* 102:4487-4492.
Duramad et al. (2005). "Inhibitors of TLR-9 Act on Multiple Cell Subsets in Mouse and Man In Vitro and Prevent Death In Vivo From Systemic Inflammation," *J. Immunol.* 174:5193-5200.
Durand et al. (1990). "Circular Dichroism Studies of an Oligodeoxyribonucleotide Containing a Hairpin Loop Made of a Hexaethylene Glycol Chain: Conformation and Stability," *Nucleic Acids Res.* 18:6353-6359.
Extended European Search Report mailed on Feb. 23, 2011, for EP Patent Application No. 10011096.4, filed on Aug. 24, 2005, 7 pages.
Extended European Search Report mailed on Jul. 22, 2011, for EP Patent Application No. 11155868.0, filed on Oct. 27, 2008, 9 pages.
Flory et al. (1996). "Nuclease-Resistant Ribozymes Decrease Stromelysin mRNA Levels in Rabbit Synovium Following Exogenous Delivery to the Knee Joint," *Proc. Natl. Acad. Sci. USA* 93:754-758.
Gao et al. (1995). "Circularization of Oligonucleotides by Disulfide Bridge Formation," *Nucleic Acids Res.* 23:2025-2029.
Geoghegan et al. (1992). "Site-Directed Conjugation of Nonpeptide Groups to Peptides and Proteins via Periodate Oxidation of a 2-Amino Alcohol. Application to Modification at N-Terminal Serine," *Bioconjug. Chem.* 3:138-146.
Gnanou et al. (1988). "Synthesis of Star-Shaped Poly(ethylene oxide)," *Makromol. Chem.* 189:2885-2892.
Godard et al. (1995). "Antisense Effects of Cholesterol-Oligodeoxynucleotide Conjugates Associated with Poly(alkylcyanoacrylate) Nanoparticles," *Eur. J. Biochem.* 232:404-410.
Goldberg et al. (2000). "Beyond Danger: Unmethylated CpG Dinucleotides and the Immunopathogensis of Disease," *Immunol. Lett.* 73:13-18.
Goodchild (1990). "Conjugates of Oligonucleotides and Modified Oligonucleotides: A Review of Their Synthesis and Properties," *Bioconjug. Chem.* 1:165-187.
Grabarek et al. (1990). "Zero-length Crosslinking Procedure with the Use of Active Esters," *Anal. Biochem.* 185:131-135.
Hagiwara et al. (1987). "A New Drug-Delivery-System of Anticancer Agents: Activated Carbon Particles Adsorbing Anticancer Agents," *In Vivo* 1:241-252.
Haralambidis et al. (1990). "The Preparation of Polyamide-oligonucelotide Probes Containing Multiple Non-Radioactive Labels," *Nucleic Acids Res.* 18:501-505.
Haralambidis et al. (1990). "The Synthesis of Polyamide-Oligonucleotide Conjugate Molecules," *Nucleic Acids Res.* 18:493-499.
Hartmann et al. (1999). "CpG DNA: A Potent Signal for Growth, Activation, and Maturation of Human Dendritic Cells," *Proc. Natl. Acad. Sci. USA* 96:9305-9310.
Hayashi et al. (2001). "The Innate Immune Response to Bacterial Flagellin is Mediated by Toll-Like Receptor 5," *Nature* 410:1099-1103.
Heil et al. (2003). "The Toll-like Receptor 7 (TLR7)-Specific Stimulus Loxoribine Uncovers a Strong Relationship Within the TLR7, 8 and 9 Subfamily," *Eur. J. Immunol.* 33:2987-2997.
Heil et al. (2004). "Species-Specific Recognition of Single-Stranded RNA via Toll-like Receptor 7 and 8," *Science* 303:1526-1529.
Hemmi et al. (2000). "A Toll-Like Receptor Recognizes Bacterial DNA," *Nature* 408:740-745.
Hemmi et al. (2002). "Small Anti-Viral Compounds Activate Immune Cells via the TLR7 MyD88-Dependent Signaling Pathway," *Nat. Immunol.* 3:196-200.
Hendry et al. (1994). "Using Linkers to Investigate the Spatial Separation of the Conserved Nucleotides $A_9$ and $G_{12}$ in the Hammerhead Ribozyme," *Biochem. Biophys. Acta* 1219:405-412.
Ho et al. (2003). "An Immunomodulatory CpG Oligonucleotide for the Treatment of Autoimmunity via the Innate and Adaptive Immune Systems," *J. Immunol.* 171:4920-4926.
Inman (1975). "Thymus-lndependent Antigens: the Preparation of Covalent, Hapten-Ficoll Conjugates," *J. Immunol.* 114:704-709.
International Preliminary Report on Patentability mailed on May 6, 2010, for PCT Patent Application No. PCT/US2008/012220, filed on Oct. 27, 2008, 13 pages.
International Search Report mailed Aug. 4, 2006 for PCT Application No. PCT/US2005/030494 filed Aug. 24, 2005, 8 pages.
International Search Report mailed Oct. 13, 2006 for PCT Application No. PCT/US2005/045433, filed Dec. 16, 2005, five pages.
International Search Report mailed on Sep. 14, 2009, or PCT Patent Application No. PCT/US2008/012220, filed on Oct. 27, 2008, 7 pages.
Iyer et al. (1990). "The Automated Synthesis of Sulfur-Containing Oligonucleotides Using 3H-1,2,Benzodithiol-3-One 1,1-Dioxide as a Sulfur-Transfer Agent," *J. Org. Chem.* 55:4693-4699.
Jäger et al. (1988). "Oligonucleotide N-Akylphosphoroamidates: Synthesis and Binding to Polynucleotides," *Biochem.* 27:7247-7246.
Jarvis et al. (1996). "Optimizing the Cell Efficacy of Synthetic Ribozymes: Site Selection and Chemical Modifications of Ribozymes Targeting the Proto-Oncogene *c-myb*," *J. Biol. Chem.* 271:29107-29112.
Jäschke et al. (1993). "Automated Incorporation of Polyethylene Glycol into Synthetic Oligonucleotides," *Tetrahedron Lett.* 34:301-304.
Jurk et al. (2002). "Human TLR7 or TLR8 Independently Confer Responsiveness to the Antiviral Compound R-848," *Nat. Immunol.* 3:499.
Kandimalla et al. (2001). "Effect of Chemical Modifications of Cytosine and Guanine in a CpG-Motif of Oligonucleotides: Structure-Immunostimulatory Activity Relationships," *Bioorg. Med. Chem.* 9:807-813.
Kessler (1992) "Nonradioactive Labeling Methods for Nucleic Acids," Chapter 2 in *Nonisotopic DNA Probe Techniques*, Kricka, L.J. ed., Academic Press: San Diego, CA, pp. 29-92.
Klinman et al. (1997). "Contribution of CpG Motifs to the Immunogenicity of DNA Vaccines," *J. Immunol.* 158:3635-3639.
Klinman et al. (2003). "Regulation of CpG-induced Immune Activation by Suppressive Oligonucelotides," *Ann. N.Y. Acad. Sci.* 1002:112-123.
Kremsky et al. (1987). "Immobilization of DNA via Oligonucleotides Containing an Aldehyde or Carboxylic Acid Group at the 5' Terminus," *Nucleic Acids Res.* 15:2891-2909.
Krieg et al. (1995). "CpG Motifs in Bacterial DNA Trigger Direct B-Cell Activation," *Nature* 374:546-549.
Lambert et al. (1998). "Effect of Polyisobutylcyanoacrylate Nanoparticles and Lipofection® Loaded with Oligonucleotides on Cell Viability and PKCα Neosynthesis in HepG2 Cells," *Biochimie* 80:969-976.
Lambrecht et al. (2000). "Induction of Rapid T Cell Activation, Division, and Recirculation by Intratracheal Injection of Dendritic Cells in a TCR Transgenic Model," *J. Immunol.* 164:2937-2946.
Leadbetter et al. (2002). "Chromatin-IgG Complexes Activate B Cells by Dual Engagement of IgM and Toll-Like Receptors," *Nature* 416:603-607.
Lee et al. (1980). "A Method for Preparing β-hCG COOH Peptide-Carrier Conjugates of Predictable Composition," *Mol. Immunol.* 17:749-756.
Lee et al. (2003). "Molecular Basis for the Immunostimulatory Activity of Guanine Nucleoside Analogs: Activation of Toll-like Receptor 7," *Proc. Natl. Acad. Sci. USA* 100:6646-6651.

(56) References Cited

OTHER PUBLICATIONS

Lenert et al. (2001). "CpG Stimulation of Primary Mouse B Cells is Blocked by Inhibitory Oligodeoxyribonucleotides at a Site Proximal to NF-κB Activation," *Antisense & Nucleic Acid Drug Development* 11:247-256.

Li et al. (2003). "Effective Induction of CF8+ T-Cell response Using CpG Oligodeoxynucleotides and HER-2/neu-Derived Peptide Co-Encapsulated in Liposomes," *Vaccine* 21:3319-3329.

Li (1992). Chapter 5 In *Capillary Electrophoresis: Principles, Practice and Application*, Journal of Chromotography Library, vol. 52, Elsevier Science Publishers: Amsterdam, The Netherlands, pp. 202-206.

Ma et al. (1993). "Design and Synthesis of RNA Miniduplexes via a Synthetic Linker Approach. 2. Generation of Covalently Closed, Double-Stranded Cyclic HIV-1 TAR RNA Analogs with High Tat-Binding Affinity," *Nucleic Acids Res.* 21:2585-2589.

Ma et al. (1993). "Design and Synthesis of RNA Miniduplexes via a Synthetic Linker Approach," *Biochemistry* 32:1751-1758.

Marshall et al. (Jun. 2003). "Identification of a Novel CpG DNA Class and Motif that Optimally Stimulate B Cell and Plasmacytoid Dendritic Cell Functions," *J. Leukoc. Biol.* 73:781-792.

McCurdy et al. (1991). "Deoxyoligonucleotides with Inverted Polarity: Synthesis and Use in Triple-Helix Formation," *Nucleosides & Nucleotides* 10:287-290.

Miller et al. (1971). "Synthesis and Properties of Adenine and Thymine Nucleoside Alkyl Phosphortriesters, the Neutral Analogs of Dinucleoside Monophosphates," *J. Am. Chem. Soc.* 93:6657-6665.

Nelson et al. (1996). "Incorporation of a Non-Nucleotide Bridge into Hairpin Oligonucleotides Capable of High-Affinity Binding to the Rev Protein of HIV-1," *Biochemistry* 35:5339-5344.

Nelson et al. (1997). "N3'→P5' Oligodeoxyribonucleotide Phosphoramidates: A New Method of Synthesis Based on a Phosphoramidite Amine-Exchange Reaction," *J. Org. Chem.* 62:7278-7287.

Nelson et al. (1989). "A New and Versatile Reagent for Incorporating Multiple Primary Aliphatic Amines into Synthetic Oligonucleotides," *Nucleic Acids Res.* 17:7179-7186.

O'Shannessy et al. (1985). "Specific Conjugation Reactions of the Oligosaccharide Moieties of Immunoglobulins," *J. Applied Biochem.* 7:347-355.

Ono et al. (1991). "DNA Triplex Formation of Oligonucleotide Analogues Consisting of Linker Groups and Octamer Segments That Have Opposite Sugar-Phosphate Backbone Polarities," *Biochemistry* 30:9914-9921.

Ozinsky et al. (2000). "Co-Operative Induction of Pro-Inflammatory Signaling by Toll-Like Receptors," *J. Endotoxin Res.* 6:393-396.

Ozinsky et al. (2000). "The Repertoire for Pattern Recognition of Pathogens by the Innate Immune System is Defined by Cooperation Between Toll-Like Receptors," *Proc. Natl. Acad. Sci. USA* 97:13766-13771.

Peyrottes et al. (1996). "Oligodeoxynucleoside Phosphoramidates (P-NH$_2$): Synthesis and Thermal Stability of Duplexes with DNA and RNA Targets," *Nucleic Acids Res.* 24:1841-1848.

Pisetsky (1996). "The Immunologic Properties of DNA," *J. Immunol.* 156:421-423.

Poltorak et al. (1998). "Defective LPS Signaling in C3H/HeJ and C57BL/10ScCr Mice: Mutations in *Tlr4* Gene," *Science* 282:2085-2088.

Puig et al. (2006). "Use of Thermolytic Protective Groups to Prevent G-Tetrad Formation in CpG ODN Type D: Structural Studies and Immunomodulatory Activity in Primates," *Nucleic Acids Research* 34:6488-6495.

Rein et al. (1993). "New Developments in Synthesis of Star Polymers with Poly(ethylene oxide) Arms," *Acta Polymer* 44:225-229.

Reynolds et al. (1996). "Antisense Oligonucleotides Containing an Internal Non-Nucleotide-Based Linker Promote Site-Specific Cleavage of RNA," *Nucleic Acids Res.* 24:760-765.

Richardson et al. (1991). "Tethered Oligonucleotide Probes. A Strategy for the Recognition of Structured RNA," *J. Am. Chem. Soc.* 113:5109-5111.

Roget et al. (1989). "Synthesis and Use of Labelled Nucleoside Phosphoramidite Building Blocks Bearing a Reporter Group: Biotinyl, Dinitrophenyl, Pyrenyl and Dansyl," *Nucleic Acids Res.* 17:7643-7651.

Roman et al. (1997). "Immunostimulatory DNA Sequences Function as T Helper-1-Promoting Adjuvants," *Nature Med.* 3:849-854.

Salunkhe et al. (1992). "Control of Folding and Binding of Oligonucleotides by Use of a Nonnucleotide Linker," *J. Am. Chem. Soc.* 114:8768-8772.

Santeliz et al. (2002). "Amb a 1-Linked CpG Oligodeozynucleotides Reverse Established Airway Hyperresponsiveness in a Murine Model of Asthma," *J. Aller. Clin. Immunol.* 109:455-462.

Schacht et al. (1996). "Biomedical Applications of Degradable Polyphosphazenes," *Biotechnol. Bioeng.* 52:102-108.

Schroeder et al. (1998). "Efficacy of Oral Dalargin-Loaded Nanoparticle Delivery Across the Blood-Brain Barrier," *Peptides* 19:777-780.

Schultz et al. (1996). "Oligo-2'-fluoro-2'-deoxynucelotide N3'→P5' Phosphoramidates: Synthesis and Properties," *Nucleic Acids Res.* 24:2966-2973.

Shevach et al. (2001). "Control of T-Cell Activation by CD4$^+$ CD25$^+$ Suppressor T Cells," *Immunol. Rev.* 182:58-67.

Shirota et al. (2000). "Regulation of Murine Airway Eosinophilia and TH2 Cells by Antigen-Conjugated CPG Oligonucleotides as a Novel Antigen-Specific Immunomodulator," *J. Immunol.* 164:5575-5582.

Staros et al. (1986). "Enhancement by *N*-Hydroxysulfosuccinimide of Water-Soluble Carbodiimide-Mediated Coupling Reactions," *Anal. Biochem.* 156:220-222.

Stirchak et al. (1989). "Uncharged Stereoregular Nucleic Acid Analogs: 2. Morpholino Nucleoside Oligomers with Carbamate Internucleoside Linkages," *Nucleic Acids Res.* 17:6129-6141.

Stunz et al. (2002). "Inhibitory Oligonucleotides Specifically Block Effects of Stimulatory CpG Oligonucleotides in B Cells," *Eur. J. Immunol.* 32:1212-1222.

Takeshita et al. (2001). "Cutting Edge: Role of Toll-Like Receptor 9 in CpG DNA-induced Activation of Human Cells," *J. Immunol.* 167:3555-3558.

Tang et al. (2000). "Large-Scale Synthesis of Oligonucleotide Phosphorothioates Using 3-Amino-1,2,4-dithiazole-5-thione as an Efficient Sulfur-Transfer Reagent," *Org. Process Res. Dev.* 4:194-198.

Tomalia et al. (1990). "Starburst Dendrimers: Molecular-Level Control of Size, Shape, Surface Chemistry, Topology, and Flexibility from Atoms to Macroscopic Matter," *Angew. Chem. Int. Ed. Engl.* 29:138-175.

Tung et al. (1991). "Preparation of Oligonucleotide-Peptide Conjugates," *Bioconjug. Chem.* 2:464-465.

Waldner et al. (2004). "Activation of Antigen-Presenting Cells by Microbial Products Breaks Self Tolerance and Induces Autoimmune Disease," *J. Clin. Invest.* 113:990-997.

Walker et al. (2002). "The Enemy Within: Keeping Self-reactive T Cells at bay in the Periphery," *Nat. Rev. Immunol.* 2:11-19.

Wang et al. (1994). "Circular RNA Oligonucleotides. Synthesis, Nucleic Acid Binding Properties, and a Comparison with Circular DNAs," *Nucleic Acids Res.* 22:2326-2333.

Wang et al. (1991). "Multinuclear Nuclear Magnetic Resonance Studies of Na Cation-Stabilized Complex Formed by d(G-G-T-T-T-T-C-G-G) in Solution. Implications for G-tetrad Structures," *J. Mol. Biol.* 222:819-832.

Wang et al. (1994). "Solution Structure of the *Tetrahymena* Telomeric Repeat d(T$_2$G$_4$)$_4$ G-Tetraplex," *Structure* 2:1141-1156.

Warner et al. (1984). "Construction and Evaluation of an Instrument for the Automated Synthesis of Oligodeoxyribonucleotides," *DNA* 3:401-411.

(56) References Cited

OTHER PUBLICATIONS

Watwe et al. (1995). "Manufacture of Liposomes: A Review," *Curr. Sci.* 68:715-724.

Wyrzykiewicz et al. (1994). "Efficiency of Sulfhurization in the Synthesis of Oligodeoxyribonucleotide Phosphorothioates Utilizing Various Sulfhurizing Reagents," *Bioorg. & Med. Chem. Lett.* 4:1519-1522.

Yamada et al. (2002). "Effect of Suppressive DNA on CpG-Induced Immune Activation," *J. Immunol.* 169:5590-5594.

Yamamoto et al. (1992). "Unique Palindromic Sequences in Synthetic Oligonucleotides are Required to Induce INF and Augment INF-Mediated Natural Killer Activity," *J. Immunol.* 148:4072-4076.

Yanagawa et al. (1988). "Analysis of Superhelical Structures of Nucleic Acid-Lipid Conjugates by Image Processing," *Nucleic Acids Symp. Ser.* 19:189-192.

Zon (1993). "Oligonucleoside Phosphorothioates," Chapter 8 In *Methods in Microbiology: Protocols for Oliqonucleotides and Analogs: Synthesis and Properties*, Agrawal, S. ed., Humana Press: Totowa, NJ, 20:165-189.

Zuckermann et al. (1987). "Efficient Methods for Attachment of Thiol Specific Probes to the 3'-ends of Synthetic Oligodeoxyribonucleotides," *Nucleic Acids Res.* 15:5305-5321.

Barrat et al. (2007). "Treatment of Lupus-prone Mice with a Dual Inhibitor of TLR7 and TLR9 Leads to Reduction of Autoantibody Production and Amelioration of Disease Symptoms," *Eur. J. Immunol.* 37:3582-3586.

Guiducci et al. (2009). "Signalling Pathways Leading to IFN-α Production in Human Plasmacytoid Dendritic Cell and the Possible Use of Agonists or Antagonists of TLR7 and TLR9 in Clinical Indications," J. Intern. Med. 265:43-57.

Morel et al. (2000) In situ Hybridization in light Microscopy. CRC Press Publisher. p. 58.

TLR7 (R848)

TLR9 (ISS)

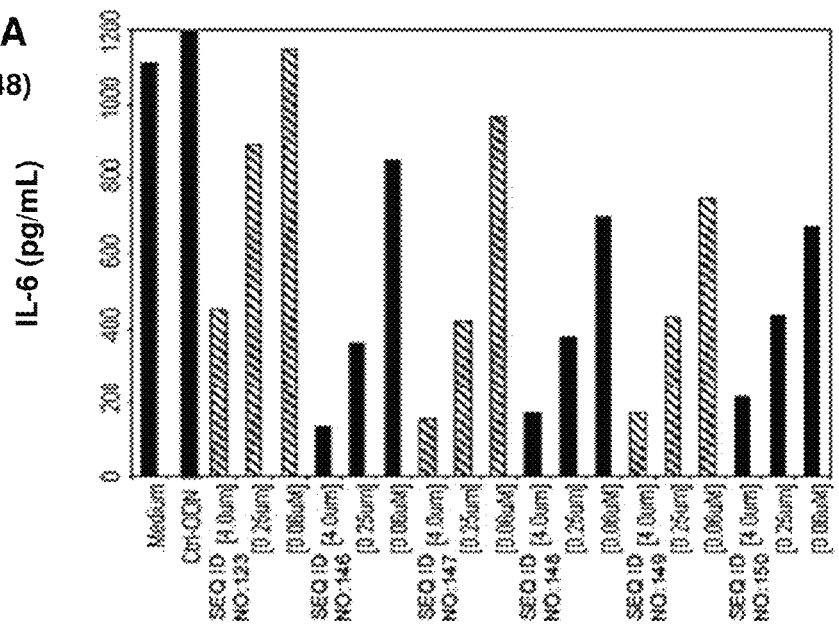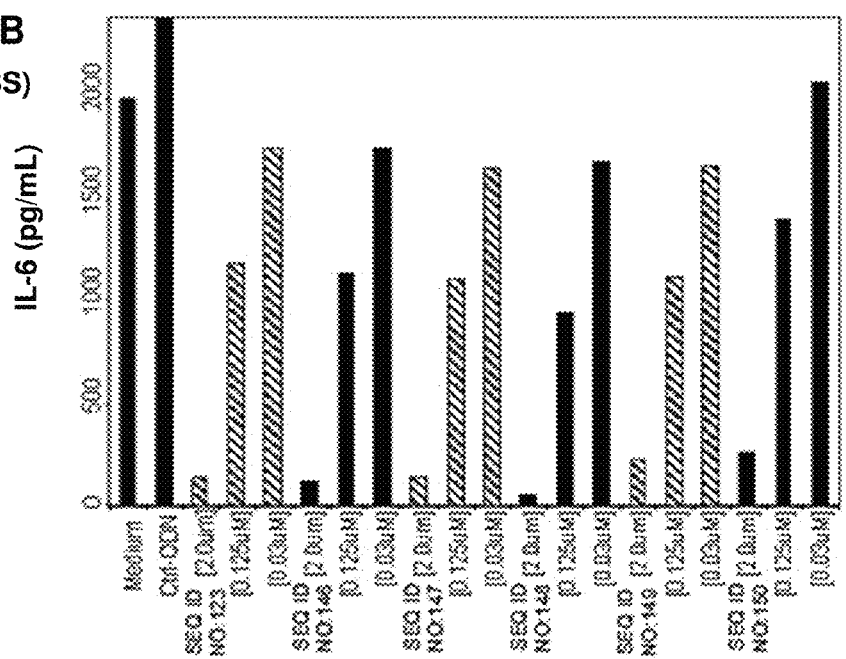

TLR7 (R848)

TLR9 (ISS)

TLR7 (R848)

TLR9 (ISS)

TLR7 (R848)

TLR9 (ISS)

TLR7 (R848)

TLR9 (ISS)

TLR7 (R848)

TLR9 (ISS)

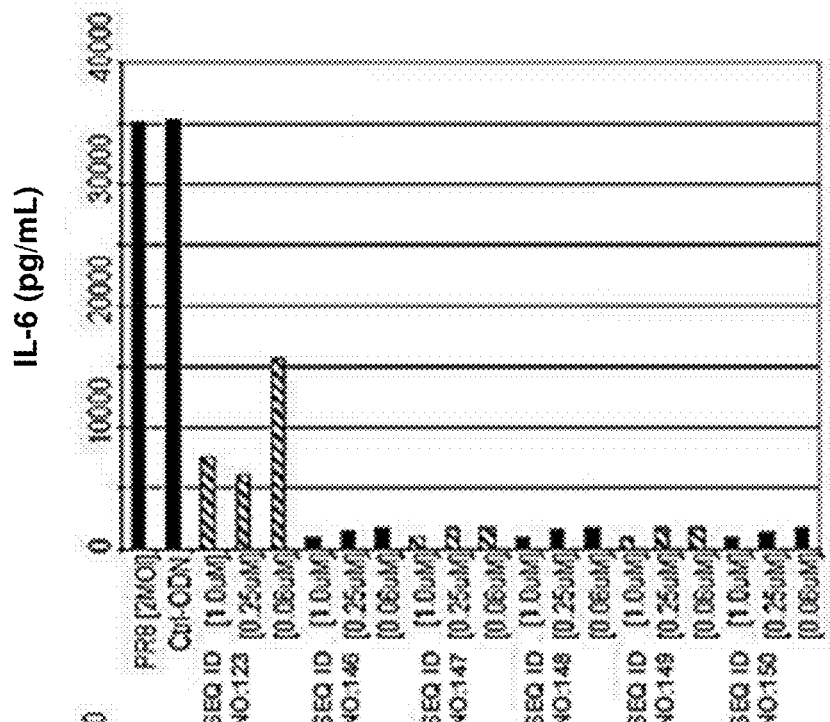
FIG. 20A TLR7 (R848)
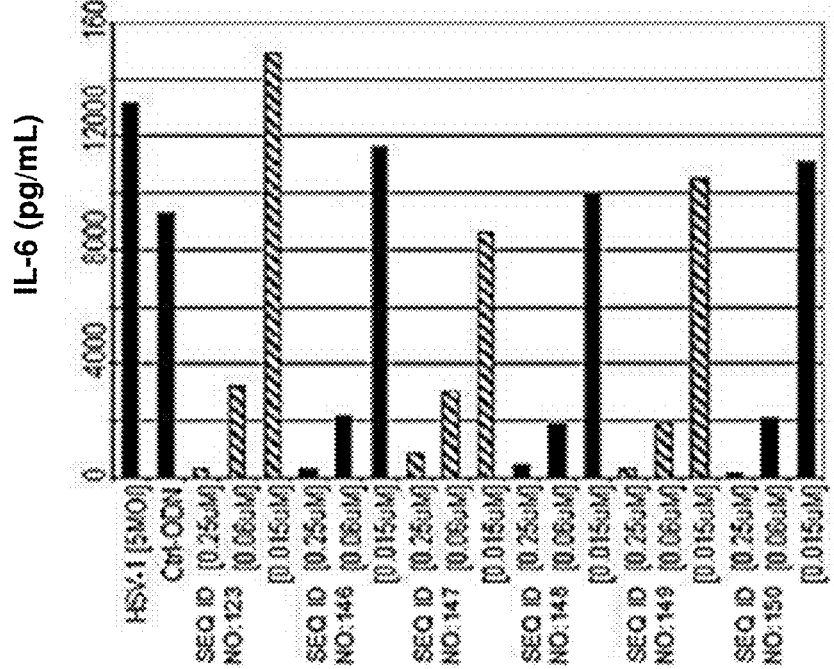
FIG. 20B TLR9 (ISS)

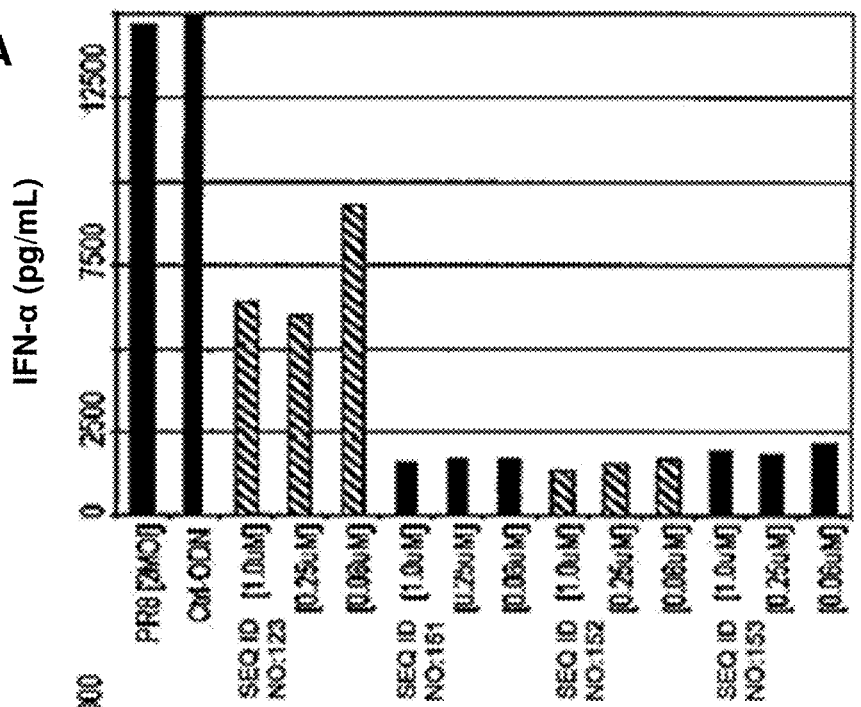
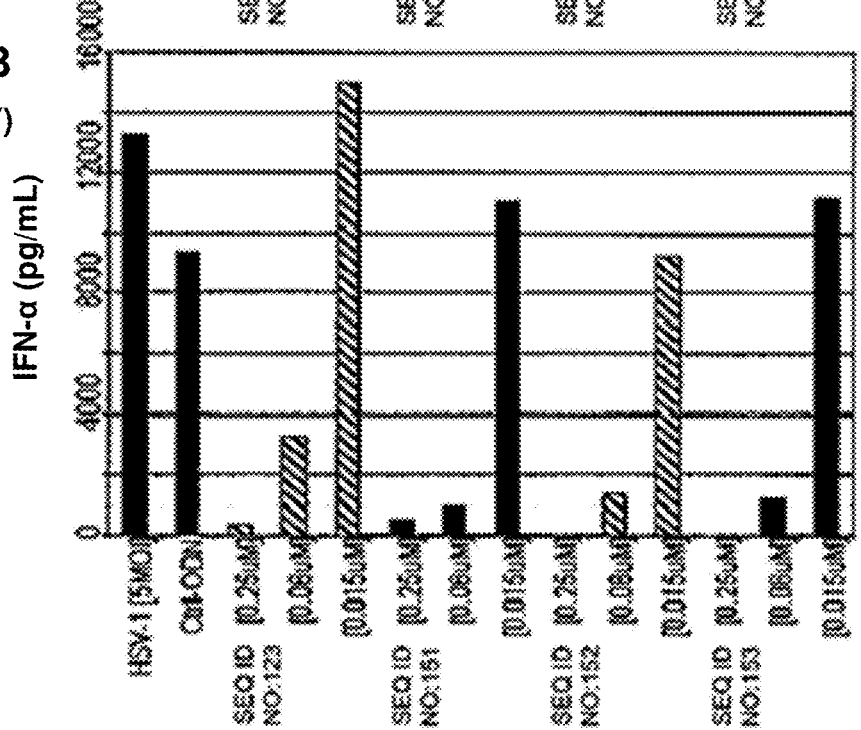

FIG. 40A 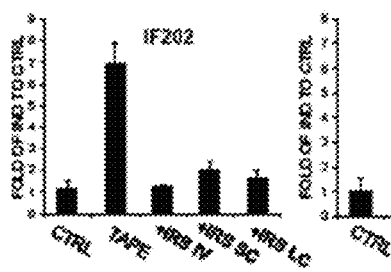 FIG. 40B FIG. 40C 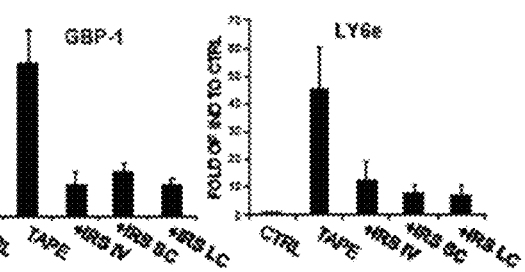 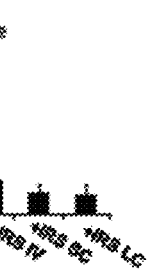
FIG. 40D 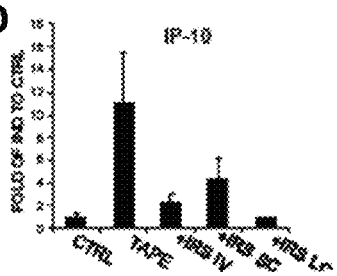 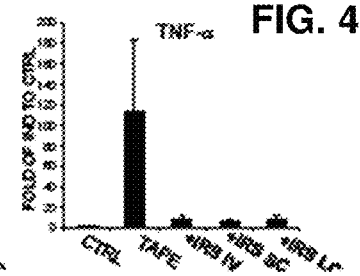 FIG. 40E
FIG. 40F 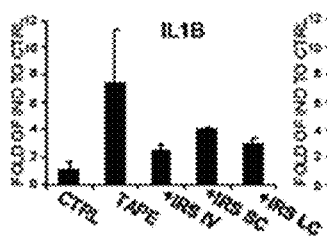 FIG. 40G FIG. 40H 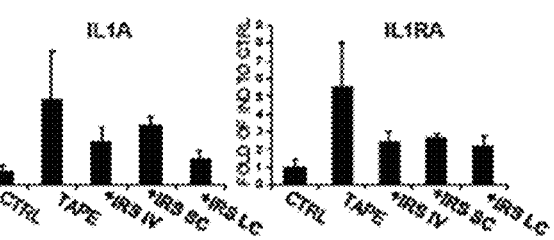 

METHODS AND COMPOSITIONS FOR INHIBITION OF IMMUNE RESPONSES AND AUTOIMMUNITY

CROSS-REFERENCE TO RELATED APPLICATIONS

This application is a continuation of U.S. application Ser. No. 12/767,692, filed Apr. 26, 2010, now U.S. Pat. No. 8,962,579, which is a continuation of International Application No. PCT/US2008/012220, filed Oct. 27, 2008, which claims the priority benefit of U.S. Provisional Application 60/983,073 filed Oct. 26, 2007, which are hereby incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 377882003901SubSeqList.txt, date recorded: Jun. 8, 2015, size: 67 KB 377882003901SeqList.txt, date recorded: Apr. 20, 2015, size: 71 KB).

TECHNICAL FIELD

The application relates to the use of immunoregulatory polynucleotides and/or immunoregulatory compounds in combination with other therapeutic agents. The application further relates to immunoregulatory polynucleotides and/or immunoregulatory compounds comprising a modified immunoregulatory sequence. It also relates to the administration of the immunoregulatory polynucleotides and/or immunoregulatory compounds comprising a modified immunoregulatory sequence to regulate an immune response.

BACKGROUND

Immunity can generally be classified as innate immunity or as adaptive immunity. Innate immune responses typically occur immediately upon infection to provide an early barrier to infectious disease whereas adaptive immune responses occur later with the generation of antigen-specific effector cells and often long term protective immunity. Innate immune responses do not generate lasting protective immunity but appear to play a role in the generation of the later arising adaptive immune response.

Innate immunity uses germ-line encoded receptors to recognize features that are common to many pathogens and to activate signaling events that result in the expression of effector molecules. Some of these effector molecules may eventually induce an adaptive immune response. The family of Toll-like receptors (TLRs) have been associated with innate immune response signaling and microbial ligands have been identified for several mammalian TLRs. For example, TLR2 interacts with peptidoglycan, bacterial lipopeptides and certain types of lipopolysaccharide (LPS), TLR3 interacts with double-stranded RNA, TLR4 interacts with LPS and TLR-5 interacts with bacterial flagellin. See, for example, Poltorak et al. (1998) Science 282:2085-2088; Akira et al. (2003) Immunol. Lett. 85:85-95; Alexopoulou et al. (2001) Nature 413:732-738; Hayashi et al. (2001) Nature 410:1099-1103. TLR-7 is activated by guanosine analogs, by small antiviral compounds such as imidazoquinolines, imiquimod and R-848, and by single-stranded viral RNA, and TLR-8 is also activated by R-848 and single-stranded viral RNA. See, for example, Lee et al. (2003) Proc. Natl. Acad. Sci. USA 100:6646-6651; Hemmi et al. (2002) Nat. Immunol. 3:196-200; Jurk et al. (2002) Nat. Immunol. 3:499; Heil et al. (2004) Science 303:1526-1529; Diebold et al. (2004) Science 303:1529-1531. TLR-9 has been shown to recognize immunostimulatory nucleic acid molecules such as bacterial DNA and immunostimulatory DNA containing a 5'-CG-3' sequence. See, for example, Hemmi et al. (2000) Nature 408:740-745; Bauer et al. (2001) Proc. Natl. Acad. Sci. USA 98:9237-9242; Takeshita et al. (2001) J. Immunol. 167:3555-3558. In addition, certain TLRs (for example, TLR-1, TLR-2 and TLR-6) can heterodimerize, interact with their microbial ligands and lead to cell activation, thus expanding the ligand repertoire of the TLR family. Ozinsky et al. (2000) J. Endotoxin Res. 6:393-396; Ozinsky et al. (2000) Proc. Natl. Acad. Sci. USA 97:13766-13771.

Immunostimulatory nucleic acid (ISNA) molecules, such as bacterial DNA or a polynucleotide containing unmethylated 5'-CG-3' sequences, can stimulate innate immune responses, such as cytokine production, and dendritic cell and macrophage activation, and then lead to a Th1-type immune response. Immunostimulatory nucleic acid molecules stimulate the immune response through interaction with and signaling through the mammalian TLR9 receptor. See Hemmi et al. (2000), Supra. Mammalian DNA does not generally possess immunostimulatory activity due apparently to a low frequency of CG sequences and to most of the CG sequences having a methylated cytosine. Mammalian immune system cells thus appear to distinguish bacterial DNA from self DNA through the TLR9 receptor.

Immunostimulatory nucleic acid molecules have been implicated in the pathogenesis of arthritis. Immunostimulatory nucleic acid has been shown to play a role in activation of autoreactive B cells such as those produce a class of autoantibodies known as rheumatoid factor (RF). Thus, such immunostimulatory nucleic acids appear to play a role in systemic autoimmunity. In addition, immunostimulatory nucleic acid can enhance toxicity of LPS and contribute to adverse effects of administration of vectors for gene therapy. See, for example, Deng et al. (1999) Nature Med. 5:702-705, Leadbetter et al. (2002) Nature 416:603-607, Cowdery et al. (1996) J. Immunol. 156:4570-4575, U.S. Pat. No. 6,225,292.

There remains a need to identify strategies to control unwanted immune activation, including unwanted activation of the innate immune response.

All patents, patent applications, and publications cited herein are hereby incorporated by reference in their entirety.

SUMMARY

The invention relates to immunoregulatory polynucleotides and/or immunoregulatory compounds and methods for inhibiting an immune response in individuals using these polynucleotides and compounds, and particularly, methods for inhibiting an immune response in humans. The invention further relates to the use of immunoregulatory polynucleotides and/or immunoregulatory compounds in combination with other therapeutic agents. In some variations, the immunoregulatory polynucleotides and/or immunoregulatory compounds comprise a modified immunoregulatory sequence. In some variations, the immunoregulatory polynucleotides and/or immunoregulatory compounds comprise an unmodified immunoregulatory sequence.

The invention provides methods of regulating an immune response in an individual, comprising administering to the individual a polynucleotide in an amount sufficient to regulate an immune response in the individual, wherein the polynucleotide consists of a nucleotide sequence of the formula: 5'-JGCN$_z$-3' (SEQ ID NO:119), wherein J is U or T, the sequence 5'-JGC-3' comprises a modification, each N is a nucleotide, and z is an integer from 1 to about 100.

In some variations, the modification is selected from the group consisting of a 2'-sugar modification, a 3'-terminal internucleotide phosphodiester linkage modification, and a 5'-methyl-cytosine modification. In some variations, the 3'-terminal internucleotide phosphodiester linkage modification is selected from the group consisting of an alkyl or aryl phosphotriester, alkyl or aryl phosphonate, hydrogen phosphonate, phosphoramidate, and phosphoroselenate linkage modification. In some variations, the 3'-terminal internucleotide phosphodiester linkage modification is a phosphoramidate modification. In some variations, the modification is a 2'-sugar modification. In some variations, the 2'-sugar modification is a 2'-O-methyl sugar modification or 2'-O-methoxyethyl sugar modification. In some variations, the modification is a 2'-O-methyl sugar modification. In some variations, the modification is a 5'-methyl-cytosine modification.

In some variations, the each nucleotide N comprises a modification. In some variations, the sequence N$_z$ comprises a modification. In some variations, the modification of nucleotide N or the sequence N$_z$ is selected from the group consisting of a 2'-sugar modification, a 3'-terminal internucleotide phosphodiester linkage modification, and a 5'-methyl-cytosine modification. In some variations, the modification is a 2'-sugar modification. In some variations, the 2'-sugar modification is a 2'-O-methyl sugar modification or 2'-O-methoxyethyl sugar modification. In some variations, the modification is a 2'-O-methyl sugar modification. In some variations, the each nucleotide N consists of a modification and said modification is a 2'-O-methyl sugar modification.

In some variations, the polynucleotide further comprises 5'-TGC-3', wherein 5'-TGC-3' is unmodified. In some variations, the polynucleotide comprises 5'-JGCTGC-3' (SEQ ID NO:189), wherein J is U or T and the sequence 5'-JGC-3' comprises a modification. In some variations, the modification is a 2'-O-methyl sugar modification or 2'-O-methoxyethyl sugar modification. In some variations, the modification is a 2'-O-methyl sugar modification.

In some variations, the polynucleotide further comprises a nucleotide sequence of the formula: 5'-S$_1$S$_2$S$_3$S$_4$Q$_y$M$_r$-3' (SEQ ID NO:190), wherein S$_1$, S$_2$, S$_3$, and S$_4$ are independently G, I, or 7-deaza-dG, each Q is a nucleotide, each M is a nucleotide comprising a modification, y is an integer greater than 1, and r is an integer from 1 to about 50. In some variations, the modification of nucleotide M is selected from the group consisting of a 2'-O-methyl sugar modification, a 3'-terminal internucleotide phosphodiester linkage modification, and a 5'-methyl-cytosine modification. In some variations, the modification is a 2'-sugar modification. In some variations, the 2'-sugar modification is a 2'-O-methyl sugar modification or 2'-O-methoxyethyl sugar modification. In some variations, the modification is a 2'-O-methyl sugar modification. In some variations, one or more of S$_1$, S$_2$, S$_3$, and S$_4$ are G. In some variations, one or more of S$_1$, S$_2$, S$_3$, and S$_4$ are I. In some variations, S$_1$, S$_2$, S$_3$, and S$_4$ are G.

In some variations, the immune response is inhibited. In some variations, the immune response is a TLR7 dependent immune response. In some variations, the immune response is a TLR9 dependent immune response and a TLR7 dependent immune response. In some variations, the immune response is a TLR7 dependent immune response and is independent of TLR9 dependent immune response. In some variations, the immune response is associated with an autoimmune disease. In some variations, regulating the immune response ameliorates one or more symptoms of the autoimmune disease. In some variations, regulating the immune response prevents or delays development of the autoimmune disease. In some variations, the autoimmune disease is selected from the group consisting of systemic lupus erythematosus (SLE) and rheumatoid arthritis. In some variations, the immune response is associated with chronic pathogen stimulation.

The invention also provides methods of regulating an immune response in an individual, comprising administering to the individual a polynucleotide in an amount sufficient to regulate an immune response in the individual, wherein the polynucleotide comprising a nucleotide sequence of the formula: 5'-S$_1$S$_2$S$_3$S$_4$Q$_y$M$_r$-3' (SEQ ID NO:190), wherein S$_1$, S$_2$, S$_3$, and S$_4$ are independently G, I, or 7-deaza-dG, each Q is a nucleotide, each M is a nucleotide comprising a modification, y is an integer greater than 1, and r is an integer from 1 to about 100.

In some variations, the modification of nucleotide M is selected from the group consisting of a 2'-sugar modification, a 3'-terminal internucleotide phosphodiester linkage modification, and a 5'-methyl-cytosine modification. In some variations, the modification is a 2'-sugar modification. In some variations, the 2'-sugar modification is a 2'-O-methyl sugar modification or 2'-O-methoxyethyl sugar modification. In some variations, the modification is a 2'-O-methyl sugar modification. In some variations, one or more of S$_1$, S$_2$, S$_3$, and S$_4$ are G. In some variations, one or more of S$_1$, S$_2$, S$_3$, and S$_4$ are I. In some variations, S$_1$, S$_2$, S$_3$, and S$_4$ are G.

In some variations, the immune response is inhibited. In some variations, the immune response is a TLR9 dependent immune response. In some variations, the immune response is associated with an autoimmune disease. In some variations, regulating the immune response ameliorates one or more symptoms of the autoimmune disease. In some variations, regulating the immune response prevents or delays development of the autoimmune disease. In some variations, the autoimmune disease is selected from the group consisting of systemic lupus erythematosus (SLE) and rheumatoid arthritis. In some variations, the immune response is associated with chronic pathogen stimulation.

The invention further provides polynucleotides consisting of a nucleotide sequence of the formula: 5'-JGCN$_z$-3' (SEQ ID NO:119), wherein J is U or T, the sequence 5'-JGC-3' comprises a modification, each N is a nucleotide, and z is an integer from 1 to about 100.

In some variations, the modification is selected from the group consisting of a 2'-sugar modification, a 3'-terminal internucleotide phosphodiester linkage modification, and a 5'-methyl-cytosine modification. In some variations, the 3'-terminal internucleotide phosphodiester linkage modification is selected from the group consisting of an alkyl or aryl phosphotriester, alkyl or aryl phosphonate, hydrogen phosphonate, phosphoramidate, and phosphoroselenate linkage modification. In some variations, the 3'-terminal internucleotide phosphodiester linkage modification is a phosphoramidate modification. In some variations, the modification is a 2'-sugar modification. In some variations, the 2'-sugar modification is a 2'-O-methyl sugar modification or 2'-O-methoxyethyl sugar modification. In some variations, the modification is a 2'-O-methyl sugar modification. In some variations, the modification is a 5'-methyl-cytosine modification.

In some variations, each nucleotide N comprises a modification. In some variations, the sequence $N_z$ comprises a modification. In some variations, the modification of the nucleotide N or the sequence $N_z$ is selected from the group consisting of a 2'-sugar modification, a 3'-terminal internucleotide phosphodiester linkage modification, and a 5'-methyl-cytosine modification. In some variations, the modification is a 2'-sugar modification. In some variations, the 2'-sugar modification is a 2'-O-methyl sugar modification or 2'-O-methoxyethyl sugar modification. In some variations, the modification is a 2'-O-methyl sugar modification. In some variations, each nucleotide N consists of a modification and said modification is a 2'-O-methyl sugar modification.

In some variations, the polynucleotide further comprises 5'-TGC-3', wherein 5'-TGC-3' is unmodified. In some variations, the polynucleotide comprises 5'-JGCTGC-3' (SEQ ID NO:189), wherein J is U or T and the sequence 5'-JGC-3' comprises a modification. In some variations, the modification is a 2'-O-methyl sugar modification or 2'-O-methoxyethyl sugar modification. In some variations, the modification is a 2'-O-methyl sugar modification.

In some variations, the polynucleotide further comprises a nucleotide sequence of the formula: 5'-$S_1S_2S_3S_4Q_yM_r$-3' (SEQ ID NO:190), wherein $S_1$, $S_2$, $S_3$, and $S_4$ are independently G, I, or 7-deaza-dG, each Q is a nucleotide, each M is a nucleotide comprising a modification, y is an integer greater than 1, and r is an integer from 1 to about 50. In some variations, the modification of nucleotide M is selected from the group consisting of a 2'-O-methyl sugar modification, a 3'-terminal internucleotide phosphodiester linkage modification, and a 5'-methyl-cytosine modification. In some variations, the modification is a 2'-sugar modification. In some variations, the 2'-sugar modification is a 2'-O-methyl sugar modification or 2'-O-methoxyethyl sugar modification. In some variations, the modification is a 2'-O-methyl sugar modification. In some variations, one or more of $S_1$, $S_2$, $S_3$, and $S_4$ are G. In some variations, one or more of $S_1$, $S_2$, $S_3$, and $S_4$ are I. In some variations, $S_1$, $S_2$, $S_3$, and $S_4$ are G.

The invention further provides a polynucleotide comprising the nucleotide sequence of the formula: 5'-$S_1S_2S_3S_4Q_yM_r$-3' (SEQ ID NO:190), wherein $S_1$, $S_2$, $S_3$, and $S_4$ are independently G, I, or 7-deaza-dG, each Q is a nucleotide, each M is a nucleotide comprising a modification, y is an integer greater than 1, and r is an integer from 1 to about 100.

In some variations, the modification of nucleotide M is selected from the group consisting of a 2'-sugar modification, a 3'-terminal internucleotide phosphodiester linkage modification, and a 5'-methyl-cytosine modification. In some variations, the modification is a 2'-sugar modification. In some variations, the 2'-sugar modification is a 2'-O-methyl sugar modification or 2'-O-methoxyethyl sugar modification. In some variations, the modification is a 2'-O-methyl sugar modification. In some variations, one or more of $S_1$, $S_2$, $S_3$, and $S_4$ are G. In some variations, one or more of $S_1$, $S_2$, $S_3$, and $S_4$ are I. In some variations, $S_1$, $S_2$, $S_3$, and $S_4$ are G.

In some variations, immunoregulatory polynucleotides (IRP) are provided. In some variations, the compositions may comprise any of the immunoregulatory polynucleotides described herein. In some variations, the IRP comprises a modified IRS. In some variations, the IRP comprises an unmodified IRS. In some variations, the IRPs comprise both modified and unmodified IRSs. The compositions may also include, for example, a pharmaceutically acceptable excipient or any of a number of other components.

In some variations, immunoregulatory compounds (IRC) are provided. In certain variations, the compositions may comprise any of the immunoregulatory compounds described herein. In some variations, the IRC comprises a modified IRS. In some variations, the IRC comprises an unmodified IRS. In some variations, the IRCs comprise both modified and unmodified IRSs. The compositions may also include, for example, a pharmaceutically acceptable excipient or any of a number of other components.

The invention further relates to kits, preferably for carrying out the methods of the invention. The kits of the invention generally comprise an immunoregulatory polynucleotide and/or an immunoregulatory compound of the invention (generally in a suitable container), and may further include instructions for use of the immunoregulatory polynucleotide and/or immunoregulatory compound in immunoregulation of an individual. In some variations, the kit further comprises an other therapeutic agent. In some variations, the other therapeutic agent is a corticosteroid. In some variations, the IRP and/or IRC comprises a modified IRS. In some variations, the IRP and/or IRC comprises an unmodified IRS. In some variations, the IPR and/or IRC comprises both modified and unmodified IRSs.

BRIEF DESCRIPTION OF THE DRAWINGS

FIGS. 5A and B depict IL-6 levels (pg/ml) in mouse splenocytes following TLR7 ligand stimulation by R848 or TLR9 ligand stimulation by 1018 ISS (SEQ ID NO:122) either alone or in the presence of tested IRPs.

FIGS. 20A and B depict IFN-α levels (pg/ml) in human plasmacytoid dendritic cells following TLR7 ligand stimulation by influenza virus or TLR9 ligand stimulation by HSV-1 either alone or in the presence of tested IRPs.

FIGS. 21A and B depict IFN-α levels (pg/ml) in human plasmacytoid dendritic cells following TLR7 ligand stimulation by influenza virus or TLR9 ligand stimulation by HSV-1 either alone or in the presence of tested IRPs.

PDC stands for plasmacytoid dendritic cells, CD11c/for dendritic cells, B220 for B-cells, and CD11b for monocytes.

Figure 36A:
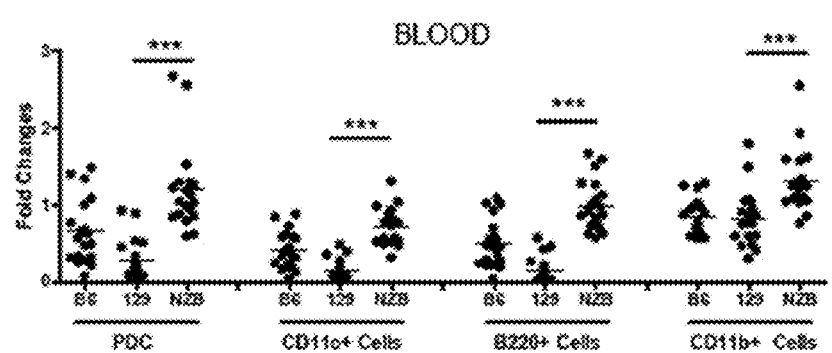

FIGS. 36A and B depict the survival of different cells subsets after in vivo treatment with glucocorticoid Dexthametasone (DEX) in lupus prone mice (NZB×NZW) F1 mice and in the wild type strains, 129 and B6. PDC stands for plasmacytoid dendritic cells, CD11c for dendritic cells, B220 for B-cells, and CD11b for monocytes.

Figure 37:
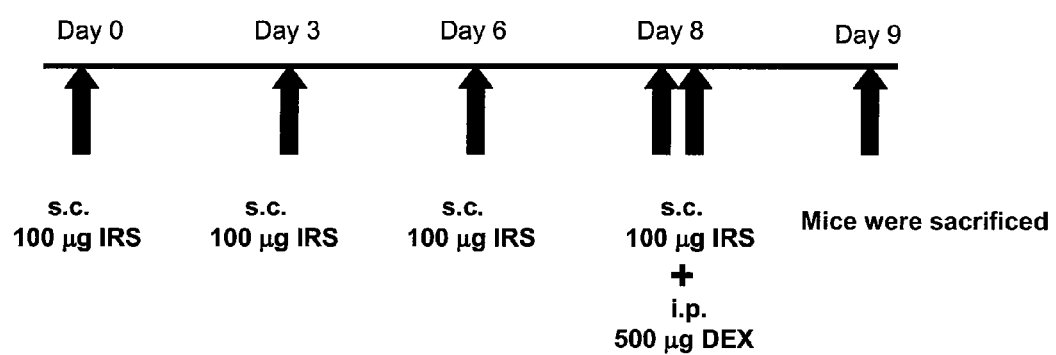
Figure 38A:
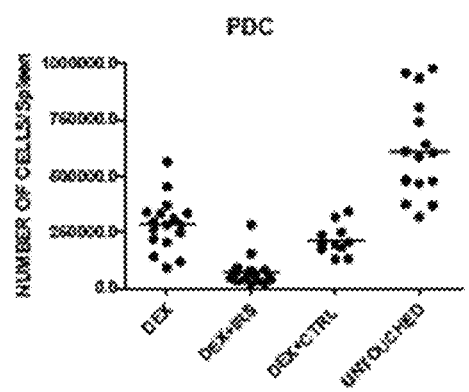
Figure 38B:
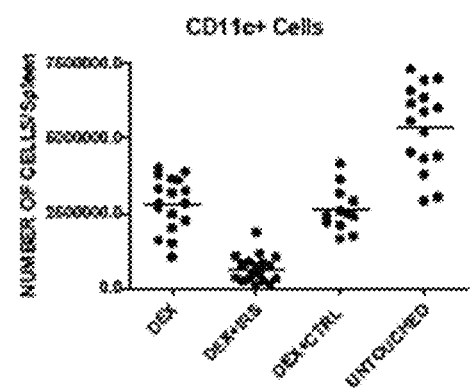
Figure 38C:
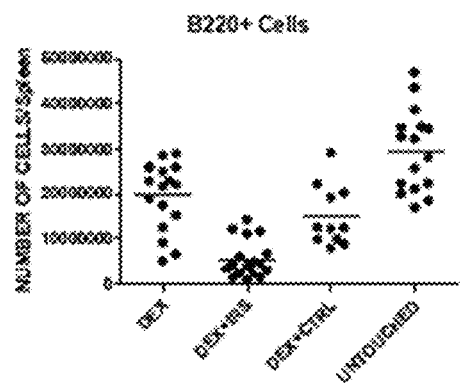
Figure 38D:
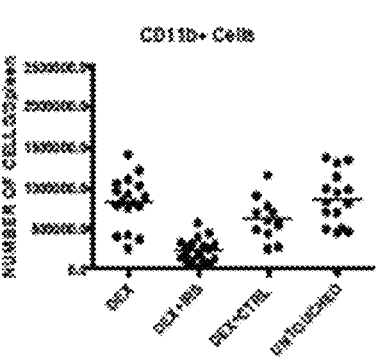

FIG. 37 depicts a schematic of the experimental design for evaluating the ability of immunoregulatory sequences to restore responsiveness to glucocorticoid treatment in lupus prone mice (NZB×NZW)F1.

FIG. 38 depicts the survival of different cells subsets after in vivo treatment with glucocorticoid Dexthametasone (DEX) or DEX plus IRS (SEQ ID NO:123) in lupus prone mice (NZB×NZW)F1 mice. Results shown refer to spleen cells. Similar results were obtained in the blood. PDC stands for plasmacytoid dendritic cells, CD11c for dendritic cells, B220 for B cells and CD11b for monocytes.

Figure 39A:
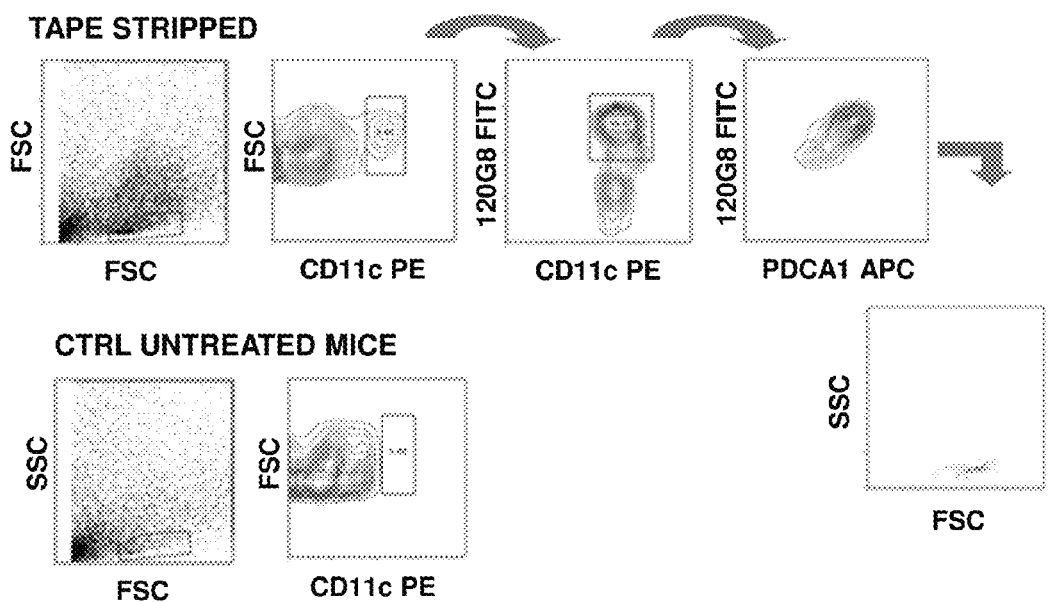
Figure 39B:
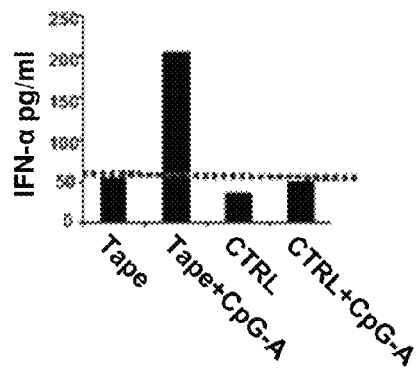

FIGS. 39A-B. FIG. 39A depicts the infiltration as determined by flow cytometry of plasmacytoid dendritic cells infiltrating the skin of mice that were inflamed by mechanical stripping. PDC were defined to be CD11c+, PDCA1+, 120G8+. FIG. 39B depicts cells infiltrating the skin were stimulated in vitro with an immunostimulatory sequence CpG-A ISS C264 ("ISS" 5'-GGtgcatcgatgcagGGGGG-3' (SEQ ID NO:125), wherein upper case letters represent PS linkages and lower case letters represent PO linkages) and IFN-α was measured in the supernatant by ELISA.

FIGS. 40A-H depict the gene expression profile of cells infiltrating inflamed skin either left untreated or treated with IRS (SEQ ID NO:123) administered i.v. or s.c. or locally on the inflamed skin. CTRL stands for un-inflamed skin.

Figure 41:
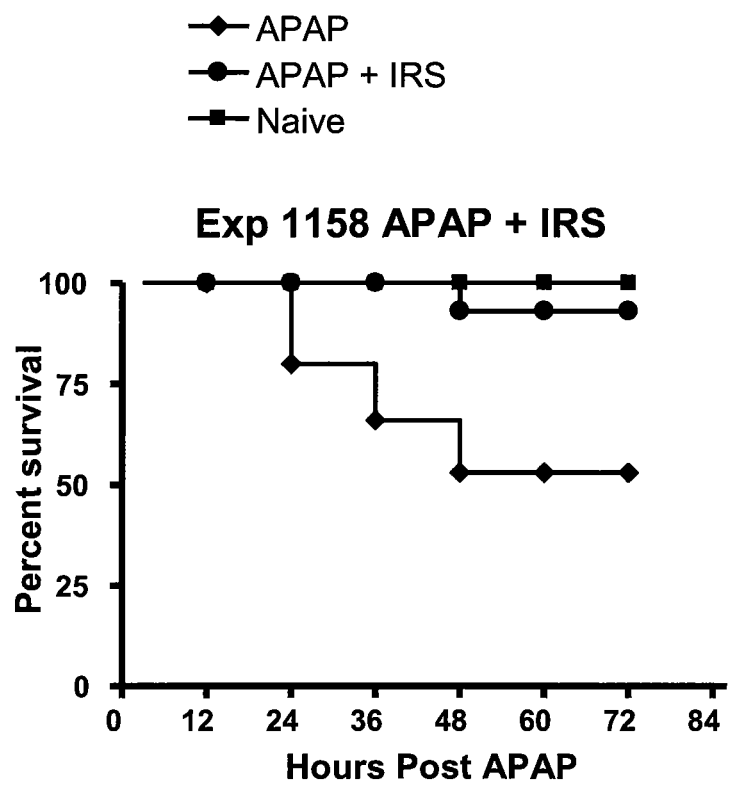

FIG. 41 depicts the percent survival of mice treated with acetaminophen (APA) either alone or in the presence of a single injection of IRS (SEQ ID NO:173) given s.c.

DETAILED DESCRIPTION

The invention provides immunoregulatory polynucleotides and/or immunoregulatory compounds and methods of regulating immune responses in individuals, particularly humans, using these immunoregulatory polynucleotides and/or immunoregulatory compounds. In some variations, the immunoregulatory polynucleotides and/or immunoregulatory compounds comprise a modified IRS. In some variations, the immunoregulatory polynucleotides and/or immunoregulatory compounds comprise an unmodified IRS. In some variations, the immunoregulatory polynucleotides and/or immunoregulatory compounds comprise both modified and unmodified IRSs. The immunoregulatory polynucleotides and/or immunoregulatory compounds of the invention particularly inhibit innate immune responses, including those responses that involve signaling through TLR7 and/or TLR9.

The invention further provides immunoregulatory polynucleotides and/or immunoregulatory compounds of the invention efficiently regulate immune cells, including human cells, in a variety of ways. Immunoregulatory polynucleotides and/or immunoregulatory compounds of the invention can effectively suppress cytokine production, including IFN-α, and/or IL-6, from human cells. Immunoregulatory polynucleotides and/or immunoregulatory compounds of the invention suppress cell responses, including cytokine production, stimulated through TLR7 and/or TLR9 receptors. Immunoregulatory polynucleotides and/or immunoregulatory compounds described herein also can effectively suppress proliferation and/or maturation of cells stimulated with an immunostimulatory nucleic acid, including B cells and plasmacytoid dendritic cells. In some variations, the immunoregulatory polynucleotides and/or the immunoregulatory compounds comprise at least one modified immunoregulatory compounds. Thus, the IRP and/or IRC described herein are of use in the suppression of immune responses to ISNA such as microbial DNA present due to an infection or suppression of nucleic acid vectors administered for gene therapy purposes.

Provide herein are also methods of treating and preventing autoimmune disorders and chronic inflammatory disorders in an individual by administering an immunoregulatory polynucleotide and/or immunoregulatory compound described herein to the individual. In some variations, the immunoregulatory polynucleotide and/or immunoregulatory compound is administered in combination with another therapeutic agent. In some variations, the other therapeutic agent is a corticosteroid. In some variations, the immunoregulatory compounds and/or the immunoregulatory polynucleotides comprise at least one modified immunoregulatory compounds.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); and *Methods of Immunological Analysis* (R. Masseyeff, W. H. Albert, and N. A. Staines, eds., Weinheim: VCH Verlags gesellschaft mbH, 1993).

DEFINITIONS

As used herein, the singular form "a", "an", and "the" includes plural references unless indicated otherwise. For example, "an" IRP includes one or more IRP.

As used interchangeably herein, the terms "nucleic acid," "polynucleotide" and "oligonucleotide" include single-stranded DNA (ssDNA), double-stranded DNA (dsDNA), single-stranded RNA (ssRNA) and double-stranded RNA (dsRNA), modified polynucleotides and polynucleosides or combinations thereof. The polynucleotide can be linearly or circularly configured, or the polynucleotide can contain both linear and circular segments. Polynucleotides are polymers of nucleosides joined, generally, through phosphodiester linkages, although alternate linkages, such as phosphorothioate esters may also be used in polynucleotides. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

The term "immunostimulatory nucleic acid" or "immunostimulatory polynucleotide" as used herein refers to a nucleic acid molecule (e.g., polynucleotide) that effects and/or contributes to a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4+ T lymphocytes, CD8+ T lymphocytes, B lymphocytes, and the like. Immunostimulatory nucleic acid (ISNA) sequences are known to stimulate innate immune responses, in particular, those response occur through TLR-9 signaling in the cell. As known in the art, immunostimulatory nucleic acid (ISNA) molecules can be isolated from microbial sources, such as bacteria, can be present in nucleic acid vectors for use in gene therapy, or can be synthesized using techniques and equipment described herein and known in the art. Generally, an immunostimulatory nucleic acid sequence include at least one CG dinucleotide, with the C of this dinucleotide being unmethylated. Accordingly, microbial infection and administered DNA can in some cases result in stimulation of innate immune responses.

The term "immunostimulatory" or "stimulating an immune response" as used herein includes stimulation of cell types that participate in immune reactions and enhancement of an immune response to a specific antigenic substance. An immune response that is stimulated by an immunostimulatory nucleic acid is generally a "Th1-type" immune response, as opposed to a "Th2-type" immune response. Th1-type immune responses are normally characterized by "delayed-type hypersensitivity" reactions to an antigen and activated macrophage function and can be detected at the biochemical level by increased levels of Th1-associated cytokines such as IFN-γ, IL-2, IL-12, and TNF-β. Th2-type immune responses are generally associated with high levels of antibody production, especially IgE antibody production and enhanced eosinophils numbers and activation, as well as expression of Th2-associated cytokines such as IL-4, IL-5 and IL-13.

The term "innate immune response" or "innate immunity" as used herein includes a variety of innate resistance mechanisms by which a cell or individual recognizes and responds to the presence of a pathogen. As used herein, an "innate immune response" includes the intracellular and intercellular events and reactions that occur when the cell recognizes pathogen associated molecular patterns or signals. Cellular receptors active in an innate immune response include a family of Toll-like receptors (TLRs) and microbial ligands have been identified for several TLRs, as described herein.

The term "immunoregulatory sequence" or "IRS", as used herein, refers to a nucleic acid sequence that inhibits and/or suppresses a measurable innate immune response as measured in vitro, in vivo, and/or ex vivo. The term "immunoregulatory sequence" or "IRS", as used herein, refers to both nucleic acid sequence that comprise a modification (i.e., modified IRS) as well as nucleic acids which do not comprise a modification (i.e., unmodified IRS).

The term "immunoregulatory polynucleotide" or "IRP", as used herein, refers to a polynucleotide comprising at least one IRS that inhibits and/or suppresses a measurable innate immune response as measured in vitro, in vivo, and/or ex vivo. The term "immunoregulatory polynucleotide" or "IRP", as used herein, may comprise a modified and/or unmodified IRS. Inhibition of a TLR, e.g., TLR-7 or 9, includes without limitation inhibition at the receptor site, e.g., by blocking ligand—receptor binding, and inhibition of the downstream signal pathway after ligand-receptor binding. Examples of measurable innate immune responses include, but are not limited to, secretion of cytokines, activation or expansion of lymphocyte populations such as NK cells, CD4+ T lymphocytes, CD8+ T lymphocytes, B lymphocytes, maturation of cell populations such as plasmacytoid dendritic cells and the like.

The term "immunoregulatory compound" or "IRC", as used herein, refers to a molecule which has immunoregulatory activity and which comprises a nucleic acid moiety comprising an IRS. The IRC may consist of a nucleic acid moiety that comprises more than one IRS, consists of an IRS, or has no immunostimulatory activity on its own. The IRC may comprise a modified and/or unmodified IRS. The IRC may consist of a polynucleotide (a "polynucleotide IRC") or it may comprise additional moieties. Accordingly, the term IRC includes compounds which incorporate one or more nucleic acid moieties, at least one of which comprises an IRC, covalently linked to a non-nucleotide spacer moiety.

The term "modified immunoregulatory sequence" or "modified IRS" as used herein refers to a polynucleotide comprising at least one modified nucleotide, that inhibits and/or suppresses a measurable innate immune response as measured in vitro, in vivo, and/or ex vivo. The term "modified immunoregulatory polynucleotide" or "modified IRP" as used herein refers to a polynucleotide comprising at least one modified IRS, that inhibits and/or suppresses a measurable innate immune response as measured in vitro, in vivo, and/or ex vivo. The modified IRP may consist of a nucleic acid moiety that comprises more than one modified IRS, comprises one or more modified IRS and one or more unmodified IRS, or consists of a modified IRS. Inhibition of a TLR, e.g., TLR-7 or 9, includes without limitation inhibition at the receptor site, e.g., by blocking ligand-receptor binding, and inhibition of the downstream signal pathway after ligand-receptor binding. Examples of measurable innate immune responses include, but are not limited to, secretion of cytokines, activation or expansion of lymphocyte populations such as NK cells, CD4+ T lymphocytes, CD8+ T lymphocytes, B lymphocytes, maturation of cell populations such as plasmacytoid dendritic cells and the like.

The term "modified immunoregulatory compound" or "modified IRC", as used herein, refers to a molecule which has immunoregulatory activity and which comprises a nucleic acid moiety comprising at least one modified IRS. The modified IRC may consist of a nucleic acid moiety that comprises more than one modified IRS, comprises one or more modified IRS and one or more unmodified IRS, consists of a modified IRS, or has no immunostimulatory activity on its own. The modified IRC may consist of a polynucleotide (a "modified polynucleotide IRC") or it may comprise additional moieties. Accordingly, the term modified IRC includes compounds which incorporate one or more nucleic acid moieties, at least one of which comprises a modified IRC, covalently linked to a non-nucleotide spacer moiety.

The term "unmodified immunoregulatory sequence" or "unmodified IRS" as used herein refers to a nucleic acid sequence consisting of no modifications (i.e. absent of modifications) of the nucleic acid sequence, that inhibits and/or suppresses a measurable innate immune response as measured in vitro, in vivo and/or ex vivo. Inhibition of a TLR, e.g., TLR-7 or 9, includes without limitation inhibition at the receptor site, e.g., by blocking ligand—receptor binding, and inhibition of the downstream signal pathway after ligand—receptor binding. Examples of measurable innate immune responses include, but are not limited to, secretion of cytokines, activation or expansion of lymphocyte populations such as NK cells, CD4+ T lymphocytes, CD8+ T lymphocytes, B lymphocytes, maturation of cell populations such as plasmacytoid dendritic cells and the like.

The term "palindromic sequence" or "palindrome" refers to a nucleic acid sequence that is an inverted repeat, e.g., ABCDD'C'B'A', where the bases, e.g., A, and A', B and B', C and C', D and D', are capable of forming the Watson-Crick base pairs. Such sequences may be single-stranded or may form double-stranded structures or may form hairpin loop structures under some conditions. For example, as used herein, "an 8 base palindrome" refers to a nucleic acid sequence in which the palindromic sequence is 8 bases in length, such as ABCDD'C'B'A'. A palindromic sequence may be part of a polynucleotide which also contains non-palindromic sequences. A polynucleotide may contain one or more palindromic sequence portions and one or more non-palindromic sequence portions. Alternatively, a polynucleotide sequence may be entirely palindromic. In a polynucleotide with more than one palindromic sequence portions, the palindromic sequence portions may overlap with each other or the palindromic sequence portions may not overlap with each other.

The term "3'" generally refers to a region or position in a polynucleotide or oligonucleotide 3' (downstream) from another region or position in the same polynucleotide or oligonucleotide. The term "3' end" refers to the 3' terminus of the polynucleotide.

The term "5'" generally refers to a region or position in a polynucleotide or oligonucleotide 5' (upstream) from another region or position in the same polynucleotide or oligonucleotide. The term "5' end" refers to the 5' terminus of the polynucleotide.

The term "conjugate" refers to a complex in which an IRP and/or an IRC are linked. Such conjugate linkages include covalent and/or non-covalent linkages.

"Adjuvant" refers to a substance which, when added to an immunogenic agent such as antigen, nonspecifically enhances or potentiates an immune response to the agent in the recipient host upon exposure to the mixture.

The term "peptide" are polypeptides that are of sufficient length and composition to effect a biological response, e.g., antibody production or cytokine activity whether or not the peptide is a hapten. Typically, the peptides are at least six amino acid residues in length. The term "peptide" further includes modified amino acids (whether or not naturally or non-naturally occurring), such modifications including, but not limited to, phosphorylation, glycosylation, pegylation, lipidization and methylation.

A "delivery molecule" or "delivery vehicle" is a chemical moiety which facilitates, permits, and/or enhances delivery of an IRP and/or IRC to a particular site and/or with respect to particular timing.

An "individual" is a vertebrate, such as avian, and is preferably a mammal, more preferably a human. Mammals include, but are not limited to, humans, primates, farm animals, sport animals, rodents and pets.

An "effective amount" or a "sufficient amount" of a substance is that amount sufficient to effect beneficial or desired results, including clinical results, and, as such, an "effective amount" depends upon the context in which it is being applied. In the context of administering a composition that suppresses a TLR9 dependent immune response, an effective amount of an IRP and/or IRC is an amount sufficient to inhibit or decrease a cellular response to stimulation through TLR9. In the context of administering a composition that suppresses a TLR7 dependent immune response, an effective amount of an IRP and/or IRC is an amount sufficient to inhibit or decrease a cellular response to stimulation through TLR7. An effective amount can be administered in one or more administrations.

The term "co-administration" as used herein refers to the administration of at least two different substances sufficiently close in time to regulate an immune response. Preferably, co-administration refers to simultaneous administration of at least two different substances.

"Suppression" or "inhibition" of a response or parameter includes decreasing that response or parameter when compared to otherwise same conditions except for a condition or parameter of interest, or alternatively, as compared to another condition. For example, a composition comprising an IRP which suppresses immunostimulatory nucleic acid induced cytokine production reduces cytokine production as compared to, for example, cytokine production induced by the immunostimulatory nucleic acid alone. As another example, a composition comprising an IRP which suppresses cytokine production associated with an innate immune response reduces the extent and/or levels of cytokine production as compared to, for example, extent and/or levels of cytokine produced by the innate immune response alone. B cell "suppression" includes, for example, reduced B cell proliferation, reduced B cell activation and/or reduced production of cytokines, such as IL-6 and/or TNF-α, from the stimulated B cell. Inhibition of a TLR response, e.g., a TLR7 or 9 response, includes, but is not limited to, inhibition at the receptor site, e.g., by preventing or blocking effective ligand—receptor binding, and inhibition of the downstream signal pathway, e.g., after effective ligand—receptor binding.

"Stimulation" of a response or parameter includes eliciting and/or enhancing that response or parameter. For example, "stimulation" of an immune response, such as innate immune response or Th1 response, means an increase in the response, which can arise from eliciting and/or enhancement of a response. Similarly, "stimulation" of a cytokine or cell type (such as CTLs) means an increase in the amount or level of cytokine or cell type. B cell "stimulation" includes, for example, enhanced B cell proliferation, induced B cell activation and/or increased production of cytokines, such as IL-6 and/or TNF-α, from the stimulated B cell.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder. Especially in the autoimmune disease context, as is well understood by those skilled in the art, palliation may occur upon regulation or reduction of the unwanted immune response. Further, palliation does not necessarily occur by administration of one dose, but often occurs upon administration of a series of doses. Thus, an amount sufficient to palliate a response or disorder may be administered in one or more administrations.

As used herein, the term "comprising" and its cognates are used in their inclusive sense; that is, equivalent to the term "including" and its corresponding cognates.

Compositions of the Invention

Immunoregulatory sequences (IRS), immunoregulatory polynucleotides (IRPs) and immunoregulatory compounds (IRCs) are provided herein for regulating innate immune responses in individuals. Each IRP and IRC described herein comprises at least one IRS. In some variations, the IRS is modified. In some variations, the IRS is unmodified. In some variations, the IRP and/or IRC described herein comprises both modified and unmodified IRSs.

Compositions provided herein comprise an immunoregulatory polynucleotide or an immunoregulatory compound alone (or a combination of two or more IRPs and/or IRCs). In some variations, the IRPs and/or the IRCs comprise a modified IRS. In some variations, the IRPs and/or the IRCs comprise an unmodified IRS. In some variations, the IRPs and/or IRCs comprise both modified and unmodified IRSs. Compositions provided herein may comprise an IRP or IRC and a pharmaceutically acceptable excipient. Pharmaceutically acceptable excipients, including buffers, are described herein and well known in the art. *Remington: The Science and Practice of Pharmacy,* 20th edition, Mack Publishing (2000).

Immunoregulatory polynucleotides and Immunoregulatory Compounds

In accordance with the present invention, an IRP or an IRC contains at least one IRS. In some instances, an IRS comprises a 5'-G,C-3' sequence. In some instances, an IRS includes at least one TGC trinucleotide sequence at or near the 5' end of the polynucleotide (i.e., 5'-TGC). In some variations, the TGC trinucleotide sequence is about any of 0, 1, 2, 3, 4, 5, 6, 7, 8, 9, or 10 nucleotides from the 5' end of the polynucleotide. In some variations, the TGC trinucleotide sequence is less than about any of 1, 2, 3, 4, 5, 6, 7, 8, 9, or 10 nucleotides from the 5' end of the polynucleotide. In some instances, an IRS comprises a 5'-GGGG-3' sequence. In some instances, an IRS does not comprise a 5'-GGGG-3' sequence. Accordingly, in some instances, an IRP or IRC does not comprise a 5'-GGGG-3' sequence. In some instances, an IRP or IRC comprising a 5'-GGGG-3' sequence is particularly effective when used in the single-stranded form. In some instances, an IRP or IRC comprising a 5'-GGGG-3' sequence is particularly effective when made with a phosphothioate backbone.

As demonstrated herein, particular IRPs and IRCs inhibit TLR-7 dependent cell responses. Also, particular IRPs and IRCs inhibit TLR9 dependent cell responses. In some variations, particular IRPs and IRCs inhibit TLR7 dependent cell responses and TLR-9 dependent cell responses. Accordingly, as used herein, "TLR7/9" refers to "TLR7 and TLR9." In some variations, certain IRPs do not inhibit TLR4 dependent cell responses.

Immunostimulatory nucleic acids and other stimulators of an innate immune response have been described in the art and their activity may be readily measured using standard assays which indicate various aspects of an innate immune response, such as cytokine secretion, antibody production, NK cell activation, B cell proliferation, T cell proliferation, dendritic cell maturation. See, e.g. Krieg et al. (1995) *Nature* 374:546-549; Yamamoto et al. (1992) *J. Immunol.* 148: 4072-4076; Klinman et al. (1997) *J. Immunol.* 158:3635-3639; Pisetsky (1996) *J. Immunol.* 156:421-423; Roman et al. (1997) *Nature Med.* 3:849-854; Hemmi et al. (2000), Supra; Lee et al. (2003), Supra; WO 98/16247; WO 98/55495; WO 00/61151 and U.S. Pat. No. 6,225,292. Accordingly, these and other methods can be used to identify, test and/or confirm immunoregulatory sequences, polynucleotides and/or compounds. For example, the effect of IRP or IRC can be determined when cells or individuals in which an innate immune response has been stimulated are contacted with the IRP or IRC.

As is clearly conveyed herein, it is understood that, with respect to formulae described herein, any and all parameters are independently selected. For example, if x=0-2, y may be independently selected regardless of the values of x (or any other selectable parameter in a formula).

As demonstrated herein, one class of IRS discovered is particularly effective in inhibiting TLR9 dependent cell stimulation. Accordingly, IRS with this activity are referred to as "TLR9 class" IRS.

In some variations, an IRS may comprise a sequence of the formula: $X_1GGGGX_2X_3$ (SEQ ID NO:1) wherein $X_1$, $X_2$, and $X_3$ are nucleotides, provided that if $X_1$=C or A, then $X_2X_3$ is not AA. In some variations, an IRS may comprise a sequence of the formula SEQ ID NO:1 wherein $X_1$ is C or A. In some variations, an IRS may comprise a sequence of the formula: $X_1GGGGX_2X_3$ (SEQ ID NO:2) wherein $X_1$, $X_2$, and $X_3$ are nucleotides, provided that if $X_1$=C or A, then $X_2X_3$ is not AA, and wherein $X_1$ is C or A.

In some variations, an IRS may comprise a sequence of the formula: $GGN_nX_1GGGGX_2X_3$ (SEQ ID NO:3), wherein n is an integer from 1 to about 100 (preferably from 1 to about 20), each N is a nucleotide, and $X_1$, $X_2$, and $X_3$ are nucleotides, provided that if $X_1$=C or A, then $X_2X_3$ is not AA. In some variations, an IRS may comprise a sequence of the formula SEQ ID NO:3 wherein $X_1$ is C or A.

In some variations, an IRS may comprise a sequence of the formula: $N_iTCCN_j(GG)_kN_mX_1GGGGX_2X_3$ (SEQ ID NO: 4), wherein each N is a nucleotide, wherein i is an integer from 1 to about 50, wherein j is an integer from 1 to about 50, k is 0 or 1, m is an integer from 1 to about 20, and $X_1$, $X_2$, and $X_3$ are nucleotides, provided that if $X_1$=C or A, then $X_2X_3$ is not AA. In some variations, an IRS may comprise a sequence of the formula SEQ ID NO:4 wherein $X_1$ is C or A.

In some variations, an IRS may comprise a sequence of the formula: $X_1X_2X_3GGGGAA$ (SEQ ID NO:5), wherein $X_1$, $X_2$, and $X_3$ are nucleotides, provided that if $X_3$=C or A, then $X_1X_2$ is not GG.

In some variations, SEQ ID NO:1-5 further comprise at least one 5'-TGC-3'. In some variations, the 5'-TGC-3' is about 0-10 nucleotides from the 5' end IRS and/or IRP. In some variations, the TGC trinucleotide sequence is about any of 0, 1, 2, 3, 4, 5, 6, 7, 8, 9, or 10 nucleotides from the 5' end of the polynucleotide. In some variations, the TGC trinucleotide sequence is less than about any of 1, 2, 3, 4, 5, 6, 7, 8, 9, or 10 nucleotides from the 5' end of the polynucleotide. In some variations, the 5'-TGC-3' is a 5'-TGC nucleotide sequence at the 5' end.

Examples of oligonucleotide sequences comprising SEQ ID NO:1, 2, 3, 4, or 5 include the following sequences:

```
5'-TCCTAACGGGGAAGT-3';    (SEQ ID NO: 10)

5'-TCCTAAGGGGGAAGT-3';    (SEQ ID NO: 11)

5'-TCCTAACGGGGTTGT-3';    (SEQ ID NO: 12)

5'-TCCTAACGGGGCTGT-3';    (SEQ ID NO: 13)

5'-TCCTCAAGGGGCTGT-3';    (SEQ ID NO: 14)

5'-TCCTCAAGGGGTTGT-3';    (SEQ ID NO: 15)

5'-TCCTCATGGGGTTGT-3';    (SEQ ID NO: 16)

5'-TCCTGGAGGGGTTGT-3';    (SEQ ID NO: 17)

5'-TCCTGGAGGGGCTGT-3';    (SEQ ID NO: 18)

5'-TCCTGGAGGGGCCAT-3';    (SEQ ID NO: 19)

5'-TCCTGGAGGGGTCAT-3';    (SEQ ID NO: 20)

5'-TCCGGAAGGGGAAGT-3';    (SEQ ID NO: 21)
and

5'-TCCGGAAGGGGTTGT-3'.    (SEQ ID NO: 22)
```

As shown herein, some IRS are particularly effective in inhibiting TLR7 dependent cell stimulation. Accordingly, IRS with this activity are referred to as "TLR7 class" IRS. For example, an oligonucleotide comprising the sequence 5'-TGCTTGCAAGCTTGCAAGCA-3' (SEQ ID NO:27) inhibits TLR7 dependent cell stimulation.

In some variations, an IRS comprises a fragment of SEQ ID NO:27 and includes at least a 10 base palindromic portion thereof. In some variations, the IRP consists of SEQ ID NO:27. For example, such sequences include the following sequences:

```
5'-TGCTTGCAAGCTTGCAAG-3';    (SEQ ID NO: 28)

5'-TGCTTGCAAGCTTGCA-3';      (SEQ ID NO: 29)

5'-GCTTGCAAGCTTGCAAGCA-3';   (SEQ ID NO: 30)

5'-CTTGCAAGCTTGCAAGCA-3';    (SEQ ID NO: 31)
and

5'-TTGCAAGCTTGCAAGCA-3'.     (SEQ ID NO: 32)
```

In some variations, an IRP effective in inhibiting TLR7 dependent cell stimulation consists of a sequence of the formula: 5'-TGCN$_m$-3' (SEQ ID NO:126), where N is a nucleotide, m is an integer from 5 to about 50 and wherein the sequence N$_1$-N$_m$ comprises at least one GC dinucleotide. In some variations, such an IRP consists of the sequence 5'-TGCN$_m$A-3' (SEQ ID NO:127), the sequence 5'-TGCN$_m$CA-3'(SEQ ID NO:128), or the sequence 5'-TGCN$_m$GCA-3' (SEQ ID NO:129). For example, in some variations, the IRP may consist of the following sequences:

```
5'-TGCTTGCAAGCTAGCAAGCA-3';    (SEQ ID NO: 33)

5'-TGCTTGCAAGCTTGCTAGCA-3';    (SEQ ID NO: 34)

5'-TGCTTGACAGCTTGACAGCA-3';    (SEQ ID NO: 35)

5'-TGCTTAGCAGCTATGCAGCA-3';    (SEQ ID NO: 36)
or

5'-TGCAAGCAAGCTAGCAAGCA-3'.    (SEQ ID NO: 37)
```

In some variations, the IRP comprises a sequence of the formula: 5'-TGCN$_m$-3' (SEQ ID NO:194), where each N is a nucleotide, m is an integer from 5 to about 50 and wherein the sequence N$_1$-N$_m$. In some variations, the IRP further comprises the nucleotide sequence 5'-S$_1$S$_2$S$_3$S$_4$-3', wherein S$_1$, S$_2$, S$_3$, and S$_4$ are independently G or a molecule that is capable of preventing G-tetrad formation and/or preventing Hoogsteen base pairing. In some variations, the molecule that is capable of preventing G-tetrad formation and/or preventing Hoogsteen base pairing disrupts or prevents formation of tetrameric/quadruplex structure of G-quadruplexes. In some variations, the molecule that is capable of preventing G-tetrad formation and/or preventing Hoogsteen base pairing is a nucleotide or derivative thereof. Examples of molecules that are capable of preventing G-tetrad formation and/or preventing Hoogsteen base pairing included, but are not limited to, I, 7-deaza-dG, 7-deaza-2'-deoxyxanthosine, 7-deaza-8-aza-2'-deoxyguanosine, 2'-deoxynebularine, isodeoxyguanosine, 8-oxo-2'-deoxyguanosine. In some variations, at least one, two, three, or four of S$_1$, S$_2$, S$_3$, and S$_4$ are G. In some variations, at least one, two, three, or four of S$_1$, S$_2$, S$_3$, and S$_4$ are a molecule that are capable of preventing G-tetrad formation and/or preventing Hoogsteen base pairing. In some variations, at least one, two, three, or four of S$_1$, S$_2$, S$_3$, and S$_4$ are I. In some variations, at least one, two, three, or four of S$_1$, S$_2$, S$_3$, and S$_4$ are 7-deaza-dG. In some variations, S$_1$, S$_2$, S$_3$, and S$_4$ are G.

Other IRS sequences which are also effective in inhibiting TLR7 dependent cell signaling include the following:

```
                                 (SEQ ID NO: 38)
5'-TGCAAGCTTGCAAGCTTG CAA GCT T-3';

(SEQ ID NO: 39)
5'-TGCTGCAAGCTTGCAGAT GAT-3';

(SEQ ID NO: 40)
5'-TGCTTGCAAGCTTGCAAGC-3';

(SEQ ID NO: 41)
5'-TGCAAGCTTGCAAGCTTGCAAT-3';

(SEQ ID NO: 42)
5'-TGCTTGCAAGCTTG-3';

(SEQ ID NO: 43)
5'-AGCTTGCAAGCTTGCAAGCA-3';

(SEQ ID NO: 44)
5'-TACTTGCAAGCTTGCAAGCA-3';

(SEQ ID NO: 45)
5'-TGATTGCAAGCTTGCAAGCA-3';

(SEQ ID NO: 46)
5'-AAATTGCAAGCTTGCAAGCA-3';

(SEQ ID NO: 47)
5'-TGCTGGAGGGGTTGT-3';

(SEQ ID NO: 48)
5'-AAATTGACAGCTTGACAGCA-3';

(SEQ ID NO: 49)
5'-TGATTGACAGCTTGACAGCA-3';
```

```
                                        (SEQ ID NO: 50)
5'-TGATTGACAGATTGACAGCA-3';
and (SEQ ID NO: 51)
5'-TGATTGACAGATTGACAGAC-3'.
```

IRPs comprising SEQ ID NO:1, 2, 3, 4, or 5 or an IRP comprising SEQ ID NO:1, 2, 3, 4, or 5, wherein at least one G is replaced by 7-deaza-dG are particularly effective in inhibiting TLR9 dependent cell stimulation. For example, in some variations, the IRS may comprise the sequence 5'-TCCTGGAGZ'GGTTGT-3' (Z'=7-deaza-dG; SEQ ID NO:23). Other IRS sequences which are also effective in inhibiting TLR9 dependent cell signaling include the following:

```
                                        (SEQ ID NO: 24)
5'-TGACTGTAGGCGGGGAAGATGA-3';

(SEQ ID NO: 25)
5'-GAGCAAGCTGGACCTTCCAT-3';
and (Z' = 7-deaza-dG; SEQ ID NO: 26)
5'-CCTCAAGCTTGAGZ'GG-3'.
```

In some variations, an IRS may comprise a sequence comprising inosine such as wherein at least one G is replaced with an inosine. In some variations, the inosine is deoxy-inosine. In some variations, the IRS may comprise the sequence 5'-TGC TGC TCC TTG AGI GGT TGT TTG T-3', wherein I is deoxy-inosine (SEQ ID NO:169). In some variations, the IRS may comprise the sequence 5'TGC TCC TTG AGI GGT TGT TTG T-3', wherein I is deoxy-inosine (SEQ ID NO:172).

Another class of IRS include those which are particularly effective in inhibiting both TLR7 and TLR9 dependent cell stimulation. Accordingly, IRS with this activity are referred to as "TLR7/9 class" IRS. In some instances, a combination of a TLR7 class IRS with a TLR9 class IRS results in an IRS of the TLR7/9 class.

The TLR7/9 class of IRS include those comprising the sequence TGCN$_m$TCCTGGAGGGGTTGT-3' (SEQ ID NO:6) where each N is a nucleotide and m is an integer from 0 to about 100, in some instances from 0 to about 50, preferably from 0 to about 20.

In some variations, an IRS comprises SEQ ID NO:6, wherein the sequence N$_1$—N$_m$ comprises a fragment of the sequence 5'-TTGACAGCTTGACAGCA-3' (SEQ ID NO:7). A fragment of SEQ ID NO:7 is any portion of that sequence, for example, TTGAC or GCTTGA. In some variations, the fragment of SEQ ID NO:7 is from the 5' end of SEQ ID NO:7, including, for example, TTGAC or TTG.

In some variations, the IRS comprises asequence 5'-TGCRRZNYY-3' (SEQ ID NO:8), wherein Z is any nucleotide except C, wherein N is any nucleotide, wherein when Z is not G or inosine, N is guanosine or inosine. In other variations, the IRS comprises the sequence 5'-TGCRRZNpoly(Pyrimidine)-3' (SEQ ID NO:9), wherein Z is any nucleotide except C, wherein N is any nucleotide, wherein when Z is not G or inosine, N is guanosine or inosine.

Examples of IRS sequences which are also effective in inhibiting TLR7/9 dependent cell signaling include the following:

```
                                        (SEQ ID NO: 52)
5'-TGCTCCTGGAGGGGTTGT-3';

(SEQ ID NO: 53)
5'-TGCTTGTCCTGGAGGGGTTGT-3';

(SEQ ID NO: 54)
5'-TGCTTGACATCCTGGAGGGGTTGT-3';

(SEQ ID NO: 55)
5'-TGCTTGACAGCTTGACAGTCCTGGAGGGGTTGT-3';

(SEQ ID NO: 56)
5'-TGCTTGACAGCTTGATCCTGGAGGGGTTGT-3';

(SEQ ID NO: 57)
5'-TGCTTGACAGCTTCCTGGAGGGGTTGT-3';

(SEQ ID NO: 58)
5'-TGCTTGACAGCTTGCTCCTGGAGGGGTTGT-3';

(SEQ ID NO: 59)
5'-TGCTTGACAGCTTGCTTGTCCTGGAGGGGTTGT-3';

(SEQ ID NO: 60)
5'-TGCTTGACAGCTTGACAGCATCCTGGAGGGGTTGT-3';

(SEQ ID NO: 61)
5'-TGCTTGACAGCTTGACAGCATCCTGGAGGGGTTGT-3';

(SEQ ID NO: 62)
5'-TGCTTGACAGCTTGACAGCATCCTGGAGGGGT-3';

(SEQ ID NO: 63)
5'-TGCTTGACAGCTTGACAGCATCCTGGAGGGG-3';

(SEQ ID NO: 64)
5'-TGCTTGCAAGCTTGCTCCTGGAGGGGTTGT-3';

(SEQ ID NO: 65)
5'-TGCTTGCAAGCTTCCTGGAGGGGTTGT-3';
and (SEQ ID NO: 66)
5'-TGCTTGCAAGCTTGCAAGCATCCTGGAGGGGTTGT-3'.
```

In some embodiments, the IRS sequence is any of the following sequences:

```
                                        (SEQ ID NO: 164)
5'-TGC TGC TCC TGG AGG GGT TGT TTG T-3'

(SEQ ID NO: 165)
5'-TGC TGC TCC TTG AGG GGT TGT TTG T-3'

(SEQ ID NO: 166)
5'-TGC TGC TCC TTG AGG GGT TGT-3';
or (SEQ ID NO: 167)
5'-TGC TGC TCC TGG AGG GGT TGT-3'.
```

As described herein, some IRPs are particularly effective in suppressing TLR9 dependent cell responses. Such IRPs include, but are not limited to, SEQ ID NO:24; SEQ ID NO:25; SEQ ID NO:86; SEQ ID NO:91; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23, and SEQ ID NO:66.

As described herein, some IRPs are particularly effective in suppressing TLR7 dependent cell responses. Such IRPs include, but are not limited to, SEQ ID NO:17; SEQ ID NO:23; SEQ ID NO:27; SEQ ID NO:38; SEQ ID NO:29; SEQ ID NO:33; SEQ ID NO:34; SEQ ID NO:40; SEQ ID NO:28; SEQ ID NO:29; SEQ ID NO:41, and SEQ ID NO:66.

Exemplary examples of IRPs effective in suppressing TLR7 and/or TLR9 are found, for example, in PCT/US2005/030494, which is hereby incorporated by reference in its entirety.

IRPs used in the invention can comprise one or more ribonucleotides (containing ribose as the only or principal sugar component) and/or deoxyribonucleotides (containing deoxyribose as the principal sugar component). The heterocyclic bases, or nucleic acid bases, which are incorporated in the IRP can be the naturally-occurring principal purine and pyrimidine bases, (namely uracil, thymine, cytosine, adenine and guanine). An IRP may be single stranded or double stranded DNA, as well as single or double-stranded RNA. An IRP may be linear, may be circular or include circular portions and/or may include a hairpin loop.

In some variations, an immunoregulatory polynucleotide is less than about any of the following lengths (in bases or base pairs): 10,000; 5,000; 2500; 2000; 1500; 1250; 1000; 750; 500; 300; 250; 200; 175; 150; 125; 100; 75; 60; 50; 40; 30; 25; 20; 15; 14; 13; 12; 11; 10; 9; 8; 7; 6; 5; 4. In some variations, an immunoregulatory polynucleotide is greater than about any of the following lengths (in bases or base pairs): 4; 5; 6, 7, 8, 9, 10; 11; 12; 13; 14; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the immunoregulatory polynucleotide can be any of a range of sizes having an upper limit of 10,000; 5,000; 2500; 2000; 1500; 1250; 1000; 750; 500; 300; 250; 200; 175; 150; 125; 100; 75; 60; 50; 40; 30; 25; 20; 15; 14; 13; 12; 11; 10; 9; 8; 7; 6; 5; 4 and an independently selected lower limit of 4; 5; 6; 7; 8; 9; 10; 11; 12; 13; 14; 15; 20; 25; 30; 40; 50; 60; 75; 100; 125; 150; 175; 200; 250; 300; 350; 400; 500; 750; 1000; 2000; 5000; 7500, wherein the lower limit is less than the upper limit. In some variations, an IRP is preferably about 200 or less bases in length.

Modified Immunoregulatory Polynucleotides and Modified Immunoregulatory Compounds The invention further provides IRPs and IRCs comprising at least one modified IRS. A modified IRS comprises at least one modified nucleotide. The modification of at least one nucleotide may be a modified base, a modified sugar, and/or a modified phosphate. In some variations, the modification of at least one nucleotide may be a naturally-occurring modified. In some variations, the modification of at least one nucleotide may be a synthetic modification. In some variations, the modifications may be imparted before or after assembly of the polynucleotide. In some variations, the modified nucleotide comprises one or more modified nucleosides. "Modified nucleotide" or "modified nucleosides" are herein defined as being synonymous with nucleoside or nucleotide "analogs."

In some variations, the modification of at least one nucleotide comprises a modified base. As used herein, the term "modified base" is synonymous with "base analog", for example, "modified cytosine" is synonymous with "cytosine analog." Examples of base modifications include, but are not limited to, addition of an electron-withdrawing moiety to C-5 and/or C-6 of a cytosine of the IRP. Preferably, the electron-withdrawing moiety is a halogen, e.g., 5-bromocytosine, 5-chlorocytosine, 5-fluorocytosine, 5-iodocytosine. In some variations, the base modifications include, but are not limited to, addition of an electron-withdrawing moiety to C-5 and/or C-6 of a uracil of the immunoregulatory polynucleotide. Preferably, the electron-withdrawing moiety is a halogen. Such modified uracils can include, but are not limited to, 5-bromouracil, 5-chlorouracil, 5-fluorouracil, 5-iodouracil. In some variations, the base modifications include the addition of one or more thiol groups to the base including, but not limited to, 6-thio-guanine, 4-thio-thymine, and 4-thio-uracil. In some variations, the base modifications include, but are not limited to, N4-ethylcytosine, 7-deazaguanine, and 5-hydroxycytosine. See, for example, Kandimalla et al. (2001) Bioorg. Med. Chem. 9:807-813. In some variations, the IRS may include 2'-deoxyuridine and/or 2-amino-2'-deoxyadenosine. In some variations, the modified base comprises a methylation modification. In some variations, the methylation modification comprises a 5'-methyl-cytosine modification. In some variations, an IRS comprises multiple base modifications. In some variations, the base modifications are the same. In some variations, the base modifications are different. In some variations, the IRS comprises any of about 1, about 2, about 3, about 4, about 5 different base modifications. Base modifications may also be made and combined with any phosphate modification and/or sugar modification in the preparation of a modified IRS.

In some variations, the modification of at least one nucleotide comprises a modified phosphate. In some variations, the modified phosphate is a phosphodiester linkage modification. For example, phosphate modifications may include, but are not limited to, methyl phosphonate, phosphorothioate, phosphoamidates, phosphoramidate (bridging or non-bridging), phosphotriester and phosphorodithioate and may be used in any combination. In some variations, the modified phosphate is a 3'-terminal internucleotide phosphodiester linkage modification. For example, the 3'-terminal internucleotide phosphodiester linkage modifications include, but are not limited to, an alkyl or aryl phosphotriester, an alkyl or aryl phosphonate, a hydrogen phosphonate, a phosphoramidate, and/or a phosphoroselenate linkage modification. In some variations, the 3'-terminal internucleotide phophodiester linkage modification is a phosphoramidate modification. In some variations, the modified phosphate includes, but is not limited to, variations wherein the phosphate is replaced by P(O)S ("thioate"), P(S)S ("dithioate"), (O)NR2 ('amidate"), P(O)R, P(R)OR', CO or CH2 ("formacetal"), in which each R or R' is independently H or substituted or unsubstituted alkyl (1-20 C), optionally containing an ether (—O—) linkage, aryl, alkenyl, cycloaklyl, cycloalkenyl, or araldyl.

In some variations, an IRS may comprise at least one nucleotide comprising at least phosphothioate backbone linkage. In some variations, polynucleotides of the IRS comprise only phosphorothioate backbones. In some variations, polynucleotides of the IRS comprise only phosphodiester backbones. In some variations, an IRS may comprise a combination of phosphate linkages in the phosphate backbone including, but not limited to, a combination of phosphodiester and phosphorothioate linkages.

The IRS can contain phosphate-modified polynucleotides, some of which may stabilize the polynucleotide. Accordingly, some variations include a stabilized immunoregulatory polynucleotides. In some variations, an IRS comprises multiple phosphate modifications. In some variations, the phosphate modifications are the same. In some variations, the phosphate modifications are different. In some variations, the IRS comprises any of about 1, about 2, about 3, about 4, about 5 different phosphate modifications. Phosphate modifications may also be made and combined with any base modification and/or sugar modification in the preparation of a modified IRS.

In some variations, the modification of at least one nucleotide comprises a modified sugar. IRPs used in the invention may comprise one or more modified sugars or sugar analogs. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the IRS, the sugar moiety is preferably the furanoside of ribose, deoxyribose, arabinose or 2'-O-alkylribose. In some variations, the sugar can be attached to the respective heterocyclic bases either in ƒ or ᴠ anomeric configuration. In some variations, the sugar is modified by replacing a hydroxyl group ordinarily present. The hydroxyl group ordinarily present in the sugar may be replaced by, for example, but not limited to, phosphonate groups or phosphate groups. The 5' and 3' terminal hydroxyl group can additionally be phosphorylated or substituted with amines or organic capping group moieties of from 1 to 20 carbon atoms. In some variations, the modified sugars are 2'-sugar modifications including, but are not limited to, 2'-alkoxy-RNA analogs, 2'-amino-RNA analogs, 2'-fluoro-DNA, and 2'-alkoxy- or amino-RNA/DNA chimeras. In some variations, the modified sugars include, but are not limited to, 2'-O-methyl-, 2'-O-allyl, or 2'-azido-sugar modification. In some variations, the 2'-modified sugar is 2'-O-methyl sugar modification. In some variations, the 2'-modified sugar is 2'-O-methoxyethyl sugar modification. For example, a sugar modification in the IRS includes, but is not limited to, 2'-O-methyl-uridine, 2'-O-methyl-thymidine, 2'-O-methyl-adenine, 2'-O-methyl-guanine, or 2'-O-methyl-cytidine. In some variations, the sugar-modified nucleotide comprises one or more sugar modified nucleosides. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. In some variations, an IRS comprises multiple sugar modifications. In some variations, the sugar modifications are the same. In some variations, the sugar modifications are different. In some variations, the IRS comprises any of about 1, about 2, about 3, about 4, about 5 different sugar modifications. Sugar modifications may also be made and combined with any base modification and/or phosphate modification in the preparation of a modified IRS.

As demonstrated herein, particular IRPs and/or IRCs comprising a modified IRS inhibit TLR7 dependent cell responses. In some variations, the IRPs and/or IRCs comprising a modified IRS inhibit TLR7 dependent cell responses independent of TLR9 dependent cell responses. In some variations, the IRPs and/or IRCs comprising a modified IRS inhibit TLR9 dependent cell responses. In some variations, the IRPs and/or IRCs comprising a modified IRS inhibit TLR7 dependent cell responses and TLR9 dependent cell responses.

Any of the modified polynucleotides described herein may comprise a modification any where in the polynucleotide sequence. In some variations, the modification is a modification of the nucleotides at or near the 5' end of the polynucleotide sequence. In some variations, at the 5' end of the polynucleotide sequence, about any of 1, 2, 3, 4, 5, 6, 7, 8, 9, or 10 nucleotides are modified. In some variations, at the 5' end of the polynucleotide sequence, at least about any of 1, 2, 3, 4, 5, 6, 7, 8, 9, or 10 nucleotides are modified. In some variations, the modification is a modification of the nucleotides at or near the 3' end of the polynucleotide sequence. In some variations, at the 3' end of the polynucleotide sequence, about any of 1, 2, 3, 4, 5, 6, 7, 8, 9, or 10 nucleotides are modified. In some embodiments, at the 3' end of the polynucleotide sequence, at least about any of 1, 2, 3, 4, 5, 6, 7, 8, 9, or 10 nucleotides are modified. In some variations, both the nucleotides at or near the 5' end of the polynucleotide sequence and the nucleotides at or near the 3' end of the polynucleotide sequence are modified. In some variations, at the 5' end of the polynucleotide sequence and at the 3' end of the polynucleotide sequence, about any of 1, 2, 3, 4, 5, 6, 7, 8, 9, or 10 nucleotides are modified. In some embodiments, at the 5' end of the polynucleotide sequence and at the 3' end of the polynucleotide sequence, at least about any of 1, 2, 3, 4, 5, 6, 7, 8, 9, or 10 nucleotides are modified.

Immunostimulatory nucleic acids and other stimulators of an innate immune response have been described in the art and their activity may be readily measured using standard assays which indicate various aspects of an innate immune response, such as cytokine secretion, antibody production, NK cell activation, B cell proliferation, T cell proliferation, dendritic cell maturation. See, e.g. Krieg et al. (1995) Nature 374:546-549; Yamamoto et al. (1992) J. Immunol. 148: 4072-4076; Klinman et al. (1997) J. Immunol. 158:3635-3639; Pisetsky (1996) J. Immunol. 156:421-423; Roman et al. (1997) Nature Med. 3:849-854; Hemmi et al. (2000), Supra; Lee et al. (2003), Supra; WO 98/16247; WO 98/55495; WO 00/61151 and U.S. Pat. No. 6,225,292. Accordingly, these and other methods can be used to identify, test and/or confirm immunoregulatory sequences, polynucleotides and/or compounds. For example, the effect of IRP or IRC comprising a modified IRS can be determined when cells or individuals in which an innate immune response has been stimulated are contacted with the IRP or IRC comprising a modified IRS.

In some variations, an IRS may comprise a sequence comprising 7-deaza-dG, such as wherein at least one G is replaced with a 7-deaza-dG. In some variations, the IRS may comprise the sequence 5'-TGC TGC TCC TTG AGZ' GGT TGT TTG T-3', wherein Z' is 7-deaza-dG (SEQ ID NO:168).

As described herein, some IRPs comprising a modified IRS are particularly effective in suppressing TLR7 and/or TLR9 dependent cell responses.

The invention provides polynucleotides consisting of a nucleotide sequence of the formula: 5'-JGCN$_z$-3' (SEQ ID NO:130), wherein J is U or T, the sequence 5'-JGC-3' comprises a modification, each N is a nucleotide, and z is an integer from about 1 to about 1000. In some embodiments, the polynucleotide is effective in suppressing TLR7 and/or TLR9 dependent cell responses. In some variations, the sequence 5'-JGC-3' is modified.

The modification may be any described above, for example, a modified base, a modified sugar, a modified phosphate. In some variations, modification includes a 2'-sugar modification, a 3'-terminal internucleotide phosphodiester linkage modification, and/or a 5'-methyl-cytosine modification. In some variations, the modification may be a phosphate or termini modification. In some variations, the phosphate or termini modification may be a 3'terminal internucletide phosphodiester linkage modification. In some variations, the 3'-terminal internucleotide phosphodiester linkage modification is selected from the group consisting of an alkyl or aryl phosphotriester, alkyl or aryl phosphonate, hydrogen phosphonate, phosphoramidate, and phosphoroselenate linkage modification. In some variations, 3'-terminal internucleotide phosphodiester linkage modification is a phosphoramidate modification. In some variations, the modification may be a sugar modification. In some variations, the sugar modification is a 2'-sugar modification as described herein. In some variations, the 2'-sugar modification is a 2'-O-methyl sugar modification or 2'-O-methoxyethyl sugar modification. In some variations, the modification is a base modified, for example, a 5'-methyl-cytosine modification.

In some variations, every nucleotide of the polynucleotide comprises at least one modification (i.e., nucleotide N comprises a modification). In some variations, the at least one modification is the same modification for each nucleotide. In some variations, every nucleotide of the polynucleotide is modified and the modification is a 2'-O-methyl sugar modification (i.e., nucleotide N consists of a modification and said modification is a 2'-O-methyl sugar modification). In some variations, the at least one modification comprises more than one different type of modifications. In some variations, one or more nucleotides of the polynucleotide comprise a modification (i.e., sequence $N_z$ comprises a modification).

In some variations, z is an integer of any of about between about 1 to about 750, between about 1 to about 500, between about 1 to about 250, between about 1 to about 200, between about 1 to about 150, between about 1 to about 125, between about 1 to about 100, between about 1 to about 75, between about 1 to about 50, between about 1 to about 25, between about 1 to about 20, between about 1 to about 15, between about 1 to about 10, or between about 1 to about 5. In some variation, z is an integer between about 1 to about 100. In some variations, z is an integer between 1 and 100. In some variations, z is an integer less than any of about 200, about 175, about 150, about 125, about 100, about 75, about 50, about 40, about 30, about 25, about 20, about 15 or about 10. In some variations, z is an integer less than 100. In some variations, z is an integer greater than any of about 1, about 2, about 3, about 4, about 5, about 10, about 15, or about 20.

In some variations, the polynucleotide, such as 5'-JGCN$_z$-3' (SEQ ID NO:130), comprises a modification of the nucleotides at or near the 3' end of the polynucleotide sequence. In some variations, at the 3' end of the polynucleotide sequence, about any of 1, 2, 3, 4, 5, 6, 7, 8, 9, or 10 nucleotides are modified. In some embodiments, at the 3' end of the polynucleotide sequence, at least about any of 1, 2, 3, 4, 5, 6, 7, 8, 9, or 10 nucleotides are modified.

In some variations, the polynucleotide, such as 5'-JGCN$_z$-3' (SEQ ID NO:130), further comprises a nucleotide sequence 5'-TGC-3', wherein 5'-TGC-3' is unmodified. In some variations, the TGC trinucleotide sequence is about any of 0, 1, 2, 3, 4, 5, 6, 7, 8, 9, or 10 nucleotides from the 5' end of the polynucleotide. In some variations, the TGC trinucleotide sequence is less than about any of 1, 2, 3, 4, 5, 6, 7, 8, 9, or 10 nucleotides from the 5' end of the polynucleotide. In some variations, the polynucleotide consists of a nucleotide sequence 5'-JGCTGC-3' (SEQ ID NO:189), wherein J is U or T and the sequence 5'-JGC-3' comprises a modification. In some variations, the modification is any 2'-sugar modification described herein. In some variations, the 2'-sugar modification is a 2'O-methoxyethyl sugar modification.

In some variations, the polynucleotide, such as 5'-JGCN$_z$-3' (SEQ ID NO:130), further comprises a nucleotide sequence of the formula: 5'-S$_1$S$_2$S$_3$S$_4$-3', wherein S$_1$, S$_2$, S$_3$, and S$_4$ are independently G or a molecule that is capable of preventing G-tetrad formation and/or preventing Hoogsteen base pairing, each Q is an unmodified nucleotide, each M is a nucleotide comprising a modification, y is an integer greater than 1, and r is an integer from 1 to about 1000. In some variations, the molecule that is capable of preventing G-tetrad formation and/or preventing Hoogsteen base pairing disrupts or prevents formation of tetrameric/quadruplex structure of G-quadruplexes. In some variations, the molecule that is capable of preventing G-tetrad formation and/or preventing Hoogsteen base pairing is a nucleotide or derivative thereof. Examples of molecules that are capable of preventing G-tetrad formation and/or preventing Hoogsteen base pairing included, but are not limited to, I, 7-deaza-dG, 7-deaza-2'-deoxyxanthosine, 7-deaza-8-aza-2'-deoxyguanosine, 2'-deoxynebularine, isodeoxyguanosine, 8-oxo-2'-deoxyguanosine. In some variations, at least one, two, three, or four of S$_1$, S$_2$, S$_3$, and S$_4$ are molecules that are capable of preventing G-tetrad formation and/or preventing Hoogsteen base pairing. In some variations, at least one, two, three, or four of S$_1$, S$_2$, S$_3$, and S$_4$ are I. In some variations, at least one, two, three, or four of S$_1$, S$_2$, S$_3$, and S$_4$ are 7-deaza-dG. In some variations, at least one, two, three, or four of S$_1$, S$_2$, S$_3$, and S$_4$ are G. In some variations, S$_1$, S$_2$, S$_3$, and S$_4$ are G. In some variations, S$_1$, S$_2$, S$_3$, and S$_4$ are not modified and/or not further modified. In some variations, the polynucleotide comprises the nucleotide sequence of the formula: 5'-GS$_5$GGQ$_y$M$_r$-3' (SEQ ID NO:187), wherein S$_5$ is G or a molecule that is capable of preventing G-tetrad formation and/or preventing Hoogsteen base pairing pairing such as I or 7-deaza-dG, each Q is an unmodified nucleotide, each M is a nucleotide comprising a modification, y is an integer greater than 1, and r is an integer from 1 to about 1000. In some variations, the polynucleotide comprises the nucleotide sequence of the formula: 5'-GGGGQ$_y$M$_r$-3' (SEQ ID NO:131), wherein each Q is an unmodified nucleotide, each M is a nucleotide comprising a modification, y is an integer greater than 1, and r is an integer from 1 to about 1000.

The modification of nucleotide M may be any described above, including, but not limited to, a modified base, a modified sugar, a modified phosphate. In some variations, the modification of nucleotide M is selected from the group consisting of a 2'-sugar modification, a 3'-terminal internucleotide phosphodiester linkage modification, and a 5'-methyl-cytosine modification. In some variations, the modification is any 2'-sugar modification described herein. In some variations, the 2'-sugar modification is a 2'O-methoxyethyl sugar modification.

In some variations, r is an integer of any of about between about 1 to about 750, between about 1 to about 500, between about 1 to about 250, between about 1 to about 200, between about 1 to about 150, between about 1 to about 125, between about 1 to about 100, between about 1 to about 75, between about 1 to about 50, between about 1 to about 25, between about 1 to about 20, between about 1 to about 15, between about 1 to about 10, or between about 1 to about 5. In some variation, r is an integer between about 1 to about 50. In some variations, r is an integer between 1 and 50. In some variations, r is an integer less than any of about 200, about 175, about 150, about 125, about 100, about 75, about 50, about 40, about 30, about 25, about 20, about 15 or about 10. In some variations, r is an integer less than 50. In some variations, r is an integer greater than any of about 1, about 2, about 3, about 4, about 5, about 10, about 15, or about 20.

In some variations, y is an integer greater than any of about 1, about 2, about 3, about 4, about 5, about 6, about 7, about 8, about 9, about 10, about 11, about 12, about 13, about 14, or about 15. In some variations, y is an integer any of about 1, about 2, about 3, about 4, about 5, about 6, about 7, about 8, about 9, about 10, about 11, about 12, about 13, about 14, or about 15.

Provided herein are also polynucleotides consisting of the nucleotide sequence of the formula: 5'-M$_\alpha$TGCN$_\beta$-3' (SEQ ID NO:198), wherein each M is a nucleotide comprising a modification, a is an integer from about 1 to about 10, each N is a nucleotide, and β is an integer from about 1 to about 1000.

The modification may be any described above, for example, a modified base, a modified sugar, a modified phosphate. In some variations, modification includes a 2'-sugar modification, a 3'-terminal internucleotide phosphodiester linkage modification, and/or a 5'-methyl-cytosine modification. In some variations, the modification may be a phosphate or termini modification. In some variations, the phosphate or termini modification may be a 3'terminal internucletide phosphodiester linkage modification. In some variations, the 3'-terminal internucleotide phosphodiester linkage modification is selected from the group consisting of an alkyl or aryl phosphotriester, alkyl or aryl phosphonate, hydrogen phosphonate, phosphoramidate, and phosphoroselenate linkage modification. In some variations, 3'-terminal internucleotide phosphodiester linkage modification is a phosphoramidate modification. In some variations, the modification may be a sugar modification. In some variations, the sugar modification is any 2'-sugar modification described herein. In some variations, the 2'-sugar modification is a 2'O-methoxyethyl sugar modification.

In some variations, every nucleotide of the polynucleotide comprises at least one modification (i.e., nucleotide N comprises a modification). In some variations, the at least one modification is the same modification for each nucleotide. In some variations, every nucleotide of the polynucleotide is modified and the modification is a 2'-O-methyl sugar modification (i.e., nucleotide N consists of a modification and said modification is a 2'-O-methyl sugar modification). In some variations, the at least one modification comprises more than one different types of modifications. In some variations, one or more nucleotides of the polynucleotide comprise a modification (e.g., sequence $M_\alpha$ and/or $N_\beta$ comprises a modification).

In some variations, a is an integer of any of about between about 1 to about 7, about 1 to about 5, about 1 to about 4, about 1 to about 3, or about 1 to about 2. In some variations, α is an integer of about any of 1, 2, 3, 4, 5, 6, 7, 8, 9, or 10.

In some variations, β is an integer of any of about between about 1 to about 750, between about 1 to about 500, between about 1 to about 250, between about 1 to about 200, between about 1 to about 150, between about 1 to about 125, between about 1 to about 100, between about 1 to about 75, between about 1 to about 50, between about 1 to about 25, between about 1 to about 20, between about 1 to about 15, between about 1 to about 10, or between about 1 to about 5. In some variation, z is an integer between about 1 to about 100. In some variations, β is an integer between 1 and 100. In some variations, β is an integer less than any of about 200, about 175, about 150, about 125, about 100, about 75, about 50, about 40, about 30, about 25, about 20, about 15 or about 10. In some variations, z is an integer less than 100. In some variations, 0 is an integer greater than any of about 1, about 2, about 3, about 4, about 5, about 10, about 15, or about 20.

In some variations, the polynucleotide, such as 5'-$M_\alpha$TGCN$_\beta$-3' (SEQ ID NO:198), comprises a modification of the nucleotides at or near the 3' end of the polynucleotide sequence. In some variations, at the 3' end of the polynucleotide sequence, about any of 1, 2, 3, 4, 5, 6, 7, 8, 9, or 10 nucleotides are modified. In some embodiments, at the 3' end of the polynucleotide sequence, at least about any of 1, 2, 3, 4, 5, 6, 7, 8, 9, or 10 nucleotides are modified.

In some variations, the polynucleotide, such as 5'-$M_\alpha$TGCN$_\beta$-3' (SEQ ID NO:198), further comprises a nucleotide sequence of the formula: 5'-$S_1S_2S_3S_4$-3', wherein $S_1$, $S_2$, $S_3$, and $S_4$ are independently G or a molecule that is capable of preventing G-tetrad formation and/or preventing Hoogsteen base pairing, each Q is an unmodified nucleotide, each M is a nucleotide comprising a modification, y is an integer greater than 1, and r is an integer from 1 to about 1000. In some variations, the molecule that is capable of preventing G-tetrad formation and/or preventing Hoogsteen base pairing disrupts or prevents formation of tetrameric/quadruplex structure of G-quadruplexes. In some variations, the molecule that is capable of preventing G-tetrad formation and/or preventing Hoogsteen base pairing is a nucleotide or derivative thereof. Examples of molecules that are capable of preventing G-tetrad formation and/or preventing Hoogsteen base pairing included, but are not limited to, I, 7-deaza-dG, 7-deaza-2'-deoxyxanthosine, 7-deaza-8-aza-2'-deoxyguanosine, 2'-deoxynebularine, isodeoxyguanosine, 8-oxo-2'-deoxyguanosine. In some variations, at least one, two, three, or four of $S_1$, $S_2$, $S_3$, and $S_4$ are molecules that are capable of preventing G-tetrad formation and/or preventing Hoogsteen base pairing. In some variations, at least one, two, three, or four of $S_1$, $S_2$, $S_3$, and $S_4$ are I. In some variations, at least one, two, three, or four of $S_1$, $S_2$, $S_3$, and $S_4$ are 7-deaza-dG. In some variations, at least one, two, three, or four of $S_1$, $S_2$, $S_3$, and $S_4$ are G. In some variations, $S_1$, $S_2$, $S_3$, and $S_4$ are G. In some variations, $S_1$, $S_2$, $S_3$, and $S_4$ are not modified and/or not further modified. In some variations, the polynucleotide comprises the nucleotide sequence of the formula: 5'-$GS_5GGQ_yM_r$-3' (SEQ ID NO:187), wherein $S_5$ is G or a molecule that is capable of preventing G-tetrad formation and/or preventing Hoogsteen base pairing such as I or 7-deaza-dG, each Q is an unmodified nucleotide, each M is a nucleotide comprising a modification, y is an integer greater than 1, and r is an integer from 1 to about 1000. In some variations, inosine is deoxyinosine. In some variations, the polynucleotide comprises the nucleotide sequence of the formula: 5'-$GGGGQ_yM_r$-3' (SEQ ID NO:131), wherein each Q is an unmodified nucleotide, each M is a nucleotide comprising a modification, y is an integer greater than 1, and r is an integer from 1 to about 1000.

The modification of nucleotide M may be any described above, including, but not limited to, a modified base, a modified sugar, a modified phosphate. In some variations, the modification of nucleotide M is selected from the group consisting of a 2'-sugar modification, a 3'-terminal internucleotide phosphodiester linkage modification, and a 5'-methyl-cytosine modification. In some variations, the sugar modification is any 2'-sugar modification described herein. In some variations, the 2'-sugar modification is a 2'O-methoxyethyl sugar modification.

In some variations, r is an integer of any of about between about 1 to about 750, between about 1 to about 500, between about 1 to about 250, between about 1 to about 200, between about 1 to about 150, between about 1 to about 125, between about 1 to about 100, between about 1 to about 75, between about 1 to about 50, between about 1 to about 25, between about 1 to about 20, between about 1 to about 15, between about 1 to about 10, or between about 1 to about 5. In some variation, r is an integer between about 1 to about 50. In some variations, r is an integer between 1 and 50. In some variations, r is an integer less than any of about 200, about 175, about 150, about 125, about 100, about 75, about 50, about 40, about 30, about 25, about 20, about 15 or about 10. In some variations, r is an integer less than 50. In some variations, r is an integer greater than any of about 1, about 2, about 3, about 4, about 5, about 10, about 15, or about 20.

In some variations, y is an integer greater than any of about 1, about 2, about 3, about 4, about 5, about 6, about 7, about 8, about 9, about 10, about 11, about 12, about 13, about 14, or about 15. In some variations, y is an integer any of about 1, about 2, about 3, about 4, about 5, about 6, about 7, about 8, about 9, about 10, about 11, about 12, about 13, about 14, or about 15.

Provided herein are also polynucleotides consisting of a nucleotide sequence of the formula: 5'-JGCL$_p$K$_w$S$_1$S$_2$S$_3$S$_4$Q$_y$M$_r$-3' (SEQ ID NO:191), wherein J is U or T, the sequence 5'-JGC-3' comprises a modification, each L is a nucleotide, p is an integer from about 1 to about 1000, each K is an unmodified nucleotide, w is an integer greater than 1, S$_1$, S$_2$, S$_3$, and S$_4$ are independently G or a molecule that is capable of preventing G-tetrad formation and/or preventing Hoogsteen base pairing each Q is an unmodified nucleotide, each M is a nucleotide comprising a modification, y is an integer greater than 1, and r is an integer from 1 to about 1000. In some variations, the sequence 5'-JGC-3' is modified. In some variations, the molecule that is capable of preventing G-tetrad formation and/or preventing Hoogsteen base pairing disrupts or prevents formation of tetrameric/quadruplex structure of G-quadruplexes. In some variations, the molecule that is capable of preventing G-tetrad formation and/or preventing Hoogsteen base pairing is a nucleotide or derivative thereof. Examples of molecules that are capable of preventing G-tetrad formation and/or preventing Hoogsteen base pairing included, but are not limited to, I, 7-deaza-dG, 7-deaza-2'-deoxyxanthosine, 7-deaza-8-aza-2'-deoxyguanosine, 2'-deoxynebularine, isodeoxyguanosine, 8-oxo-2'-deoxyguanosine. In some variations, at least one, two, three, or four of S$_1$, S$_2$, S$_3$, and S$_4$ are molecules that are capable of preventing G-tetrad formation and/or preventing Hoogsteen base pairing. In some variations, at least one, two, three, or four of S$_1$, S$_2$, S$_3$, and S$_4$ are I. In some variations, at least one, two, three, or four of S$_1$, S$_2$, S$_3$, and S$_4$ are 7-deaza-dG. In some variations, at least one, two, three, or four of S$_1$, S$_2$, S$_3$, and S$_4$ are G. In some variations, S$_1$, S$_2$, S$_3$, and S$_4$ are G. In some variations, S$_1$, S$_2$, S$_3$, and S$_4$ are not modified and/or not further modified. In some variations, the polynucleotide consists of a nucleotide sequence of the formula: 5'-JGCL$_p$K$_w$GS$_5$GGQ$_y$M$_r$-3' (SEQ ID NO:188), wherein J is U or T, the sequence 5'-JGC-3' comprises a modification, each L is a nucleotide, p is an integer from about 1 to about 1000, each K is an unmodified nucleotide, w is an integer greater than 1, S$_5$ is G or a molecule that is capable of preventing G-tetrad formation and/or preventing Hoogsteen base pairing such as I or 7-deaza-dG, each Q is an unmodified nucleotide, each Q is an unmodified nucleotide, each M is a nucleotide comprising a modification, y is an integer greater than 1, and r is an integer from 1 to about 1000. In some variations, the inosine is deoxy-inosine. In some variations, the polynucleotide consists of a nucleotide sequence of the formula: 5'-JGCL$_p$K$_w$GGGGQ$_y$M$_r$-3' (SEQ ID NO:132), wherein J is U or T, the sequence 5'-JGC-3' comprises a modification, each L is a nucleotide, p is an integer from about 1 to about 1000, each K is an unmodified nucleotide, w is an integer greater than 1, each Q is an unmodified nucleotide, each M is a nucleotide comprising a modification, y is an integer greater than 1, and r is an integer from 1 to about 1000.

In some variations, L is modified. The modification of nucleotide M and/or L may be any described above, for example, a modified base, a modified sugar, a modified phosphate. In some variations, the modification of nucleotide M and/or L is selected from the group consisting of a 2'-sugar modification, a 3'-terminal internucleotide phosphodiester linkage modification, and a 5'-methyl-cytosine modification. In some variations, the sugar modification is any 2'-sugar modification described herein. In some variations, the 2'-sugar modification is a 2'O-methoxyethyl sugar modification.

In some variations, r is an integer of any of about between about 1 to about 750, between about 1 to about 500, between about 1 to about 250, between about 1 to about 200, between about 1 to about 150, between about 1 to about 125, between about 1 to about 100, between about 1 to about 75, between about 1 to about 50, between about 1 to about 25, between about 1 to about 20, between about 1 to about 15, between about 1 to about 10, or between about 1 to about 5. In some variation, r is an integer between about 1 to about 50. In some variations, r is an integer between 1 and 50. In some variations, r is an integer less than any of about 200, about 175, about 150, about 125, about 100, about 75, about 50, about 40, about 30, about 25, about 20, about 15 or about 10. In some variations, r is an integer less than 50. In some variations, r is an integer greater than any of about 1, about 2, about 3, about 4, about 5, about 10, about 15, or about 20.

In some variations, p is an integer of any of about between about 1 to about 750, between about 1 to about 500, between about 1 to about 250, between about 1 to about 200, between about 1 to about 150, between about 1 to about 125, between about 1 to about 100, between about 1 to about 75, between about 1 to about 50, between about 1 to about 25, between about 1 to about 20, between about 1 to about 15, between about 1 to about 10, or between about 1 to about 5. In some variation, p is an integer between about 1 to about 50. In some variations, p is an integer between 1 and 50. In some variations, p is an integer less than any of about 200, about 175, about 150, about 125, about 100, about 75, about 50, about 40, about 30, about 25, about 20, about 15 or about 10. In some variations, p is an integer less than 50. In some variations, p is an integer greater than any of about 1, about 2, about 3, about 4, about 5, about 10, about 15, or about 20.

In some variations, y is an integer greater than any of about 1, about 2, about 3, about 4, about 5, about 6, about 7, about 8, about 9, about 10, about 11, about 12, about 13, about 14, or about 15. In some variations, y is an integer any of about 1, about 2, about 3, about 4, about 5, about 6, about 7, about 8, about 9 or about 10, about 11, about 12, about 13, about 14, or about 15.

In some variations, w is an integer greater than any of about 1, about 2, about 3, about 4, about 5, about 6, about 7, about 8, about 9, about 10, about 11, about 12, about 13, about 14, or about 15. In some variations, w is an integer any of about 1, about 2, about 3, about 4, about 5, about 6, about 7, about 8, about 9, about 10, about 11, about 12, about 13, about 14, or about 15.

Provided herein are also polynucleotides comprising a nucleotide sequence of the formula: 5'-S$_1$S$_2$S$_3$S$_4$Q$_y$M$_r$-3' (SEQ ID NO:192), wherein S$_1$, S$_2$, S$_3$, and S$_4$ are independently G or a molecule that is capable of preventing G-tetrad formation and/or preventing Hoogsteen base pairing, each Q is an unmodified nucleotide, each M is a nucleotide comprising a modification, y is an integer greater than 1, and r is an integer from 1 to about 1000. In some variations, the molecule that is capable of preventing G-tetrad formation and/or preventing Hoogsteen base pairing disrupts or prevents formation of tetrameric/quadruplex structure of G-quadruplexes. In some variations, the molecule that is capable of preventing G-tetrad formation and/or preventing Hoogsteen base pairing is a nucleotide or derivative thereof. Examples of molecules that are capable of preventing G-tetrad formation and/or preventing Hoogsteen base pairing included, but are not limited to, I, 7-deaza-dG, 7-deaza-2'-deoxyxanthosine, 7-deaza-8-aza-2'-deoxyguanosine, 2'-deoxynebularine, isodeoxyguanosine, 8-oxo-2'-deoxyguanosine. In some variations, at least one, two, three, or four of $S_1$, $S_2$, $S_3$, and $S_4$ are molecules that are capable of preventing G-tetrad formation and/or preventing Hoogsteen base pairing. In some variations, at least one, two, three, or four of $S_1$, $S_2$, $S_3$, and $S_4$ are I. In some variations, at least one, two, three, or four of $S_1$, $S_2$, $S_3$, and $S_4$ are 7-deaza-dG. In some variations, at least one, two, three, or four of $S_1$, $S_2$, $S_3$, and $S_4$ are G. In some variations, $S_1$, $S_2$, $S_3$, and $S_4$ are G. In some variations, $S_1$, $S_2$, $S_3$, and $S_4$ are not modified and/or not further modified. The nucleotide sequence of the formula: 5'-$S_1S_2S_3S_4Q_yM_r$-3' (SEQ ID NO:192) can be found any where in the polynucleotide sequence. In some variation, the nucleotide sequence of the formula: 5'-$S_1S_2S_3S_4Q_yM_r$-3' (SEQ ID NO:192) is found internally in the polynucleotide sequence, i.e., not at the 5' end or 3' end of the nucleotide sequence. In some variations, the polynucleotides comprising a nucleotide sequence of the formula: 5'-$GS_5GGQ_yM_r$-3' (SEQ ID NO:193), wherein $S_5$ is G or a molecule that is capable of preventing G-tetrad formation and/or preventing Hoogsteen base pairing such as I or 7-deaza-dG, each Q is an unmodified nucleotide, each M is a nucleotide comprising a modification, y is an integer greater than 1, and r is an integer from 1 to about 1000. In some variation, the polynucleotides comprising a nucleotide sequence of the formula: 5'-$GGGGQ_yM_r$-3' (SEQ ID NO:133), wherein each Q is an unmodified nucleotide, each M is a nucleotide comprising a modification, y is an integer greater than 1, and r is an integer from 1 to about 1000.

The modification of nucleotide M may be any described above, for example, a modified base, a modified sugar, a modified phosphate. In some variations, the modification of nucleotide M is selected from the group consisting of a 2'-sugar modification, a 3'-terminal internucleotide phosphodiester linkage modification, and a 5'-methyl-cytosine modification. In some variations, the sugar modification is any 2'-sugar modification described herein. In some variations, the 2'-sugar modification is a 2'O-methoxyethyl sugar modification.

In some variations, r is an integer of any of about between about 1 to about 750, between about 1 to about 500, between about 1 to about 250, between about 1 to about 200, between about 1 to about 150, between about 1 to about 125, between about 1 to about 100, between about 1 to about 75, between about 1 to about 50, between about 1 to about 25, between about 1 to about 20, between about 1 to about 15, between about 1 to about 10, or between about 1 to about 5. In some variation, r is an integer between about 1 to about 50. In some variations, r is an integer between 1 and 50. In some variations, r is an integer less than any of about 200, about 175, about 150, about 125, about 100, about 75, about 50, about 40, about 30, about 25, about 20, about 15 or about 10. In some variations, r is an integer less than 50. In some variations, r is an integer greater than any of about 1, about 2, about 3, about 4, about 5, about 10, about 15, or about 20.

In some variations, y is an integer greater than any of about 1, about 2, about 3, about 4, about 5, about 6, about 7, about 8, about 9, about 10, about 11, about 12, about 13, about 14, or about 15. In some variations, y is an integer any of about 1, about 2, about 3, about 4, about 5, about 6, about 7, about 8, about 9, about 10, about 11, about 12, about 13, about 14, or about 15.

In some variations, the polynucleotide further comprises at least one trinucleotide sequence 5'-TGC-3'. In some variations, the 5'-TGC-3' is about 0-10 nucleotides from the 5' end IRS and/or IRP. The 5'-TGC-3' may be between about any of 1-7, 1-5, 1-3, or 1-2 nucleotides from the 5' end of the IRS and/or IRP. In some variations, the 5'-TGC-3' is a 5'-TGC nucleotide sequence at the 5' end.

Further provided herein are polynucleotides comprising the nucleotide sequence of the formula: 5'-$L_pK_wS_1S_2S_3S_4$-3' (SEQ ID NO:195), wherein each L is a nucleotide, p is an integer from about 1 to about 1000, each K is an unmodified nucleotide, w is an integer greater than 1, and $S_1$, $S_2$, $S_3$, and $S_4$ are independently G or a molecule that is capable of preventing G-tetrad formation and/or preventing Hoogsteen base pairing. In some variations, the molecule that is capable of preventing G-tetrad formation and/or preventing Hoogsteen base pairing disrupts or prevents formation of tetrameric/quadruplex structure of G-quadruplexes. In some variations, the molecule that is capable of preventing G-tetrad formation and/or preventing Hoogsteen base pairing is a nucleotide or derivative thereof. Examples of molecules that are capable of preventing G-tetrad formation and/or preventing Hoogsteen base pairing included, but are not limited to, I, 7-deaza-dG, 7-deaza-2'-deoxyxanthosine, 7-deaza-8-aza-2'-deoxyguanosine, 2'-deoxynebularine, isodeoxyguanosine, 8-oxo-2'-deoxyguanosine. In some variations, at least one, two, three, or four of $S_1$, $S_2$, $S_3$, and $S_4$ are molecules that are capable of preventing G-tetrad formation and/or preventing Hoogsteen base pairing. In some variations, at least one, two, three, or four of $S_1$, $S_2$, $S_3$, and $S_4$ are I. In some variations, at least one, two, three, or four of $S_1$, $S_2$, $S_3$, and $S_4$ are 7-deaza-dG. In some variations, at least one, two, three, or four of $S_1$, $S_2$, $S_3$, and $S_4$ are G. In some variations, $S_1$, $S_2$, $S_3$, and $S_4$ are G. In some variations, polynucleotides comprising the nucleotide sequence of the formula: 5'-$L_pK_wGS_5GG$-3' (SEQ ID NO:196), wherein each L is a nucleotide, p is an integer from about 1 to about 1000, each K is an unmodified nucleotide, w is an integer greater than 1, and $S_5$ is G or a molecule that is capable of preventing G-tetrad formation and/or preventing Hoogsteen base pairing such as I or 7-deaza-dG. In some variations the polynucleotides comprising a nucleotide sequence of the formula: 5'-$L_pK_wGGGG$-3' (SEQ ID NO:134), wherein each L is a nucleotide, p is an integer from about 1 to about 1000, each K is an unmodified nucleotide, and w is an integer greater than 1.

In some variations, L is modified. The modification of nucleotide L may be any described above, for example, a modified base, a modified sugar, a modified phosphate. In some variations, the modification of nucleotide L is selected from the group consisting of a 2'-O-methyl sugar modification, a 3'-terminal internucleotide phosphodiester linkage modification, and a 5'-methyl-cytosine modification. In some variations, the sugar modification is any 2'-sugar modification described herein. In some variations, the 2'-sugar modification is a 2'O-methoxyethyl sugar modification.

In some variations, p is an integer of any of about between about 1 to about 750, between about 1 to about 500, between about 1 to about 250, between about 1 to about 200, between about 1 to about 150, between about 1 to about 125, between about 1 to about 100, between about 1 to about 75, between about 1 to about 50, between about 1 to about 25, between about 1 to about 20, between about 1 to about 15, between about 1 to about 10, or between about 1 to about 5. In some variation, p is an integer between about 1 to about 50. In some variations, p is an integer between 1 and 50. In some variations, p is an integer less than any of about 200, about 175, about 150, about 125, about 100, about 75, about 50, about 40, about 30, about 25, about 20, about 15 or about 10.

In some variations, p is an integer less than 50. In some variations, p is an integer greater than any of about 1, about 2, about 3, about 4, about 5, about 10, about 15, or about 20.

In some variations, w is an integer greater than any of about 1, about 2, about 3, about 4, about 5, about 6, about 7, about 8, about 9, about 10, about 11, about 12, about 13, about 14, or about 15. In some variations, w is an integer any of about 1, about 2, about 3, about 4, about 5, about 6, about 7, about 8, about 9, about 10, about 11, about 12, about 13, about 14, or about 15.

In some variations, the polynucleotide further comprises at least one trinucleotide sequence 5'-TGC-3'. In some variations, the 5'-TGC-3' is about 0-10 nucleotides from the 5' end IRS and/or IRP. The 5'-TGC-3' may be between about any of 1-7, 1-5, 1-3, or 1-2 nucleotides from the 5' end of the IRS and/or IRP. In some variations, the 5'-TGC-3' is a 5'-TGC nucleotide sequence at the 5' end.

In some variations, the modified IRS is C999 (SEQ ID NO:135) 5'-UGC UCC UGG AGG GGU UGU-3', wherein all nucleotides are modified with a 2'-O-Me modification, a sugar modification). In some variations, the modified IRS is DV017 (SEQ ID NO:136) 5'-UGC UCC UGG AGG GGU UGU-3', wherein all nucleotides are modified with phosphoramidate modification, a phosphate modification). In some variations, the modified IRS is DV031 (SEQ ID NO:137) 5'-UGC UCC UGG AGG GGU UGU-3', wherein all cytosines are modified with a 5-methyl dC (M) modification, a base modification).

In some variations, the modified IRS is modified with a 2'-O-Me modification. In some variations, the modified IRS modified with a 2'-O-Me modification is any of:

*UGC* TCC TGG AGG GGT TGT; (SEQ ID NO: 138)

TGC TCC TGG AGG GG *U UGU*; (SEQ ID NO: 139)

*UGC* TCC TGG AGG GG *U UGU*; (SEQ ID NO: 140)

TGC TCC TGG A *GG G*GT TGT; (SEQ ID NO: 141)

*UGC* TTG TCC TGG AGG GGT TGT; (SEQ ID NO: 142)

TGC TCC TGG AGG GGA AGT *UUG U*; (SEQ ID NO: 143)

*UGC* TTG TCC TGG AGG GG *U UGU*; (SEQ ID NO: 144)

*UGC* TTG TCC TGG AGG GGA AGT *UUG U*; (SEQ ID NO: 145)

*UGC* TG TCC TGG AGG GGA AGT *UUG U*; (SEQ ID NO: 146)

*UGC* G TCC TGG AGG GGA AGT *UUG U*; (SEQ ID NO: 147)

*UGC* TTG TCC TGG AGG GG TG *UUG U*; (SEQ ID NO: 148)

*UGC* TG TCC TGG AGG GG TG *UUG U*; (SEQ ID NO: 149)

*UGC* G TCC TGG AGG GG TG *UUG U*; (SEQ ID NO: 150)

*UGC* TTG TCC TGG AGG GGT *UGU*; (SEQ ID NO: 151)

*UGC* TG TCC TGG AGG GGT *UGU*; (SEQ ID NO: 152)

*UGC* G TCC TGG AGG GGT *UGU*; (SEQ ID NO: 153)

*UGC* TTG TCC TGG AGG GGT TGT *UUG U*; (SEQ ID NO: 154)

*UGC* TTG TCC TGG AGG GGT T *GU UUG U*; (SEQ ID NO: 155)

*UGC* TGC TCC TGG AGG GGT TGT *UUG U*; (SEQ ID NO: 156)

*UGC* TGC TCC TTG AGG GGT TGT *UUG U*; (SEQ ID NO: 157)

*UGC* TGC TCC TTG AGG GGT G *UU GU*; (SEQ ID NO: 158)

*UGC* TGC TCC TTG AGG GGT T *GU UUG U*; (SEQ ID NO: 159)

*UGC UGC UCC UUG AGA GGU UGU*; (SEQ ID NO: 160)

*UGC* TGC TCC TGG AGG GGT T *GU UUG U*; (SEQ ID NO: 163)

*UGC* TGC TCC TTG AGG GGT TGT TTG T; (SEQ ID NO: 170)

or

*UGC* TGC TCC TTG AGG GGT TGT TTG T; (SEQ ID NO: 171)

wherein the bolded and italicized nucleotides are modified with a 2'-O-Me sugar modification.

In some variations, the modified IRS is modified with a 2'-O-Me modification and further comprises the nucleoside inosine and/or deoxy-inosine. In some variations, the modified IRS is modified with a 2'-O-Me modification and further comprises 7-deaza-dG. In some variations, the modified IRS is any of:

5'-*UGC* TGC TCC TTG AGI GGT TGT TTG T-3', wherein I is deoxy-inosine (SEQ ID NO:173);

5'-*UGC* TGC TCC TTG AGZ' GGT TGT TTG T-3', wherein Z' is 7-deaza-dG (SEQ ID NO:174)

5'-*UGC* TGC TCC TTG AGI GGT TGT TTG-3', wherein I is deoxy-inosine (SEQ ID NO:175);

5'-*UGC* TGC TCC TTG AGI GGT TGT TT-3', wherein I is deoxy-inosine (SEQ ID NO:176);

5'-*UGC* TGC TCC TTG AGI GGT TGT T-3', wherein I is deoxy-inosine (SEQ ID NO:177);

5'-*UGC* TGC TCC TTG AGI GGT TGT-3', wherein I is deoxy-inosine (SEQ ID NO:178);

5'-*UGC* TGC TCC TTG AGI GGT T-3', wherein I is deoxy-inosine (SEQ ID NO:179);

5'-*UGC* TGC TCC TTG AGI GGT-3', wherein I is deoxy-inosine (SEQ ID NO:180);

5'-*UGC* TGC TCC TTG AGI GG-3', wherein I is deoxy-inosine (SEQ ID NO:181);

5'-*UGC* TGC TCC TTG AGI G-3', wherein I is deoxy-inosine (SEQ ID NO:182);

5'-*UGC* TGC TCC TTG AGI-3', wherein I is deoxy-inosine (SEQ ID NO:183);

5'-*GC* TGC TCC TTG AGI GGT TGT TTG T-3', wherein I is deoxy-inosine (SEQ ID NO:184);

5'-*C* TGC TCC TTG AGI GGT TGT TTG T-3', wherein I is deoxy-inosine (SEQ ID NO:185); or 5'-*UGC* TGC TCC TTG AGI GGT TG-3', wherein I is deoxy-inosine (SEQ ID NO:186); wherein the bolded and italicized nucleotides are modified with a 2'-O-Me sugar modification.

An IRP comprising a modified IRS may be single stranded or double stranded DNA, as well as single or double-stranded RNA. An IRP comprising a modified IRS may be linear, may be circular or include circular portions and/or may include a hairpin loop.

In some variations of any of the modified immunoregulatory sequences, a uridine (U) nucleoside of the modified IRS may be substituted with a thymidine (T) nucleoside. In some variations, all uridine (U) nucleoside of the modified IRS may be substituted with a thymidine (T) nucleoside. In some variations of any of the modified immunoregulatory sequences, a thymidine (T) nucleoside of the modified IRS may be substituted with a uridine (U) nucleoside. In some variations, all thymidine (T) nucleoside of the modified IRS may be substituted with a uridine (U) nucleoside. In some variations, the modified IRS may comprise both uridine (U) nucleosides and thymidine (T) nucleosides.

In some variations, a modified immunoregulatory polynucleotide is less than about any of the following lengths (in bases or base pairs): 10,000; 5,000; 2500; 2000; 1500; 1250; 1000; 750; 500; 300; 250; 200; 175; 150; 125; 100; 75; 60; 50; 40; 30; 25; 20; 15; 14; 13; 12; 11; 10; 9; 8; 7; 6; 5; 4. In some variations, a modified immunoregulatory polynucleotide is greater than about any of the following lengths (in bases or base pairs): 4; 5; 6, 7, 8, 9, 10; 11; 12; 13; 14; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the modified immunoregulatory polynucleotide can be any of a range of sizes having an upper limit of 10,000; 5,000; 2500; 2000; 1500; 1250; 1000; 750; 500; 300; 250; 200; 175; 150; 125; 100; 75; 60; 50; 40; 30; 25; 20; 15; 14; 13; 12; 11; 10; 9; 8; 7; 6; 5; 4 and an independently selected lower limit of 4; 5; 6; 7; 8; 9; 10; 11; 12; 13; 14; 15; 20; 25; 30; 40; 50; 60; 75; 100; 125; 150; 175; 200; 250; 300; 350; 400; 500; 750; 1000; 2000; 5000; 7500, wherein the lower limit is less than the upper limit. In some variations, a modified IRP is preferably about 200 or less bases in length.

In some variations, IRPs and/or IRCs comprising a modified IRS, as described herein, inhibits and/or suppresses a measurable immune response as measured in vitro, in vivo, and/or ex vivo. In some variations, the immune response is an innate immune response. In some variations, the immune response is an adaptive immune response. In some variations, an IRP and/or an IRC comprising a modified IRS result in increased inhibition of a measurable immune response as measured in vitro, in vivo, and/or ex vivo compared to an IRP and/or an IRC comprising an unmodified IRS. In some variations, the immune response is an innate immune response. In some variations, the immune response is an adaptive immune response. In some variations, the nucleotide sequence of the modified and unmodified IRS is the same, and the only difference is the modification of at least one nucleotide. In some variations, inhibition of a measurable immune response as measured in vitro, in vivo, and/or ex vivo by an IRP and/or an IRC comprising a modified IRS is increased by greater than any of about 5%, about 10%, about 15%, about 20%, about 25%, about 30%, about 35%, about 40%, about 45%, about 50%, about 60%, about 70%, about 80%, or about 90% compared to an IRP and/or an IRC comprising an unmodified IRS. In some variations, inhibition of a measurable immune response as measured in vitro, in vivo, and/or ex vivo by an IRP and/or an IRC comprising a modified IRS is increased by any of about 10%, about 15%, about 20%, or about 25% compared to an IRP and/or an IRC comprising an unmodified IRS. In some variations, the nucleotide sequence of the modified and unmodified IRS is the same, and the only difference is the modification of at least one nucleotide.

In some variations, IRPs and/or IRCs comprising a modified IRS, as described herein, inhibit TLR7 dependent cell responses. In some variations, the IRPs and/or IRCs comprising a modified IRS, as described herein, TLR7 dependent cell responses independently of TLR9 dependent cell responses. In some variations, the IRPs and/or IRCs comprising a modified IRS, as described herein, inhibit TLR9 dependent cell responses. In some variations, the IRPs and/or IRCs comprising a modified IRS, as described herein, inhibit TLR7 dependent cell responses and TLR9 dependent cell responses.

In some variations, an IRP and/or an IRC comprising a modified IRS result in increased inhibition of TLR7 and/or TLR9 dependent cell responses compared to an IRP and/or an IRC comprising an unmodified IRS. In some variations, the nucleotide sequence of the modified and unmodified IRS is the same, and the only difference is the modification of at least one nucleotide. In some variations, inhibition of TLR7 and/or TLR9 dependent cell responses by an IRP and/or an IRC comprising a modified IRS is increased by greater than any of about 5%, about 10%, about 15%, about 20%, about 25%, about 30%, about 35%, about 40%, about 45%, about 50%, about 60%, about 70%, about 80%, or about 90% compared to an IRP and/or an IRC comprising an unmodified IRS. In some variations, inhibition of TLR7 and/or TLR9 dependent cell responses by an IRP and/or an IRC comprising a modified IRS is increased by any of about 10%, about 15%, about 20%, or about 25% compared to an IRP and/or an IRC comprising an unmodified IRS. In some variations, the nucleotide sequence of the modified and unmodified IRS is the same, and the only difference is the modification of at least one nucleotide.

Immunoregulatory Compounds

In certain variations, provided herein are immunoregulatory compounds (IRCs), which have immunoregulatory activity and which comprise a nucleic acid moiety comprising an IRS. In some variations, the IRC comprises a modified IRS. In some variations, the IRC comprises an unmodified IRS. In some variations, the IRC comprises both modified and unmodified IRS. IRCs provided herein contain one or more nucleic acid moieties and one or more non-nucleic acid spacer moieties. Compounds conforming to a variety of structural formulas are contemplated for use as IRCs, including the core structures described in formulas I-VII, below. Formulas I-III show core sequences for "linear IRCs." Formulas IV-VI show core sequences for "branched IRCs." Formula VII shows a core structure for "single-spacer IRCs."

In each formula provided herein, "N" designates a nucleic acid moiety (oriented in either a 5'-3' or 3'-5' orientation) and "S" designates a non-nucleic acid spacer moiety. A dash ("-") designates a covalent bond between a nucleic acid moiety and a non-nucleic acid spacer moiety. A double dash ("--") designates covalent bonds between a non-nucleic acid spacer moiety and at least 2 nucleic acid moieties. A triple dash ("---") designates covalent bonds between a non-nucleic acid spacer moiety and multiple (i.e., at least 3) nucleic acid moieties. Subscripts are used to designate differently positioned nucleic acid or non-nucleic acid spacer moieties. However, the use of subscripts to distinguish different nucleic acid moieties is not intended to indicate that the moieties necessarily have a different structure or sequence. Similarly, the use of subscripts to distinguish different spacer moieties is not intended to indicate that the moieties necessarily have different structures. For example, in formula II, infra, the nucleic acid moieties designated $N_1$ and $N_2$ can have the same or different sequences, and the spacer moieties designated $S_1$ and $S_2$ can have the same or different structures. Further, it is contemplated that additional chemical moieties (e.g., phosphate, mononucleotide, additional nucleic acid moieties, alkyl, amino, thio or disulfide groups or linking groups, and/or spacer moieties) may be covalently bound at the termini of the core structures.

Linear IRCs have structures in which the non-nucleic acid spacer moieties in the core structure are covalently bound to no more than two nucleic acid moieties. Exemplary linear IRCs conform to the following formulas:

$$N_1-S_1-N_2 \tag{I}$$

$$N_1-S_1-N_2-S_2-N_3 \tag{II}$$

$$N_1-S_1-N_2-S_2-[N_v-S_v]_A \tag{III}$$

where A is an integer between 1 and about 100 and $[N_v-S_v]$ indicates A additional iterations of nucleic acid moieties conjugated to non-nucleic acid spacer moieties. The subscript "v" indicates that N and S are independently selected in each iteration of "$[N_v-S_v]$." "A" is sometimes between 1 and about 10, sometimes between 1 and 3, sometimes exactly 1, 2, 3, 4 or 5. In some variations, A is an integer in a range defined by a lower limit of 1, 2, 3, 4, or 5, and an independently selected upper limit of 10, 20, 50 or 100 (e.g., between 3 and 10).

Exemplary linear IRCs include:

$$N_1\text{-HEG-}N_2\text{—OH} \tag{Id. at}$$

$$N_1\text{-HEG-}N_1\text{—PO}_4 \tag{Ib}$$

$$N_1\text{-HEG-}N_2\text{-HEG} \tag{Ic}$$

$$\text{HEG-}N_1\text{-HEG-}N_1\text{-HEG} \tag{Id}$$

$$N_1\text{-HEG-}N_2\text{-HEG-}N_1 \tag{Ie}$$

$$N_1\text{-HEG-}N_2\text{-(HEG)}_4\text{-}N_3 \tag{If}$$

$$(N_1)_2\text{-glycerol-}N_1\text{-HEG-}N_1 \tag{Ig}$$

$$\text{PO}_4\text{—}N_1\text{-HEG-}N_2 \tag{Ih}$$

$$N_1\text{-(HEG)}_{15}\text{-T} \tag{Ii}$$

$$(N_1\text{-HEG})_2\text{-glycerol-HEG-}N_2 \tag{Ij}$$

$$N_1\text{-HEG-T-HEG-T} \tag{Ik}$$

wherein HEG refers to hexa-(ethylene glycol). TEG refers to tetra-(ethylene glycol).

Preferred linear IRCs include:

```
                                               (SEQ ID NO: 67)
5'-TGCTTGCAAGCTTGCAAGCA-HEG-TCCTGGAGGGGTTGT-3';

(SEQ ID NO: 68)
5'-TGCTTGCAAGCTAGCAAGCA-HEG-TCCTGGAGGGGTTGT-3';

(SEQ ID NO: 69)
5'-TGCTTGCAAGCTTGCTAGCA-HEG-TCCTGGAGGGGTTGT-3';

(SEQ ID NO: 70)
5'-TGCTTGCAAGCTTGCTAGCA-HEG-TCCTGGAGZGGTTGT-3';
``` and

```
                                               (SEQ ID NO: 71)
5'-TCCTGGAGGGGTTGT-HEG-TGCTTGCAAGCTTGCAAGCA-3'.
```

Branched IRCs comprise a multivalent spacer moiety ($S_p$) covalently bound to at least three (3) nucleic acid moieties. Exemplary branched IRCs are described according to the following formulas $$[N_v]_A\text{-}S_p \tag{IV}$$

$$[S_v\text{—}N_v]_A\text{-}S_p \tag{V}$$

$$(S_1\text{—}N_1)\text{—}S_p\text{—}(N_v)_A \tag{VI}$$

where $S_p$ is a multivalent spacer covalently bonded to the quantity "A" independently selected nucleic acid moieties $N_v$, $S_v$—$N_v$ (which comprises a spacer moiety covalently bound to a nucleic acid moiety). For formulas IV and V, A is at least 3. In various variations of formulas IV and V, A is an integer between 3 and 100 (inclusive), although A may be an integer in a range defined by a lower limit of about 3, 5, 10, 50, or 100 and an independently selected upper limit of about 5, 7, 10, 50, 100, 150, 200, 250, or 500, or alternately A may be greater than 500. For formula VI, A is at least 2, an integer in a range defined by a lower limit of 2, 5, 10, 50, or 100 and an independently selected upper limit of 5, 10, 50, 100, 150, 200, 250, or 500, or greater than 500.

Exemplary Branched IRCs include:

$$(N_1)_2\text{-glycerol-}N_1 \tag{IVa}$$

$$(N_2\text{-HEG})_2\text{-glycerol-}N_1 \tag{IVb}$$

$$(N_1\text{-HEG-}N_2)_2\text{-glycerol-}N_1 \tag{IVc}$$

$$[(N_1)_2\text{-glycerol-}N_1]_2\text{-glycerol-}N_1 \tag{IVd}$$

Preferred branched IRCs include $(5'\text{-}N_1\text{-}3'\text{-HEG})_2\text{-glycerol-HEG-}5'\text{-}N_1\text{-}3'$ and $(5'\text{-}N_1\text{-}3'\text{-HEG})_2\text{-glycerol-HEG-}5'\text{-}N_1'$.

Single spacer IRCs comprise a structure in which there is a single nucleic acid moiety covalently conjugated to a single spacer moiety, i.e., $$N_1\text{—}S_1 \tag{VII}$$

In a preferred variation $S_1$ has the structure of a multimer comprising smaller units (e.g., HEG, TEG, glycerol, 1'2'-dideoxyribose, C2 alkyl-C12 alkyl subunits, and the like), typically connected by an ester linkage (e.g., phosphodiester or phosphorothioate ester), e.g., as described infra. See, e.g., formula VIIa, infra. The multimer can be heteromeric or homomeric. In one variation, the spacer is a heteromer of monomeric units (e.g., HEG, TEG, glycerol, 1'2'-dideoxyribose, C2 alkyl to C12 alkyl linkers, and the like) linked by an ester linkage (e.g., phosphodiester or phosphorothioate ester). See, e.g., formula VIIb, infra.

Exemplary single spacer IRCs include:

$$N_1\text{-(HEG)}_{15} \tag{VIIa}$$

$$N_1\text{-HEG-propyl-HEG-propyl-HEG} \tag{VIIb}$$

In certain variations, the terminal structures of the IRC are covalently joined (e.g., nucleic acid moiety-to-nucleic acid moiety; spacer moiety-to-spacer moiety, or nucleic acid moiety-to-spacer moiety), resulting in a circular conformation.

IRCs for use in the immunoregulatory compositions provided herein include at least one nucleic acid moiety. The term "nucleic acid moiety," as used herein, refers to a nucleotide monomer (i.e., a mononucleotide) or polymer (i.e., comprising at least 2 contiguous nucleotides). As used herein, a nucleotide comprises (1) a purine or pyrimidine base linked to a sugar that is in an ester linkage to a phosphate group, or (2) an analog in which the base and/or sugar and/or phosphate ester are replaced by analogs, e.g., as described infra. In an IRC comprising more than one nucleic acid moiety, the nucleic acid moieties may be the same or different.

Nucleic acid moieties used in IRCs incorporated in the immunoregulatory compositions may comprise any of the IRS sequences disclosed herein, and may additionally be sequences of six base pairs or less. It is contemplated that in an IRC comprising multiple nucleic acid moieties, the nucleic acid moieties can be the same or different lengths. In some variations where the IRC comprises more than one nucleic acid moiety, only one of the moieties need comprise the IRS. In some variations, the IRS is a modified IRS. In some variations, the IRS is an unmodified IRS.

It is contemplated that in an IRC comprising multiple nucleic acid moieties, the nucleic acid moieties can be the same or different. Accordingly, in various variations, IRCs incorporated into the immunoregulatory compositions comprise (a) nucleic acid moieties with the same sequence, (b) more than one iteration of a nucleic acid moiety, or (c) two or more different nucleic acid moieties. Additionally, a single nucleic acid moiety may comprise more than one IRS, which may be adjacent, overlapping, or separated by additional nucleotide bases within the nucleic acid moiety.

As described herein, some IRPs are particularly effective in suppressing TLR9 dependent cell responses and some IRPs are particularly effective in suppressing TLR7 dependent cell responses. Since an IRC may comprise more than one IRP, IRPs with various activities can be combined to create an IRC with a particular activity for a particular use.

In some instances, the combination of two IRPs in an IRC leads to an immunoregulatory activity of the IRC different from either of the IRPs alone. For example, IRC SEQ ID NO:68 contains IRP SEQ ID NO:33 linked to IRP SEQ ID NO:17 through a HEG moiety. IRP SEQ ID NO:33 inhibits TLR7 dependent cell responses but not TLR9 dependent cell responses. IRP SEQ ID NO:17 have greater inhibitory activity for TLR9 dependent cell responses than for TLR-7/8 dependent cell responses. The IRC SEQ ID NO:68 however is very active in inhibiting both TLR7 dependent cell responses and TLR-9 dependent cell responses. The same is also true for IRC SEQ ID NO:69 and its component IRPs SEQ ID NO:34 and SEQ ID NO:17.

The IRCs comprise one or more non-nucleic acid spacer moieties covalently bound to the nucleic acid moieties. For convenience, non-nucleic acid spacer moieties are sometimes referred to herein simply as "spacers" or "spacer moieties." Spacers are generally of molecular weight about 50 to about 50,000, typically from about 75 to about 5000, most often from about 75 to about 500, which are covalently bound, in various variations, to one, two, three, or more than three nucleic acid moieties. A variety of agents are suitable for connecting nucleic acid moieties. For example, a variety of compounds referred to in the scientific literature as "non-nucleic acid linkers," "non-nucleotidic linkers," or "valency platform molecules" may be used as spacers in an IRC. In certain variations, a spacer comprises multiple covalently connected subunits and may have a homopolymeric or heteropolymeric structure. It will be appreciated that mononucleotides and polynucleotides are not included in the definition of non-nucleic acid spacers, without which exclusion there would be no difference between nucleic acid moiety and an adjacent non-nucleic acid spacer moiety.

In certain variations, a spacer may comprise one or more abasic nucleotides (i.e., lacking a nucleotide base, but having the sugar and phosphate portions). Exemplary abasic nucleotides include 1'2'-dideoxyribose, 1'-deoxyribose, 1'-deoxyarabinose and polymers thereof.

Other suitable spacers comprise optionally substituted alkyl, optionally substituted polyglycol, optionally substituted polyamine, optionally substituted polyalcohol, optionally substituted polyamide, optionally substituted polyether, optionally substituted polyimine, optionally substituted polyphosphodiester (such as poly(l-phospho-3-propanol), and the like. Optional substituents include alcohol, alkoxy (such as methoxy, ethoxy, and propoxy), straight or branched chain alkyl (such as C1-C12 alkyl), amine, aminoalkyl (such as amino C1-C12 alkyl), phosphoramidite, phosphate, thiophosphate, hydrazide, hydrazine, halogen, (such as F, Cl, Br, or I), amide, alkylamide (such as amide C1-C12 alkyl), carboxylic acid, carboxylic ester, carboxylic anhydride, carboxylic acid halide, sulfonyl halide, imidate ester, isocyanate, isothiocyanate, haloformate, carbodiimide adduct, aldehydes, ketone, sulfhydryl, haloacetyl, alkyl halide, alkyl sulfonate, NR1R2 wherein R1R2 is —C(=O) CH=CHC(=O) (maleimide), thioether, cyano, sugar (such as mannose, galactose, and glucose), α,β-unsaturated carbonyl, alkyl mercurial, α,β-unsaturated sulfone.

Suitable spacers may comprise polycyclic molecules, such as those containing phenyl or cyclohexyl rings. The spacer may be a polyether such as polyphosphopropanediol, polyethyleneglycol, polypropylene glycol, a bifunctional polycyclic molecule such as a bifunctional pentalene, indene, naphthalene, azulene, heptalene, biphenylene, asymindacene, sym-indacene, acenaphthylene, fluorene, phenalene, phenanthrene, anthracene, fluoranthene, acephenathrylene, aceanthrylene, triphenylene, pyrene, chrysene, naphthacene, thianthrene, isobenzofuran, chromene, xanthene, phenoxathiin, which may be substituted or modified, or a combination of the polyethers and the polycyclic molecules. The polycyclic molecule may be substituted or polysubstituted with C1-C5 alkyl, C6 alkyl, alkenyl, hydroxyalkyl, halogen or haloalkyl group. Nitrogen-containing polyheterocyclic molecules (e.g., indolizine) are typically not suitable spacers. The spacer may also be a polyalcohol, such as glycerol or pentaerythritol. In one variation, the spacer comprises 1-phosphopropane$_3$-phosphate or 1-phosphopropane$_4$-phosphate (also called tetraphosphopropanediol and pentaphosphopropanediol). In one variation, the spacer comprises derivatized 2,2'-ethylenedioxydiethylamine (EDDA).

Specific examples of non-nucleic acid spacers useful in IRCs include "linkers" described by Cload et al. (1991) *J. Am. Chem. Soc.* 113:6324; Richardson et al. (1991) *J. Am. Chem. Soc.* 113:5109; Ma et al. (1993) *Nucleic Acids Res.* 21:2585; Ma et al. (1993) *Biochemistry* 32:1751; McCurdy et al. (1991) *Nucleosides & Nucleotides* 10:287; Jaschke et al. (1993) *Tetrahedron Lett.* 34:301; Ono et al. (1991) *Biochemistry* 30:9914; and International Publication No. WO 89/02439.

Other suitable spacers include linkers described by Salunkhe et al. (1992) *J. Am. Chem. Soc.* 114:8768; Nelson et al. (1996) *Biochemistry* 35:5339-5344; Bartley et al. (1997) *Biochemistry* 36:14502-511; Dagneaux et al. (1996) *Nucleic Acids Res.* 24:4506-12; Durand et al. (1990) *Nucleic Acids Res.* 18:6353-59; Reynolds et al. (1996) *Nucleic Acids Res.* 24:760-65; Hendry et al. (1994) *Biochem. Biophys. Acta* 1219:405-12; Altmann et al. (1995) *Nucleic Acids Res.*

23:4827-35. Still other suitable spacers are described in European Pat. No. EP0313219B1 and U.S. Pat. No. 6,117,657.

Exemplary non-nucleic acid spacers comprise oligo-ethylene glycol (e.g., triethylene glycol, tetraethylene glycol, hexaethylene glycol spacers, and other polymers comprising up to about 10, about 20, about 40, about 50, about 100 or about 200 ethylene glycol units), alkyl spacers (e.g., propyl, butyl, hexyl, and other C2-C12 alkyl spacers, e.g., usually C2-C10 alkyl, most often C2-C6 alkyl), abasic nucleotide spacers, symmetric or asymmetric spacers derived from glycerol, pentaerythritol or 1,3,5-trihydroxycyclohexane (e.g., symmetrical doubler and trebler spacer moieties described herein). Spacers can also comprise heteromeric or homomeric oligomers and polymers of the aforementioned compounds (e.g., linked by an amide, ester, ether, thioether, disulfide, phosphodiester, phosphorothioate, phosphoramidate, phosphotriester, phosphorodithioate, methyl phosphonate or other linkage).

Suitable spacer moieties can contribute charge and/or hydrophobicity to the IRC, contribute favorable pharmacokinetic properties (e.g., improved stability, longer residence time in blood) to the IRC, and/or result in targeting of the IRC to particular cells or organs. Spacer moieties can be selected or modified to tailor the IRC for desired pharmacokinetic properties or suitability for desired modes of administration (e.g., oral administration). It will be appreciated by the reader that, for convenience, a spacer (or spacer component) is sometimes referred to by the chemical name of the compound from which the spacer component is derived (e.g., hexaethylene glycol), with the understanding that the IRC actually comprises the conjugate of the compound and adjacent nucleic acid moieties or other spacer moiety components.

In an IRC comprising more than one spacer moiety, the spacers may be the same or different. Thus, in one variation all of the non-nucleic acid spacer moieties in an IRC have the same structure. In one variation, an IRC comprises non-nucleic acid spacer moieties with at least 2, at least 3, at least 4, at least 5, or at least 6 or more different structures.

In some contemplated variations, the spacer moiety of an IRC is defined to exclude certain structures. Thus, in some variations, a spacer is other than an abasic nucleotide or polymer of abasic nucleotides. In some variations, a spacer is other than a oligo(ethyleneglycol) (e.g., HEG, TEG and the like) or poly(ethyleneglycol). In some variations a spacer is other than a C3 alkyl spacer. In some variations, a spacer is other than a polypeptide. Thus, in some variations, an immunogenic molecule, e.g., a protein or polypeptide, is not suitable as a component of spacer moieties. However, as discussed infra, it is contemplated that in certain variations, an IRC is a "proteinaceous IRC" i.e., comprising a spacer moiety comprising a polypeptide. However, in some variations, the spacer moiety is not proteinaceous and/or is not an antigen (i.e., the spacer moiety, if isolated from the IRC, is not an antigen).

Generally, suitable spacer moieties do not render the IRC of which they are a component insoluble in an aqueous solution (e.g., PBS, pH 7.0). Thus, the definition of spacers excludes microcarriers or nanocarriers. In addition, a spacer moiety that has low solubility, such as a dodecyl spacer (solubility <5 mg/ml when measured as dialcohol precursor 1,12-dihydroxydodecane) is not preferred because it can reduce the hydrophilicity and activity of the IRC. Preferably, spacer moieties have solubility much greater than 5 mg/ml (e.g., 20 mg/ml, ≤50 mg/ml or 100 mg/ml) when measured as dialcohol precursors.

The charge of an IRC may be contributed by phosphate, thiophosphate, or other groups in the nucleic acid moieties as well as groups in non-nucleic acid spacer moieties. In some variations, a non-nucleic acid spacer moiety carries a net charge (e.g., a net positive charge or net negative charge when measured at pH 7). In one useful variation, the IRC has a net negative charge. In some variations, the negative charge of a spacer moiety in an IRC is increased by derivatizing a spacer subunit described herein to increase its charge. For example, glycerol can be covalently bound to two nucleic acid moieties and the remaining alcohol can be reacted with an activated phosphoramidite, followed by oxidation or sulfurization to form a phosphate or thiophosphate, respectively. In certain variations the negative charge contributed by the non-nucleic acid spacer moieties in an IRC (i.e., the sum of the charges when there is more than one spacer) is greater than the negative charge contributed by the nucleic acid moieties of the IRC. Charge can be calculated based on molecular formula, or determined experimentally, e.g., by capillary electrophoresis (Li, ed., 1992, *Capillary electrophoresis, Principles, Practice and Application* Elsevier Science Publishers, Amsterdam, The Netherlands, pp 202-206).

As is noted supra, suitable spacers can be polymers of smaller non-nucleic acid (e.g., non-nucleotide) compounds, such as those described herein, that are themselves useful as spacers, including compounds commonly referred to as non-nucleotide "linkers." Such polymers (i.e., "multiunit spacers") may be heteromeric or homomeric, and often comprise monomeric units (e.g., HEG, TEG, glycerol, 1'2'-dideoxyribose, and the like) linked by an ester linkage (e.g., phosphodiester or phosphorothioate ester). Thus, in one variation the spacer comprises a polymeric (e.g., heteropolymeric) structure of non-nucleotide units (e.g., from 2 to about 100 units, alternatively 2 to about 50, e.g., 2 to about 5, alternatively e.g., about 5 to about 50, e.g., about 5 to about 20).

For illustration, IRCs containing SEQ ID NO:17 (C869) and multiunit spacers include

5'-TCCTGGAGGGGTTGT-(C3)$_{15}$-T

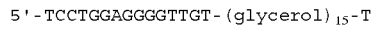
5'-TCCTGGAGGGGTTGT-(glycerol)$_{15}$-T

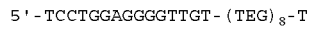
5'-TCCTGGAGGGGTTGT-(TEG)$_{8}$-T

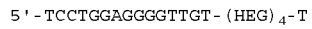
5'-TCCTGGAGGGGTTGT-(HEG)$_{4}$-T where (C3)$_{15}$ means 15 propyl linkers connected via phosphorothioate esters; (glycerol)$_{15}$ means 15 glycerol linkers connected via phosphorothioate esters; (TEG)$_{8}$ means 8 triethyleneglycol linkers connected via phosphorothioate esters; and (HEG)$_{4}$ means 4 hexaethyleneglycol linkers connected via phosphorothioate esters. It will be appreciated that certain multiunit spacers have a net negative charge, and that the negative charge can be increased by increasing the number of e.g., ester-linked monomeric units.

In certain variations, a spacer moiety is a multivalent non-nucleic acid spacer moiety (i.e., a "multivalent spacer"). As used in this context, an IRC containing a multivalent spacer contains a spacer covalently bound to three (3) or more nucleic acid moieties. Multivalent spacers are sometimes referred to in the art as "platform molecules." Multivalent spacers can be polymeric or nonpolymeric. Examples of suitable molecules include glycerol or substituted glycerol (e.g., 2-hydroxymethyl glycerol, levulinyl-glycerol); tetraaminobenzene, heptaaminobetacyclodextrin, 1,3,5-trihydroxycyclohexane, pentaerythritol and derivatives of pentaerythritol, tetraaminopentaerythritol, 1,4,8,11-tetraazacyclo tetradecane (Cyclam), 1,4,7,10-tetraazacyclododecane (Cyclen), polyethyleneimine, 1,3-diamino-2-propanol and substituted derivatives, propyloxymethyl]ethyl compounds (e.g., "trebler"), polyethylene glycol derivatives such as so-called "Star PEGs" and "bPEG" (see, e.g., Gnanou et al. (1988) *Makromol. Chem.* 189:2885; Rein et al. (1993) *Acta Polymer* 44:225; U.S. Pat. No. 5,171,264), and dendrimers.

Dendrimers are known in the art and are chemically defined globular molecules, generally prepared by stepwise or reiterative reaction of multifunctional monomers to obtain a branched structure (see, e.g., Tomalia et al. (1990) *Angew. Chem. Int. Ed. Engl.* 29:138-75). A variety of dendrimers are known, e.g., amine-terminated polyamidoamine, polyethyleneimine and polypropyleneimine dendrimers. Exemplary dendrimers useful include "dense star" polymers or "starburst" polymers such as those described in U.S. Pat. Nos. 4,587,329; 5,338,532; and 6,177,414, including so-called "poly(amidoamine) ("PAMAM") dendrimers." Still other multimeric spacer molecules suitable for use include chemically-defined, non-polymeric valency platform molecules such as those disclosed in U.S. Pat. No. 5,552,391; and PCT application publications WO 00/75105, WO 96/40197, WO 97/46251, WO 95/07073, and WO 00/34231. Many other suitable multivalent spacers can be used and will be known to those of skill in the art.

Conjugation of a nucleic acid moiety to a platform molecule can be effected in any number of ways, typically involving one or more crosslinking agents and functional groups on the nucleic acid moiety and platform molecule. Linking groups are added to platforms using standard synthetic chemistry techniques. Linking groups can be added to nucleic acid moieties using standard synthetic techniques.

Multivalent spacers with a variety of valencies are useful, and in various variations the multivalent spacer of an IRC is bound to between about 3 and about 400 nucleic acid moieties, often from 3 to 100, sometimes from 3-50, frequently from 3-10, and sometimes more than 400 nucleic acid moieties. In various variations, the multivalent spacer is conjugated to more than 10, more than 25, more than 50, or more than 500 nucleic acid moieties (which may be the same or different). It will be appreciated that, in certain variations in which an IRC comprises a multivalent spacer, provided herein is a population of IRCs with slightly different molecular structures. For example, when an IRC is prepared using a dendrimer as a high valency the multivalent spacer, a somewhat heterogeneous mixture of molecules is produced, i.e., comprising different numbers (within or predominantly within a determinable range) of nucleic acid moieties joined to each dendrimer molecule.

Polysaccharides derivatized to allow linking to nucleic acid moieties can be used as spacers in IRCs. Suitable polysaccharides include naturally occurring polysaccharides (e.g., dextran) and synthetic polysaccharides (e.g., ficoll). For instance, aminoethylcarboxymethyl-ficoll (AECM-Ficoll) can be prepared by the method of Inman (1975) *J. Imm.* 114:704-709. AECM-Ficoll can then be reacted with a heterobifunctional crosslinking reagent, such as 6-maleimido caproic acyl N-hydroxysuccinimide ester, and then conjugated to a thiol-derivatized nucleic acid moiety (see Lee et al. (1980) *Mol. Imm.* 17:749-56). Other polysaccharides may be modified similarly.

It will be well within the ability of one of skill, guided by this specification and knowledge in the art, to prepare IRCs using routine methods. Techniques for making nucleic acid moieties (e.g., oligonucleotides and modified oligonucleotides) are known. Nucleic acid moieties can be synthesized using techniques including, but not limited to, enzymatic methods and chemical methods and combinations of enzymatic and chemical approaches. For example, DNA or RNA containing phosphodiester linkages can be chemically synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Useful solid supports for DNA synthesis include Controlled Pore Glass (Applied Biosystems, Foster City, Calif.), polystyrene bead matrix (Primer Support, Amersham Pharmacia, Piscataway, N.J.) and Tent-Gel (Rapp Polymere GmbH, Tubingen, Germany). Once the desired oligonucleotide sequence has been synthesized, the oligonucleotide is removed from the support, the phosphate triester groups are deprotected to phosphate diesters and the nucleoside bases are deprotected using aqueous ammonia or other bases.

For instance, DNA or RNA polynucleotides (nucleic acid moieties) containing phosphodiester linkages are generally synthesized by repetitive iterations of the following steps: a) removal of the protecting group from the 5'-hydroxyl group of the 3'-solid support-bound nucleoside or nucleic acid, b) coupling of the activated nucleoside phosphoramidite to the 5'-hydroxyl group, c) oxidation of the phosphite triester to the phosphate triester, and d) capping of unreacted 5'-hydroxyl groups. DNA or RNA containing phosphorothioate linkages is prepared as described above, except that the oxidation step is replaced with a sulfurization step. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in PROTOCOLS FOR OLIGONUCLEOTIDES AND ANALOGS, SYNTHESIS AND PROPERTIES (Agrawal, ed.) Humana Press, Totowa, N.J.; Warner et al. (1984) *DNA* 3:401; Tang et al. (2000) *Org. Process Res. Dev.* 4:194-198; Wyrzykiewica et al. (1994) *Bioorg. & Med. Chem. Lett.* 4:1519-1522; Radhakrishna et al. (1989) *J. Org. Chem.* 55:4693-4699. and U.S. Pat. No. 4,458,066. Programmable machines that automatically synthesize nucleic acid moieties of specified sequences are widely available. Examples include the Expedite 8909 automated DNA synthesizer (Perseptive Biosystem, Framington Mass.); the ABI 394 (Applied Biosystems, Inc., Foster City, Calif.); and the OligoPilot II (Amersham Pharmacia Biotech, Piscataway, N.J.).

Polynucleotides can be assembled in the 3' to 5' direction, e.g., using base-protected nucleosides (monomers) containing an acid-labile 5'-protecting group and a 3'-phosphoramidite. Examples of such monomers include 5'-O-(4,4'-dimethoxytrityl)-protected nucleoside-3'-O-(N,N-diisopropylamino) 2-cyanoethyl phosphoramidite, where examples of the protected nucleosides include, but are not limited to, N6-benzoyladenosine, N4-benzoylcytidine, N2-isobutryrylguanosine, thymidine, and uridine. In this case, the solid support used contains a 3'-linked protected nucleoside. Alternatively, polynucleotides can be assembled in the 5' to 3' direction using base-protected nucleosides containing an acid-labile 3'-protecting group and a 5'-phosphoramidite. Examples of such monomers include 3'-O-(4, 4'-dimethoxytrityl)-protected nucleoside-5'-O-(N,N-diisopropylamino) 2-cyanoethyl phosphoramidite, where examples of the protected nucleosides include, but are not limited to, N6-benzoyladenosine, N4-benzoylcytidine, N2-isobutryrylguanosine, thymidine, and uridine (Glen Research, Sterling, Va.). In this case, the solid support used contains a 5'-linked protected nucleoside. Circular nucleic acid components can be isolated, synthesized through recombinant methods, or chemically synthesized. Chemical synthesis can be performed using any method described in the literature. See, for instance, Gao et al. (1995) *Nucleic Acids Res.* 23:2025-2029 and Wang et al. (1994) *Nucleic Acids Res.* 22:2326-2333.

Addition of non-nucleic acid spacer moieties can be accomplished using routine methods. Methods for addition of particular spacer moieties are known in the art and, for example, are described in the references cited supra. See, e.g., Durand et al. (1990) *Nucleic Acids Res.* 18:6353-6359. The covalent linkage between a spacer moiety and nucleic acid moiety can be any of a number of types, including phosphodiester, phosphorothioate, amide, ester, ether, thioether, disulfide, phosphoramidate, phosphotriester, phosphorodithioate, methyl phosphonate and other linkages. It will often be convenient to combine a spacer moiety(s) and a nucleic acid moiety(s) using the same phosphoramidite-type chemistry used for synthesis of the nucleic acid moiety. For example, IRCs described herein can be conveniently synthesized using an automated DNA synthesizer (e.g., Expedite 8909; Perseptive Biosystems, Framington, Mass.) using phosphoramidite chemistry (see, e.g., Beaucage, 1993, supra; *Current Protocols in Nucleic Acid Chemistry*, supra). However, one of skill will understand that the same (or equivalent) synthesis steps carried out by an automated DNA synthesizer can also be carried out manually, if desired. In such a synthesis, typically, one end of the spacer (or spacer subunit for multimeric spacers) is protected with a 4,4'-dimethyoxytrityl group, while the other end contains a phosphoramidite group.

A variety of spacers with the requisite protecting and reacting groups are commercially available, for example:

triethylene glycol spacer or "TEG spacer" 9-O-(4,4'-dimethoxytrityl)triethyleneglycol-1-O-[(2-cyanoethyl) N,N-diisopropylphosphoramidite] (Glen Research, 22825 Davis Drive, Sterling, Va.)

hexaethylene glycol spacer or "HEG spacer" 18-O-(4,4'-dimethoxytrityl)hexaethyleneglycol-1-O-[(2-cyanoethyl) N,N-diisopropylphosphoramidite] (Glen Research, Sterling, Va.)

propyl spacer 3-(4,4'-dimethoxytrityloxy)propyloxy-1-O-[(2-cyanoethyl) N,N-diisopropylphosphoramidite] (Glen Research, Sterling, Va.);

butyl spacer 4-(4,4'-dimethoxytrityloxy)butyloxy-1-O-[(2-cyanoethyl) N,N-diisopropylphosphoramidite] (Chem Genes Corporation, Ashland Technology Center, 200 Homer Ave, Ashland, Mass.)

Hexyl spacer or "HME spacer" 6-(4,4'-dimethoxytrityloxy)hexyloxy-1-O-[(2-cyanoethyl) N,N-diisopropylphosphoramidite] 2-(hydroxymethyl)ethyl 1-(4,4'-dimethoxytrityloxy)-3-(levulinyloxy)-spacer propyloxy-2-O-[(2-cyanoethyl) N,N-diisopropylphosphoramidite]; also called "asymmetrical branched" spacer "abasic nucleotide spacer" or "abasic spacer" 5-O-(4,4'-dimethoxytrityl)-1,2-dideoxyribose-3-O-[(2-cyanoethyl) N,N-diisopropylphosphoramidite] (Glen Research, Sterling, Va.)

"symmetrical branched spacer" or "glycerol spacer" 1,3-O,O-bis(4,4'-dimethoxytrityl)glycerol-2-O-[(2-cyanoethyl) N,N-diisopropylphosphoramidite] (Chem Genes, Ashland, Mass.)

"trebler spacer" 2,2,2-O,O,O-tris[3-O-(4,4'-dimethoxytrityloxy)propyloxymethyl]ethyl-1-O-[(2-cyanoethyl) N,N-diisopropylphosphoramidite] (Glen Research, Sterling, Va.)

"symmetrical doubler spacer" 1,3-O,O-bis[5-O-(4,4'-dimethoxytrityloxy)pentylamido]propyl-2-O-[(2-cyanoethyl) N,N-diisopropylphosphoramidite] (Glen Research, Sterling, Va.)

"dodecyl spacer" 12-(4,4'-dimethoxytrityloxy)dodecyloxy-1-O-[(2-cyanoethyl) N,N-diisopropylphosphoramidite] (Glen Research, Sterling, Va.)

These and a large variety of other protected spacer moiety precursors (e.g., comprising DMT and phosphoramidite group protecting groups) can be purchased or can be synthesized using routine methods for use in preparing IRCs disclosed herein. The instrument is programmed according to the manufacturer's instructions to add nucleotide monomers and spacers in the desired order.

Although use of phosphoramidite chemistry is convenient for the preparation of certain IRCs, it will be appreciated that the IRCs described herein are not limited to compounds prepared by any particular method of synthesis or preparation.

In one variation, IRCs with multivalent spacers conjugated to more than one type of nucleic acid moiety are prepared. For instance, platforms containing two maleimide groups (which can react with thiol-containing polynucleotides), and two activated ester groups (which can react with amino-containing nucleic acids) have been described (see, e.g., PCT application publication WO 95/07073). These two activated groups can be reacted independently of each other. This would result in an IRC containing a total of 4 nucleic acid moieties, two of each sequence.

IRCs with multivalent spacers containing two different nucleic acid sequences can also be prepared using the symmetrical branched spacer, described above, and conventional phosphoramidite chemistry (e.g., using manual or automated methods). The symmetrical branched spacer contains a phosphoramidite group and two protecting groups that are the same and are removed simultaneously. In one approach, for example, a first nucleic acid is synthesized and coupled to the symmetrical branched spacer, the protecting groups are removed from the spacer. Then two additional nucleic acids (of the same sequence) are synthesized on the spacer (using double the amount of reagents used for synthesis of a single nucleic acid moiety in each step).

A similar method can be used to connect three different nucleic acid moieties (referred to below as Nucleic acids I, II, and III) to a multivalent platform (e.g., asymmetrical branched spacer). This is most conveniently carried out using an automated DNA synthesizer. In one variation, the asymmetrical branched spacer contains a phosphoramidite group and two orthogonal protecting groups that can be removed independently. First, nucleic acid I is synthesized, then the asymmetrical branched spacer is coupled to nucleic acid I, then nucleic acid II is added after the selective removal of one of the protecting groups. Nucleic acid II is deprotected, and capped, and then the other protecting group on the spacer is removed. Finally, nucleic acid III is synthesized.

In some variations, a nucleic acid moiety(s) is synthesized, and a reactive linking group (e.g., amino, carboxylate, thio, disulfide, and the like) is added using standard synthetic chemistry techniques. The reactive linking group (which is considered to form a portion of the resulting spacer moiety) is conjugated to additional non-nucleic acid compounds to form the spacer moiety. Linking groups are added to nucleic acids using standard methods for nucleic acid synthesis, employing a variety of reagents described in the literature or commercially available. Examples include reagents that contain a protected amino group, carboxylate group, thiol group, or disulfide group and a phosphoramidite group. Once these compounds are incorporated into the nucleic acids, via the activated phosphoramidite group, and are deprotected, they provide nucleic acids with amino, carboxylate, or thiol reactivity.

Hydrophilic linkers of variable lengths are useful, for example to link nucleic acids moieties and platform molecules. A variety of suitable linkers are known. Suitable linkers include, without limitation, linear oligomers or polymers of ethylene glycol. Such linkers include linkers with the formula $R^1S(CH_2CH_2O)_nCH_2CH_2O$ $(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. The order of attachment can vary, i.e., the thioether bond can be formed before or after the amide bond is formed. Other useful linkers include Sulfo-SMCC (sulfosuccinimidyl 4-[N-maleimidomethyl]-cyclohexane-1-carboxylate) Pierce Chemical Co. product 22322; Sulfo-EMCS (N-ℓ-maleimidocaproyloxyl sulfosuccinimide ester) Pierce Chemical Co. product 22307; Sulfo-GMBS (N-[ɓ-maleimidobutyryloxy] sulfosuccinimide ester) Pierce Chemical Co. product 22324 (Pierce Chemical Co., Rockford, Ill.), and similar compounds of the general formula maleimido-R—C(O)NHS ester, where R=alkyl, cyclic alkyl, polymers of ethylene glycol, and the like.

Particularly useful methods for covalently joining nucleic acid moieties to multivalent spacers are described in the references cited supra.

In certain variations, a polypeptide is used as a multivalent spacer moiety to which a plurality of nucleic acid moieties are covalently conjugated, directly or via linkers, to form a "proteinaceous IRC." The polypeptide can be a carrier (e.g., albumin). Typically, a proteinaceous IRC comprises at least one, and usually several or many nucleic acid moieties that (a) are between 2 and 7, more often between 4 and 7 nucleotides in length, alternatively between 2 and 6, 2 and 5, 4 and 6, or 4 and 5 nucleotides in length and/or (b) have inferior isolated immunomodulatory activity or do not have isolated immunomodulatory activity. Methods of making a proteinaceous IRC will be apparent to one of skill upon review of the present disclosure. A nucleic acid, for example, can be covalently conjugated to a polypeptide spacer moiety by art known methods including linkages between a 3' or 5' end of a nucleic acid moiety (or at a suitably modified base at an internal position in the a nucleic acid moiety) and a polypeptide with a suitable reactive group (e.g., an N-hydroxysuccinimide ester, which can be reacted directly with the $N^4$ amino group of cytosine residues). As a further example, a polypeptide can be attached to a free 5'-end of a nucleic acid moiety through an amine, thiol, or carboxyl group that has been incorporated into nucleic acid moiety. Alternatively, the polypeptide can be conjugated to a spacer moiety, as described herein. Further, a linking group comprising a protected amine, thiol, or carboxyl at one end, and a phosphoramidite can be covalently attached to a hydroxyl group of a polynucleotide, and, subsequent to deprotection, the functionality can be used to covalently attach the IRC to a peptide.

IRP and/or IRC Complexes and Compositions

IRPs or IRCs can be directly administered to the individual or they can be administered in a composition or complex to enhance IRP or IRC delivery to cells and/or uptake by cells. Compositions or complexes can also be use to enhance co-delivery of two of more different IRP and/or IRC species to a cell. In some variations, a mixture of IRCs and IRPs may be complexed so as to deliver at least one IRC and IRP species. In some variations, the IRP and/or IRC comprises a modified IRS. In some variation, the IRP and/or IRC comprises an unmodified IRS. In some variations, the IRP and/or IRC comprises both modified and unmodified IRSs. Such delivery compositions or complexes include, but are not limited to, encapsulating complexes and colloidal dispersion systems as described herein and known in the art. Examples of such delivery compositions include oil-in-water emulsions, micelles, and liposomes. Delivery compositions or complexes also include IRP and/or IRC linked to a linker molecules, a platform molecule, a nanoparticle or a microparticle, as described herein. Such linkages include both covalent and non-covalent linkages. Unless otherwise noted, complex and composition formulations described herein for use with IRPs are also appropriate for use with IRCs.

In some variations, the IRP and/or IRC is conjugated with a linker molecule. The IRP and/or IRC portion can be coupled with the linker portion of a conjugate in a variety of ways, including covalent and/or non-covalent interactions.

The link between the portions can be made at the 3' or 5' end of the IRP and/or IRC, or at a suitably modified base at an internal position in the IRP and/or IRC. If the linker is a peptide and contains a suitable reactive group (e.g., an N-hydroxysuccinimide ester) it can be reacted directly with the $N^4$ amino group of cytosine residues. Depending on the number and location of cytosine residues in the IRP and/or IRC, specific coupling at one or more residues can be achieved.

Alternatively, modified oligonucleosides, such as are known in the art, can be incorporated at either terminus, or at internal positions in the IRP and/or IRC. These can contain blocked functional groups which, when deblocked, are reactive with a variety of functional groups which can be present on, or attached to, the linker of interest.

Where the linker is a peptide, this portion of the conjugate can be attached to the 3'-end of the IRP and/or IRC through solid support chemistry. For example, the IRP portion can be added to a peptide portion that has been pre-synthesized on a support. Haralambidis et al. (1990a) *Nucleic Acids Res.* 18:493-499; and Haralambidis et al. (1990b) *Nucleic Acids Res.* 18:501-505. Alternatively, the IRP can be synthesized such that it is connected to a solid support through a cleavable linker extending from the 3'-end. Upon chemical cleavage of the IRP from the support, a terminal thiol group is left at the 3'-end of the oligonucleotide (Zuckermann et al. (1987) *Nucleic Acids Res.* 15:5305-5321; and Corey et al. (1987) *Science* 238:1401-1403) or a terminal amino group is left at the 3'-end of the oligonucleotide (Nelson et al. (1989) *Nucleic Acids Res.* 17:1781-1794). Conjugation of the amino-modified IRP and/or IRC to amino groups of the peptide can be performed as described in Benoit et al. (1987) *Neuromethods* 6:43-72. Conjugation of the thiol-modified IRP and/or IRC to carboxyl groups of the peptide can be performed as described in Sinah et al. (1991) *Oligonucleotide Analogues: A Practical Approach*, IRL Press. Coupling of an oligonucleotide carrying an appended maleimide to the thiol side chain of a cysteine residue of a peptide has also been described. Tung et al. (1991) *Bioconjug. Chem.* 2:464-465.

The peptide linker portion of the conjugate can be attached to the 5'-end of the IRP and/or IRC through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) *Nucleic Acids Res.* 14:6227-6245; Connolly (1985) *Nucleic Acids Res.* 13:4485-4502; Kremsky et al. (1987) *Nucleic Acids Res.* 15:2891-2909; Connolly (1987) *Nucleic Acids Res.* 15:3131-3139; Bischoff et al. (1987) *Anal. Biochem.* 164:336-344; Blanks et al. (1988) *Nucleic Acids Res.* 16:10283-10299; and U.S. Pat. Nos. 4,849,513, 5,015,733, 5,118,800, and 5,118,802. Subsequent to deprotection, the amine, thiol, and carboxyl functionalities can be used to covalently attach the oligonucleotide to a peptide. Benoit et al. (1987); and Sinah et al. (1991).

An IRP and/or IRC conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an IRP and/or IRC. Roget et al. (1989) *Nucleic Acids Res.* 17:7643-7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an IRP and/or IRC through the use of a linker portion comprising charged residues that can interact with an oligonucleotide. For example, non-covalent conjugation can occur between a generally negatively-charged IRP and/or IRC and positively-charged amino acid residues of a peptide linker, e.g., polylysine, polyarginine and polyhistidine residues.

The linkage of the IRP and/or IRC to a lipid can be formed using standard methods. These methods include, but are not limited to, the synthesis of oligonucleotide-phospholipid conjugates (Yanagawa et al. (1988) *Nucleic Acids Symp. Ser.* 19:189-192), oligonucleotide-fatty acid conjugates (Grabarek et al. (1990) *Anal. Biochem.* 185:131-135; and Staros et al. (1986) *Anal. Biochem.* 156:220-222), and oligonucleotide-sterol conjugates. Boujrad et al. (1993) *Proc. Natl. Acad. Sci. USA* 90:5728-5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347-355.

The linkage of a circular IRP and/or IRC to a peptide linker can be formed in several ways. Where the circular IRP and/or IRC is synthesized using recombinant or chemical methods, a modified nucleoside is suitable. Ruth (1991) in *Oligonucleotides and Analogues: A Practical Approach*, IRL Press. Standard linking technology can then be used to connect the circular IRP and/or IRC to the peptide. Goodchild (1990) *Bioconjug. Chem.* 1:165. Where the circular IRP and/or IRC is isolated, or synthesized using recombinant or chemical methods, the linkage can be formed by chemically activating, or photoactivating, a reactive group (e.g. carbene, radical) that has been incorporated into the peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) *Nonisotopic DNA Probe Techniques*, Academic Press; and Geoghegan et al. (1992) *Bioconjug. Chem.* 3:138-146.

An IRP and/or IRC may be proximately associated in other ways. In some variations, an IRP and/or IRC are proximately associated by encapsulation. In other variations, an IRP and/or IRC are proximately associated by linkage to a platform molecule. A "platform molecule" (also termed "platform") is a molecule containing sites which allow for attachment of the IRP and/or IRC. In other variations, an IRP and/or IRC are proximately associated by adsorption onto a surface, preferably a carrier particle.

In some variations, the methods described herein employ an encapsulating agent in association with the IRP and/or IRC. Preferably, the composition comprising IRP and/or IRC and encapsulating agent is in the form of adjuvant oil-in-water emulsions, microparticles and/or liposomes. More preferably, adjuvant oil-in-water emulsions, microparticles and/or liposomes encapsulating an IRP and/or IRC are in the form of particles from about 0.04 μm to about 100 μm in size, preferably any of the following ranges: from about 0.1 μm to about 20 μm; from about 0.15 μm to about 10 μm; from about 0.05 μm to about 1.00 ⊠ m; from about 0.05 ⊠ m to about 0.5 ⊠ m.

Colloidal dispersion systems, such as microspheres, beads, macromolecular complexes, nanocapsules and lipid-based system, such as oil-in-water emulsions, micelles, mixed micelles and liposomes can provide effective encapsulation of IRP and/or IRC-containing compositions.

The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect an IRP and/or IRC-containing composition to preserve the immunoregulatory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of synthetic polymers which are suitable for use include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

The PEGs for use in encapsulation compositions are either purchased from chemical suppliers or synthesized using techniques known to those of skill in the art.

The term "LMS", as used herein, means lamellar lipid particles wherein polar head groups of a polar lipid are arranged to face an aqueous phase of an interface to form membrane structures. Examples of the LMSs include liposomes, micelles, cochleates (i.e., generally cylindrical liposomes), microemulsions, unilamellar vesicles, multilamellar vesicles, and the like.

An optional colloidal dispersion system is a liposome. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble chemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). For suitable lipids see e.g., Lasic (1993) "Liposomes: from Physics to Applications" Elsevier, Amsterdam.

Processes for preparing liposomes containing IRP and/or IRC compositions are known in the art. The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) *Curr. Sci.* 68:715-724. Techniques may be combined in order to provide vesicles with the most desirable attributes.

Provided herein are uses of LMSs containing tissue or cellular targeting components. Such targeting components are components of a LMS that enhance its accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The LMSs can be targeted to any cell type toward which a therapeutic treatment is to be directed, e.g., a cell type which can regulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The LMS compositions provided herein can additionally comprise surfactants. Surfactants can be cationic, anionic, amphiphilic, or nonionic. A preferred class of surfactants are nonionic surfactants; particularly preferred are those that are water soluble.

In some variations in which an IRP and/or IRC are proximately associated by linkage to a platform molecule, the platform may be proteinaceous or non-proteinaceous (i.e., organic). Examples of proteinaceous platforms include, but are not limited to, albumin, gammaglobulin, immunoglobulin (IgG) and ovalbumin. Borel et al. (1990) *Immunol. Methods* 126:159-168; Dumas et al. (1995) *Arch. Dematol. Res.* 287:123-128; Borel et al. (1995) *Int. Arch. Allergy Immunol.* 107:264-267; Borel et al. (1996) *Ann. N.Y. Acad. Sci.* 778:80-87. A platform is multi-valent (i.e., contains more than one binding, or linking, site) to accommodate binding to more than 1 IRP and/or IRC. Accordingly, a platform may contain 2 or more, 3 or more, 4 or more, 5 or more, 6 or more, 7 or more, 8 or more, 9 or more, 10 or more binding or linking sites Other examples of polymeric platforms are dextran, polyacrylamide, ficoll, carboxymethylcellulose, polyvinyl alcohol, and poly D-glutamic acid/D-lysine.

In some variations, the polymeric platform is a polymer. In some variations, the polymer is dextran, polyacrylamide, ficoll, carboxymethylcellulose, polyvinyl alcohol, or poly D-glutamic acid/D-lysine. In some variations, the polymeric platform is ficoll. In some variations, the polymeric platform is ficoll 400. In some variations, the polymeric platform is ficoll 70. In some variations, the polymeric platform is Ficoll® PM 70 (Poly(sucrose-co-epichlorhydrin)). In some variations, the polymeric platform is Ficoll® PM 400. In some variations, any of between about 1 to about 200, about 1 to about 150, about 1 to about 125, about 1 to about 100, about 1 to about 75, about 1 to about 50, or about 1 to about 25 IRPs and/or IRCs are linked to the polymeric platform. In some variations, between about 1 to about 100 IRPs and/or IRCs are linked to the polymeric platform. In some variations, the IRPs and/or IRCs comprise modified IRSs. In some variations, the IRPs and/or IRCs comprise unmodified IRSs. In some variations, the IRPs and/or IRCs include both unmodified and modified IRSs.

The principles of using platform molecules are well understood in the art. Generally, a platform contains, or is derivatized to contain, appropriate binding sites for IRP and/or IRC. In addition, or alternatively, IRP and/or IRC is derivatized to provide appropriate linkage groups. For example, a simple platform is a bi-functional linker (i.e., has two binding sites), such as a peptide. Further examples are discussed below.

Platform molecules may be biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 1,000,000, preferably any of the following ranges: from about 200 to about 500,000; from about 200 to about 200,000; from about 200 to about 50,000 (or less, such as 30,000). Examples of valency platform molecules are polymers (or are comprised of polymers) such as polyethylene glycol (PEG; preferably having a molecular weight of about 200 to about 8000), poly-D-lysine, polyvinyl alcohol, polyvinylpyrrolidone, D-glutamic acid and D-lysine (in a ratio of 3:2). Other molecules that may be used are albumin and IgG.

Other platform molecules suitable for use are the chemically-defined, non-polymeric valency platform molecules disclosed in U.S. Pat. No. 5,552,391. Other homogeneous chemically-defined valency platform molecules suitable for use are derivatized 2,2'-ethylenedioxydiethylamine (EDDA) and triethylene glycol (TEG).

Additional suitable valency platform molecules include, but are not limited to, tetraaminobenzene, heptaaminobeta-cyclodextrin, tetraaminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

Conjugation of an IRP and/or IRC to a platform molecule may be effected in any number of ways, typically involving one or more crosslinking agents and functional groups on the IRP and/or IRC and platform molecule. Platforms and IRP and/or IRC must have appropriate linking groups. Linking groups are added to platforms using standard synthetic chemistry techniques. Linking groups may be added to polypeptide platforms and IRP and/or IRC using either standard solid phase synthetic techniques or recombinant techniques. Recombinant approaches may require post-translational modification in order to attach a linker, and such methods are known in the art.

As an example, polypeptides contain amino acid side chain moieties containing functional groups such as amino, carboxyl or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s) (or if the platform is a carbohydrate), functional amino, sulfhydryl and/or aldehyde groups may be incorporated therein by conventional chemistry. For instance, primary amino groups may be incorporated by reaction of the oxidized sugar with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the platform molecule may also be derivatized to contain functional groups if it does not already possess appropriate functional groups.

Hydrophilic linkers of variable lengths are useful for connecting IRP and/or IRC to platform molecules. Suitable linkers include linear oligomers or polymers of ethylene glycol. Such linkers include linkers with the formula $R^1S(CH_2CH_2O)_mCH_2CH_2O(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. These linkers are flexible with regard to the order of attachment, i.e., the thioether can be formed first or last.

In variations in which an IRP and/or IRC are proximately associated by adsorption onto a surface, the surface may be in the form of a carrier particle (for example, a nanoparticle) made with either an inorganic or organic core. Examples of such nanoparticles include, but are not limited to, nanocrystalline particles, nanoparticles made by the polymerization of alkylcyanoacrylates and nanoparticles made by the polymerization of methylidene malonate. Additional surfaces to which an IRP and/or IRC may be adsorbed include, but are not limited to, activated carbon particles and protein-ceramic nanoplates. Other examples of carrier particles are provided herein.

Adsorption of polynucleotides and polypeptides to a surface for the purpose of delivery of the adsorbed molecules to cells is well known in the art. See, for example, Douglas et al. (1987) *Crit. Rev. Ther. Drug. Carrier Syst.* 3:233-261; Hagiwara et al. (1987) In Vivo 1:241-252; Bousquet et al. (1999) *Pharm. Res.* 16:141-147; and Kossovsky et al., U.S. Pat. No. 5,460,831. Preferably, the material comprising the adsorbent surface is biodegradable. Adsorption of an IRP and/or IRC to a surface may occur through non-covalent interactions, including ionic and/or hydrophobic interactions.

In general, characteristics of carriers such as nanoparticles, such as surface charge, particle size and molecular weight, depend upon polymerization conditions, monomer concentration and the presence of stabilizers during the polymerization process (Douglas et al., 1987). The surface of carrier particles may be modified, for example, with a surface coating, to allow or enhance adsorption of the IRP and/or IRC. Carrier particles with adsorbed IRP and/or IRC may be further coated with other substances. The addition of such other substances may, for example, prolong the half-life of the particles once administered to the subject and/or may target the particles to a specific cell type or tissue, as described herein.

Nanocrystalline surfaces to which an IRP and/or IRC may be adsorbed have been described (see, for example, U.S. Pat. No. 5,460,831). Nanocrystalline core particles (with diameters of 1 μm or less) are coated with a surface energy modifying layer that promotes adsorption of polypeptides, polynucleotides and/or other pharmaceutical agents. Another adsorbent surface are nanoparticles made by the polymerization of alkylcyanoacrylates. Alkylcyanoacrylates can be polymerized in acidified aqueous media by a process of anionic polymerization. Depending on the polymerization conditions, the small particles tend to have sizes in the range of 20 to 3000 nm, and it is possible to make nanoparticles specific surface characteristics and with specific surface charges (Douglas et al., 1987). For example, oligonucleotides may be adsorbed to polyisobutyl- and polyisohexlcyanoacrylate nanoparticles in the presence of hydrophobic cations such as tetraphenylphosphonium chloride or quaternary ammonium salts, such as cetyltrimethyl ammonium bromide. Oligonucleotide adsorption on these nanoparticles appears to be mediated by the formation of ion pairs between negatively charged phosphate groups of the nucleic acid chain and the hydrophobic cations. See, for example, Lambert et al. (1998) *Biochimie* 80:969-976, Chavany et al. (1994) *Pharm. Res.* 11:1370-1378; Chavany et al. (1992) *Pharm. Res.* 9:441-449. Another adsorbent surface are nanoparticles made by the polymerization of methylidene malonate.

IRPs or IRCs may be administered in the form of microcarrier (MC) complexes. Accordingly, provided herein are compositions comprising IRP/MC complexes or IRC/MC complexes. IRP/MC complexes comprise an IRP bound to the surface of a microcarrier (i.e., the IRP is not encapsulated in the MC), and preferably comprise multiple molecules of IRP bound to each microcarrier. In certain variations, a mixture of different IRPs may be complexed with a microcarrier, such that the microcarrier is bound to more than one IRP species. The bond between the IRP and MC may be covalent or non-covalent. As will be understood by one of skill in the art, the IRP may be modified or derivatized and the composition of the microcarrier may be selected and/or modified to accommodate the desired type of binding desired for IRP/MC complex formation. This same description applies for IRC/MC complexes. In certain variations, a mixture of IRCs and IRPs may be complexed with a microcarrier, such that the microcarrier is bound to at least one IRC and IRP species.

Microcarriers useful are less than about 150, 120 or 100 µm in size, more commonly less than about 50-60 µm in size, preferably less than about 10 µm in size, and are insoluble in pure water. Microcarriers used are preferably biodegradable, although nonbiodegradable microcarriers are acceptable. Microcarriers are commonly solid phase, such as "beads" or other particles, although liquid phase microcarriers such as oil in water emulsions comprising a biodegradable polymers or oils are also contemplated. A wide variety of biodegradable and nonbiodegradable materials acceptable for use as microcarriers are known in the art.

Microcarriers for use in the compositions or methods described herein are generally less than about 10 µm in size (e.g., have an average diameter of less than about 10 µm, or at least about 97% of the particles pass through a 10 µm screen filter), and include nanocarriers (i.e., carriers of less than about 1 µm size). Preferably, microcarriers are selected having sizes within an upper limit of about 9, 7, 5, 2, or 1 µm or 900, 800, 700, 600, 500, 400, 300, 250, 200, or 100 nm and an independently selected lower limit of about 4, 2, or 1 µm or about 800, 600, 500, 400, 300, 250, 200, 150, 100, 50, 25, or 10 nm, where the lower limit is less than the upper limit. In some variations, the microcarriers have a size of about 1.0-1.5 µm, about 1.0-2.0 µm or about 0.9-1.6 µm. In certain preferred variations, the microcarriers have a size of about 10 nm to about 5 µm or about 25 nm to about 4.5 µm, about 1 µm, about 1.2 µm, about 1.4 µm, about 1.5 µm, about 1.6 µm, about 1.8 µm, about 2.0 µm, about 2.5 µm or about 4.5 µm. When the microcarriers are nanocarriers, preferred variations include nanocarriers of about 25 to about 300 nm, 50 to about 200 nm, about 50 nm or about 200 nm.

Solid phase biodegradable microcarriers may be manufactured from biodegradable polymers including, but not limited to: biodegradable polyesters, such as poly(lactic acid), poly(glycolic acid), and copolymers (including block copolymers) thereof, as well as block copolymers of poly (lactic acid) and poly(ethylene glycol); polyorthoesters such as polymers based on 3,9-diethylidene-2,4,8,10-tetraoxaspiro[5.5]undecane (DETOSU); polyanhydrides such as poly (anhydride) polymers based on relatively hydrophilic monomers such as sebacic acid; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al., (1996) Biotechnol. Bioeng. 1996:102); and polyamides such as poly(lactic acid-co-lysine).

A wide variety of nonbiodegradable materials suitable for manufacturing microcarriers are also known, including, but not limited to polystyrene, polypropylene, polyethylene, silica, ceramic, polyacrylamide, dextran, hydroxyapatite, latex, gold, and ferromagnetic or paramagnetic materials. Certain variations exclude gold, latex, and/or magnetic beads. In certain variations, the microcarriers may be made of a first material (e.g., a magnetic material) encapsulated with a second material (e.g., polystyrene).

Solid phase microspheres are prepared using techniques known in the art. For example, they can be prepared by emulsion-solvent extraction/evaporation technique. Generally, in this technique, biodegradable polymers such as polyanhydrates, poly(alkyl-α-cyanoacrylates) and poly(α-hydroxy esters), for example, poly(lactic acid), poly(glycolic acid), poly(D,L-lactic-co-glycolic acid) and poly (caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinylalcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid microparticles are then separated by centrifugation or filtration, and dried, for example, by lyophilization or application of vacuum, before storing at 4° C.

Physico-chemical characteristics such as mean size, size distribution and surface charge of dried microspheres may be determined. Size characteristics are determined, for example, by dynamic light scattering technique and the surface charge was determined by measuring the zeta potential.

Liquid phase microcarriers include liposomes, micelles, oil droplets and other lipid or oil-based particles which incorporate biodegradable polymers or oils. In certain variations, the biodegradable polymer is a surfactant. In other variations, the liquid phase microcarriers are biodegradable due to the inclusion of a biodegradable oil such as squalene or a vegetable oil. One preferred liquid phase microcarrier is oil droplets within an oil-in-water emulsion. Preferably, oil-in-water emulsions used as microcarriers comprise biodegradable substituents such as squalene.

Covalently bonded IRP/MC complexes may be linked using any covalent crosslinking technology known in the art. Typically, the IRP portion will be modified, either to incorporate an additional moiety (e.g., a free amine, carboxyl or sulfhydryl group) or incorporate modified (e.g., phosphorothioate) nucleotide bases to provide a site at which the IRP portion may be linked to the microcarrier. The link between the IRP and MC portions of the complex can be made at the 3' or 5' end of the IRP, or at a suitably modified base at an internal position in the IRP. The microcarrier is generally also modified to incorporate moieties through which a covalent link may be formed, although functional groups normally present on the microcarrier may also be utilized. The IRP/MC is formed by incubating the IRP with a microcarrier under conditions which permit the formation of a covalent complex (e.g., in the presence of a crosslinking agent or by use of an activated microcarrier comprising an activated moiety which will form a covalent bond with the IRP).

A wide variety of crosslinking technologies are known in the art, and include crosslinkers reactive with amino, carboxyl and sulfhydryl groups. As will be apparent to one of skill in the art, the selection of a crosslinking agent and crosslinking protocol will depend on the configuration of the IRP and the microcarrier as well as the desired final configuration of the IRP/MC complex. The crosslinker may be either homobifunctional or heterobifunctional. When a homobifunctional crosslinker is used, the crosslinker exploits the same moiety on the IRP and MC (e.g., an aldehyde crosslinker may be used to covalently link an IRP and MC where both the IRP and MC comprise one or more free amines). Heterobifunctional crosslinkers utilize different moieties on the IRP and MC, (e.g., a maleimido-N-hydroxysuccinimide ester may be used to covalently link a free sulfhydryl on the IRP and a free amine on the MC), and are preferred to minimize formation of inter-microcarrier bonds. In most cases, it is preferable to crosslink through a first crosslinking moiety on the microcarrier and a second crosslinking moiety on the IRP, where the second crosslinking moiety is not present on the microcarrier. One preferred method of producing the IRP/MC complex is by 'activating' the microcarrier by incubating with a heterobifunctional crosslinking agent, then forming the IRP/MC complex by incubating the IRP and activated MC under conditions appropriate for reaction. The crosslinker may incorporate a "spacer" arm between the reactive moieties, or the two reactive moieties in the crosslinker may be directly linked.

In one preferred variation, the IRP portion comprises at least one free sulfhydryl (e.g., provided by a 5'-thiol modified base or linker) for crosslinking to the microcarrier, while the microcarrier comprises free amine groups. A heterobifunctional crosslinker reactive with these two groups (e.g., a crosslinker comprising a maleimide group and a NHS-ester), such as succinimidyl 4-(N-maleimidomethyl)cyclohexane-1-carboxylate is used to activate the MC, then covalently crosslink the IRP to form the IRP/MC complex.

Non-covalent IRP/MC complexes may be linked by any non-covalent binding or interaction, including ionic (electrostatic) bonds, hydrophobic interactions, hydrogen bonds, van der Waals attractions, or a combination of two or more different interactions, as is normally the case when a binding pair is to link the IRP and MC.

Preferred non-covalent IRP/MC complexes are typically complexed by hydrophobic or electrostatic (ionic) interactions, or a combination thereof, (e.g., through base pairing between an IRP and a polynucleotide bound to an MC use of a binding pair). Due to the hydrophilic nature of the backbone of polynucleotides, IRP/MC complexes which rely on hydrophobic interactions to form the complex generally require modification of the IRP portion of the complex to incorporate a highly hydrophobic moiety. Preferably, the hydrophobic moiety is biocompatible, nonimmunogenic, and is naturally occurring in the individual for whom the composition is intended (e.g., is found in mammals, particularly humans). Examples of preferred hydrophobic moieties include lipids, steroids, sterols such as cholesterol, and terpenes. The method of linking the hydrophobic moiety to the IRP will, of course, depend on the configuration of the IRP and the identity of the hydrophobic moiety. The hydrophobic moiety may be added at any convenient site in the IRP, preferably at either the 5' or 3' end; in the case of addition of a cholesterol moiety to an IRP, the cholesterol moiety is preferably added to the 5' end of the IRP, using conventional chemical reactions (see, for example, Godard et al. (1995) *Eur. J. Biochem.* 232:404-410). Preferably, microcarriers for use in IRP/MC complexes linked by hydrophobic bonding are made from hydrophobic materials, such as oil droplets or hydrophobic polymers, although hydrophilic materials modified to incorporate hydrophobic moieties may be utilized as well. When the microcarrier is a liposome or other liquid phase microcarrier comprising a lumen and the IRP is desired to be associated with the outer surface of the MC, the IRP/MC complex is formed by mixing the IRP and the MC after preparation of the MC, in order to avoid encapsulation of the IRP during the MC preparation process.

Non-covalent IRP/MC complexes bound by electrostatic binding typically exploit the highly negative charge of the polynucleotide backbone. Accordingly, microcarriers for use in non-covalently bound IRP/MC complexes are generally positively charged (cationic) at physiological pH (e.g., about pH 6.8-7.4). The microcarrier may intrinsically possess a positive charge, but microcarriers made from compounds not normally possessing a positive charge may be derivatized or otherwise modified to become positively charged (cationic). For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles).

For example, to prepare cationic microspheres, cationic lipids or polymers, for example, 1,2-dioleoyl-1,2,3-trimethylammoniopropane (DOTAP), cetyltrimethylammonium bromide (CTAB) or polylysine, are added either to DP or CP, as per their solubility in these phases.

IRP/MC complexes can be preformed by adsorption onto cationic microspheres by incubation of polynucleotide and the particles, preferably in an aqueous admixture. Such incubation may be carried out under any desired conditions, including ambient (room) temperature (e.g., approximately 20° C.) or under refrigeration (e.g., 4° C.). Because cationic microspheres and polynucleotides associate relatively quickly, the incubation may be for any convenient time period, such as 5, 10, 15 minutes or more, including overnight and longer incubations. For example, IRPs can be adsorbed onto the cationic microspheres by overnight aqueous incubation of polynucleotide and the particles at 4° C. However, because cationic microspheres and polynucleotides spontaneously associate, the IRP/MC complex can be formed by simple co-administration of the polynucleotide and the MC. Microspheres may be characterized for size and surface charge before and after polynucleotide association. Selected batches may then evaluated for activity against suitable controls in, for example, human peripheral blood mononuclear cell (PBMC) and mouse splenocyte assays. The formulations may also evaluated in suitable animal models.

Non-covalent IRP/MC complexes linked by nucleotide base pairing may be produced using conventional methodologies. Generally, base-paired IRP/MC complexes are produced using a microcarrier comprising a bound, preferably a covalently bound, polynucleotide (the "capture polynucleotide") that is at least partially complementary to the IRP. The segment of complementarity between the IRP and the capture nucleotide is preferably at least 6, 8, 10 or 15 contiguous base pairs, more preferably at least 20 contiguous base pairs. The capture nucleotide may be bound to the MC by any method known in the art, and is preferably covalently bound to the IRP at the 5' or 3' end. In some variations, an IRP comprising a 5'-GGGG-3' sequence will retain this portion of the sequence as single-stranded.

In other variations, a binding pair may be used to link the IRP and MC in an IRP/MC complex. The binding pair may be a receptor and ligand, an antibody and antigen (or epitope), or any other binding pair which binds at high affinity (e.g., Kd less than about 10-8). One type of preferred binding pair is biotin and streptavidin or biotin and avidin, which form very tight complexes. When using a binding pair to mediate IRP/MC complex binding, the IRP is derivatized, typically by a covalent linkage, with one member of the binding pair, and the MC is derivatized with the other member of the binding pair. Mixture of the two derivatized compounds results in IRP/MC complex formation.

Isolation and Synthesis of Immunoregulatory Polynucleotides

Provided herein are also methods of making the immunoregulatory polynucleotides described herein. In some variations, the immunoregulatory polynucleotides comprise modified immunoregulatory sequences. In some variations, the immunoregulatory polynucleotides comprise unmodified immunoregulatory sequences. The methods may be any of those described herein. For example, the method could be synthesizing the IRP (for example, using solid state synthesis) and may further comprise any purification step(s). Methods of purification are known in the art.

Also provided are methods for isolating and synthesizing immunoregulatory polynucleotide (IRP). In some variations, the IRP is a modified IRP. In some variations, the IRP is an unmodified IRP.

The IRP can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The IRP can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular immunoregulatory polynucleotide can be isolated, synthesized through recombinant methods, or chemically synthesized. Where the circular IRP is obtained through isolation or through recombinant methods, the IRP will preferably be a plasmid. The chemical synthesis of smaller circular oligonucleotides can be performed using any method described in the literature. See, for instance, Gao et al. (1995) Nucleic Acids Res. 23:2025-2029; and Wang et al. (1994) Nucleic Acids Res. 22:2326-2333.

The techniques for making polynucleotides and modified polynucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired polynucleotide sequence has been synthesized, the polynucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oligonucleotides and Analogs, Synthesis and Properties (Agrawal, ed.) Humana Press, Totowa, N.J.; Warner et al. (1984) DNA 3:401 and U.S. Pat. No. 4,458,066.

Synthesis of polynucleotides containing modified phosphate linkages or non-phosphate linkages is also known in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the polynucleotides can be a monophosphate, diphosphate, triphosphate, alkylphosphonate, phosphorothioate, phosphorodithioate, phosphoramidate or the like. The preparation of the above-noted phosphate analogs, and their incorporation into nucleotides, modified nucleotides and oligonucleotides, per se, is also known and need not be described here in detail. Peyrottes et al. (1996) Nucleic Acids Res. 24:1841-1848; Chaturvedi et al. (1996) Nucleic Acids Res. 24:2318-2323; and Schultz et al. (1996) Nucleic Acids Res. 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190). Similarly the synthesis of other phosphate analogs, such as phosphotriester (Miller et al. (1971) JACS 93:6657-6665), non-bridging phosphoramidates (Jager et al. (1988) Biochem. 27:7247-7246), N3' to P5' phosphoramidiates (Nelson et al. (1997) JOC 62:7278-7287) and phosphorodithioates (U.S. Pat. No. 5,453,496) has also been described. Other non-phosphorous based modified oligonucleotides can also be used (Stirchak et al. (1989) Nucleic Acids Res. 17:6129-6141).

Those skilled in the art will recognize that a large number of "synthetic" non-natural nucleosides comprising various heterocyclic bases and various sugar moieties (and sugar analogs) are available in the art, and that as long as other criteria of the present invention are satisfied, the IRP can include one or several heterocyclic bases other than the principal five base components of naturally-occurring nucleic acids. Preferably, however, the heterocyclic base in the IRP includes, but is not limited to, uracil-5-yl, cytosin-5-yl, adenin-7-yl, adenin-8-yl, guanin-7-yl, guanin-8-yl, 4-aminopyrrolo [2.3-d] pyrimidin-5-yl, 2-amino-4-oxopyrolo [2,3-d]pyrimidin-5-yl, 2-amino-4-oxopyrrolo [2.3-d] pyrimidin-3-yl groups, where the purines are attached to the sugar moiety of the IRP via the 9-position, the pyrimidines via the 1-position, the pyrrolopyrimidines via the 7-position and the pyrazolopyrimidines via the 1-position.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide. Nucleosides modified in their sugar moiety have also been described (including, but not limited to, e.g., U.S. Pat. Nos. 4,849,513, 5,015,733, 5,118, 800, 5,118,802) and can be used similarly.

Methods of Use

Provided herein are methods of regulating an immune response in an individual, preferably a mammal, more preferably a human, comprising administering to the individual an IRS-containing polynucleotide as described herein. Methods of immunoregulation provided by the invention include those that suppress and/or inhibit an immune response, including, but not limited to, an immune response stimulated by immunostimulatory nucleic acid molecules such as bacterial DNA. In some variations, the IRS is a modified IRS. In some variations, the IRS is an unmodified IRS. The invention also provides methods for inhibiting TLR7 and/or TLR9 induced cell response. The invention also provides methods for ameliorating symptoms associated with unwanted immune activation, including, but not limited to, symptoms associated with autoimmunity.

Provided herein are methods for regulating an immune response in an individual, comprising administering to an individual an immunoregulatory polynucleotide and/or an immunoregulatory compound described herein in an amount sufficient to regulate an immune response in said individual. In some variations, the IRP and/or IRC comprise a modified IRS. In some variations, the IRP and/or IRC comprise an unmodified IRS. In some variations, the IPR and/or IRC comprise both modified and unmodified IRSs. Immunoregulation according to the methods described herein may be practiced on individuals including those suffering from a disorder associated with an unwanted activation of an immune response. In some variations, the immune response is an innate immune response. In some variations, the immune response is an adaptive immune response.

Further provided herein are methods for inhibiting an immune response comprising contacting a cell of the immune system with a polynucleotide comprising an immunoregulatory sequence (IRS), wherein the cell is contacted with the polynucleotide in an amount effective to inhibit a response from the cell that contributes to an immune response. In some variations, the IRS comprises a modification. In some variations, the IRS does not comprise a modification (i.e., an unmodified IRS).

Methods are provided herein for ameliorating one or more symptoms of an autoimmune disease, comprising administering an effective amount of an immunoregulatory polynucleotide or immunoregulatory compound described herein to an individual having an autoimmune disease. In some variations, administration of an immunoregulatory polynucleotide or an immunoregulatory compound ameliorates one or more symptoms of the autoimmune disease, including SLE and rheumatoid arthritis. In some variations, the immunoregulatory polynucleotide or immunoregulatory compound effective for suppressing a symptom of SLE comprises an immunoregulatory sequence of the TLR7 class or TLR9 class or TLR7/9 class. In some variations, the IRP and/or IRC comprise a modified IRS. In some variations, the IRP and/or IRC comprise an unmodified IRS. In some variations, the IPR and/or IRC comprise both modified and unmodified IRSs.

Methods are also provided herein for preventing or delaying development of an autoimmune disease, comprising administering an effective amount of an immunoregulatory polynucleotide or an immunoregulatory compound described herein to an individual at risk of developing an autoimmune disease. In some variations, administration of an immunoregulatory polynucleotide or immunoregulatory compound prevents or delays development of the autoimmune disease. In some variations, the IRP and/or IRC comprise a modified IRS. In some variations, the IRP and/or IRC comprise an unmodified IRS. In some variations, the IPR and/or IRC comprise both modified and unmodified IRSs.

Methods of combination therapy are also provided herein. In some variations, methods are provided for ameliorating one or more symptoms of an autoimmune disease, comprising administering an effective amount of an immunoregulatory polynucleotide or an immunoregulatory compound described herein and an other therapeutic agent to an individual having an autoimmune disease. In some variations, the other therapeutic agent is a corticosteroid. In some variations, administration of the combination ameliorates one or more symptoms of the autoimmune disease, including SLE and rheumatoid arthritis. In some variations, the immunoregulatory polynucleotide or immunoregulatory compound used in combination therapy effective for suppressing a symptom of SLE comprises an immunoregulatory sequence of the TLR7 class or TLR9 class or TLR7/9 class. In some variations, the IRP and/or IRC used in combination therapy comprise a modified IRS. In some variations, the IRP and/or IRC used in combination therapy comprise an unmodified IRS. In some variations, the IPR and/or IRC used in combination therapy comprise both modified and unmodified IRSs.

In some variations, methods are provided for preventing or delaying development of an autoimmune disease, comprising administering an effective amount of an immunoregulatory polynucleotide or an immunoregulatory compound described herein and an other therapeutic agent to an individual at risk of developing an autoimmune disease. In some variations, the other therapeutic agent is a corticosteroid. In some variations, administration of the combination prevents or delays development of one or more symptoms of the autoimmune disease, including SLE and rheumatoid arthritis. In some variations, the IRP and/or IRC used in combination therapy comprise a modified IRS. In some variations, the IRP and/or IRC used in combination therapy comprise an unmodified IRS. In some variations, the IPR and/or IRC used in combination therapy comprise both modified and unmodified IRSs.

In certain variations, the individual suffers from a disorder associated with unwanted immune activation, such as autoimmune disease and inflammatory disease. An individual having an autoimmune disease or inflammatory disease is an individual with a recognizable symptom of an existing autoimmune disease or inflammatory disease.

Autoimmune diseases include, without limitation, rheumatoid arthritis (RA), systemic lupus erythematosus (SLE), type I diabetes mellitus, type II diabetes mellitus, multiple sclerosis (MS), immune-mediated infertility such as premature ovarian failure, scleroderma, Sjogren's disease, vitiligo, alopecia (baldness), polyglandular failure, Grave's disease, hypothyroidism, polymyositis, pemphigus vulgaris, pemphigus foliaceus, inflammatory bowel disease including Crohn's disease and ulcerative colitis, autoimmune hepatitis including that associated with hepatitis B virus (HBV) and hepatitis C virus (HCV), hypopituitarism, graft-versus-host disease (GvHD), myocarditis, Addison's disease, autoimmune skin diseases, uveitis, pernicious anemia, and hypoparathyroidism.

Autoimmune diseases may also include, without limitation, Hashimoto's thyroiditis, Type I and Type II autoimmune polyglandular syndromes, paraneoplastic pemphigus, bullus pemphigoid, dermatitis herpetiformis, linear IgA disease, epidermolysis bullosa acquisita, erythema nodosa, pemphigoid gestationis, cicatricial pemphigoid, mixed essential cryoglobulinemia, chronic bullous disease of childhood, hemolytic anemia, thrombocytopenic purpura, Goodpasture's syndrome, autoimmune neutropenia, myasthenia gravis, Eaton-Lambert myasthenic syndrome, stiff-man syndrome, acute disseminated encephalomyelitis, Guillain-Barre syndrome, chronic inflammatory demyelinating polyradiculoneuropathy, multifocal motor neuropathy with conduction block, chronic neuropathy with monoclonal gammopathy, opsonoclonus-myoclonus syndrome, cerebellar degeneration, encephalomyelitis, retinopathy, primary biliary sclerosis, sclerosing cholangitis, gluten-sensitive enteropathy, ankylosing spondylitis, reactive arthritides, polymyositis/dermatomyositis, mixed connective tissue disease, Bechet's syndrome, psoriasis, polyarteritis nodosa, allergic anguitis and granulomatosis (Churg-Strauss disease), polyangiitis overlap syndrome, hypersensitivity vasculitis, Wegener's granulomatosis, temporal arteritis, Takayasu's arteritis, Kawasaki's disease, isolated vasculitis of the central nervous system, thromboangiutis obliterans, sarcoidosis, glomerulonephritis, and cryopathies. These conditions are well known in the medical arts and are described, for example, in Harrison's Principles of Internal Medicine, 14th ed., Fauci A S et al., eds., New York: McGraw-Hill, 1998.

The systemic disease SLE is characterized by the presence of antibodies to antigens that are abundant in nearly every cell, such as anti-chromatin antibodies, anti-spliceosome antibodies, anti-ribosome antibodies and anti-DNA antibodies. Consequently, the effects of SLE are seen in a variety of tissues, such as the skin and kidneys. Autoreactive T cells also play a role in SLE. For example, studies in a murine lupus model have shown that non-DNA nucleosomal antigens, e.g. histones, stimulate autoreactive T cells that can drive anti-DNA producing B cells. Increased serum levels of IFN-α has been observed in SLE patients and shown to correlate with both disease activity and severity, including fever and skin rashes, as well as essential markers associated with the disease process (e.g., anti-dsDNA antibody titers). It has also been shown that immune complexes present in the circulation could trigger IFN-α in these patients and, thus, maintain this chronic presence of elevated IFN-α. Two different types of immune complexes have been described to trigger IFN-α from human PDC: DNA/anti-DNA antibody complexes and RNA/anti-ribonucleoprotein-RNA antibody complexes. Because DNA is a ligand of TLR-9 and RNA a ligand for TLR7, it is expected that these two pathways utilize TLR-9 and TLR-7/8 signaling, respectively, in order to chronically induce IFN-α and thus participate in the etiopathogenesis of SLE. Accordingly, IRP and/or IRC compositions which are effective in inhibiting TLR7 and TLR-9 responses may be particularly effective in treating SLE.

In certain variations, an individual is at risk of developing an autoimmune disease and an IRP or IRC is administered in an amount effective to delay or prevent the autoimmune disease. Individuals at risk of developing an autoimmune disease includes, for example, those with a genetic or other predisposition toward developing an autoimmune disease. In humans, susceptibility to particular autoimmune diseases is associated with HLA type with some being linked most strongly with particular MHC class II alleles and others with particular MHC class I alleles. For example, ankylosing spondylitis, acute anterior uveitis, and juvenile rheumatoid arthritis are associated with HLA-B27, Goodpasture's syndrome and MS are associated with HLA-DR2, Grave's disease, myasthenia gravis and SLE are associated with HLA-DR3, rheumatoid arthritis and pemphigus vulgaris are associated with HLA-DR4 and Hashimoto's thyroiditis is associated with HLA-DRS. Other genetic predispositions to autoimmune diseases are known in the art and an individual can be examined for existence of such predispositions by assays and methods well known in the art. Accordingly, in some instances, an individual at risk of developing an autoimmune can be identified.

As described herein, IRPs described herein may particularly inhibit production of a cytokine, including, but not limited to, IL-6, IL-12, TNF-α, and/or IFN-α, and may suppress B cell proliferation and/or activation of plasmacytoid dendritic cells to differentiate. Accordingly, the IRPs and IRCs described herein are particularly effective in suppressing an immune response to an immunostimulatory nucleic acid in an individual. In some variations, the IRPs and IRCs comprise a modified IRS. In some variations, the IRPs and IRCs comprise an unmodified IRS. In some variations, the IRPs and IRCs comprise both a modified IRS and an unmodified IRS.

Animal models for the study of autoimmune disease are known in the art. For example, animal models which appear most similar to human autoimmune disease include animal strains which spontaneously develop a high incidence of the particular disease. Examples of such models include, but are not limited to, the nonobeses diabetic (NOD) mouse, which develops a disease similar to type 1 diabetes, and lupus-like disease prone animals, such as New Zealand hybrid, MRL-Fas$^{lpr}$ and BXSB mice. Animal models in which an autoimmune disease has been induced include, but are not limited to, experimental autoimmune encephalomyelitis (EAE), which is a model for multiple sclerosis, collagen-induced arthritis (CIA), which is a model for rheumatoid arthritis, and experimental autoimmune uveitis (EAU), which is a model for uveitis. Animal models for autoimmune disease have also been created by genetic manipulation and include, for example, IL-2/IL-10 knockout mice for inflammatory bowel disease, Fas or Fas ligand knockout for SLE, and IL-1receptor antagonist knockout for rheumatoid arthritis.

Accordingly, animal models standard in the art are available for the screening and/or assessment for activity and/or effectiveness of the methods and compositions described herein for the treatment of autoimmune disorders.

Provided herein are methods for treating and/or ameliorating one or more symptoms of an inflammatory disease or disorder, comprising administering an effective amount of an immunoregulatory polynucleotide or an immunoregulatory compound described herein to an individual having an inflammatory disease or disorder. In some variations, administration of an immunoregulatory polynucleotide ameliorates one or more symptoms of the inflammatory disease or disorder. In some variations, the compositions described herein are effective in ameliorating a symptom of chronic inflammatory disease or disorder. In some variations, the inflammatory disease or disorder is an autoimmune disease discussed above. In some variations, the IRP and/or IRC comprise a modified IRS. In some variations, the IRP and/or IRC comprise an unmodified IRS. In some variations, the IPR and/or IRC comprise both modified and unmodified IRSs.

In certain variations, the individual suffers from a disorder associated with unwanted immune activation, such as allergic disease or condition, allergy and asthma. An individual having an allergic disease or asthma is an individual with a recognizable symptom of an existing allergic disease or asthma.

In some variations, provided herein are methods of suppressing and/or inhibiting an inflammatory response using any of the IRPs or IRCs described herein. In certain variations, the individual suffers from a disorder associated with a chronic inflammatory response. Administration of an IRP results in immunomodulation, decreasing levels of one or more immune response associated cytokines, which may result in a reduction of the inflammatory response. Immunoregulation of individuals with the unwanted immune response associated the described disorders results in a reduction or improvement in one or more of the symptoms of the disorder. In some variations, the inflammatory response inhibited and/or suppressed is drug-induced inflammation. In some variations, the drug-induced inflammation is drug-induced inflammation of the liver. In some variations, the inflammatory response inhibited and/or suppressed is infection-induced inflammation. In some variations, the disorder is an inflammatory liver disease or an inflammatory pancreatic disorder. Examples of inflammatory liver disorders include, for example, ligalactosemia, Alagille's syndrome, alpha 1-antitrypsin deficiency, neonatal hepatitis, tyrosinemia, hemorrhagic telangiectasia, Reye's syndrome, Wilson's disease, thalassemia, biliary atresia, chronic active hepatitis such as hepatitis A, hepatitis B, or hepatitis C, cancer of the liver, cirrhosis, type I glycogen storage disease, porphyria, hemochromatosis, primary sclerosing cholangitis, sarcoidosis, gallstones, fatty liver disease, alcoholic hepatitis, or alcoholic cirrhosis. Examples of inflammatory pancreatic disorders include, for example, pancreatitis or pancreatic cancer.

Other variations provided herein relate to immunoregulatory therapy of individuals having been exposed to or infected with a virus. Administration of an IRP or IRC to an individual having been exposed to or infected with a virus results in suppression of virus induced cytokine production. In some variations, the IRPs and IRCs comprise a modified IRS. In some variations, the IRPs and IRCs comprise an unmodified IRS. In some variations, the IRPs and IRCs comprise both a modified IRS and an unmodified IRS. Cytokine produced in response to a virus can contribute to an environment favorable for viral infection. Suppression of the virus-induced cytokine production may serve to limit or prevent the viral infection.

In some variations, methods are provided for suppressing chronic pathogen stimulation, comprising administering an effective amount of an immunoregulatory polynucleotide or an immunoregulatory compound described herein to an individual having a chronic pathogen infection or disease. In some variations, administration of an immunoregulatory polynucleotide or an immunoregulatory compound suppresses chronic pathogen stimulation in the individual, including that associated with malaria and chronic viral infections. IRP and/or IRC compositions which are effective in inhibiting TLR7 responses may be particularly effective in treating disease and symptoms related to chronic pathogen stimulation. In some variations, the immunoregulatory polynucleotide or immunoregulatory compound effective for suppressing chronic pathogen stimulation comprises an immunoregulatory sequence of the TLR7 class. In some variations, the IRP and/or IRC comprise a modified IRS. In some variations, the IRP and/or IRC comprise an unmodified IRS. In some variations, the IPR and/or IRC comprise both modified and unmodified IRSs.

In some situations, peripheral tolerance to an autoantigen is lost (or broken) and an autoimmune response ensues. For example, in an animal model for EAE, activation of antigen presenting cells (APCs) through the immune receptor TLR9 or TLR4 was shown to break self-tolerance and result in the induction of EAE (Waldner et al. (2004) *J. Clin. Invest.* 113:990-997).

In any of the methods described herein the IRS-containing polynucleotide may be administered in an amount sufficient to regulate an immune response. As described herein, regulation of an immune response may be humoral and/or cellular, and is measured using standard techniques in the art and as described herein.

Accordingly, in some variations, provided herein are methods for suppressing, reducing, and/or inhibiting TLR9 dependent cell stimulation. Administration of an IRP and/or IRC results in suppression of TLR9 dependent cell responses, including decreased levels of one or more TLR9-associated cytokines. IRPs and/or IRCs appropriate for use in suppressing TLR9 dependent cell stimulation are those IRP and/or IRC that inhibit or suppress cell responses associated with TLR9. In some variations, the IRPs and/or IRCs comprise a modified IRS. In some variations, the IRPs and/or IRCs comprise an unmodified IRS. In some variations, the IRPs and/or IRCs comprise both a modified IRS and an unmodified IRS.

In some variations, provided herein are methods for suppressing, reducing, and/or inhibiting TLR7 dependent cell stimulation. Administration of an IRP and/or an IRC results in suppression of TLR7 dependent cell responses, including decreased levels of one or more TLR7-associated cytokines. IRPs and/or IRCs appropriate for use in suppressing TLR7 dependent cell stimulation are those IRP and/or IRC that inhibit or suppress cell responses associated with TLR7. In some variations, the IRPs and/or IRCs comprise a modified IRS. In some variations, the IRPs and/or IRCs comprise an unmodified IRS. In some variations, the IRPs and/or IRCs comprise both a modified IRS and an unmodified IRS.

In some variations, methods are provided for inhibiting a TLR7 dependent immune response independently of TLR9 dependent immune response in an individual, comprising administering to an individual an immunoregulatory polynucleotide or an immunoregulatory compound described herein in an amount sufficient to suppress TLR7 dependent cytokine production independently of TLR9 dependent cytokine production in said individual. In some variations, the TLR7 and/or TLR9 dependent immune response is an innate immune response. In some variations, the TLR7 and/or TLR9 dependent immune response is an adaptive immune response. In some variations, the IRP and/or IRC comprise a modified IRS. In some variations, the IRP and/or IRC comprise an unmodified IRS. In some variations, the IPR and/or IRC comprise both modified and unmodified IRSs.

As demonstrated herein, some IRP and/or IRC suppress both TLR9 dependent cell responses and TLR7 dependent cell responses. In some variations, methods are provided for inhibiting a TLR9 dependent immune response and a TLR7 dependent immune response in an individual, comprising administering to an individual an immunoregulatory polynucleotide or an immunoregulatory compound described herein in an amount sufficient to suppress TLR9 dependent cytokine production and TLR7 dependent cytokine production in said individual, wherein the IRP or IRC comprises an IRS of the TLR7/9 class. In some variations, the TLR7 and/or TLR9 dependent immune response is an innate immune response. In some variations, the TLR7 and/or TLR9 dependent immune response is an adaptive immune response. In some variations, the IRP and/or IRC comprise a modified IRS. In some variations, the IRP and/or IRC comprise an unmodified IRS. In some variations, the IPR and/or IRC comprise both modified and unmodified IRSs.

In some variations, the compositions described herein inhibit a response of a B cell or a plasmacytoid dendritic cell. In some variations, immune responses inhibited by the compositions described herein include inhibition of cytokine production, such as IL-6 and/or IFN-α, by the cell, inhibition of cell maturation and/or inhibition of cell proliferation. In some variations, the compositions described herein inhibit a TLR9 dependent cell response, a TLR7 dependent cell response, and/or a TLR7/9 dependent cell response.

Administration and Assessment of the Immune Response

As with all compositions for modulation of an immune response, the effective amounts and method of administration of the particular IRP and/or IRC formulation can vary based on the individual, what condition is to be treated and other factors evident to one skilled in the art. Factors to be considered include whether or not the IRP and/or IRC will be administered with or covalently attached to a delivery molecule, route of administration and the number of doses to be administered. Such factors are known in the art and it is well within the skill of those in the art to make such determinations without undue experimentation. A suitable dosage range is one that provides the desired regulation of immune response (e.g., suppression of IFN-α or other cytokine production in response to an immunostimulatory nucleic acid). When suppression of an immune response to an immunostimulatory nucleic acid is desired, a suitable dosage range is one that provides the desired suppression of immune stimulation by the immunostimulatory nucleic acid. Generally, dosage is determined by the amount of IRP and/or IRC administered to the patient, rather than the overall quantity of IRP-containing composition administered. Useful dosage ranges of the IRP and/or IRC, given in amounts of IRP and/or IRC delivered, may be, for example, from about any of the following: 0.5 to 10 mg/kg, 1 to 9 mg/kg, 2 to 8 mg/kg, 3 to 7 mg/kg, 4 to 6 mg/kg, 5 mg/kg, 1 to 10 mg/kg, or 5 to 10 mg/kg. The absolute amount given to each patient depends on pharmacological properties such as bioavailability, clearance rate and route of administration.

The effective amount and method of administration of the particular IRP and/or IRC formulation can vary based on the individual patient, desired result and/or type of disorder, the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient IRP-containing composition to attain a tissue concentration of about 1-50 μM as measured by blood levels. The absolute amount given to each patient depends on pharmacological properties such as bioavailability, clearance rate and route of administration.

As described herein, tissues in which unwanted immune activation is occurring or is likely to occur are preferred targets for the IRP and/or IRC. Thus, administration of IRP and/or IRC to lymph nodes, spleen, bone marrow, blood, as well as tissue exposed to virus, are preferred sites of administration.

Provided herein are IRP and/or IRC formulations suitable for topical application including, but not limited to, physiologically acceptable implants, ointments, creams, rinses and gels. Exemplary routes of dermal administration are those which are least invasive such as transdermal transmission, epidermal administration and subcutaneous injection.

Transdermal administration is accomplished by application of a cream, rinse, gel, etc. capable of allowing the IRP and/or IRC to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

Parenteral routes of administration include but are not limited to electrical (iontophoresis) or direct injection such as direct injection into a central venous line, intravenous, intramuscular, intraperitoneal, intradermal, or subcutaneous injection. Formulations of IRP and/or IRC suitable for parenteral administration are generally formulated in USP water or water for injection and may further comprise pH buffers, salts bulking agents, preservatives, and other pharmaceutically acceptable excipients. Immunoregulatory polynucleotide for parenteral injection may be formulated in pharmaceutically acceptable sterile isotonic solutions such as saline and phosphate buffered saline for injection.

Gastrointestinal routes of administration include, but are not limited to, ingestion and rectal routes and can include the use of, for example, pharmaceutically acceptable powders, pills or liquids for ingestion and suppositories for rectal administration.

Naso-pharyngeal and pulmonary administration include are accomplished by inhalation, and include delivery routes such as intranasal, transbronchial and transalveolar routes. Formulations of IRP and/or IRC suitable for administration by inhalation including, but not limited to, liquid suspensions for forming aerosols as well as powder forms for dry powder inhalation delivery systems are provided. Devices suitable for administration by inhalation of IRP or IRC formulations include, but are not limited to, atomizers, vaporizers, nebulizers, and dry powder inhalation delivery devices.

As is well known in the art, solutions or suspensions used for the routes of administration described herein can include any one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

As is well known in the art, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. It may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

As is well known in the art, sterile injectable solutions can be prepared by incorporating the active compound(s) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The above-mentioned compositions and methods of administration are meant to describe but not limit the methods of administering the formulations of IRPs and IRCs described herein. The methods of producing the various compositions and devices are within the ability of one skilled in the art and are not described in detail here.

Analysis (both qualitative and quantitative) of the activity of an IRP and/or IRC in suppression of immune stimulation can be by any method described herein or known in the art, including, but not limited to, measuring suppression or a decrease in proliferation of specific cell populations such as B cells, measuring suppression of maturation of specific cell populations such as dendritic cells (including plasmacytoid dendritic cells) and T cells, and measuring suppression in production of cytokines such as, but not limited to, IFN-α, TNF-α, IL-6, and/or IL-12. Measurement of numbers of specific types of cells can be achieved, for example, with fluorescence-activated cell sorting (FACS). Measurement of maturation of particular populations of cells can be achieved by determining expression of markers, for example, cell surface markers, specific for particular stage of cell maturation. Cell marker expression can be measured, for example, by measuring RNA expression or measuring cell surface expression of the particular marker by, for example, FACS analysis. Measuring maturation of dendritic cells can be performed for instance as described in Hartmann et al. (1999) *Proc. Natl. Acad. Sci. USA* 96:9305-9310. Cytokine concentrations can be measured, for example, by ELISA. These and other assays to evaluate suppression of an immune response, including an innate immune response and/or adaptive immune response, are well known in the art.

Combination Therapy

The IRP and/or IRC can be administered in combination with other therapeutic agent, as described herein, and can be combined with a physiologically acceptable carrier thereof (and as such includes these compositions described herein). The methods described herein may be practiced in combination with other therapies which make up the standard of care for the disorder, such as administration of anti-inflammatory agents. The IRP and/or IRC can be administered in combination with a corticosteroid, as described herein, and can be combined with a physiologically acceptable carrier thereof (and as such \includes these compositions described herein). The IRP and/or IRC may be any of those described herein. In some variations, the IRP and/or IRC comprises a modified IRS. In some variations, the IRP and/or IRC comprises both unmodified and modified IRSs.

In some variations, an IRP and/or IRC is administered in combination with a corticosteroid. In some variations, the corticosteroid is a glucocorticosteroid. In some variations, the corticosteroid is a mineralocorticoid. Corticosteroids include, but are not limited to, corticosterone and derivatives, prodrugs, isomers and analogs thereof, cortisone and derivatives, prodrugs, isomers and analogs thereof (i.e., Cortone), aldosterone and derivatives, prodrugs, isomers and analogs thereof, dexamethasone and derivatives, prodrugs, isomers and analogs thereof (i.e., Decadron), prednisone and derivatives, prodrugs, isomers and analogs thereof (i.e., Prelone), fludrocortisones and derivatives, prodrugs, isomers and analogs thereof (i.e. Florinef®), hydrocortisone and derivatives, prodrugs, isomers and analogs thereof (i.e., cortisol or Cortef), hydroxycortisone and derivatives, prodrugs, isomers and analogs thereof, betamethasone and derivatives, prodrugs, isomers and analogs thereof (i.e., Celestone), budesonide and derivatives, prodrugs, isomers and analogs thereof (i.e., Entocort EC), methylprednisolone and derivatives, prodrugs, isomers and analogs thereof (i.e., Medrol), prednisolone and derivatives, prodrugs, isomers and analogs thereof (i.e., Deltasone, Crtan, Meticorten, Orasone, or Sterapred), triamcinolone and derivatives, prodrugs, isomers and analogs thereof (i.e., Kenacort or Kenalog), and the like. In some variations, the corticosteroid is fludrocortisone or a derivative, prodrug, isomer or analog thereof. In some variations, the corticosteroid is fludrocortisone. In some variations, the corticosteroid is hydroxycortisone or a derivative, prodrug, isomer or analog thereof. In some variations, the corticosteroid is hydroxycortisone.

In some variations, the corticosteroid is administered any of between about 0.001 mg to about 1 mg, about 0.5 mg to about 1 mg, about 1 mg to about 2 mg, about 2 mg to about 20 mg, about 20 mg to about 40 mg, about 40 to about 80 mg, about 80 to about 120 mg, about 120 mg to about 200 mg, about 200 mg to about 500 mg, about 500 mg to about 1000 mg per day. In some variations, the corticosteroid is administered any of between about 0.1 mg/kg to about 0.5 mg/kg, about 0.5 mg/kg to about 1 mg/kg, about 1 mg/kg to about 2 mg/kg, about 2 mg/kg to about 5 mg/kg, about 5 mg/kg to about 10 mg/kg, about 10 mg/kg to about 15 mg/kg, about 15 mg/kg to about 20 mg/kg, about 20 mg/kg to about 25 mg/kg, about 25 mg/kg to 35 mg/kg, or about 35 mg/kg to about 50 mg/kg per day.

In some variations, the IRP and/or IRC used in combination therapy, given in amounts of IRP and/or IRC delivered, may be, for example, from about any of the following: 0.5 to 10 mg/kg, 1 to 9 mg/kg, 2 to 8 mg/kg, 3 to 7 mg/kg, 4 to 6 mg/kg, 5 mg/kg, 1 to 10 mg/kg, or 5 to 10 mg/kg.

In some variations, the IRP and/or IRC is administered simultaneously with the other therapeutic agent including, but not limited to, a corticosteroid (simultaneous administration). In some variations, the IRP and/or IRC is administered sequentially with the other therapeutic agent including, but not limited to, a corticosteroid (sequential administration). In some variations, the IRP and/or IRC is administered by the same route of administration as the other therapeutic agent. In some variations, the IRP and/or IRC is administered by a different route of administration than the other therapeutic agent. In some variations, the other therapeutic agent is administered parentally (e.g., central venous line, intra-arterial, intravenous, intramuscular, intraperitoneal, intradermal, or subcutaneous injection), orally, gastrointestinally, topically, naso-pharyngeal and pulmonary (e.g. inhalation or intranasally). In some variations, the other therapeutic agent is a corticosteroid.

In some variations, the combination of an IRP and/or IRC with an other therapeutic agent reduces the effective amount (including, but not limited to, dosage volume, dosage concentration, total drug dose administered) of the IRP and/or IRC and/or the other therapeutic agents compared to the effective amount when the IRP and/or IRC or other therapeutic agent is administered alone. In some variations, the combination of an IRP and/or IRC with a corticosteroid reduces the effective amount compared to a corticosteroid administered alone. In some variations, the combination of an IRP and/or IRC with an other therapeutic agent reduces the frequency of administrations of the other therapeutic agent compared to administration of the other therapeutic agent alone. In some variations, the combination of an IRP and/or IRC with an other therapeutic agent reduces the total duration of treatment compared to administration of the other therapeutic agent alone. In some variations, the combination of an IRP and/or IRC with an other therapeutic agent reduces the side effects associated with administration of the other therapeutic agent alone. In some variations, the other therapeutic agent is a corticosteroid. In some variations, the corticosteroid is fludrocortisone or a derivative, prodrug, isomer or analog thereof. In some variations, the corticosteroid is fludrocortisone.

In some variations, the combination therapy including but not limited to the combination of an IRP and/or IRC and a corticosteroid is used in the treatment of an inflammatory disease. In some variations, the inflammatory disease is an autoimmune disease. In some variations, the autoimmune disease is rheumatoid arthritis. In some variations, the autoimmune disease is lupus. In some variations, the autoimmune disease systemic lupus erythematosus (SLE). In some variations, the lupus is associated with renal flares. In some variations, the renal flares are moderate renal flares. In some variations, the renal flares are severe renal flares.

Kits

Provided here are kits. In certain variations, the kits described herein generally comprise one or more containers comprising any IRP and/or IRC as described herein. In some variations, the kits comprise an IRP and/or IRC with a modified IRS. In some variations, the kits comprise an IRP and/or IRC with an unmodified IRS. In some variation, the kit comprises IRPs and/or IRCs with both modified and unmodified IRSs. In some variations, the kits may further provide an other therapeutic agent. In some variations, the other therapeutic agent is a corticosteroid.

The kits may further comprise a suitable set of instructions, generally written instructions, relating to the use of the IRP and/or IRC for any of the methods described herein (e.g., suppression of a response to an immunostimulatory nucleic acid, suppression of a TLR7 and/or TLR9 dependent response, ameliorating one or more symptoms of an autoimmune disease, ameliorating a symptom of chronic inflammatory disease, decreasing cytokine production in response to a virus).

The kits may comprise IRP and/or IRC packaged in any convenient, appropriate packaging. For example, if the IRP or IRC is a dry formulation (e.g., freeze dried or a dry powder), a vial with a resilient stopper is normally used, so that the IRP or IRC may be easily resuspended by injecting fluid through the resilient stopper. Ampoules with non-resilient, removable closures (e.g., sealed glass) or resilient stoppers are most conveniently used for liquid formulations of IRP or IRC. Also contemplated are packages for use in combination with a specific device, such as an inhaler, nasal administration device (e.g., an atomizer), a syringe or an infusion device such as a minipump.

The instructions relating to the use of IRP and/or IRC generally include information as to dosage, dosing schedule, and route of administration for the intended method of use. The containers of IRP or IRC may be unit doses, bulk packages (e.g., multi-dose packages) or sub-unit doses. Instructions supplied in the kits described herein are typically written instructions on a label or package insert (e.g., a paper sheet included in the kit), but machine-readable instructions (e.g., instructions carried on a magnetic or optical storage disk) are also acceptable.

In some variations, kits described herein comprise materials for production of IRP and/or IRC as complexes for administration, for example, encapsulation material, microcarrier complex material and so on. Generally, the kit includes separate containers of IRP or IRC and the complex material(s). The IRP or IRC and complexes are preferably supplied in a form which allows formation of IRP- or IRC-complex upon mixing of the supplied IRP or IRC and complex material. This configuration is preferred when the IRP- or IRC-complex is linked by non-covalent bonding. This configuration is also preferred when the IRP- or IRC-complex are to be crosslinked via a heterobifunctional crosslinker; either IRP/IRC or the complex is supplied in an "activated" form (e.g., linked to the heterobifunctional crosslinker such that a moiety reactive with the IRP/IRC is available).

EXAMPLES

The following Examples are provided to illustrate, but not limit, the invention.

Example 1

Splenocytes Stimulated with 1018 ISS (TLR9 ligand) or R848 (TLR7 Ligand) in the Presence of IRPs Modified and unmodified immunoregulatory polynucleotides (IRPs) (i.e., polynucleotides containing at least one modified or unmodified IRS) or control samples were assayed for immunoregulatory (IR) activity of innate immune responses on human and mouse cells.

For mouse cell assays, spleens from 6-12 week-old BALB/c mice spleen were harvested and mechanically dispersed by forcing the digested fragments through metal screens. The dispersed splenocytes were pelleted by centrifugation, then resuspended in fresh medium (RPMI 1640 with 10% fetal calf serum, plus 50 units/mL penicillin, 50 µg/mL streptomycin, 2 mM glutamine, and 0.05 mM β-mercaptoethanol). In a dose-dependent manner, the cells were then stimulated with 0.7-1 mM of 1018 ISS (TLR9 ligand; 5'-TGACTGTGAACGTTCGAGATGA-3' (SEQ ID NO:122)) or 1 µM of R848 (TLR7 ligand; a small molecule, an imidazoquinoline also called resiquimod) either alone or in the presence of the tested IRPs. At 48 hours, supernatants were collected and cytokine levels, IL-6, were measured using immunoassays.

The modified and unmodified IRPs tested were SEQ ID NO:123 (5'-TGCTCCTGGAGGGGTTGT-3'), SEQ ID NO:161 (5'-UGCUCCUGGAGGGG UUGU-3' a locked nucleic acid (LNA) modified version of SEQ ID NO:123, which introduces a 2'-O, 4'-C methylene bridge in the sugar ring of all nucleotides), SEQ ID NO:135 (5'-UGCUC-CUGGA GGGGUUGU-3' a 2' OMe modified version of SEQ ID NO:123, wherein all nucleotides are modified with a 2'-O-Me modification, a sugar modification), SEQ ID NO:136 (5'-UGCUCCUGGAGGGGUUGU-3' a phosphoramidate modified version of SEQ ID NO:123, wherein all nucleotides are modified with phosphoramidate modification, a phosphate modification), SEQ ID NO:137 (5'-UG-CUCCUGGAGGGGUUGU-3' a 5'-methyl dC (M) modified version of SEQ ID NO:123, wherein all cytosines are modified with a 5-methyl dC (M) modification, a base modification), and a control oligodeoxynucleotide (5'-TC-CTGCAGGTTAAGT-3' (SEQ ID NO:197)).

Figure 1:
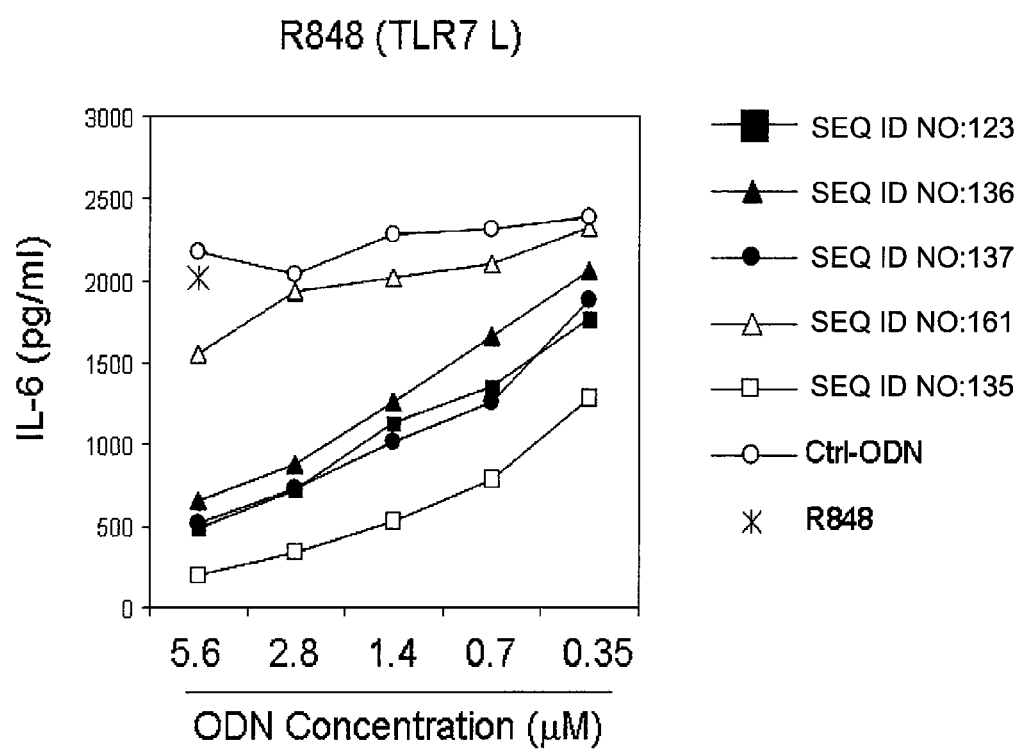
FIG. 1 depicts IL-6 levels (pg/ml) in mouse splenocytes following TLR7 ligand stimulation by R848 either alone or in the presence of tested IRPs.
Figure 2:
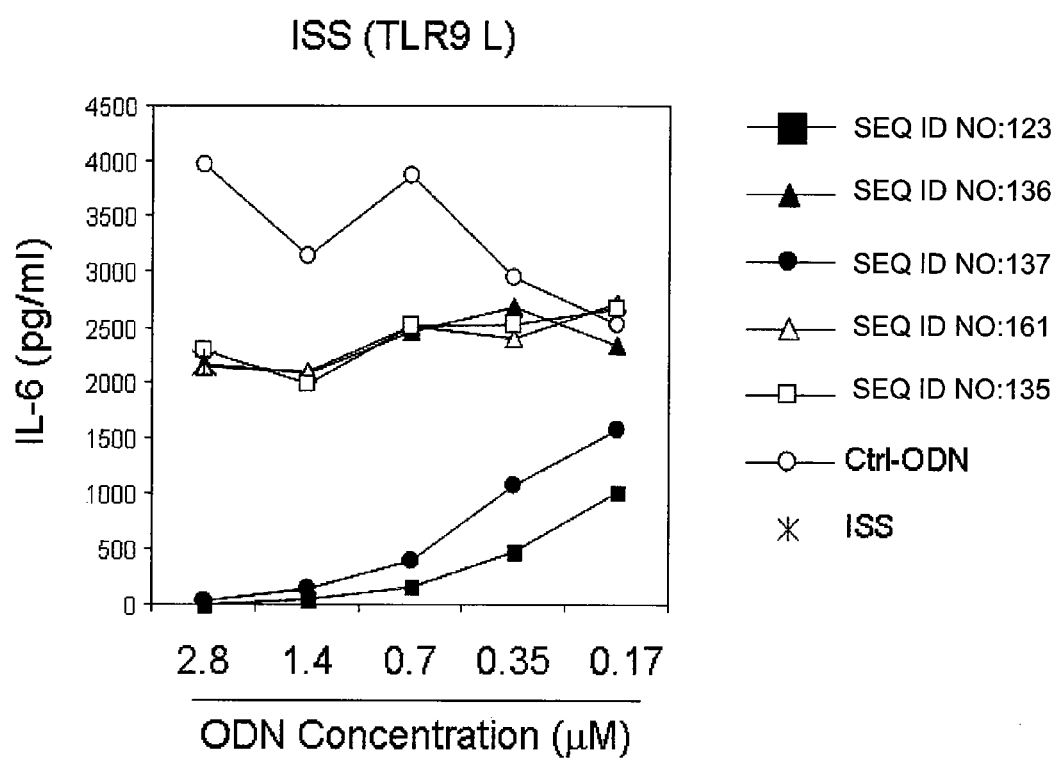
FIG. 2 depicts IL-6 levels (pg/ml) in mouse splenocytes following TLR9 ligand stimulation by 1018 ISS (SEQ ID NO:122) either alone or in the presence of tested IRPs.
Figure 3:
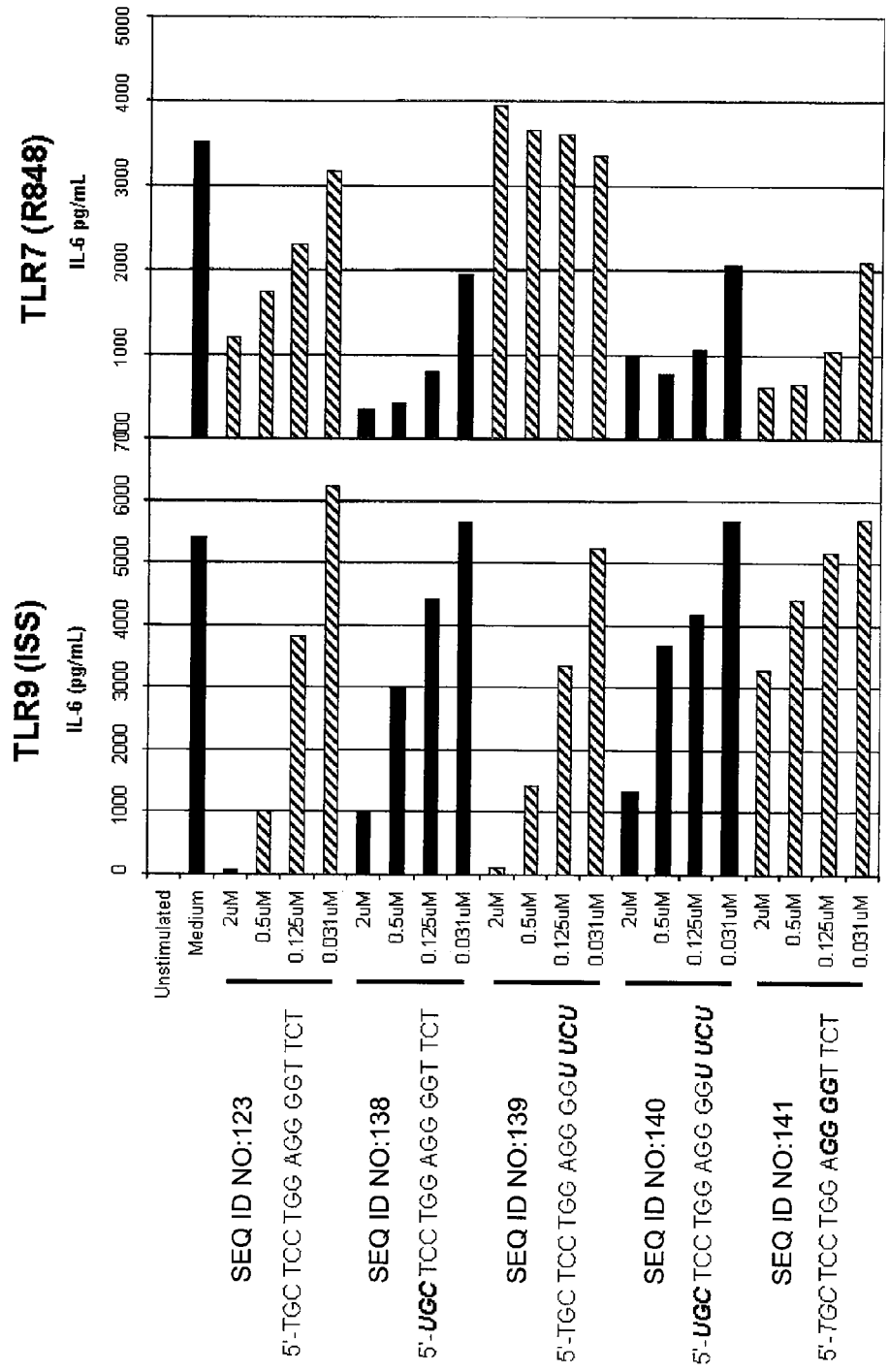
FIG. 3 depicts IL-6 levels (pg/ml) in mouse splenocytes following TLR7 ligand stimulation by R848 or TLR9 ligand stimulation by 1018 ISS (SEQ ID NO:122) either alone or in the presence of tested IRPs.
Figure 4A:
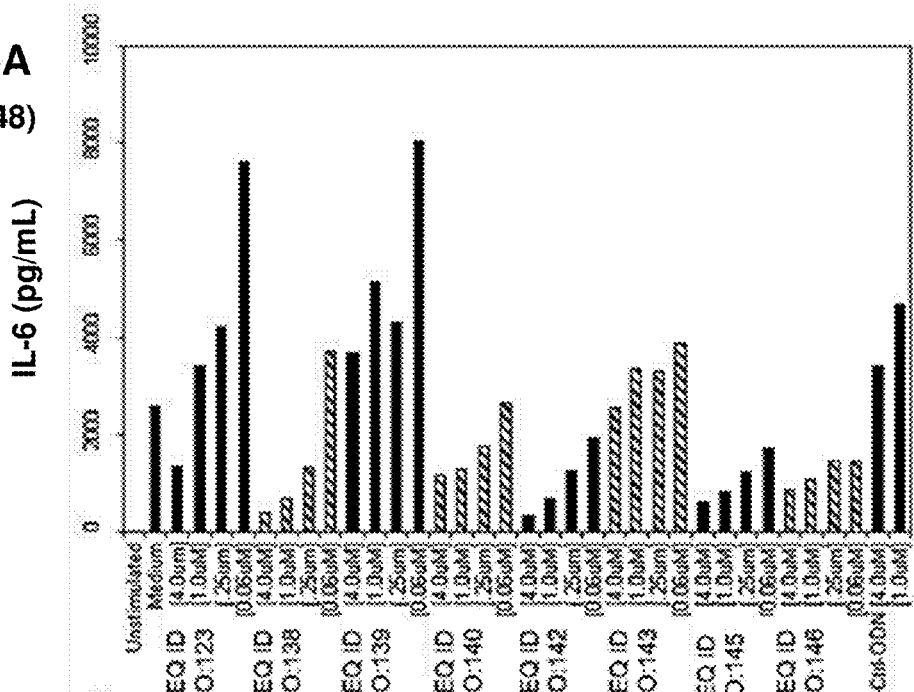
FIGS. 4A and B depict IL-6 levels (pg/ml) in mouse splenocytes following TLR7 ligand stimulation by R848 or TLR9 ligand stimulation by 1018 ISS (SEQ ID NO:122) either alone or in the presence of tested IRPs.
Figure 4B:
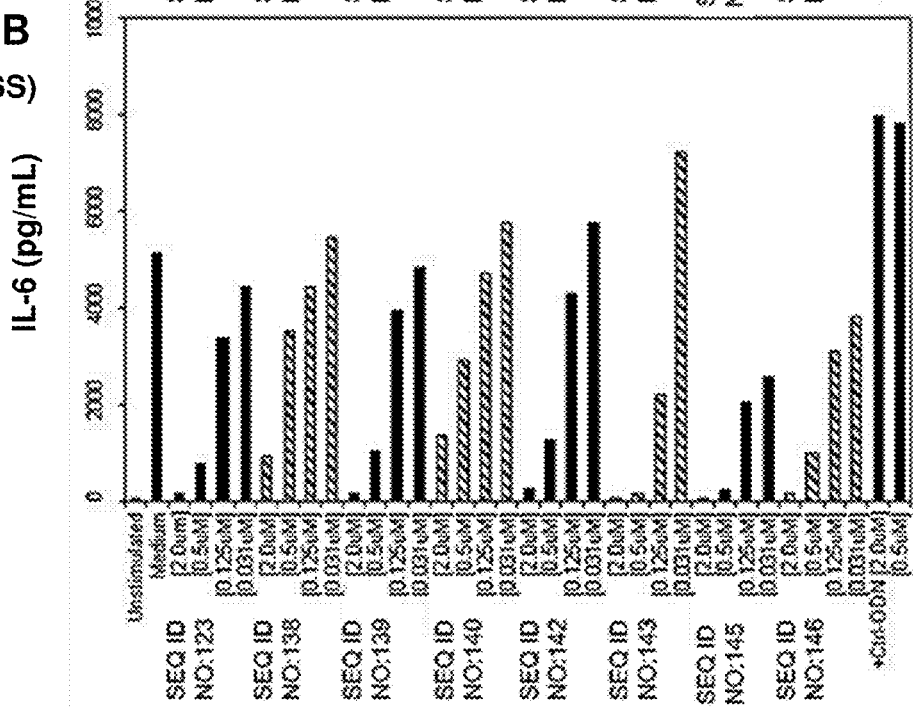
Figure 6A:
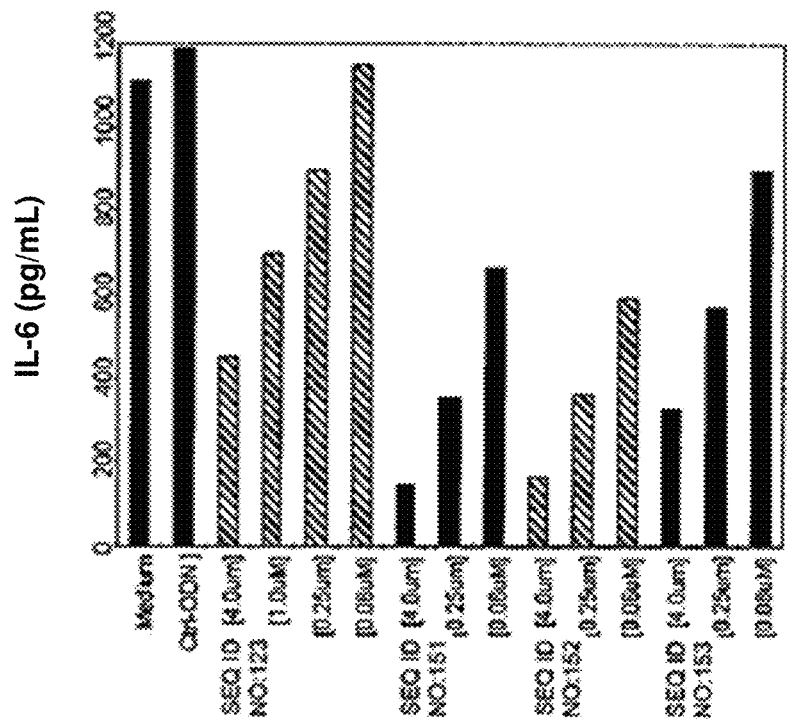
FIGS. 6A and B depict IL-6 levels (pg/ml) in mouse splenocytes following TLR7 ligand stimulation by R848 or TLR9 ligand stimulation by 1018 ISS (SEQ ID NO:122) either alone or in the presence of tested IRPs.
Figure 6B:
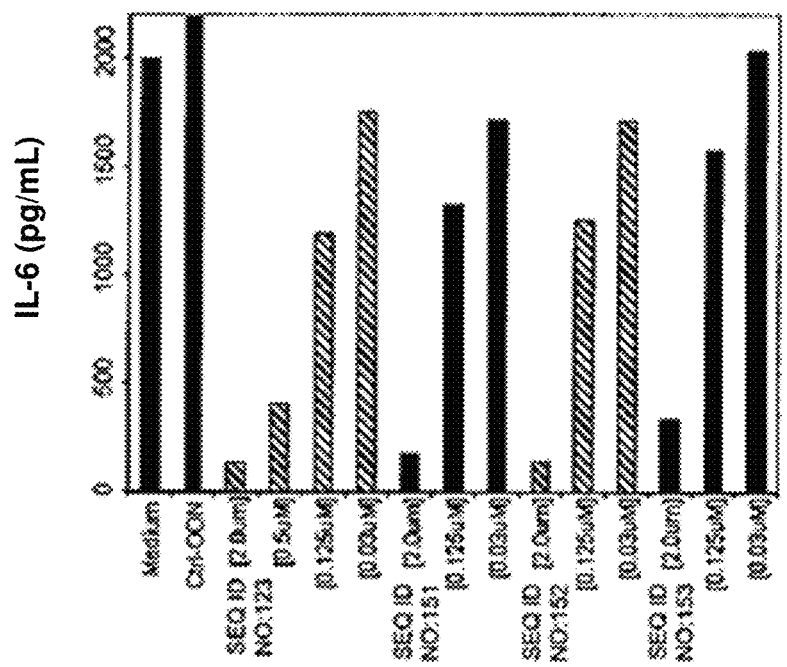
Figure 7A:
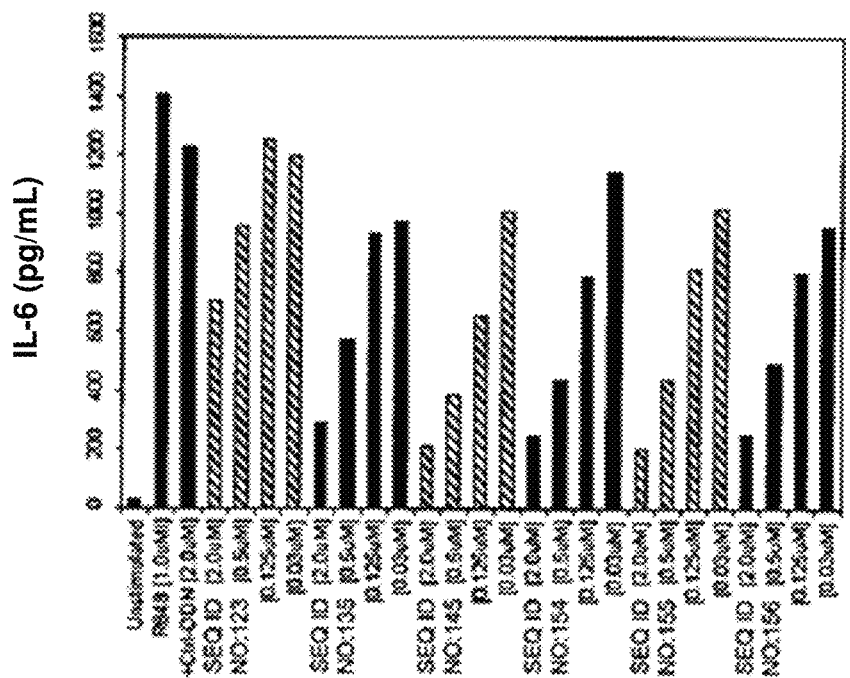
FIGS. 7A and B depict IL-6 levels (pg/ml) in mouse splenocytes following TLR7 ligand stimulation by R848 or TLR9 ligand stimulation by 1018 ISS (SEQ ID NO:122) either alone or in the presence of tested IRPs.
Figure 7B:
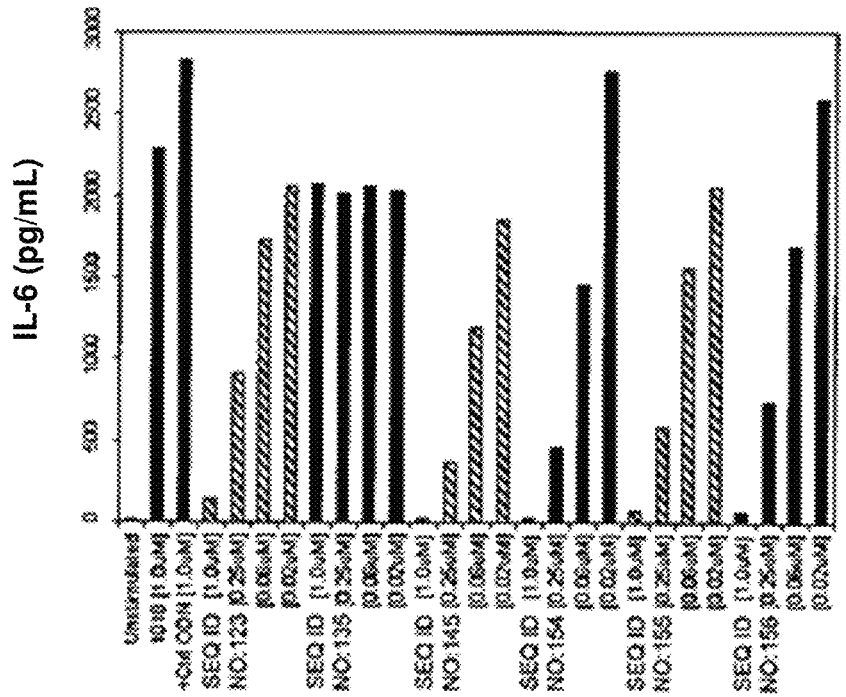
Figure 8A:
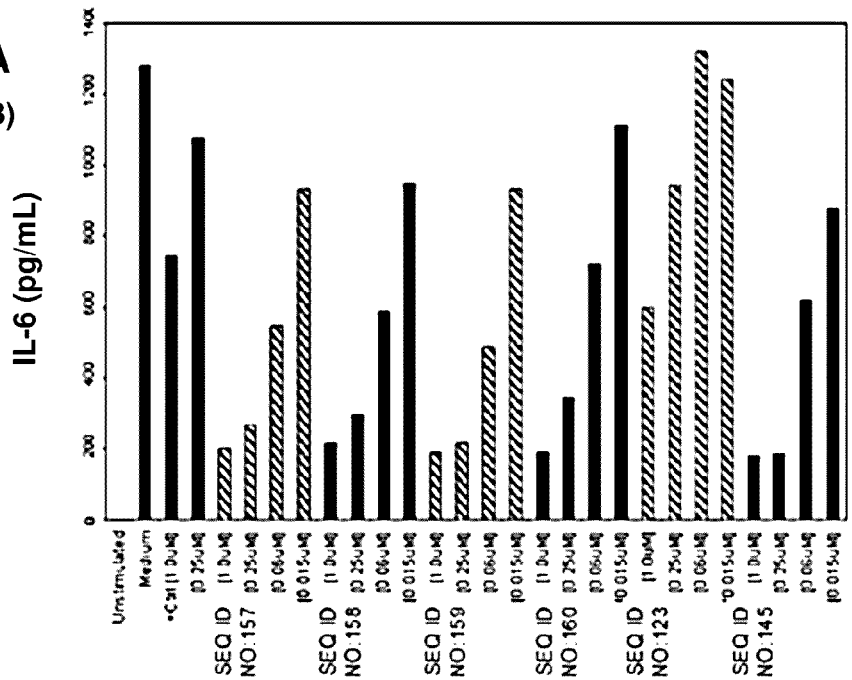
FIGS. 8A and B depict IL-6 levels (pg/ml) in mouse splenocytes following TLR7 ligand stimulation by R848 or TLR9 ligand stimulation by 1018 ISS (SEQ ID NO:122) either alone or in the presence of tested IRPs.
Figure 8B:
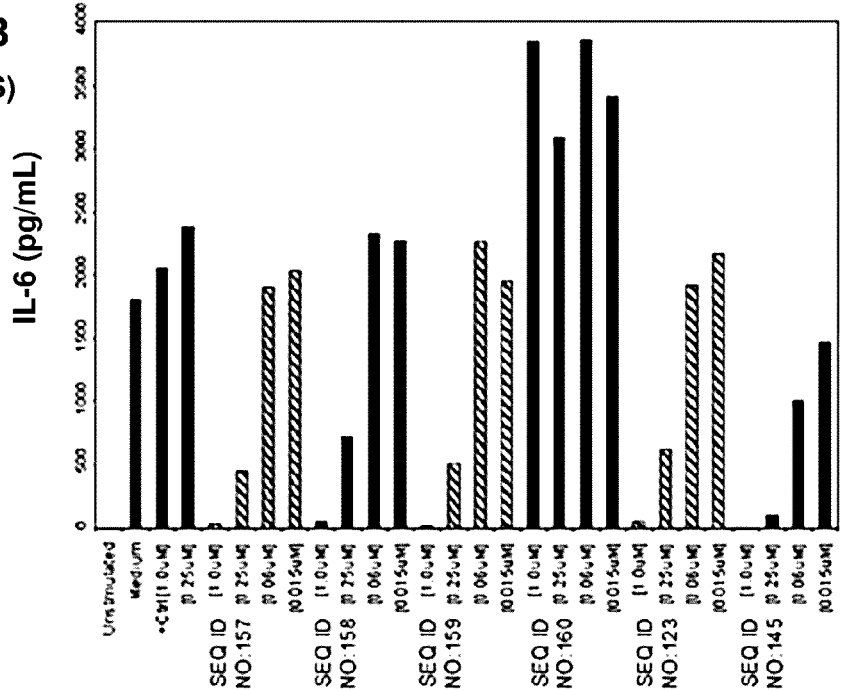
Figure 9:
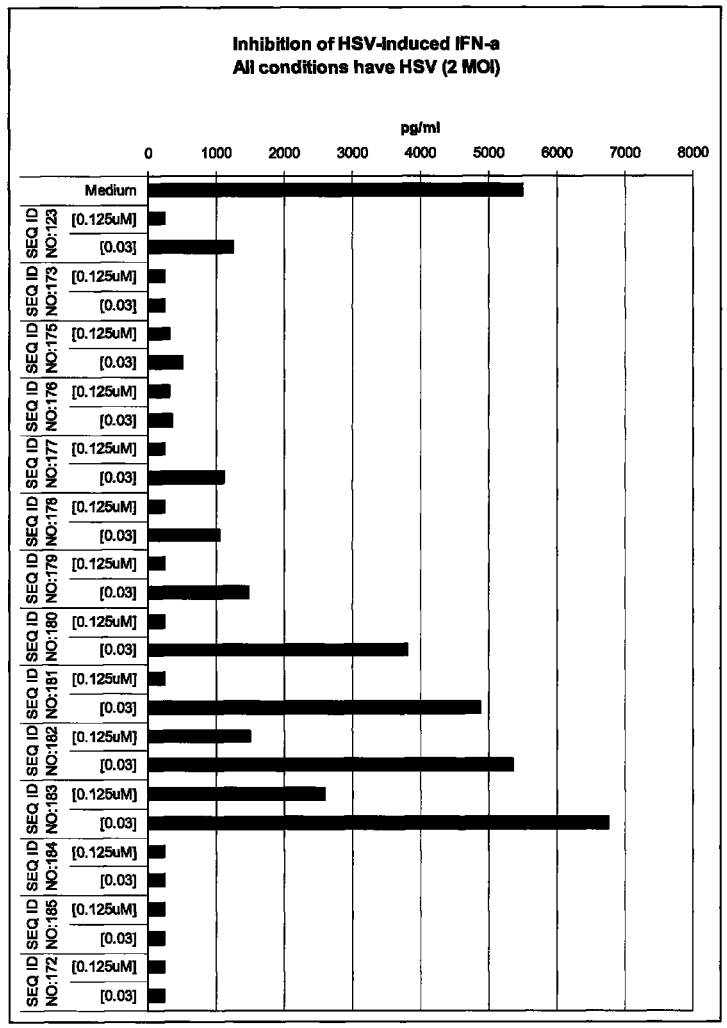
FIG. 9 depicts IFN-α levels (pg/ml) in human plasmacytoid dendritic cells following TLR9 ligand stimulation by HSV-1 either alone or in the presence of tested IRPs.
Figure 10:
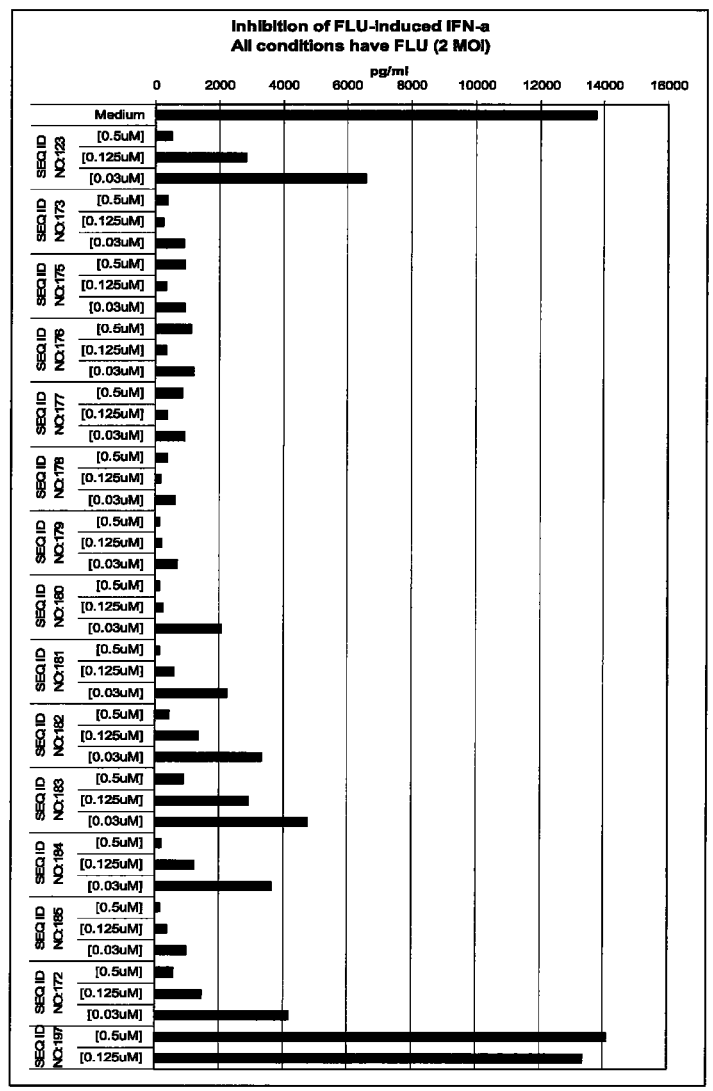
FIG. 10 depicts IFN-α levels (pg/ml) in human plasmacytoid dendritic cells following TLR7 ligand stimulation by influenza virus either alone or in the presence of tested IRPs.
Figure 11:
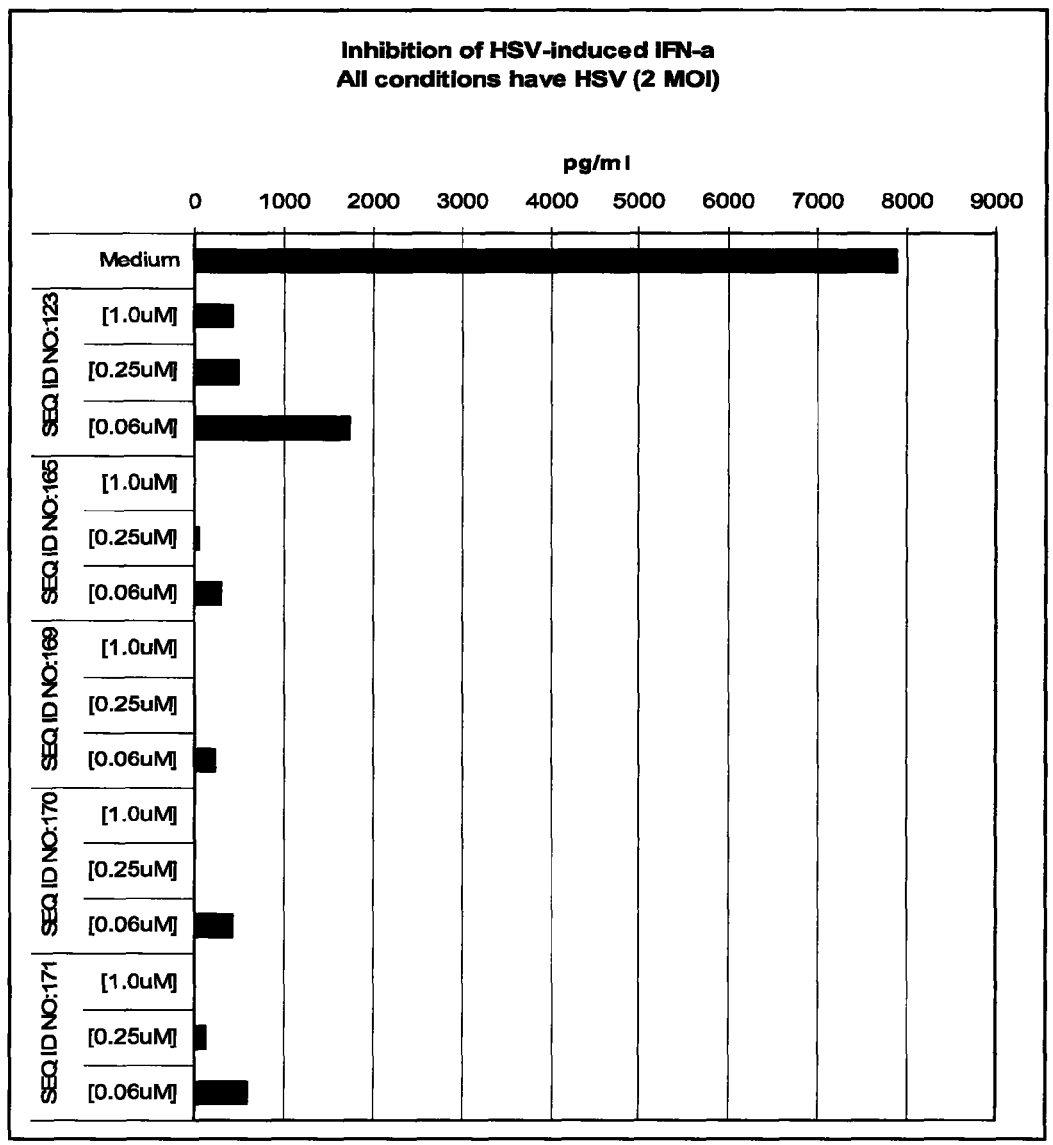
FIG. 11 depicts IFN-α levels (pg/ml) in human plasmacytoid dendritic cells following TLR9 ligand stimulation by HSV-1 either alone or in the presence of tested IRPs.
Figure 12:
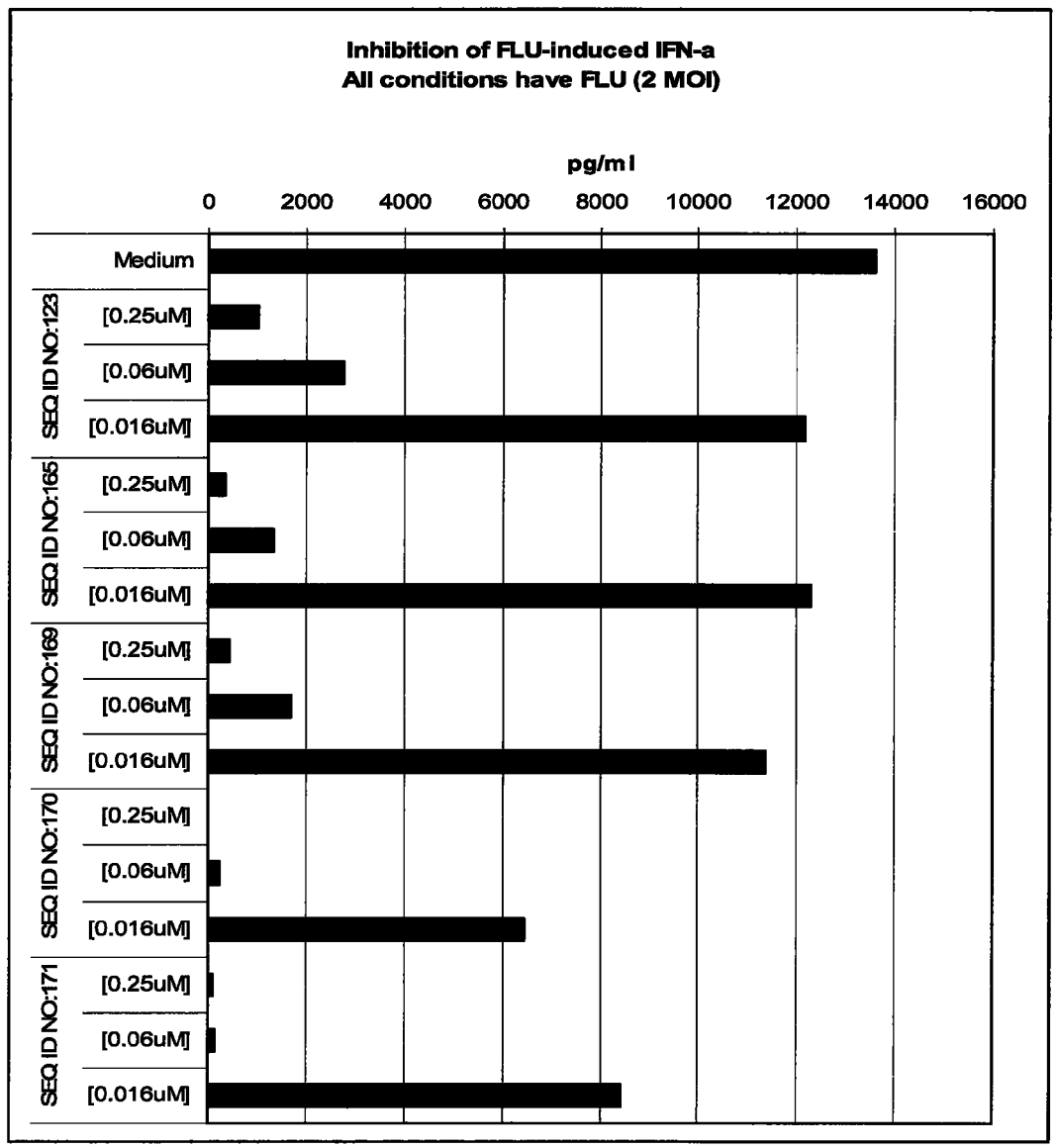
FIG. 12 depicts IFN-α levels (pg/ml) in human plasmacytoid dendritic cells following TLR7 ligand stimulation by influenza virus either alone or in the presence of tested IRPs.
Figure 13:
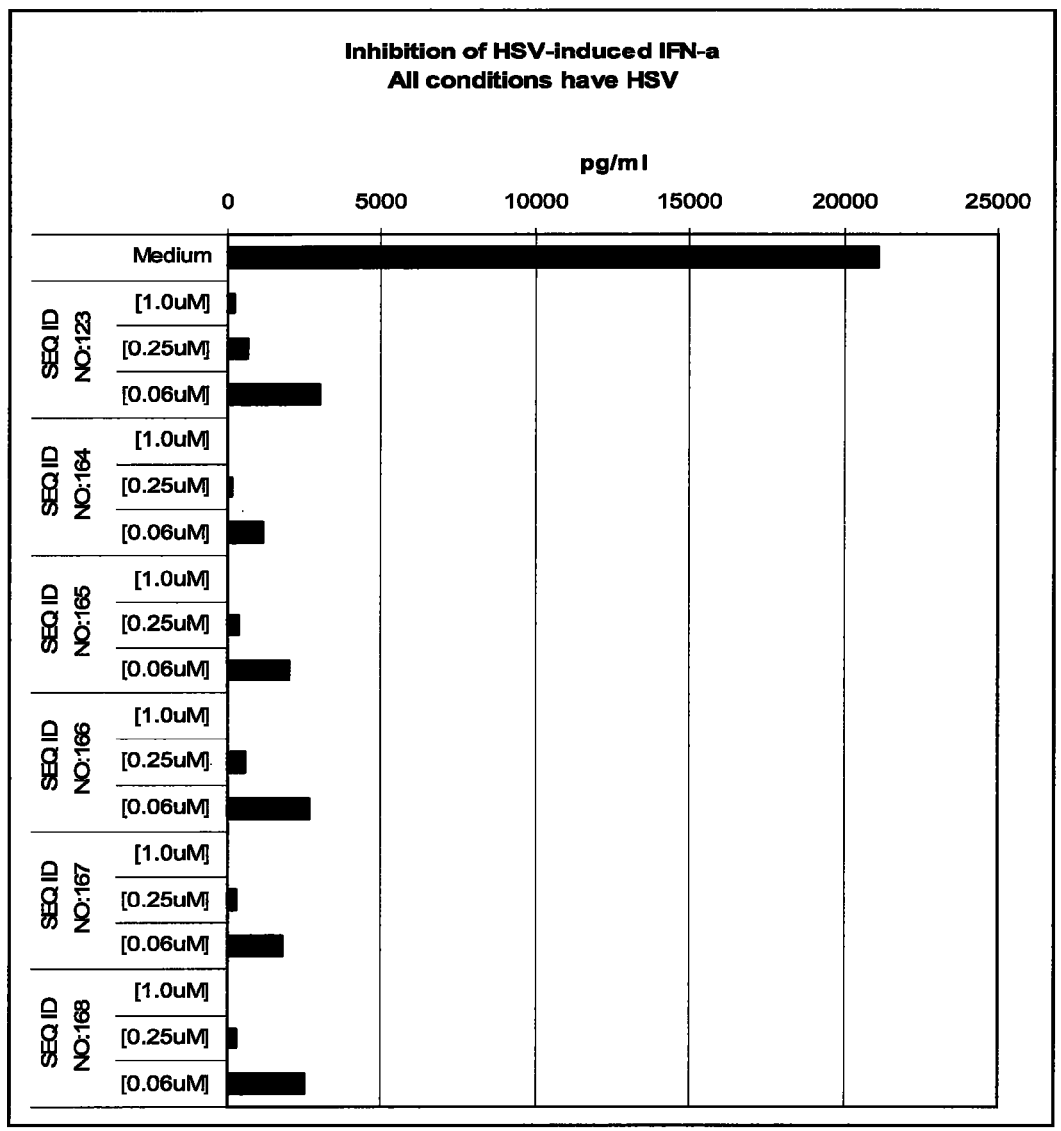
FIG. 13 depicts IFN-α levels (pg/ml) in human plasmacytoid dendritic cells following TLR9 ligand stimulation by HSV-1 either alone or in the presence of tested IRPs.
Figure 14:
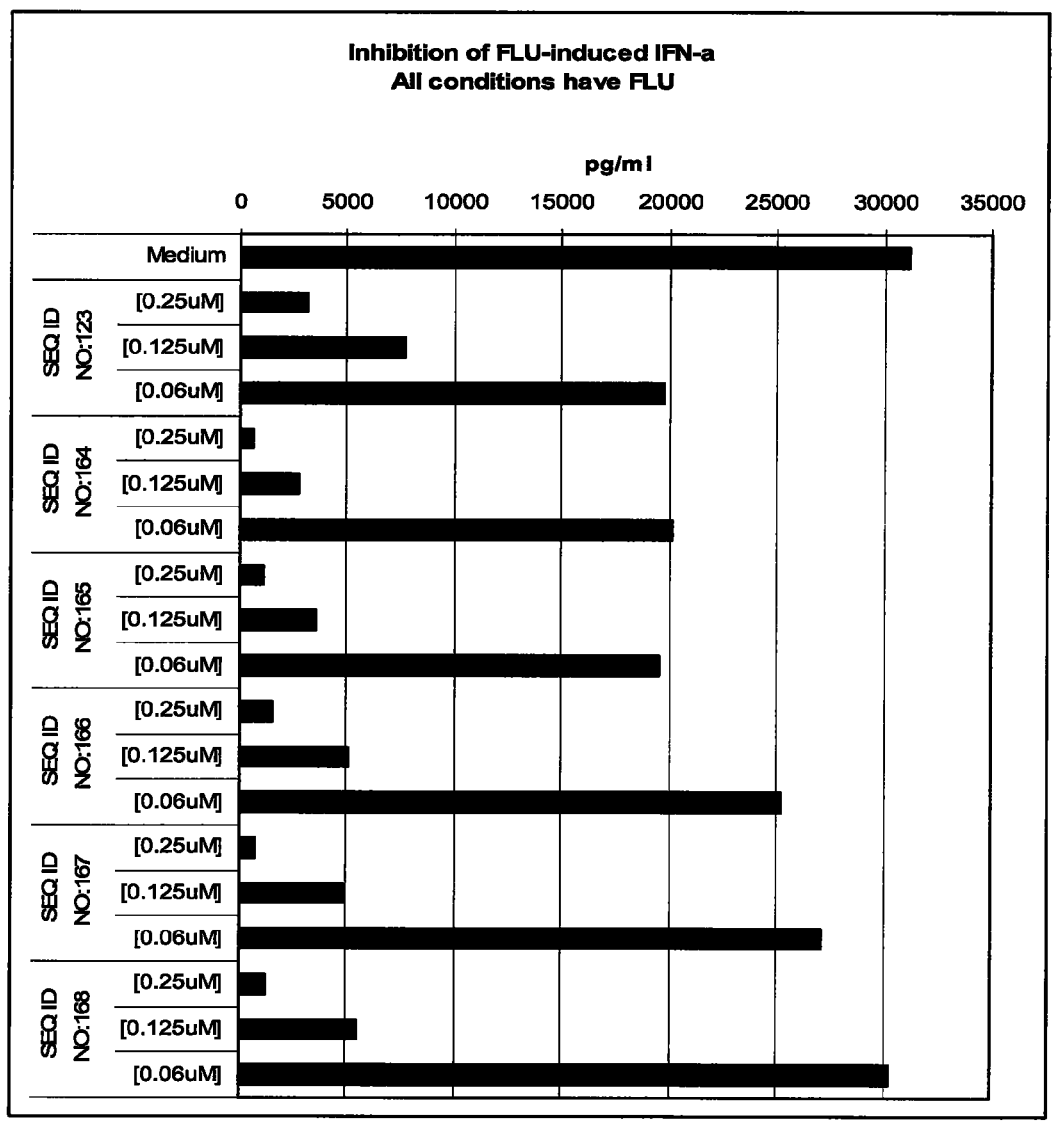
FIG. 14 depicts IFN-α levels (pg/ml) in human plasmacytoid dendritic cells following TLR7 ligand stimulation by influenza virus either alone or in the presence of tested IRPs.
Figure 15:
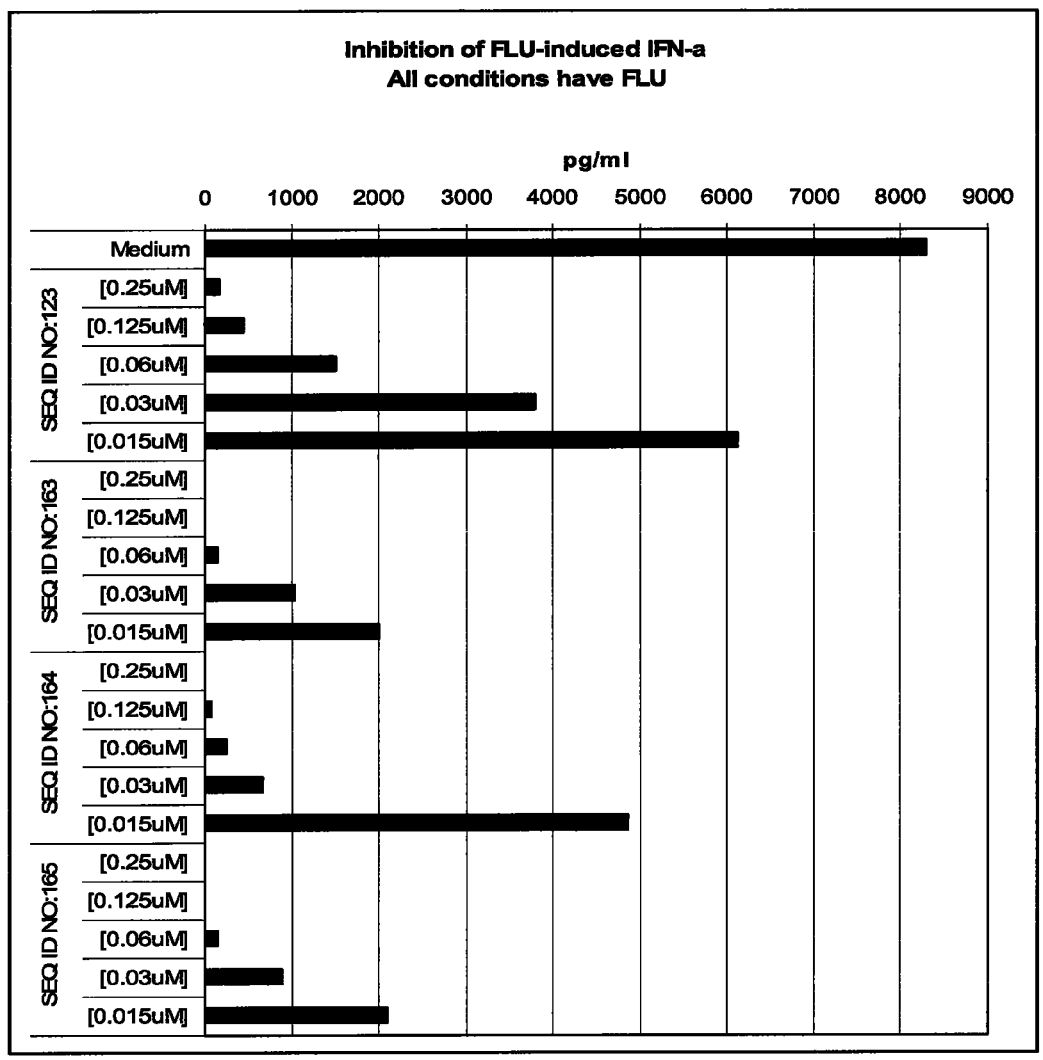
FIG. 15 depicts IFN-α levels (pg/ml) in human plasmacytoid dendritic cells following TLR7 ligand stimulation by influenza virus either alone or in the presence of tested IRPs.
Figure 16:
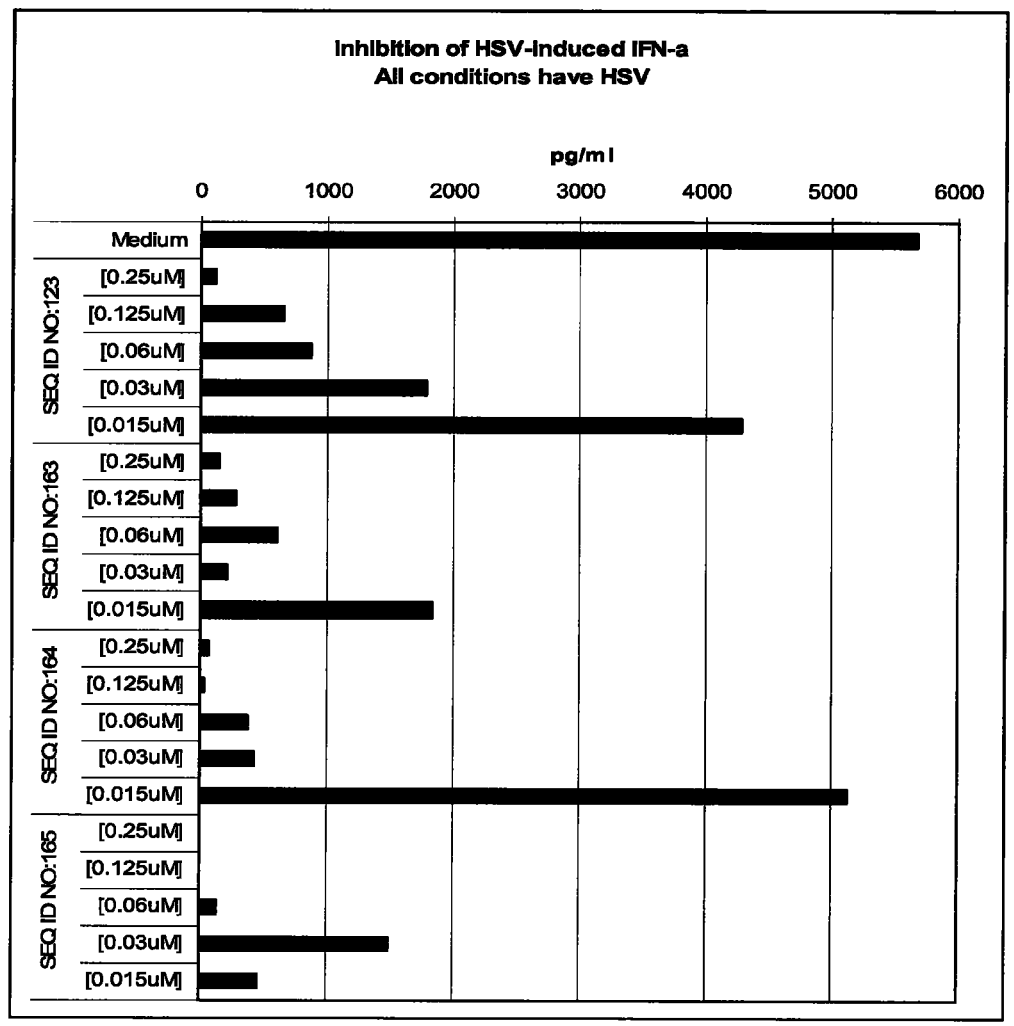
FIG. 16 depicts IFN-α levels (pg/ml) in human plasmacytoid dendritic cells following TLR9 ligand stimulation by HSV-1 either alone or in the presence of tested IRPs.

FIG. 1 shows the levels of IL-6 produced when stimulated with R848 (TLR7 ligand) either alone or in the presence of the tested IRPs. FIG. 2 shows the levels of IL-6 produced when stimulated with 1018 ISS (TLR9 ligand) either alone or in the presence of the tested modified and unmodified IRPs. Modification of the SEQ ID NO:123 sequence with 2' OMe (SEQ ID NO:135) resulted in a significant decrease in IL-6 levels compared to unmodified SEQ ID NO:123 when stimulated with R848 (TLR7). Modification of the SEQ ID NO:123 sequence with a locked nucleic acid (SEQ ID NO:161) failed to result in a significant decreased in IL-6 levels compared to unmodified SEQ ID NO:123 after either TLR7 or TLR9 stimulation. The results are summarized in Table 1.

TABLE 1

Summary of Results Related to Splenocytes activated with TLR7 and TLR9 ISS

|  | TLR7 | TLR9 |
| --- | --- | --- |
| SEQ ID NO: 123 | +++ | +++ |
| SEQ ID NO: 136 | +++ | − |
| SEQ ID NO: 137 | +++ | +++ |
| SEQ ID NO: 161 | − | − |
| SEQ ID NO: 135 | ++++ | − |

Example 2

Splenocytes Stimulated in the Presence of Modified IRPs

To further investigate the effect of 2' OMe modification of IRPs on TLR7 and TLR9 activation, various 2' OMe modified IRPs sequences or control samples were assayed for immunoregulatory (IR) activity of innate immune responses on mouse splenocyte cells.

The splenocyte assay was performed as described in Example 1. The modified and unmodified IRPs tested are found in Table 2. The bolded and italicized nucleotides represents nucleotides that have a 2'-O-Me sugar modifications.

TABLE 2

Sequence and SEQ ID NO:

TGC TCC TGG AGG GGT TGT (SEQ ID NO: 123)

*UGC UCC UGG AGG GGU UGU* (SEQ ID NO: 135)

*UGC* TCC TGG AGG GGT TGT (SEQ ID NO: 138)

TGC TCC TGG AGG GG*U UGU* (SEQ ID NO: 139)

*UGC* TCC TGG AGG GG*U UGU* (SEQ ID NO: 140)

TGC TCC TGG A*GG GG*T TGT (SEQ ID NO: 141)

*UGC* TTG TCC TGG AGG GGT TGT (SEQ ID NO: 142)

TGC TCC TGG AGG GGA AGT *UUG U* (SEQ ID NO: 143)

*UGC* TTG TCC TGG AGG GG*U UGU* (SEQ ID NO: 144)

*UGC* TTG TCC TGG AGG GGA AGT *UUG U* (SEQ ID NO: 145)

*UGC* TG TCC TGG AGG GGA AGT *UUG U* (SEQ ID NO: 146)

*UGC* G TCC TGG AGG GGA AGT *UUG U* (SEQ ID NO: 147)

*UGC* TTG TCC TGG AGG GG TG *UUG U* (SEQ ID NO: 148)

*UGC*TG TCC TGG AGG GG TG *UUG U* (SEQ ID NO: 149)

*UGC* G TCC TGG AGG GG TG *UUG U* (SEQ ID NO: 150)

*UGC* TTG TCC TGG AGG GGT *UGU* (SEQ ID NO: 151)

*UGC* TG TCC TGG AGG GGT *UGU* (SEQ ID NO: 152)

*UGC* G TCC TGG AGG GGT *UGU* (SEQ ID NO: 153)

*UGC* TTG TCC TGG AGG GGT TGT *UUG U* (SEQ ID NO: 154)

*UGC* TTG TCC TGG AGG GGT TGU *UUG U* (SEQ ID NO: 155)

*UGC* TGC TCC TGG AGG GGT TGT *UUG U* (SEQ ID NO: 156)

*UGC* TGC TCC TTG AGG GGT TGT *UUG U* (SEQ ID NO: 157)

*UGC* TGC TCC TTG AGG GGT G*UU GU* (SEQ ID NO: 158)

*UGC* TGC TCC TTG AGG GGT T*GU UUG U* (SEQ ID NO: 159)

*UGC UGC UCC UUG AGA GGU UGU* (SEQ ID NO: 160)

FIGS. 3-8 show the levels of IL-6 produced when stimulated with R848 (TLR7 ligand) or stimulated with 1018 ISS (TLR9 ligand; SEQ ID NO:122) either alone or in the presence of the tested IRPs.

Example 3

Human Plasmacytoid Dendritic Cells (PDCs) Stimulated in the Presence of Modified IRPs To further investigate the effect of 2' OMe modification of IRPs on TLR7 and TLR9 activation, various 2' OMe modified IRPs sequences or control samples were assayed for immunoregulatory (IR) activity of innate immune responses on human plasmacytoid dendritic cells (PDCs).

Human PDCs infected with herpes simplex virus type 1 (HSV-1 KOS strain) respond by producing IFN-α and this response is dependent on TLR-9 signaling. Human PDCs infected with influenza virus (H1N1, A/PR/8/34 from a patient in Puerto Rico 1934. See ATCC catalog VR-95) also respond by producing IFN-α, however, this response is dependent on TLR-7 signaling and independent of TLR-9. The effect of IRPs on innate immune response cytokine production by infected cells was examined. In a dose-dependent manner, the cells were thus stimulated with HSV-1 (2 MOI) or Influenza (2 MOI), either alone or in the presence of the tested IRPs. At 24 hours, supernatants were collected and cytokine levels, IFN-alpha, were measured using immunoassay.

The modified and unmodified IRPs tested are found in Table 3. The bolded and italicized nucleotides represents nucleotides that have a 2'-O-Me sugar modifications, Z' corresponds to 7-deaza-dG and I corresponds to deoxy-inosine. Results are shown in FIGS. 9-16. In addition, SEQ ID NO:174 resulted in similar TLR7 and TLR9 inhibition as SEQ ID NO:173 and SEQ ID NO:186 resulted in similar TLR7 and TLR9 inhibition as SEQ ID NO:178.

TABLE 3

Modified and Unmodified IRPs

| Sequence and SEQ ID NO: | Modification |
|---|---|
| 5'-*UGC* TGC TCC TGG AGG GGT T***GU UUG U*** (SEQ ID NO: 163) | 2'OMe on 5'-UGC and GU UUG U-3' |
| 5'-TGC TGC TCC TGG AGG GGT TGT TTG T (SEQ ID NO: 164) | |
| 5'-TGC TGC TCC TTG AGG GGT TGT TTG T (SEQ ID NO: 165) | |
| 5'-TGC TGC TCC TTG AGG GGT TGT (SEQ ID NO: 166) | |
| 5'-TGC TGC TCC TGG AGG GGT TGT (SEQ ID NO: 167) | |
| 5'-TGC TGC TCC TTG AGZ' GGT TGT TTG T (SEQ ID NO: 168) | Z' = 7-deaza-dG |
| 5'-TGC TGC TCC TTG AGI GGT TGT TTG T (SEQ ID NO: 169) | I = deoxy-inosine |
| 5'-*UGC* TGC TCC TTG AGG GGT TGT TTG T (SEQ ID NO: 170) | 2'OMe on 5'-UGC |
| 5'-*UGC* TGC TCC TGG AGG GGT TGT TTG T (SEQ ID NO: 171) | 2'OMe on 5'-UGC |
| 5'-*UGC* TGC TCC TTG AGI GGT TGT TTG T (SEQ ID NO: 173) | 2'OMe on 5'-UGC, I = deoxy-inosine |
| 5'-*UGC* TGC TCC TTG AGZ' GGT TGT TTG T (SEQ ID NO: 174) | 2'OMe on 5'-UGC, Z' = 7-deaza-dG |
| 5'-*UGC* TGC TCC TTG AGI GGT TGT TTG (SEQ ID NO: 175) | 2'OMe on 5'-UGC; I = deoxy-inosine |
| 5'-*UGC* TGC TCC TTG AGI GGT TGT TT (SEQ ID NO: 176) | 2'OMe on 5'-UGC; I = deoxy-inosine |
| 5'-*UGC* TGC TCC TTG AGI GGT TGT T (SEQ ID NO: 177) | 2'OMe on 5'-UGC; I = deoxy-inosine |
| 5'-*UGC* TGC TCC TTG AGI GGT TGT (SEQ ID NO: 178) | 2'OMe on 5'-UGC; I = deoxy-inosine |
| 5'-*UGC* TGC TCC TTG AGI GGT T (SEQ ID NO: 179) | 2'OMe on 5'-UGC; I = deoxy-inosine |
| 5'-*UGC* TGC TCC TTG AGI GGT (SEQ ID NO: 180) | 2'OMe on 5'-UGC; I = deoxy-inosine |
| 5'-*UGC* TGC TCC TTG AGI GG (SEQ ID NO: 181) | 2'OMe on 5'-UGC; I = deoxy-inosine |
| 5'-*UGC* TGC TCC TTG AGI G (SEQ ID NO: 182) | 2'OMe on 5'-UGC; I = deoxy-inosine |
| 5'-*UGC* TGC TCC TTG AGI (SEQ ID NO: 183) | 2'OMe on 5'-UGC; I = deoxy-inosine |

TABLE 3-continued

Modified and Unmodified IRPs

| Sequence and SEQ ID NO: | Modification |
| --- | --- |
| 5'-*GC* TGC TCC TTG AGI GGT TGT TTG T (SEQ ID NO: 184) | 2'OMe on 5'-GC; I = deoxy-inosine |
| 5'-*C* TGC TCC TTG AGI GGT TGT TTG T (SEQ ID NO: 185) | 2'OMe on 5'-C; I = deoxy-inosine |
| 5'-TGC TCC TTG AGI GGT TGT TTG T (SEQ ID NO: 172) | I = deoxy-inosine |
| 5'-*UGC* TGC TCC TTG AGI GGT TG (SEQ ID NO: 186) | 2'OMe on 5'-UGC; I = deoxy-inosine |

Example 4

Human B-cells Stimulated in the Presence of Modified IRPs

To further investigate the effect of 2'-O-Me modification of IRPs on TLR7 and TLR9 activation, various 2'-O-Me modified IRPs sequences or control samples were assayed for immunoregulatory (IR) activity of innate immune responses on human B-cells For the Human B-cell assay, B-cells were purified from total blood cells obtained from healthy donors using magnetic beads (CD19 positive). Cells were resuspended in fresh medium (RPMI 1640 with 10% fetal calf serum, 50 units/mL penicillin, 50 µg/mL streptomycin, and 2 mM glutamine). In a dose-dependent manner, the cells were then stimulated with 0.7-1 µM of 1018 ISS (TLR9 ligand; 5'-TGACTGTGAACGTTCGAGA TGA-3' (SEQ ID NO:122)) or 1 µM of R848 (TLR7 ligand; a small molecule, an imidazoquinoline also called resiquimod), either alone or in the presence of the tested IRPs. At 48 hours, supernatants were collected and cytokine levels, IL-6, were measured using immunoassay. A description for the modified and unmodified IRPs tested is found in Table 2.

Figure 17:
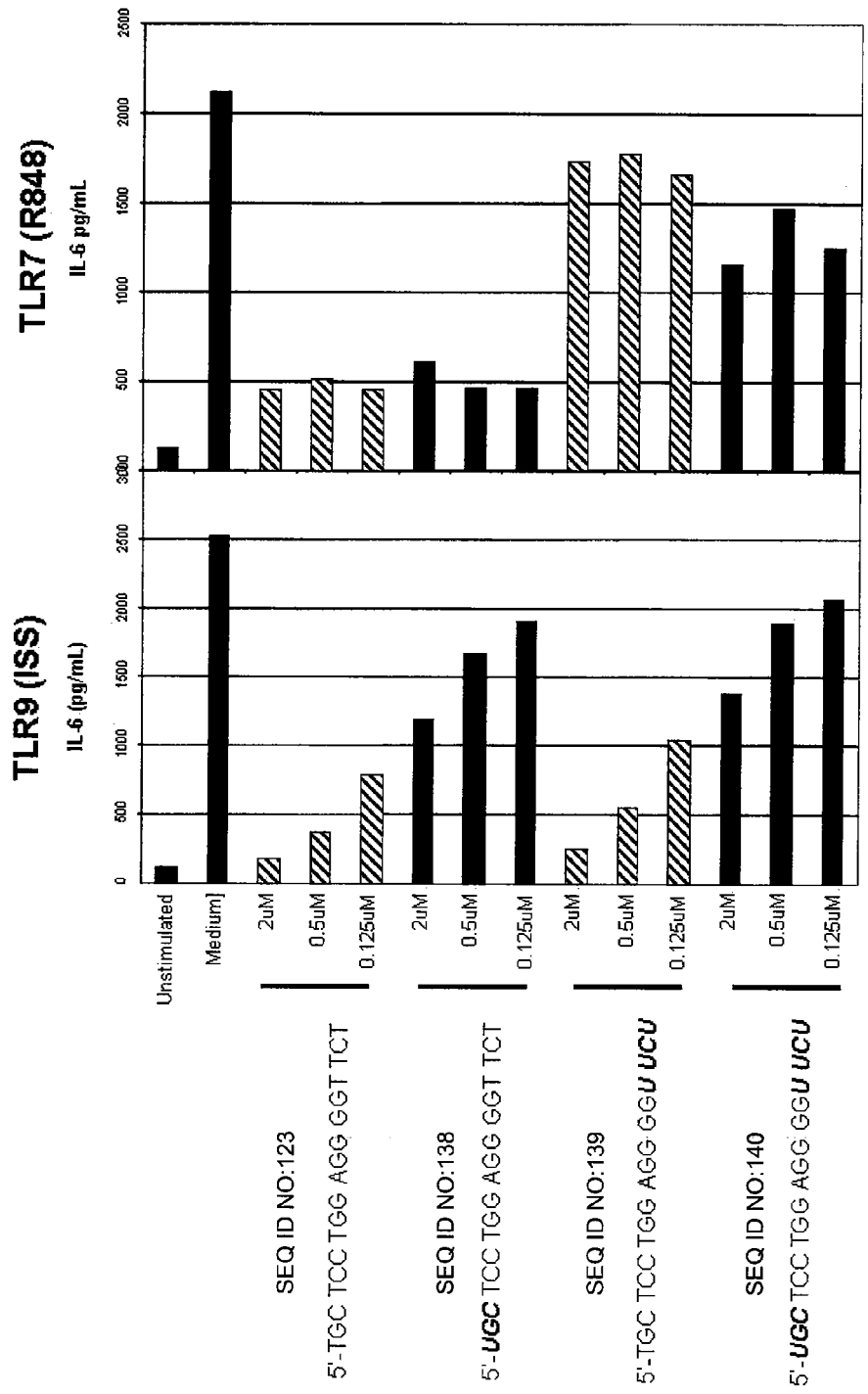
FIG. 17 depicts IL-6 levels (pg/ml) in human B-cells following TLR7 ligand stimulation by R848 or TLR9 ligand stimulation by 1018 ISS (SEQ ID NO:122) either alone or in the presence of tested IRPs.
Figure 18A:
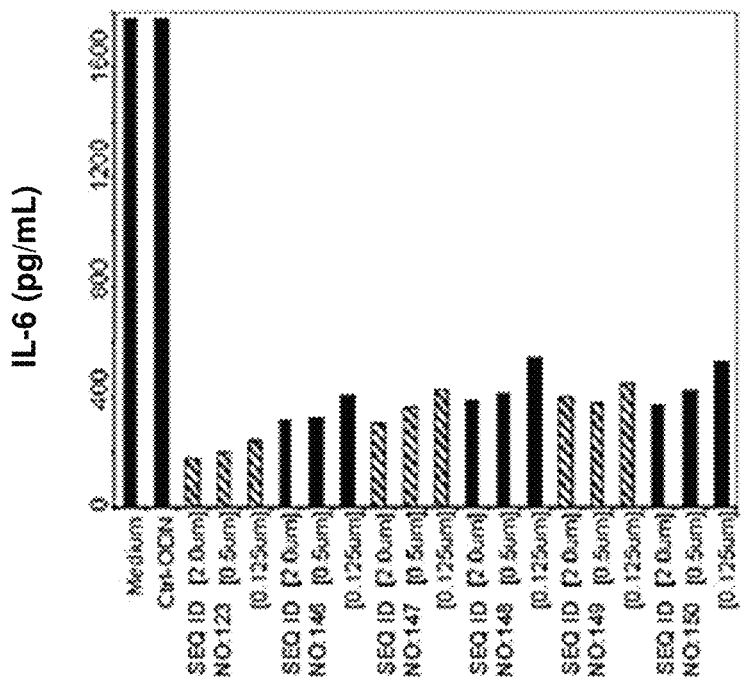
FIGS. 18A and B depict IL-6 levels (pg/ml) in human B-cells following TLR7 ligand stimulation by R848 or TLR9 ligand stimulation by 1018 ISS (SEQ ID NO:122) either alone or in the presence of tested IRPs.
Figure 18B:
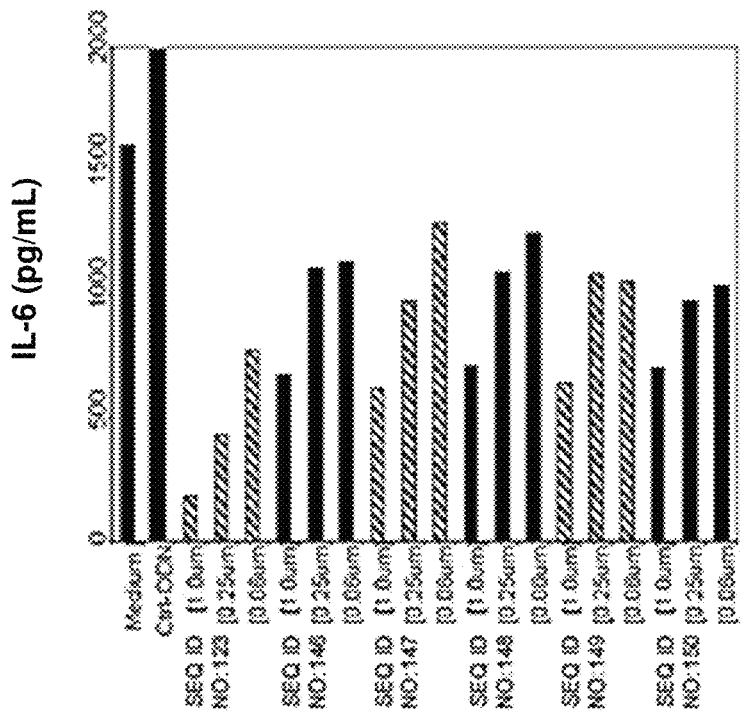
Figure 19A:
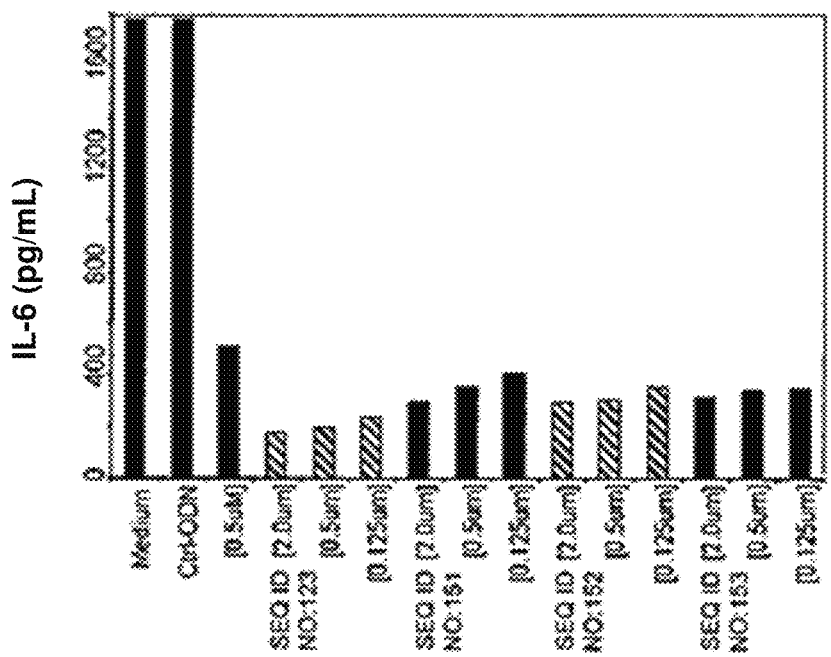
FIGS. 19A and B depict IL-6 levels (pg/ml) in human B-cells following TLR7 ligand stimulation by R848 or TLR9 ligand stimulation by 1018 ISS (SEQ ID NO:122) either alone or in the presence of tested IRPs.
Figure 19B:
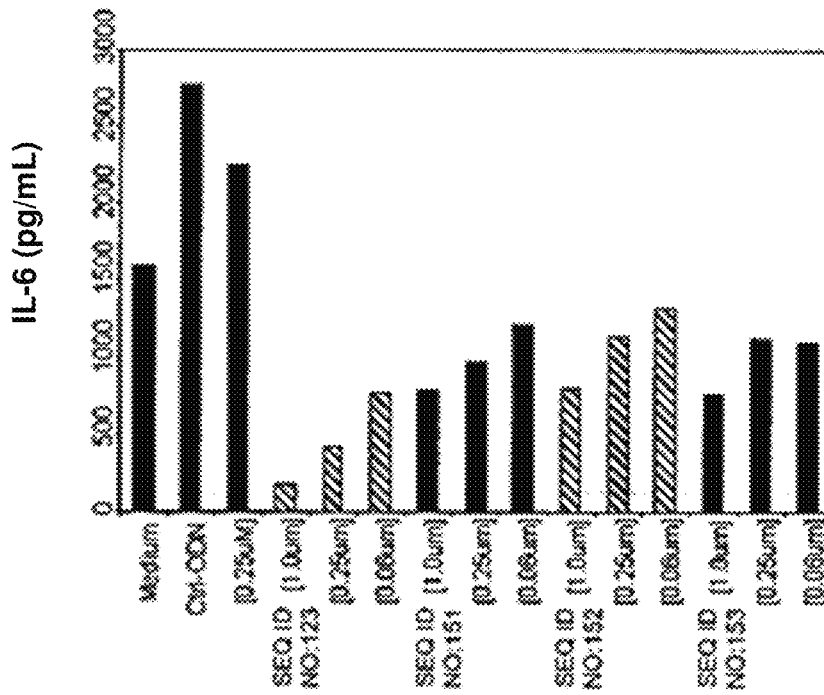

FIGS. 17-19 show the levels of IL-6 produced when stimulated with R848 (TLR7 ligand) or stimulated with 1018 ISS (TLR9 ligand; SEQ ID NO:122) either alone or in the presence of the tested IRPs.

Example 5

Human Plasmacytoid Dendritic Cells (PDCs) Stimulated in the Presence of Modified IRPs To further investigate the effect of 2'-O-Me modification of IRPs on TLR7 and TLR9 activation, various 2'-O-Me modified IRPs sequences or control samples were assayed for immunoregulatory (IR) activity of innate immune responses on human plasmacytoid dendritic cells (PDCs).

Human PDCs infected with herpes simplex virus type 1 (HSV-1 KOS strain) respond by producing IFN-α and this response is dependent on TLR-9 signaling. Human PDCs infected with influenza virus (H1N1, A/PR/8/34 from a patient in Puerto Rico 1934. See ATCC catalog VR-95) also respond by producing IFN-α, however, this response is dependent on TLR-7 signaling and independent of TLR-9. The effect of IRPs on innate immune response cytokine production by infected cells was examined. In a dose-dependent manner, the cells were thus stimulated with HSV-1 (5 MOI) or Influenza (2 MOI), either alone or in the presence of the tested IRPs. At 24 hours, supernatants were collected and cytokine levels, IFN-alpha, were measured using immunoassay.

Human PDCs from 7 donors were purified and were infected with influenza virus (strain PR/8) or HSV-1. HSV was used at 5 multiplicity of infection (MOI) while the influenza virus was used at 2 MOI. The amount of IFN-α produced by the cells was measured and compared to the amount of virus used for infection. A description for the modified and unmodified IRPs tested is found in Table 2.

Figure 22A:
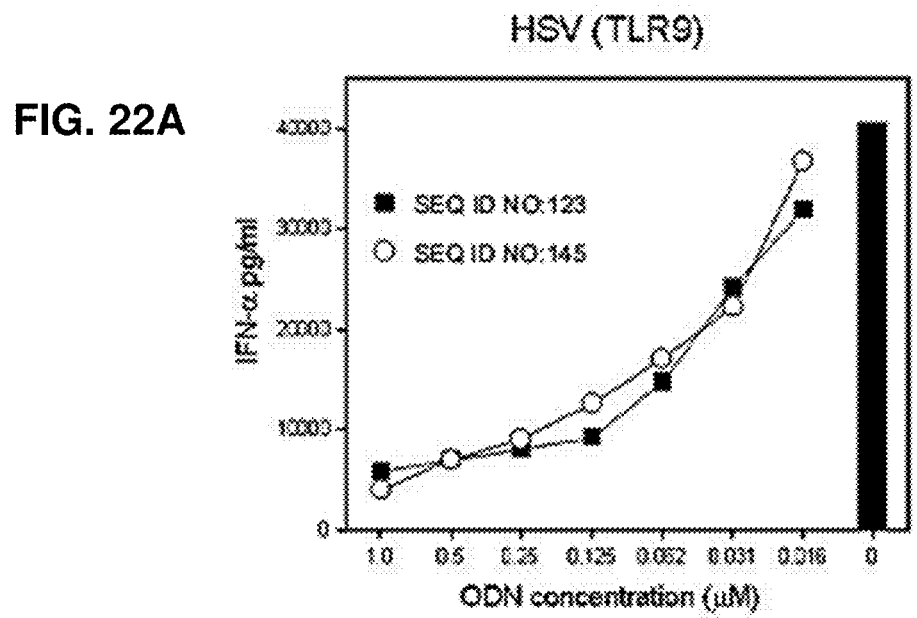
FIGS. 22A and B depict IFN-α levels (pg/ml) in human plasmacytoid dendritic cells following TLR7 ligand stimulation by influenza virus or TLR9 ligand stimulation by HSV-1 either alone or in the presence of tested IRPs.
Figure 22B:
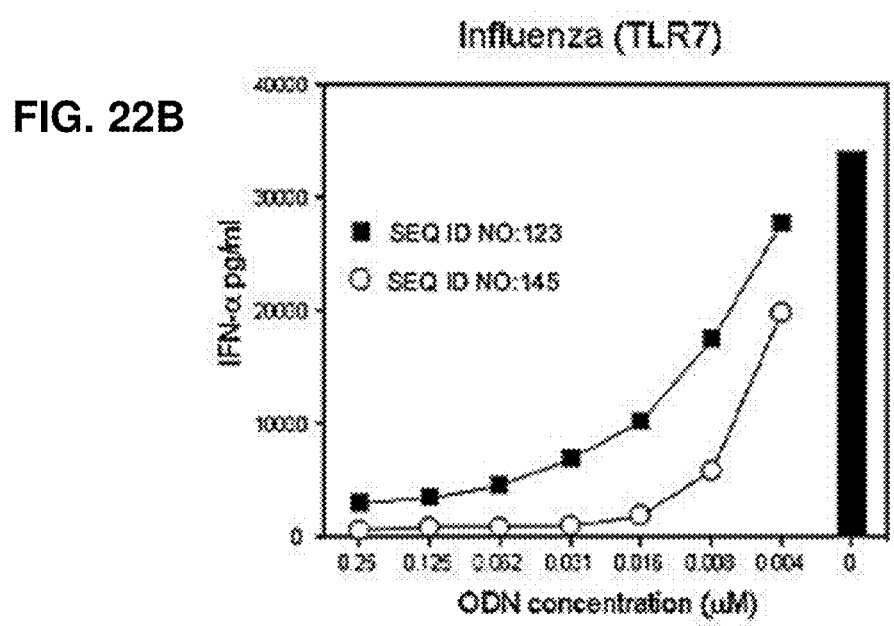

FIGS. 20-22 show the levels of IFN-α produced when stimulated with influenza virus (TLR7 ligand) or stimulated with HSV (TLR9 ligand) either alone or in the presence of the tested IRPs.

Example 6

In Vivo Activity of Modified IRPs when Stimulated by an ISS

To further investigate the effect of 2' OMe modification of IRPs on TLR7 and TLR9 activation, a 2' OMe modified IRP sequence or unmodified IRP sequence was assayed for immunoregulatory (IR) activity of innate immune responses in vivo.

Figure 23:
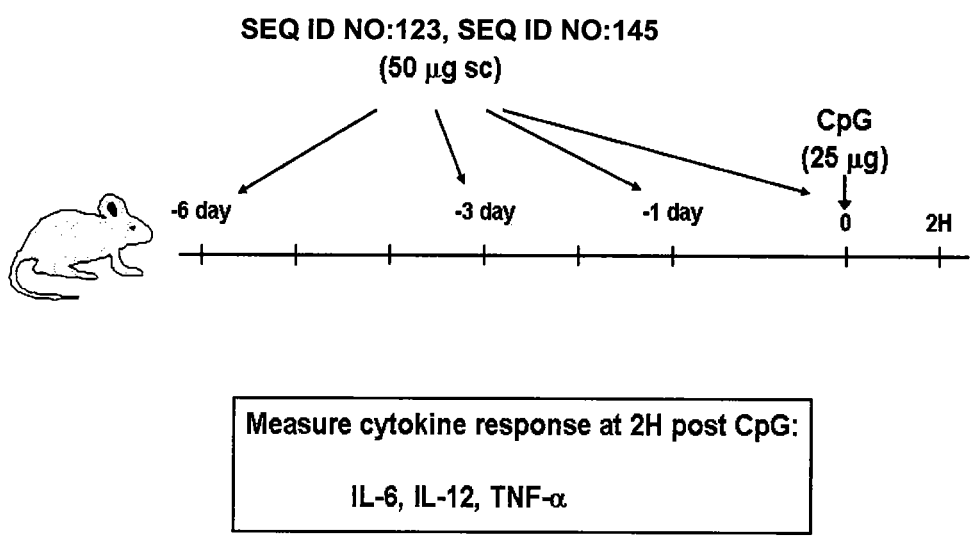
FIG. 23 depicts a schematic of the experimental design for evaluating the ability of immunoregulatory sequences to inhibit TLR9 ligand in vivo.

6 to 12 week-old BALB/c mice were used for all in vivo experiments. Mice were injected subcutaneously (s.c.) with 25 µg of 1018 ISS (5'-TGACTGTGAACGTTCG AGATGA-3' (SEQ ID NO:122)) and 50 µg of either SEQ ID NO:123 (5'-TGCTCCTGGAGGGGTT GT-3') or SEQ ID NO:145 (5'-*UGC* TTG TCC TGG AGG GGA AGT *UUG U* -3', wherein the bolded and italicized nucleotides are modified by a 2'-O-Me sugar modification), simultaneously or at different times prior to ISS stimulation (e.g., 6 days, 3 days, or 1 day prior to the administration of an ISS sequence containing a CpG). All injections used oligodeoxynucleotides in saline. Two hours following injections, blood was harvested and serum prepared using standard procedures. FIG. 23 provides a schematic of the protocol design.

Figure 24A:
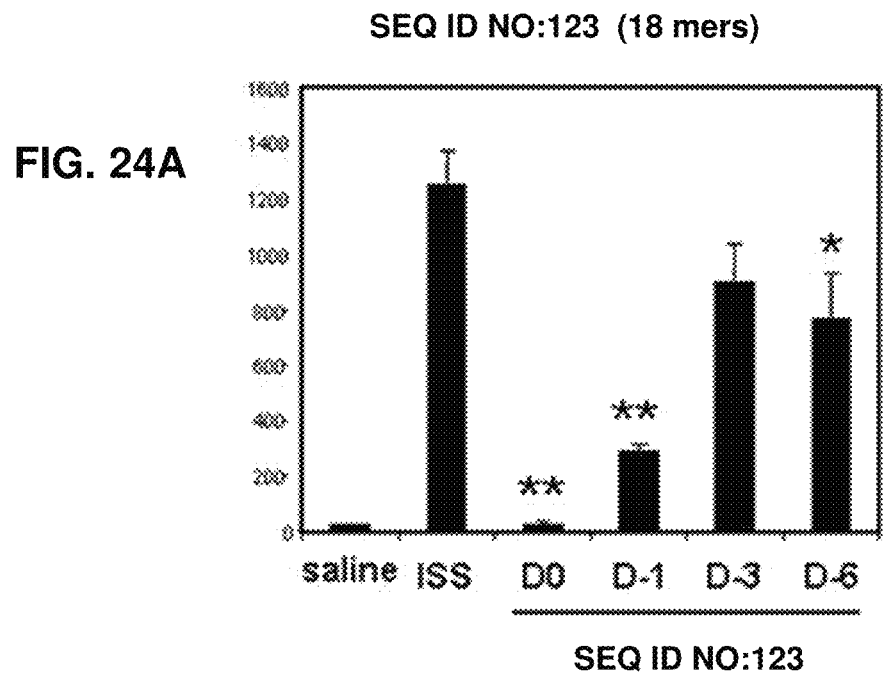
FIGS. 24A and B depict IL-6 (pg/ml) in the serum of mice two hours after activation with the TLR9 ligand ISS 1018 (SEQ ID NO:122), an immunostimulatory sequence.
Figure 24B:
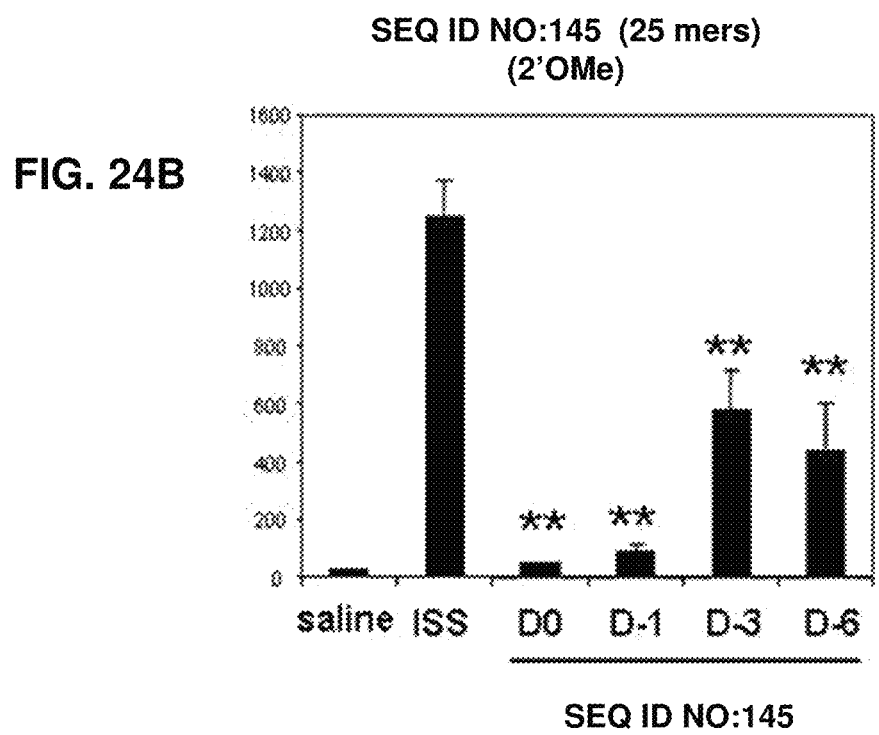
Figure 25:
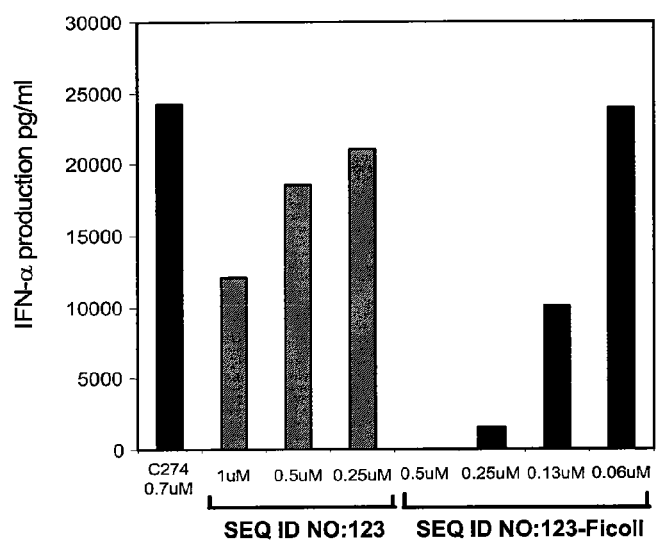
FIG. 25 depicts IFN-α levels (pg/ml) in human plasmacytoid dendritic cells following TLR9 stimulation by an immunostimulatory sequence CpG-C ISS (5'-TCG TCG AAC GTT CGA GAT GAT-3' (SEQ ID NO:99)), either alone or in the presence IRS (5'-TGCTCCTGGAGGGGTTGT-3' (SEQ ID NO:123)) or IRS-Ficoll 400 (5'-TGCTCCTGGAGGGGTTGT-3' (SEQ ID NO:123) coupled to Ficoll 400 (SEQ ID NO:124)).
Figure 26:
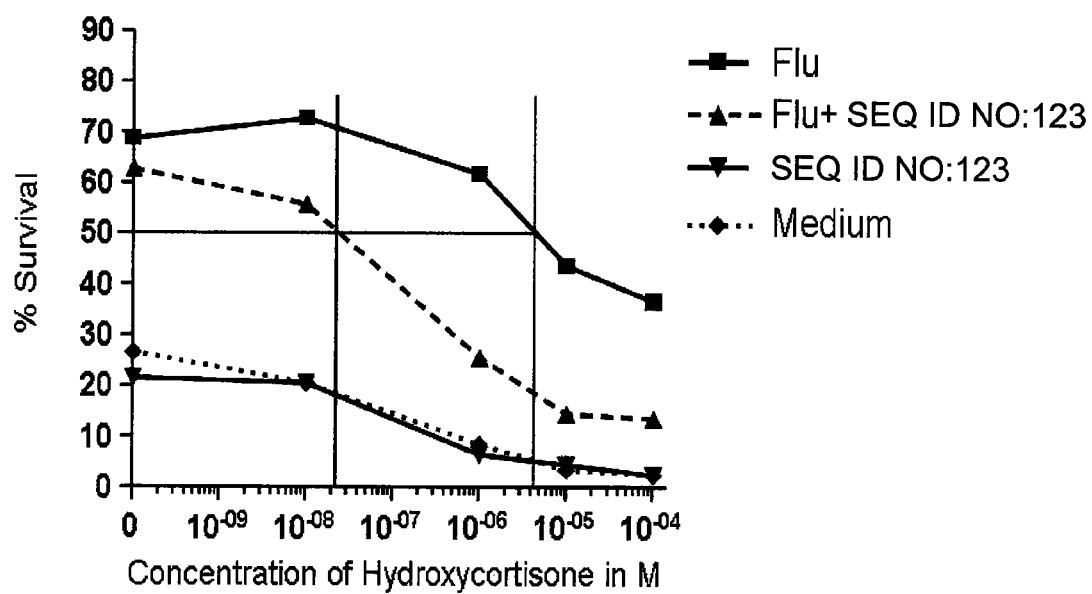
FIG. 26 depicts the percentage survival of human plasmacytoid dendritic cells at varying concentration of hydroxycortisone in the presence of media alone, IRS (5'-TGCTCCTGGAGGGGTTGT-3' (SEQ ID NO:123)), influenza virus ("Flu"), or the combination of influenza virus ("Flu") and IRS (5'-TGCTCCTGGAGGGGTTGT-3' (SEQ ID NO:123)).
Figure 27:
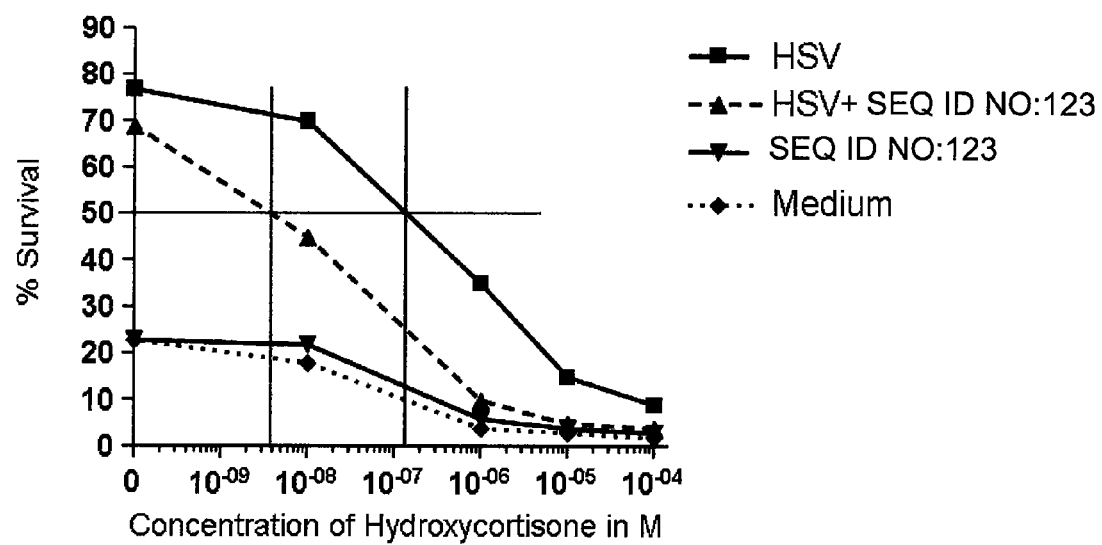
FIG. 27 depicts the percentage survival of human plasmacytoid dendritic cells at varying concentration of hydroxycortisone in the presence of media alone, IRS (5'-TGCTCCTGGAGGGGTTGT-3' (SEQ ID NO:123)), HSV-1 ("HSV"), or the combination of HSV-1 ("HSV") and IRS (5'-TGCTCCTGGAGGGGTTGT-3' (SEQ ID NO:123)).
Figure 28:
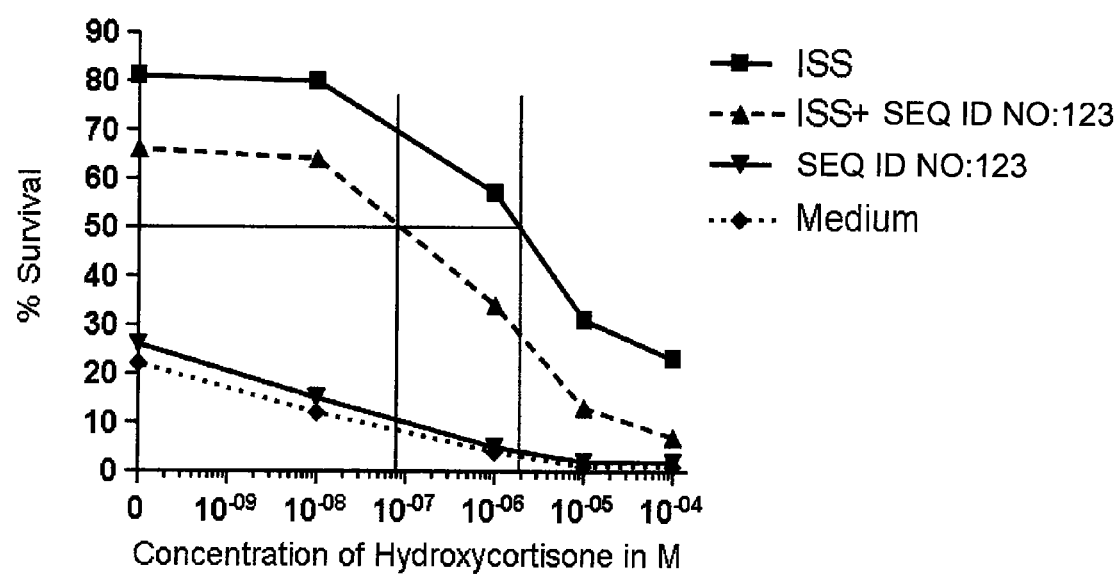
FIG. 28 depicts the percentage survival of human plasmacytoid dendritic cells at varying concentration of hydroxycortisone in the presence of media alone, IRS (5'-TGCTCCTGGAGGGGTTGT-3' (SEQ ID NO:123)), an immunostimulatory sequence CpG-C ISS C274 ("ISS"; 5'-TCG TCG AAC GTT CGA GAT GAT-3' (SEQ ID NO:99)), or the combination of ISS 1018 ("ISS"; (SEQ ID NO:122)) and IRS (5'-TGCTCCTGGAGGGGTTGT-3' (SEQ ID NO:123)).
Figure 29A:
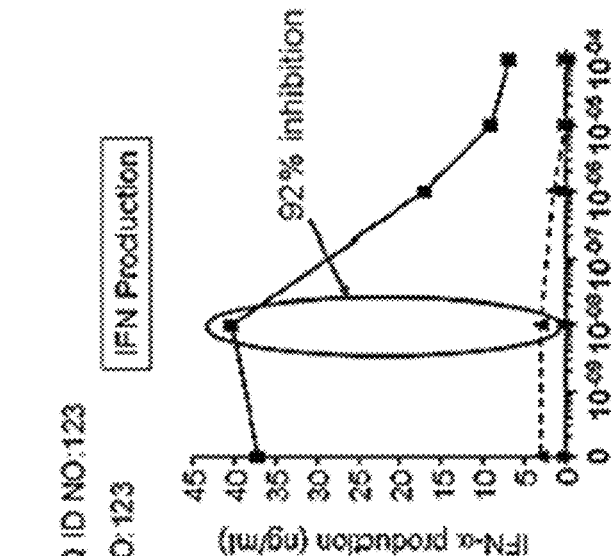
FIG. 29A depicts the percentage survival of human plasmacytoid dendritic cells at varying concentration of hydroxycortisone in the presence of media alone, IRS (5'-TGCTCCTGGAGGGGTTGT-3' (SEQ ID NO:123)), influenza virus ("Flu"), or the combination of influenza virus ("Flu") and IRS (5'-TGCTCCTGGAGGGGTTGT-3' (SEQ ID NO:123)).
Figure 29B:
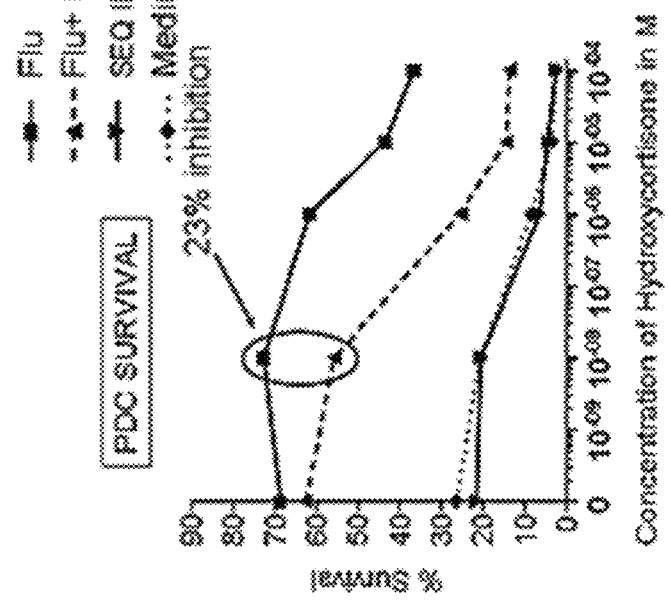
FIG. 29B depicts the levels of IFN-α (ng/ml) in human plasmacytoid dendritic cells at varying concentration of hydroxycortisone in the presence of media alone, IRS (5'-TGCTCCTGGAGGGGTTGT-3' (SEQ ID NO:123)), influenza virus ("Flu"), or the combination of influenza virus ("Flu") and IRS (5'-TGCTCCTGGAGGGGTTGT-3' (SEQ ID NO:123)).

Cytokine levels (IL-6, IL-12, and TNF-alpha) in the serum were measured. IL-6 levels of the in vivo experiments are shown in FIG. 24.

Example 7

Human Plasmacytoid Dendritic Cells (PDCs) Stimulated in the Presence of an IRS Coupled to Ficoll To further investigate whether it is possible to increase IRS activity with respect to inhibition of IFN-α production by aggregating IRS molecule onto a higher order molecule, we have generated molecules that are composed by IRS oligonucleotides that are covalently associated to Ficoll 400, a neutral, highly branched, hydrophilic polymer of sucrose. The nature of this sugar allowed us to link between 10 to over 100 IRS oligos per Ficoll molecule.

The conjugation of oligonucleotides to ficoll as practiced currently consists of four reaction steps: (I) The commercially obtained ficoll is carboxymethylated by reaction of ficoll with chloroacetic acid in base. (II) After neutralization and dialysis, product is reacted with ethylene diamine in the presence of the 1-ethyl-3-[3-(dimethylaminopropyl]carbodiimide) EDC to give product (III). After dialysis Product (III) is reacted with (sulfosuccinimidal 4-[N-maleimidyl]-cyclohexane-1-carboxylate) SMCC to give the ficoll-maleimide product (IV). The thiol-reactive species (IV) is then reacted with the oligonucleotide thiol to give the final product (V), a multioligonucleotide conjugate of ficoll.

The aggregation of IRS molecule in such structure leads to a molecule that has a much increased activity for blocking IFN-α production by PDC when activated with an immunostimulatory sequence CpG-C ISS C274 ("ISS"; 5'-TCG TCG AAC GTT CGA GAT GAT-3' (SEQ ID NO:99)). See FIG. 25. Thus, it is possible to increase IRS activity with respect to inhibition of IFN-α production by aggregating IRS molecule onto a higher order molecule.

Example 8

Use of IRP in Combination with Corticosteroids to Treat Autoimmune Diseases

Corticosteroids are the most widely used anti-inflammatory drugs in lupus. A SLE patient with a severe disease flare can receive up to 1 g/day of corticosteroids for about a week. Patients with "milder flares" are treated with about 0.5-1 mg/kg/day of corticosteroids while patients with chronic mild, non-organ-threatening disease are treated with about 10-40 mg/day of corticosteroids for long periods of time. The side effects associated with corticosteroid administration depend on the dose and length of treatment.

Some studies in both adult and pediatric SLE patients showed 70% decrease in circulating plasmacytoid dendritic cells (PDCs) in response to high dosages of corticosteroids. PBMC from healthy donors treated for 3 days with low dose of corticosteroids (30 mg/day) are unresponsive to TLR9 stimulation (HSV) and PDCs are reduced. However, corticosteroid treatment represses the IFN-signature in lupus patients. TLR7 and TLR9 by activating PDC may reduce the potency of corticosteroid to repress the IFN-signature. PDC activated by TLR7/9 are more resistant to corticosteroid-induced apoptosis. Blocking TLR7 and/or TLR9 could thus facilitate the corticosteroid effect on PDC resulting in increased PDC depletion and reduction of the IFN-signature Percentage PDC Death Upon Varying Concentrations of the Corticosteroid, Hydroxycortisone, in the Presence of Immunoregulatory Sequences To investigate whether administration of an IRS could facilitate the killing of PDC by corticosteroids via the inhibition of TLR signaling and thereby reduce doses of corticosteroid required in the treatment of lupus, the dosage of corticosteroid required to induce apoptosis in TLR-activated PDC was evaluated.

Purified PDC (50-100,000 cells) were cultured for 24-48H either alone or in the presence of TLR7 or TLR9 ligands as depicted either alone or in the presence of SEQ ID NO:123. Hydroxycortisone was added at various concentrations and cell survival measured at the end of the culture. The number of viable cells was evaluated by flow cytometry by comparing to a fixed amount of microbeads that was added in equal amount in all samples prior to the measure on the flow cytometer.

As shown in FIG. 26, the percentage PDC death using vary concentrations of the corticosteroid, hydroxycortisone, was increased in the presence of an immunoregulatory sequence (SEQ ID NO:123). The concentration of hydroxycortisone necessary to achieve 50% death of PDCs was $4.5\times10^{-6}$ M in the presence of influenza virus (H1N1, A/PR/8/34 from a patient in Puerto Rico 1934. See ATCC catalog VR-95). In comparison, the concentration of hydroxycortisone necessary to achieve 50% death of PDCs was $2.2\times10^{-8}$ M in the presence of influenza virus and the immunoregulatory sequence, SEQ ID NO:123. This represented a 204-fold reduction in the amount of hydroxycortisone necessary to achieve 50% death of PDCs.

As also indicated in FIG. 27, the percentage PDC death using vary concentrations of the corticosteroid, hydroxycortisone, was increased in the presence of an immunoregulatory sequence (SEQ ID NO:123). The concentration of hydroxycortisone necessary to achieve 50% death of PDCs was $1.5\times10^{-7}$ M in the presence of HSV (HSV-1 KOS strain). In comparison, the concentration of hydroxycortisone necessary to achieve 50% death of PDCs was $4\times10^{-9}$ M in the presence of HSV and the immunoregulatory sequence, SEQ ID NO:123. This represented a 37-fold reduction in the amount of hydroxycortisone necessary to achieve 50% death of PDCs.

As further indicated in FIG. 28, the percentage PDC death using vary concentrations of the corticosteroid, hydroxycortisone, was increased in the presence of an immunoregulatory sequence (SEQ ID NO:123). The concentration of hydroxycortisone necessary to achieve 50% death of PDCs was $2\times10^{-6}$ M in the presence of an immunostimulatory sequence, an immunostimulatory sequence CpG-C ISS C274 ("ISS"; 5'-TCG TCG AAC GTT CGA GAT GAT-3' (SEQ ID NO:99)). In comparison, the concentration of hydroxycortisone necessary to achieve 50% death of PDCs was $8.5\times10^{-8}$ M in the presence of the ISS and the immunoregulatory sequence, SEQ ID NO:123. This represented a 23-fold reduction in the amount of hydroxycortisone necessary to achieve 50% death of PDCs.

The decrease in percentage PDC survival following administration of an immunoregulatory sequence such as SEQ ID NO:123, was not solely due to inhibition of IFN-α. Supernatant from the cultures shown in FIG. 26 and shown as FIG. 29A were measured for their content in IFN-α using immunoassay (FIG. 29B). As depicted, the reduction in IFN-α production did not correlate with cell survival suggesting that IRS is affecting other pathways involved in cell survival than just blocking IFN-α.

As shown in FIGS. 29A and 29B, IFN-α production was inhibited by 92% in PDC cells when the combination of influenza virus and SEQ ID NO:123 was used compared to influenza virus alone when hydroxycortisone was used at $1\times10^{-8}$ M; however, there was only a 23% decrease of in survival of PDC cells when the combination of influenza virus and SEQ ID NO:123 was used compared to influenza virus alone when hydroxycortisone was used at $1\times10^{-8}$ M. If IFN-α inhibition was solely responsible for the change in survival. When there was no hydroxycortisone present, IFN-α was completely inhibited by IRS but there was no difference in PDC survival. The experiments indicate that the blocking of IFN-α alone did not account for the entire effect of the IRS on increased susceptibility to cortisone.

As further support for the fact that the decrease in percentage PDC survival following administration of an immunoregulatory sequence such as SEQ ID NO:123, was not solely due to inhibition of IFN-α, IFN-β, IFNR, or TNF-α, purified PDC were cultured for 48H with hydroxycortisone concentration of $1\times10^{-6}$ M in medium, with SEQ ID NO:123, with influenza virus either alone or with SEQ ID NO:123, a cocktail of anti-IFN blocking antibodies (polyclonal anti-IFN-α, polyclonal anti-IFN-β, and monoclonal mouse anti-IFN-αβ receptor antibodies (PBL Biomedical Labs Inc., Piscataway, N.J.)) or a cocktail of anti-TNF-α blocking antibodies (anti-TNF-α and anti-TNFR). Cell survival was evaluated by flow cytometry by comparing to a fixed amount of microbeads that was added in equal amount in all samples prior to the measure on the flow cytometer.

Figure 30:
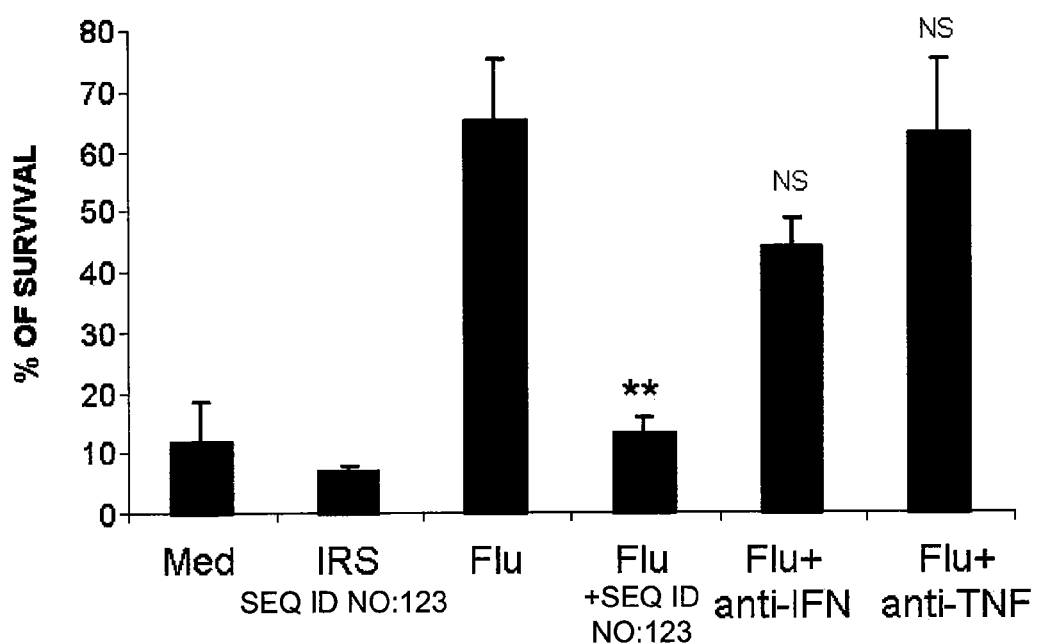
FIG. 30 depicts the percentage survival of human plasmacytoid dendritic cells at a hydroxycortisone concentration of $1 \times 10^{-6}$ M in the presence of media alone, IRS (5'-TGCTCCTGGAGGGGTTGT-3' (SEQ ID NO:123)), influenza virus ("Flu"), the combination of influenza virus ("Flu") and IRS (5'-TGCTCCTGGAGGGGTTGT-3' (SEQ ID NO:123)), the combination of influenza virus ("Flu") and an anti-TNF-α antibody, or the combination of influenza virus ("Flu") and an anti-IFN-α/β and IFNR antibody.

As shown in FIG. 30, the combination of influenza virus and SEQ ID NO:123 at a hydroxycortisone concentration of $1\times10^{-6}$ M resulted in a statistically significant decrease in the percent survival of PDCs compared to influenza virus alone at a hydroxycortisone concentration of $1\times10^{-6}$ M. Use of the combination of influenza virus and antibodies that inhibit either type I IFN or TNF-α did not result in a statistically significant decrease in the percent survival of PDCs compared to influenza virus alone at a hydroxycortisone concentration of $1\times10^{-6}$ M.

The results indicate that corticosteroids induce apoptosis of PDC in vitro. TLR7 and/or TLR9 stimulation confer some resistance to corticosteroid-induced apoptosis. Administration of an IRS and inhibition of TLR7 and/or TLR9 increases susceptibility of PDC to corticosteroids, and an IRS, if used in combination, may reduce the doses of corticosteroids needed to control inflammation.

Example 9

IRPs Comprising an IRS Inhibits NF-kB Transcriptional Activity in Human PDC Stimulated with CpG-C To investigate whether IRPs comprising an IRS inhibits NF-kB transcriptional activity in human PDC stimulated with CpG-C, $1\times10^6$ PDC were stimulated for three hours in the presence of glucocorticoid, hydroxycortisone, and an immunostimulatory sequence CpG-C ISS C274 ("ISS"; 5'-TCG TCG AAC GTT CGA GAT GAT-3' (SEQ ID NO:99)), CpG-C (1 μM) plus hydroxycortisone ($1\times10^{-6}$ M), CpG-C (1 μM) plus IRS (1 μM; SEQ ID NO:123), CpG-C (1 μM) plus NF-kB inhibitor IKK (1 μM), or left untreated.

Figure 31:
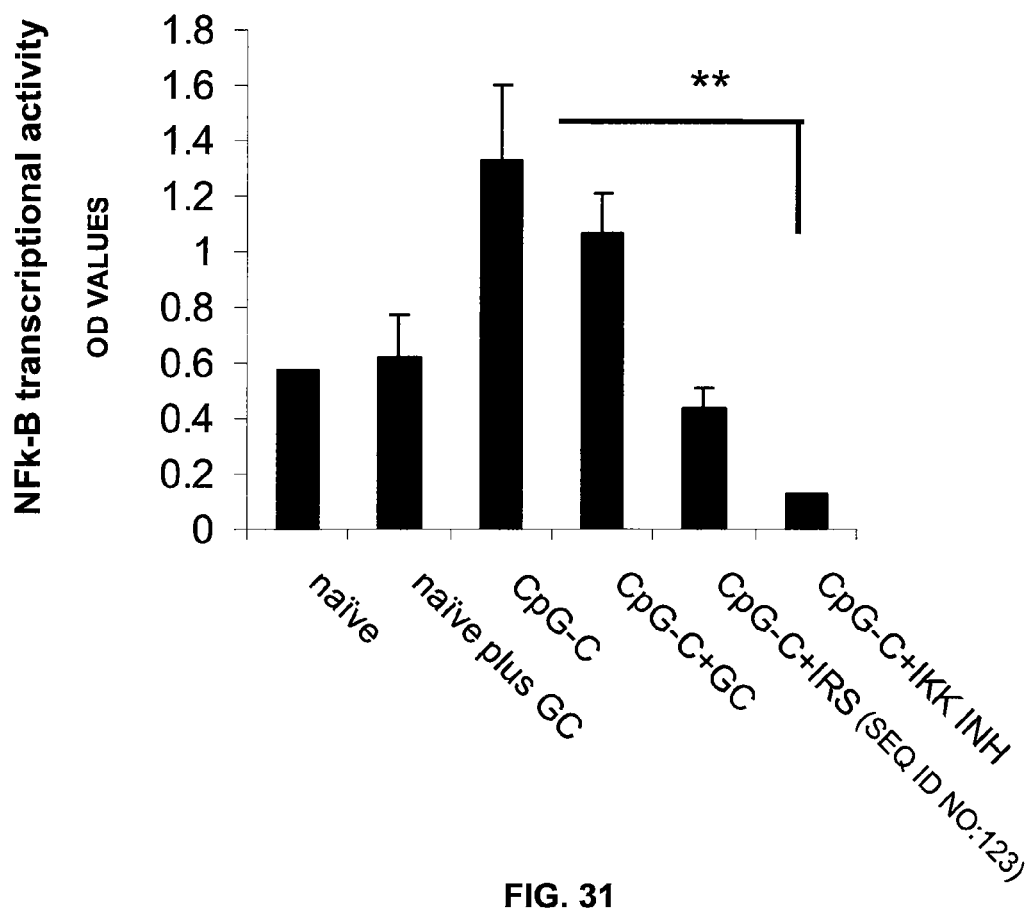
FIG. 31 depicts the level of NF-kB transcriptional activity in human PDC treated for three hours in the presence of glucocorticoid, an immunostimulatory sequence CpG-C ISS C274 ("ISS"; 5'-TCG TCG AAC GTT CGA GAT GAT-3' (SEQ ID NO:99)), CpG-C plus glucocorticoid, CpG-C plus IRS (SEQ ID NO:123), CpG-C plus NF-kB inhibitor IKK or left untreated.
Figure 32A:
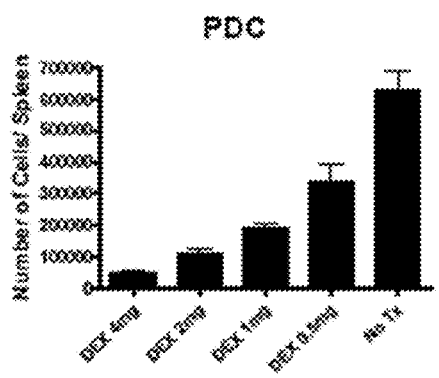
FIGS. 32A-D depict the survival of different cells subsets after in vivo treatment with escalating dose of glucocorticoid Dexthametasone. Mice are 129 strain.
Figure 32B:
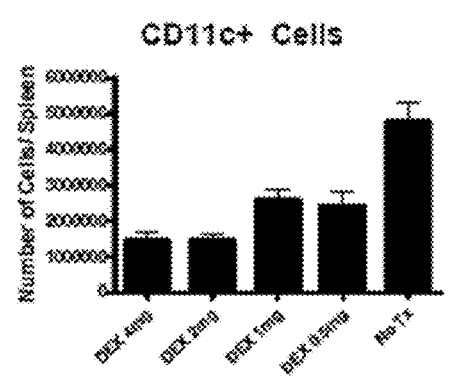
Figure 32C:
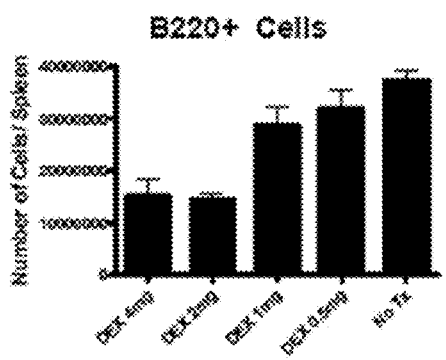
Figure 32D:
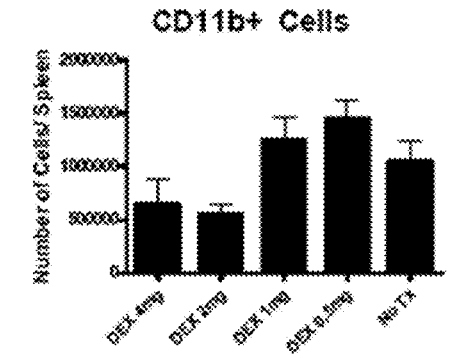
Figure 33A:
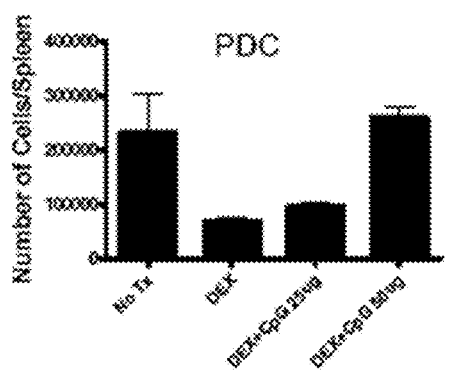
FIGS. 33A-D depict the survival of different cells subsets after in vivo treatment with glucocorticoid Dexthametasone (DEX), DEX plus an immunostimulatory sequence CpG-C ISS C274 ("ISS"; 5'-TCG TCG AAC GTT CGA GAT GAT-3' (SEQ ID NO:99)) at 25 µg and 50 µg. Mice are 129 strain. Results shown refer to spleen cells. Similar results were obtained in the blood. PDC stands for plasmacytoid dendritic cells, CD11c for dendritic cells, B220 for B-cells, and CD11b for monocytes.
Figure 33B:
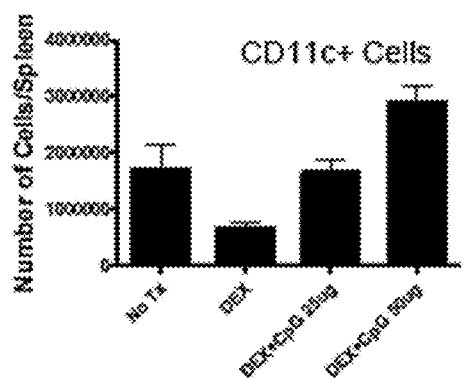
Figure 33C:
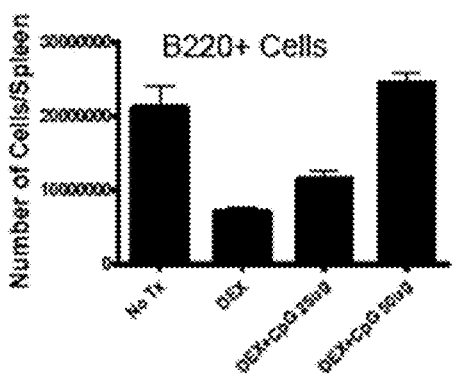
Figure 33D:
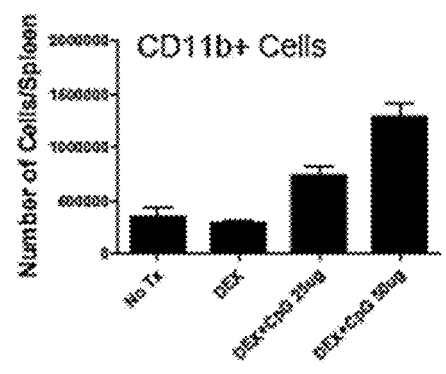

Cells were then collected by centrifugation and nuclear extract was prepared using the nuclear extraction kit (Manufacture from Chemicon). Level of p65 transcriptional activity was evaluated using a sandwich based assay from Active motif that measure level of binding of the p65 NF-kB complex to a consensus DNA motif. The levels of NF-KB transcriptional activity in human PDC under various conditions in FIG. 31.

Example 10

PDC are Sensitive to Glucorticoid Induced Death In Vivo

To investigate whether PDC are sensitive to glucorticoid induced death in vivo, 129 mice were treated with escalating dose of Dexthametasone (0.5 mg-4 mg) and after 16 hours spleen and blood was harvest. Cell survival was measured by flow cytometry. The number of viable cells was evaluated by flow cytometry by comparing to a fixed amount of microbeads that was added in equal amount in all samples prior to the measure on the flow cytometry.

Specific markers were used to identify specific subsets. Cells were identified to be PDC by the surface presence of B220, CD11c, and PDCA1 marker. Myeloid dendritic cells were identified as to be CD11c positive and B220 negative. B-cells were identified as B220 positive cells and CD11c negative. Monocytes were identified as CD11b positive. Cell viability using cells from spleen tissue under increasing Dexthametason dose was evaluated and results are shown in FIG. 32. Similar results were obtained using blood (data not shown). PDC were sensitive to glucorticoid induced death in vivo.

Example 11

TLR9 Signaling Rescue PDC from GC Induced Death

To investigate whether TLR9 signaling rescue PDC from GC induced death, 129 mice were treated with the glucocorticoid Dexthametasone (DEX; 1000 μg) alone or DEX (1000 μg) plus an immunostimulatory sequence CpG-C ISS C274 ("ISS"; 5'-TCG TCG AAC GTT CGA GAT GAT-3' (SEQ ID NO:99)) at 25 μg and 50 μg. Viability of the different cell type was evaluated as described in Example 9.

Cells were identified to be PDC by the surface presence of B220, CD11c, and PDCA1 marker. Myeloid dendritic cells were identified as to be CD11c positive and B220 negative. B-cells were identified as B220 positive cells and CD11c negative. Monocytes were identified as CD11b positive. Cell viability of cells from spleen tissue under various conditions was evaluated and results are shown in FIG. 33. Similar results were obtained using blood (data not shown). TLR9 signaling rescued PDC from GC induced death.

Example 12

IRPs Comprising an IRS Restore In Vivo PDC Sensitivity to Glucocorticoid in Mice Treated with CpG-TLR9 Ligand To investigate whether IRPs comprising an IRS restore in vivo PDC sensitivity to glucocorticoid in mice treated with CpG-TLR9 ligand, 129 mice were treated with the glucocorticoid Dexthametasone (DEX; 1000 μg) alone or DEX (1000 μg) plus a immunostimulatory sequence CpG-C ISS C274 ("ISS"; 5'-TCG TCG AAC GTT CGA GAT GAT-3' (SEQ ID NO:99)) (50 μg) and DEX (1000 μg) plus CpG (50 μg) plus IRS (SEQ ID NO: 123) (100 μg). Viability of the different cell type was evaluated as described in Example 9.

Figure 34A:
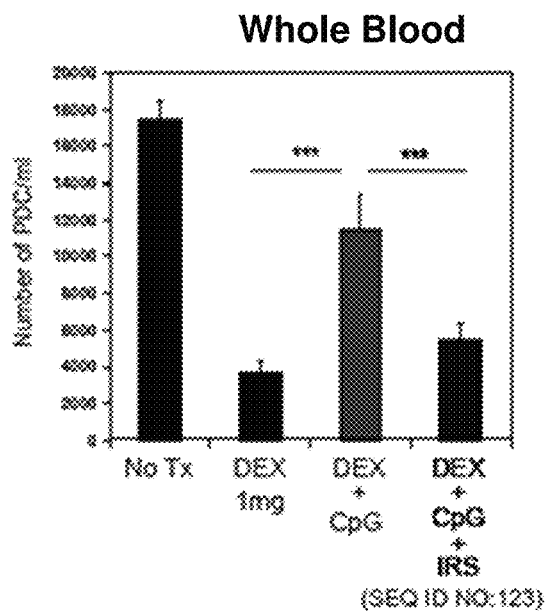
FIGS. 34A and B depict the survival of plasmacytoid dendritic cells (PDC) after in vivo treatment with glucocorticoid Dexthametasone (DEX), DEX plus an immunostimulatory sequence CpG-C ISS C274 ("ISS"; 5'-TCG TCG AAC GTT CGA GAT GAT-3' (SEQ ID NO:99)) at 50 µg and DEX plus CpG plus IRS (SEQ ID NO:123). Mice are 129 strain. Results shown refer to blood and spleen.
Figure 34B:
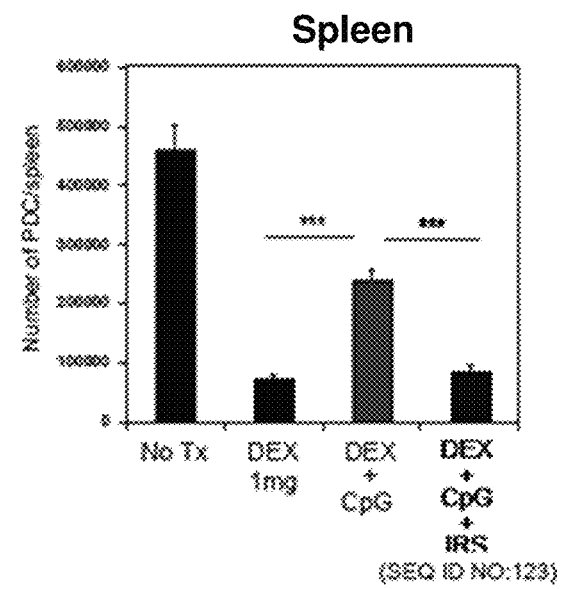
Figure 35A:
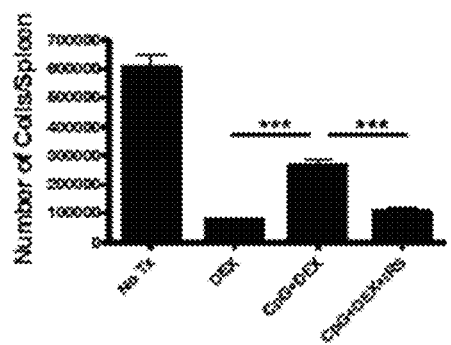
FIGS. 35A-C depict the survival of different cells subsets after in vivo treatment with glucocorticoid Dexthametasone (DEX), DEX plus an immunostimulatory sequence CpG-C ISS C274 ("ISS"; 5'-TCG TCG AAC GTT CGA GAT GAT-3' (SEQ ID NO:99)) and DEX plus CpG plus IRS (SEQ ID NO:123). Mice are 129 strain. Results shown refer to spleen cells. Similar results were obtained in the blood.
Figure 35B:
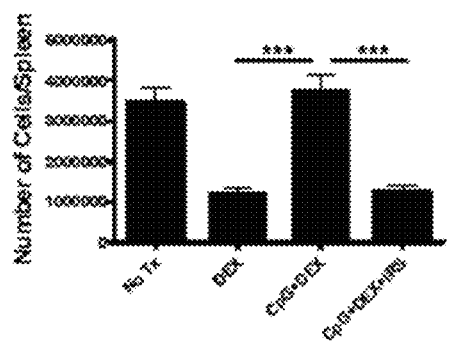
Figure 35C:
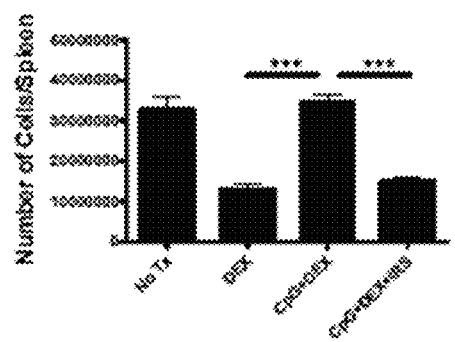

Cells were identified to be PDC by the surface presence of B220, CD11c, and PDCA1 marker. Myeloid dendritic cells were identified as to be CD11c positive and B220 negative. B-cells were identified as B220 positive cells and CD11c negative. Monocytes were identified as CD11b positive. PDC viability from the spleen or blood was evaluated under various conditions and results are shown in FIG. 34. Cell viability of cells from spleen tissue under various conditions was also evaluated and results are shown in FIG. 35. Similar results were obtained using blood (data not shown). IRS SEQ ID NO:173 was also tested and similar results were obtained as with IRS SEQ ID NO:123 (data not shown). IRPs comprising an IRS restored in vivo PDC sensitivity to glucocorticoid in mice treated with CpG-TLR9 ligand.

Example 13

IRPs Comprising an IRS Restores Sensitiveness to Glucocorticoid Induced Cell Death in Autoimmune Prone Animals First, the sensitivity of autoimmune prone animals to glucocorticoid-induced cell death was evaluated. Lupus prone mice (NZB×NZW)F1 mice and the wild type strains, 129 and B6, were treated with 500 µg of Dexthametasone (DEX). Viability of the different cell type was evaluated as described in Example 9.

Figure 36B:
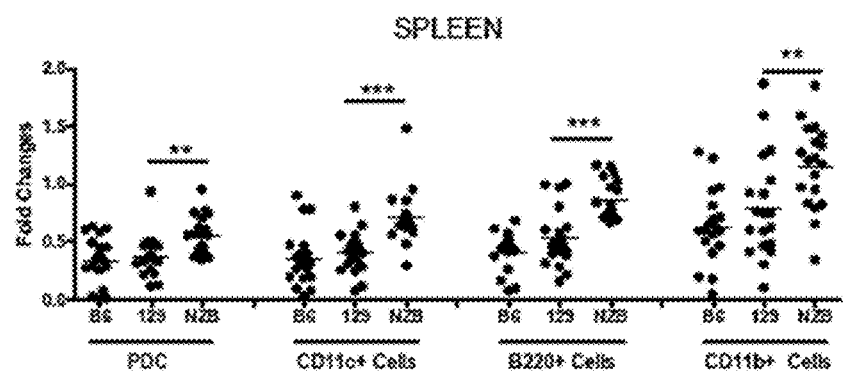

Cells were identified to be PDC by the surface presence of B220, CD11c, and PDCA1 marker. Myeloid dendritic cells were identified as to be CD11c positive and B220 negative. B-cells were identified as B220 positive cells and CD11c negative. Monocytes were identified as CD11b positive. Cell viability of cells from blood and spleen tissue from various mice strains under various conditions was evaluated and results are shown in FIG. 36.

Next, the ability of immunoregulatory sequences to restore responsiveness to glucocorticoid treatment in lupus prone mice (NZB×NZW)F1 was evaluated. A schematic of the experimental design is shown in FIG. 37.

To test whether IRPs comprising an IRS restore sensitiveness to glucocorticoid induced cell death in autoimmune prone animals, Lupus prone mice (NZB×NZW)F1 mice treated with 500 µg of Dexthametasone (DEX) alone or DEX (500 µg) plus IRS (SEQ ID NO: 123) (100 µg) or DEX (500 µg) plus IRS (SEQ ID NO: 123) (100 µg) or DEX (500 µg) plus CTRL oligo (100 µg). Viability of the different cell type was evaluated as described in Example 9.

Cells were identified to be PDC by the surface presence of B220, CD11c, and PDCA1 marker. Myeloid dendritic cells were identified as to be CD11c positive and B220 negative. B-cells were identified as B220 positive cells and CD11c negative. Monocytes were identified as CD11b positive. Cell viability of cells from spleen tissue under various conditions was evaluated and results are shown in FIG. 38. IRS SEQ ID NO:173 was also tested and similar results were obtained as with IRS SEQ ID NO:123 (data not shown). IRS restored sensitiveness to glucocorticoid induced cell death in autoimmune prone animals.

Example 14

IRPs Comprising an IRS can Target Skin Inflammation in vivo

PDC infiltrate the inflamed mouse skin. 129 mice were mechanical stripped 12 times with tape or left untreated as control. After 16 hr mice were euthanized and the skin was collected and digested for 1 hr with a solution containing Liberase 0.28 u/ml and the cellular content was analyzed by flow cytometry. A) depicts an example of the facs plot of plasmacytoid dendritic cells PDC were defined to be CD11c+, PDCA1+, 120G8+. B) Cells infiltrating the skin were stimulated in vitro with an immunostimulatory sequence CpG-A ISS ("ISS" 5'-GGtgcatcgatgcagGGGGG-3' (SEQ ID NO:125), wherein upper case letters represent PS inkages and lower case letters represent PO linkages) (1 µM) and IFN-α was measured in the supernatant by ELISA.

Cells infiltrating inflamed skin show an IFN-α inflammatory gene signature which is preventable by treatment with IRS. Skin of 129 mice was mechanical inflamed by tape stripping as described in FIG. 39. Mice were stripped only or stripped and treated with IRS (SEQ ID NO:123) (100 µg) either administered s.c. or i.v. or locally on the inflamed skin. A group of mice was left completely untreated to serve as controls. Skin was processed as described in FIG. 39 and RNA was extracted from the infiltrating cells using an RNA kit from Quiagen according to manufacture instruction. Gene expression of specific genes was measured by Taqman. Results are shown in FIG. 40. IRS SEQ ID NO:173 was also tested and similar results were obtained as with IRS SEQ ID NO:123 (data not shown). IRS can target skin inflammation in vivo.

Male mice of the C57BL/6 strain (15 mice/group) were injected intraperitoneally with 750 ug of acetaminophen (APA) either alone or in the presence of a single injection of 200 µg of the IRS of SEQ ID NO:173 given s.c. Mice were surveyed overtime and percentage survival evaluated as shown in FIG. 41. The tape stripping model closely mimics aspects of human skin autoimmune disease including abundant infiltration of plasmacytoid dendritic cells and neutrophils, the upregulation of Type I IFN-α inducible genes, and inflammatory cytokines such as TNF-α, IL1A/B, and IP-10.

Although the foregoing invention has been described in some detail by way of illustration and example for purposes of clarity and understanding, it will be apparent to those skilled in the art that certain changes and modifications may be practiced. Therefore, descriptions and examples should not be construed as limiting the scope of the invention.

What is claimed is:

1. A polynucleotide consisting of a nucleotide sequence of the formula: 5'-$N_n$UGC$N_m$-3', wherein 5'-UGC-3' is a TLR7-inhibitory sequence located at or 1 nucleotide from the 5' end of the polynucleotide, each N is a nucleotide, n is 0 or 1, m is an integer from 5 to 50, and $N_m$ comprises 5'-$S_1S_2S_3S_4$-3', wherein 5'-$S_1S_2S_3S_4$-3' is a TLR9-inhibitory sequence, at least one of $S_1$, $S_2$, $S_3$, and $S_4$ is inosine, wherein remaining $S_1$, $S_2$, $S_3$, and $S_4$, if any, are G, and wherein the polynucleotide does not comprise a CG dinucleotide.

2. A method of inhibiting an immune response in an individual, comprising administering to the individual the polynucleotide of claim 1 in an amount sufficient to inhibit an immune response in the individual.

3. The method of claim 2, wherein the immune response comprises a TLR7 dependent immune response.

4. The method of claim 2, wherein the immune response is a TLR9 dependent immune response and/or TLR7 dependent immune response.

5. The method of claim 2, wherein the immune response is associated with an autoimmune disease.

6. The method of claim 5, wherein inhibiting the immune response ameliorates one or more symptoms of the autoimmune disease.

7. The method of claim 5, wherein inhibiting the immune response prevents or delays development of the autoimmune disease.

8. The method of claim 5, wherein the autoimmune disease is selected from the group consisting of systemic lupus erythematosus (SLE), autoimmune skin disease and rheumatoid arthritis.

9. The method of claim 2, wherein the immune response is associated with chronic pathogen stimulation.

10. A kit comprising the polynucleotide of claim 1 in a suitable container and instructions for use of the polynucleotide in inhibiting an immune response in an individual.

11. The method of claim 2, wherein the immune response is associated with drug-induced inflammation of the liver, or pancreatitis.

12. The method of claim 2, wherein the individual is a human.

13. The method of claim 5, further comprising administering a corticosteroid to the individual.

14. The polynucleotide of claim 1, wherein the sequence 5'-$N_n$UGC$N_m$-3' comprises a modification, wherein said modification comprises a modified base, a modified sugar, and/or a modified phosphate.

15. The polynucleotide of claim 14, wherein said modified phosphate comprises a methyl phosphonate, a phosphorothioate, a phosphoroamidate, a phosphotriester, and/or a phosphorodithioate modification.

16. The polynucleotide of claim 15, wherein said modified phosphate is a phosphorothioate modification.

17. The polynucleotide of claim 16, wherein each nucleotide N comprises the phosphorothioate modification.

18. The polynucleotide of claim 14, wherein said modified sugar is a 2'-sugar modification.

19. The polynucleotide of claim 18, wherein said 2'-sugar modification is a 2'-O-methyl sugar modification or a 2'-O-methoxyethyl sugar modification.

20. The polynucleotide of claim 14, wherein said modified base is a 5'-methyl-cytosine modification.

21. The polynucleotide of claim 1, wherein the 5'-UGC-3' is located 1 nucleotide from the 5' end of the polynucleotide.

22. The polynucleotide of claim 1, wherein the 5'-UGC-3' is located at the 5' end of the polynucleotide.

23. The polynucleotide of claim 1, wherein two, three or four of $S_1$, $S_2$, $S_3$, and $S_4$ are inosine.

24. The polynucleotide of claim 1, wherein inosine is deoxyinosine.

25. The polynucleotide of claim 1, wherein $N_m$ comprises a non-nucleic acid spacer moiety.

26. The polynucleotide of claim 25, wherein the non-nucleic acid spacer moiety comprises hexa-(ethylene glycol).

27. The polynucleotide of claim 1, wherein only one of $S_1$, $S_2$, $S_3$, and $S_4$ is inosine.

28. The polynucleotide of claim 27, wherein inosine is deoxyinosine.

29. The polynucleotide of claim 28, wherein 5'-$S_1S_2S_3S_4$-3' is 5'-GIGG-3'.

30. The polynucleotide of claim 1, wherein said polynucleotide is single-stranded DNA.

31. The polynucleotide of claim 1, wherein said polynucleotide is double-stranded DNA.

32. The polynucleotide of claim 29, wherein said polynucleotide is single-stranded DNA.

33. A pharmaceutical composition comprising the polynucleotide of claim 1 and a pharmaceutically acceptable excipient.

34. A pharmaceutical composition comprising the polynucleotide of claim 29 and a pharmaceutically acceptable excipient.

35. The polynucleotide of claim 32, wherein said polynucleotide is selected from the group consisting of SEQ ID NO:173, SEQ ID NO:175, SEQ ID NO:176, SEQ ID NO:177, SEQ ID NO:178, SEQ ID NO:179, SEQ ID NO:180, SEQ ID NO:181, and SEQ ID NO:186.

36. A pharmaceutical composition comprising the polynucleotide of claim 35 and a pharmaceutically acceptable excipient.

37. The pharmaceutical composition of claim 36, wherein the polynucleotide is less than 25 bases in length.

\* \* \* \* \*

SEQUENCE LISTING

```
<160> NUMBER OF SEQ ID NOS: 198

<210> SEQ ID NO 1
<211> LENGTH: 7
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = A, T, C or G
<220> FEATURE:
<221> NAME/KEY: misc_feature
<222> LOCATION: 6,7
<223> OTHER INFORMATION: n = A, T, C or G and if base at position 1 is C
      or A then bases at positions 6 and 7 cannot both be A

<400> SEQUENCE: 1
``` ngggnn                                                              7

<210> SEQ ID NO 2
<211> LENGTH: 7
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = A or C
<220> FEATURE:
<221> NAME/KEY: misc_feature
<222> LOCATION: 6,7
<223> OTHER INFORMATION: n = A, T, C or G, but bases at positions 6 and
      7 cannot both be A

<400> SEQUENCE: 2 ngggnn                                                              7

<210> SEQ ID NO 3
<211> LENGTH: 109
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 3
<223> OTHER INFORMATION: n = A, T, C or G
<220> FEATURE:
<221> NAME/KEY: misc_feature
<222> LOCATION: (4)...(102)
<223> OTHER INFORMATION: n = absent or A, T, C or G
<220> FEATURE:
<221> NAME/KEY: misc_feature
<222> LOCATION: 103
<223> OTHER INFORMATION: n = A, T, C or G
<220> FEATURE:
<221> NAME/KEY: misc_feature
<222> LOCATION: 108,109
<223> OTHER INFORMATION: n = A, T, C or G and if base at position 103 is
      A or C then bases at positions 108 and 109 cannot
      both be A

<400> SEQUENCE: 3
ggnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnngggnn                 109

<210> SEQ ID NO 4
<211> LENGTH: 132
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = A, T, C or G
<220> FEATURE:
<221> NAME/KEY: misc_feature
<222> LOCATION: (2)...(50)
<223> OTHER INFORMATION: n = absent or A, T, C or G
<220> FEATURE:
<221> NAME/KEY: misc_feature
<222> LOCATION: 54
<223> OTHER INFORMATION: n = A, T, C or G
<220> FEATURE:
<221> NAME/KEY: misc_feature
<222> LOCATION: (55)...(103)
<223> OTHER INFORMATION: n = absent or A, T, C or G

```
<220> FEATURE:
<221> NAME/KEY: misc_feature
<222> LOCATION: 104,105
<223> OTHER INFORMATION: n = sequence absent or G
<220> FEATURE:
<221> NAME/KEY: misc_feature
<222> LOCATION: 106
<223> OTHER INFORMATION: n = A, T, C or G
<220> FEATURE:
<221> NAME/KEY: misc_feature
<222> LOCATION: (107)...(125)
<223> OTHER INFORMATION: n = absent or A, T, C or G
<220> FEATURE:
<221> NAME/KEY: misc_feature
<222> LOCATION: 126
<223> OTHER INFORMATION: n = A, T, C or G
<220> FEATURE:
<221> NAME/KEY: misc_feature
<222> LOCATION: 131,132
<223> OTHER INFORMATION: n = A, T, C or G and if base at position 126 is
     A or C then bases at positions 131 and 132 cannot
     both be A

<400> SEQUENCE: 4
nnnnnnnnnn nnnnnnnnnn nnnnnnnnnn nnnnnnnnnn nnnnnnnnnn tcnnnnnnnn    60
nnnnnnnnnn nnnnnnnnnn nnnnnnnnnn nnnnnnnnnn nnnnnnnnnn nnnnnnnnnn   120
nnnnnngggg nn                                                       132

<210> SEQ ID NO 5
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1,2
<223> OTHER INFORMATION: n = A, T, C or G and if base at position 3 is C
     or A then bases at positions 1 and 2 cannot both be
     G
<220> FEATURE:
<221> NAME/KEY: misc_feature
<222> LOCATION: 3
<223> OTHER INFORMATION: n = A, T, C or G

<400> SEQUENCE: 5 nnngggaa                                                              9

<210> SEQ ID NO 6
<211> LENGTH: 118
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)...(103)
<223> OTHER INFORMATION: n = absent or A, T, C or G

<400> SEQUENCE: 6
tgcnnnnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnntcctgga ggggttgt    118

<210> SEQ ID NO 7
<211> LENGTH: 17
<212> TYPE: DNA
<213> ORGANISM: Artificial Sequence
<220> FEATURE:
<223> OTHER INFORMATION: Synthetic construct
```

```
<400> SEQUENCE: 7
ttgacagctt gacagca                                                    17

<210> SEQ ID NO 8
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 4,5
<223> OTHER INFORMATION: n = A or G
<220> FEATURE:
<221> NAME/KEY: misc_feature
<222> LOCATION: 6
<223> OTHER INFORMATION: n = A, T or G or inosine
<220> FEATURE:
<221> NAME/KEY: misc_feature
<222> LOCATION: 7
<223> OTHER INFORMATION: n = A, T, C, G or inosine and when base at
      position 6 is not G or inosine then base at position 7 is
      guanosine or inosine
<220> FEATURE:
<221> NAME/KEY: misc_feature
<222> LOCATION: 8,9
<223> OTHER INFORMATION: n = T or C

<400> SEQUENCE: 8 tgcnnnnnn                                                              9

<210> SEQ ID NO 9
<211> LENGTH: 107
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 4,5
<223> OTHER INFORMATION: n = G or A
<220> FEATURE:
<221> NAME/KEY: misc_feature
<222> LOCATION: 6
<223> OTHER INFORMATION: n = A, T, G or inosine
<220> FEATURE:
<221> NAME/KEY: misc_feature
<222> LOCATION: 7
<223> OTHER INFORMATION: n = A, T, C, G or inosine and when base at
      position 6 is not G or inosine the base at position 7 is
      guanosine or inosine
<220> FEATURE:
<221> NAME/KEY: misc_feature
<222> LOCATION: 8,9
<223> OTHER INFORMATION: n = C or T
<220> FEATURE:
<221> NAME/KEY: misc_feature
<222> LOCATION: (10)...(107)
<223> OTHER INFORMATION: n = absent, C or T

<400> SEQUENCE: 9
tgcnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnn                  107

<210> SEQ ID NO 10
<211> LENGTH: 15
<212> TYPE: DNA
<213> ORGANISM: Artificial Sequence
<220> FEATURE:
<223> OTHER INFORMATION: Synthetic construct

<400> SEQUENCE: 10
```
tcctaacggg gaagt                                                       15

<210> SEQ ID NO 11
<211> LENGTH: 15
<212> TYPE: DNA
<213> ORGANISM: Artificial Sequence
<220> FEATURE:
<223> OTHER INFORMATION: Synthetic construct

<400> SEQUENCE: 11
tcctaagggg gaagt                                                       15

<210> SEQ ID NO 12
<211> LENGTH: 15
<212> TYPE: DNA
<213> ORGANISM: Artificial Sequence
<220> FEATURE:
<223> OTHER INFORMATION: Synthetic construct

<400> SEQUENCE: 12
tcctaacggg gttgt                                                       15

<210> SEQ ID NO 13
<211> LENGTH: 15
<212> TYPE: DNA
<213> ORGANISM: Artificial Sequence
<220> FEATURE:
<223> OTHER INFORMATION: Synthetic construct

<400> SEQUENCE: 13
tcctaacggg gctgt                                                       15

<210> SEQ ID NO 14
<211> LENGTH: 15
<212> TYPE: DNA
<213> ORGANISM: Artificial Sequence
<220> FEATURE:
<223> OTHER INFORMATION: Synthetic construct

<400> SEQUENCE: 14
tcctcaaggg gctgt                                                       15

<210> SEQ ID NO 15
<211> LENGTH: 15
<212> TYPE: DNA
<213> ORGANISM: Artificial Sequence
<220> FEATURE:
<223> OTHER INFORMATION: Synthetic construct

<400> SEQUENCE: 15
tcctcaaggg gttgt                                                       15

<210> SEQ ID NO 16
<211> LENGTH: 15
<212> TYPE: DNA
<213> ORGANISM: Artificial Sequence
<220> FEATURE:
<223> OTHER INFORMATION: Synthetic construct

<400> SEQUENCE: 16
tcctcatggg gttgt                                                       15

<210> SEQ ID NO 17
<211> LENGTH: 15
<212> TYPE: DNA

```
<213> ORGANISM: Artificial Sequence
<220> FEATURE:
<223> OTHER INFORMATION: Synthetic construct

<400> SEQUENCE: 17
tcctggaggg gttgt                                                         15

<210> SEQ ID NO 18
<211> LENGTH: 15
<212> TYPE: DNA
<213> ORGANISM: Artificial Sequence
<220> FEATURE:
<223> OTHER INFORMATION: Synthetic construct

<400> SEQUENCE: 18
tcctggaggg gctgt                                                         15

<210> SEQ ID NO 19
<211> LENGTH: 15
<212> TYPE: DNA
<213> ORGANISM: Artificial Sequence
<220> FEATURE:
<223> OTHER INFORMATION: Synthetic construct

<400> SEQUENCE: 19
tcctggaggg gccat                                                         15

<210> SEQ ID NO 20
<211> LENGTH: 15
<212> TYPE: DNA
<213> ORGANISM: Artificial Sequence
<220> FEATURE:
<223> OTHER INFORMATION: Synthetic construct

<400> SEQUENCE: 20
tcctggaggg gtcat                                                         15

<210> SEQ ID NO 21
<211> LENGTH: 15
<212> TYPE: DNA
<213> ORGANISM: Artificial Sequence
<220> FEATURE:
<223> OTHER INFORMATION: Synthetic construct

<400> SEQUENCE: 21
tccggaaggg gaagt                                                         15

<210> SEQ ID NO 22
<211> LENGTH: 15
<212> TYPE: DNA
<213> ORGANISM: Artificial Sequence
<220> FEATURE:
<223> OTHER INFORMATION: Synthetic construct

<400> SEQUENCE: 22
tccggaaggg gttgt                                                         15

<210> SEQ ID NO 23
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 9
<223> OTHER INFORMATION: n = 7-deaza-dG
```

<400> SEQUENCE: 23
tcctggagng gttgt                                                    15

<210> SEQ ID NO 24
<211> LENGTH: 22
<212> TYPE: DNA
<213> ORGANISM: Artificial Sequence
<220> FEATURE:
<223> OTHER INFORMATION: Synthetic construct

<400> SEQUENCE: 24
tgactgtagg cggggaagat ga                                            22

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
gagcaagctg gaccttccat                                               20

<210> SEQ ID NO 26
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 14
<223> OTHER INFORMATION: n = 7-deaza-dG

<400> SEQUENCE: 26
cctcaagctt gagngg                                                   16

<210> SEQ ID NO 27
<211> LENGTH: 20
<212> TYPE: DNA
<213> ORGANISM: Artificial Sequence
<220> FEATURE:
<223> OTHER INFORMATION: Synthetic construct

<400> SEQUENCE: 27
tgcttgcaag cttgcaagca                                               20

<210> SEQ ID NO 28
<211> LENGTH: 18
<212> TYPE: DNA
<213> ORGANISM: Artificial Sequence
<220> FEATURE:
<223> OTHER INFORMATION: Synthetic construct

<400> SEQUENCE: 28
tgcttgcaag cttgcaag                                                 18

<210> SEQ ID NO 29
<211> LENGTH: 16
<212> TYPE: DNA
<213> ORGANISM: Artificial Sequence
<220> FEATURE:
<223> OTHER INFORMATION: Synthetic construct

<400> SEQUENCE: 29

```
tgcttgcaag cttgca                                                    16

<210> SEQ ID NO 30
<211> LENGTH: 19
<212> TYPE: DNA
<213> ORGANISM: Artificial Sequence
<220> FEATURE:
<223> OTHER INFORMATION: Synthetic construct

<400> SEQUENCE: 30
gcttgcaagc ttgcaagca                                                 19

<210> SEQ ID NO 31
<211> LENGTH: 18
<212> TYPE: DNA
<213> ORGANISM: Artificial Sequence
<220> FEATURE:
<223> OTHER INFORMATION: Synthetic construct

<400> SEQUENCE: 31
cttgcaagct tgcaagca                                                  18

<210> SEQ ID NO 32
<211> LENGTH: 17
<212> TYPE: DNA
<213> ORGANISM: Artificial Sequence
<220> FEATURE:
<223> OTHER INFORMATION: Synthetic construct

<400> SEQUENCE: 32
ttgcaagctt gcaagca                                                   17

<210> SEQ ID NO 33
<211> LENGTH: 20
<212> TYPE: DNA
<213> ORGANISM: Artificial Sequence
<220> FEATURE:
<223> OTHER INFORMATION: Synthetic construct

<400> SEQUENCE: 33
tgcttgcaag ctagcaagca                                                20

<210> SEQ ID NO 34
<211> LENGTH: 20
<212> TYPE: DNA
<213> ORGANISM: Artificial Sequence
<220> FEATURE:
<223> OTHER INFORMATION: Synthetic construct

<400> SEQUENCE: 34
tgcttgcaag cttgctagca                                                20

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
tgcttgacag cttgacagca                                                20

<210> SEQ ID NO 36
<211> LENGTH: 20
<212> TYPE: DNA
<213> ORGANISM: Artificial Sequence
```

```
<220> FEATURE:
<223> OTHER INFORMATION: Synthetic construct

<400> SEQUENCE: 36
tgcttagcag ctatgcagca                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic construct

<400> SEQUENCE: 37
tgcaagcaag ctagcaagca                                              20

<210> SEQ ID NO 38
<211> LENGTH: 25
<212> TYPE: DNA
<213> ORGANISM: Artificial Sequence
<220> FEATURE:
<223> OTHER INFORMATION: Synthetic construct

<400> SEQUENCE: 38
tgcaagcttg caagcttgca agctt                                        25

<210> SEQ ID NO 39
<211> LENGTH: 21
<212> TYPE: DNA
<213> ORGANISM: Artificial Sequence
<220> FEATURE:
<223> OTHER INFORMATION: Synthetic construct

<400> SEQUENCE: 39
tgctgcaagc ttgcagatga t                                            21

<210> SEQ ID NO 40
<211> LENGTH: 19
<212> TYPE: DNA
<213> ORGANISM: Artificial Sequence
<220> FEATURE:
<223> OTHER INFORMATION: Synthetic construct

<400> SEQUENCE: 40
tgcttgcaag cttgcaagc                                               19

<210> SEQ ID NO 41
<211> LENGTH: 22
<212> TYPE: DNA
<213> ORGANISM: Artificial Sequence
<220> FEATURE:
<223> OTHER INFORMATION: Synthetic construct

<400> SEQUENCE: 41
tgcaagcttg caagcttgca at                                           22

<210> SEQ ID NO 42
<211> LENGTH: 14
<212> TYPE: DNA
<213> ORGANISM: Artificial Sequence
<220> FEATURE:
<223> OTHER INFORMATION: Synthetic construct

<400> SEQUENCE: 42
tgcttgcaag cttg                                                    14
```

<210> SEQ ID NO 43
<211> LENGTH: 20
<212> TYPE: DNA
<213> ORGANISM: Artificial Sequence
<220> FEATURE:
<223> OTHER INFORMATION: Synthetic construct

<400> SEQUENCE: 43
agcttgcaag cttgcaagca                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic construct

<400> SEQUENCE: 44
tacttgcaag cttgcaagca                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic construct

<400> SEQUENCE: 45
tgattgcaag cttgcaagca                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic construct

<400> SEQUENCE: 46
aaattgcaag cttgcaagca                                              20

<210> SEQ ID NO 47
<211> LENGTH: 15
<212> TYPE: DNA
<213> ORGANISM: Artificial Sequence
<220> FEATURE:
<223> OTHER INFORMATION: Synthetic construct

<400> SEQUENCE: 47
tgctggaggg gttgt                                                   15

<210> SEQ ID NO 48
<211> LENGTH: 20
<212> TYPE: DNA
<213> ORGANISM: Artificial Sequence
<220> FEATURE:
<223> OTHER INFORMATION: Synthetic construct

<400> SEQUENCE: 48
aaattgacag cttgacagca                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic construct

<400> SEQUENCE: 49
tgattgacag cttgacagca                                        20

<210> SEQ ID NO 50
<211> LENGTH: 20
<212> TYPE: DNA
<213> ORGANISM: Artificial Sequence
<220> FEATURE:
<223> OTHER INFORMATION: Synthetic construct

<400> SEQUENCE: 50
tgattgacag attgacagca                                        20

<210> SEQ ID NO 51
<211> LENGTH: 20
<212> TYPE: DNA
<213> ORGANISM: Artificial Sequence
<220> FEATURE:
<223> OTHER INFORMATION: Synthetic construct

<400> SEQUENCE: 51
tgattgacag attgacagac                                        20

<210> SEQ ID NO 52
<211> LENGTH: 18
<212> TYPE: DNA
<213> ORGANISM: Artificial Sequence
<220> FEATURE:
<223> OTHER INFORMATION: Synthetic construct

<400> SEQUENCE: 52
tgctcctgga ggggttgt                                          18

<210> SEQ ID NO 53
<211> LENGTH: 21
<212> TYPE: DNA
<213> ORGANISM: Artificial Sequence
<220> FEATURE:
<223> OTHER INFORMATION: Synthetic construct

<400> SEQUENCE: 53
tgcttgtcct ggaggggttg t                                      21

<210> SEQ ID NO 54
<211> LENGTH: 24
<212> TYPE: DNA
<213> ORGANISM: Artificial Sequence
<220> FEATURE:
<223> OTHER INFORMATION: Synthetic construct

<400> SEQUENCE: 54
tgcttgacat cctggagggg ttgt                                   24

<210> SEQ ID NO 55
<211> LENGTH: 33
<212> TYPE: DNA
<213> ORGANISM: Artificial Sequence
<220> FEATURE:
<223> OTHER INFORMATION: Synthetic construct

<400> SEQUENCE: 55
tgcttgacag cttgacagtc ctggaggggt tgt                         33

<210> SEQ ID NO 56

```
<211> LENGTH: 30
<212> TYPE: DNA
<213> ORGANISM: Artificial Sequence
<220> FEATURE:
<223> OTHER INFORMATION: Synthetic construct

<400> SEQUENCE: 56
tgcttgacag cttgatcctg gaggggttgt                                      30

<210> SEQ ID NO 57
<211> LENGTH: 27
<212> TYPE: DNA
<213> ORGANISM: Artificial Sequence
<220> FEATURE:
<223> OTHER INFORMATION: Synthetic construct

<400> SEQUENCE: 57
tgcttgacag cttcctggag gggttgt                                         27

<210> SEQ ID NO 58
<211> LENGTH: 30
<212> TYPE: DNA
<213> ORGANISM: Artificial Sequence
<220> FEATURE:
<223> OTHER INFORMATION: Synthetic construct

<400> SEQUENCE: 58
tgcttgacag cttgctcctg gaggggttgt                                      30

<210> SEQ ID NO 59
<211> LENGTH: 33
<212> TYPE: DNA
<213> ORGANISM: Artificial Sequence
<220> FEATURE:
<223> OTHER INFORMATION: Synthetic construct

<400> SEQUENCE: 59
tgcttgacag cttgcttgtc ctggaggggt tgt                                  33

<210> SEQ ID NO 60
<211> LENGTH: 35
<212> TYPE: DNA
<213> ORGANISM: Artificial Sequence
<220> FEATURE:
<223> OTHER INFORMATION: Synthetic construct

<400> SEQUENCE: 60
tgcttgacag cttgacagca tcctggaggg gttgt                                35

<210> SEQ ID NO 61
<211> LENGTH: 35
<212> TYPE: DNA
<213> ORGANISM: Artificial Sequence
<220> FEATURE:
<223> OTHER INFORMATION: Synthetic construct

<400> SEQUENCE: 61
tgcttgacag cttgacagca tcctggaggg gttgt                                35

<210> SEQ ID NO 62
<211> LENGTH: 32
<212> TYPE: DNA
<213> ORGANISM: Artificial Sequence
<220> FEATURE:
<223> OTHER INFORMATION: Synthetic construct

<400> SEQUENCE: 62
```
tgcttgacag cttgacagca tcctggaggg gt                                          32

<210> SEQ ID NO 63
<211> LENGTH: 31
<212> TYPE: DNA
<213> ORGANISM: Artificial Sequence
<220> FEATURE:
<223> OTHER INFORMATION: Synthetic construct

<400> SEQUENCE: 63
tgcttgacag cttgacagca tcctggaggg g                                           31

<210> SEQ ID NO 64
<211> LENGTH: 30
<212> TYPE: DNA
<213> ORGANISM: Artificial Sequence
<220> FEATURE:
<223> OTHER INFORMATION: Synthetic construct

<400> SEQUENCE: 64
tgcttgcaag cttgctcctg gaggggttgt                                             30

<210> SEQ ID NO 65
<211> LENGTH: 27
<212> TYPE: DNA
<213> ORGANISM: Artificial Sequence
<220> FEATURE:
<223> OTHER INFORMATION: Synthetic construct

<400> SEQUENCE: 65
tgcttgcaag cttcctggag gggttgt                                                27

<210> SEQ ID NO 66
<211> LENGTH: 35
<212> TYPE: DNA
<213> ORGANISM: Artificial Sequence
<220> FEATURE:
<223> OTHER INFORMATION: Synthetic construct

<400> SEQUENCE: 66
tgcttgcaag cttgcaagca tcctggaggg gttgt                                       35

<210> SEQ ID NO 67
<211> LENGTH: 35
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 20,21
<223> OTHER INFORMATION: Bases at positions 20 and 21 are linked by a
      hexa-(ethylene glycol) moiety

<400> SEQUENCE: 67
tgcttgcaag cttgcaagca tcctggaggg gttgt                                       35

<210> SEQ ID NO 68
<211> LENGTH: 35
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 20,21
<223> OTHER INFORMATION: Bases at positions 20 and 21 are linked by a

```
                              hexa-(ethylene glycol) moiety

<400> SEQUENCE: 68
tgcttgcaag ctagcaagca tcctggaggg gttgt                            35

<210> SEQ ID NO 69
<211> LENGTH: 35
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 20,21
<223> OTHER INFORMATION: Bases at positions 20 and 21 are linked by a
      hexa-(ethylene glycol) moiety

<400> SEQUENCE: 69
tgcttgcaag cttgctagca tcctggaggg gttgt                            35

<210> SEQ ID NO 70
<211> LENGTH: 35
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 20,21
<223> OTHER INFORMATION: Bases at positions 20 and 21 are linked by a
      hexa-(ethylene glycol) moiety
<220> FEATURE:
<221> NAME/KEY: misc_feature
<222> LOCATION: 29
<223> OTHER INFORMATION: n = 7-deaza-dG

<400> SEQUENCE: 70
tgcttgcaag cttgctagca tcctggagng gttgt                            35

<210> SEQ ID NO 71
<211> LENGTH: 35
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 15,16
<223> OTHER INFORMATION: Bases at positions 15 and 16 are linked by a
      hexa-(ethylene glycol) moiety

<400> SEQUENCE: 71
tcctggaggg gttgttgctt gcaagcttgc aagca                            35

<210> SEQ ID NO 72
<211> LENGTH: 21
<212> TYPE: DNA
<213> ORGANISM: Artificial Sequence
<220> FEATURE:
<223> OTHER INFORMATION: Synthetic construct

<400> SEQUENCE: 72
tcgtcgaacg ttcgagatga t                                           21

<210> SEQ ID NO 73
<400> SEQUENCE: 73

000
```

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
000

<210> SEQ ID NO 89
<400> SEQUENCE: 89
000

<210> SEQ ID NO 90
<400> SEQUENCE: 90
000

<210> SEQ ID NO 91
<400> SEQUENCE: 91
000

<210> SEQ ID NO 92
<400> SEQUENCE: 92
000

<210> SEQ ID NO 93
<400> SEQUENCE: 93
000

<210> SEQ ID NO 94
<400> SEQUENCE: 94
000

<210> SEQ ID NO 95
<400> SEQUENCE: 95
000

<210> SEQ ID NO 96

```
<400> SEQUENCE: 96

000

<210> SEQ ID NO 97

<400> SEQUENCE: 97

000

<210> SEQ ID NO 98

<400> SEQUENCE: 98

000

<210> SEQ ID NO 99
<211> LENGTH: 21
<212> TYPE: DNA
<213> ORGANISM: Artificial Sequence
<220> FEATURE:
<223> OTHER INFORMATION: Synthetic Construct

<400> SEQUENCE: 99
tcgtcgaacg ttcgagatga t                                            21

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000
```

-continued

<210> SEQ ID NO 107
<400> SEQUENCE: 107
000

<210> SEQ ID NO 108
<400> SEQUENCE: 108
000

<210> SEQ ID NO 109
<400> SEQUENCE: 109
000

<210> SEQ ID NO 110
<400> SEQUENCE: 110
000

<210> SEQ ID NO 111
<400> SEQUENCE: 111
000

<210> SEQ ID NO 112
<400> SEQUENCE: 112
000

<210> SEQ ID NO 113
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118

<400> SEQUENCE: 118

000

<210> SEQ ID NO 119
<211> LENGTH: 103
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n= U or T
<220> FEATURE:
<221> NAME/KEY: misc_feature
<222> LOCATION: 4-103
<223> OTHER INFORMATION: n = absent or any nucleotide
<220> FEATURE:
<221> NAME/KEY: misc_feature
<222> LOCATION: 1-3
<223> OTHER INFORMATION: nucleotides at position 1-3 comprise a
      modification

<400> SEQUENCE: 119
ngcnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnn                        103

<210> SEQ ID NO 120

<400> SEQUENCE: 120

000

<210> SEQ ID NO 121

<400> SEQUENCE: 121

000

<210> SEQ ID NO 122
<211> LENGTH: 22
<212> TYPE: DNA
<213> ORGANISM: Artificial Sequence
<220> FEATURE:
<223> OTHER INFORMATION: Synthetic Construct

<400> SEQUENCE: 122
tgactgtgaa cgttcgagat ga                                                22

<210> SEQ ID NO 123
<211> LENGTH: 18
<212> TYPE: DNA
<213> ORGANISM: Artificial Sequence
<220> FEATURE:
<223> OTHER INFORMATION: Synthetic Construct

<400> SEQUENCE: 123
tgctcctgga ggggttgt                                                     18

<210> SEQ ID NO 124
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature

```
<222> LOCATION: 1, 21
<223> OTHER INFORMATION: nucleotide either at position 1 or 21 is
      coupled to Ficoll 400

<400> SEQUENCE: 124
tcgtcgaacg ttcgagatga t                                              21

<210> SEQ ID NO 125
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1,2, 17-21
<223> OTHER INFORMATION: PS Linkage
<220> FEATURE:
<221> NAME/KEY: misc_feature
<222> LOCATION: 3-15
<223> OTHER INFORMATION: PO Linkage

<400> SEQUENCE: 125
ggtgcatcga tgcagggggg                                                20

<210> SEQ ID NO 126
<211> LENGTH: 53
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)...(53)
<223> OTHER INFORMATION: n = absent or any nucleotide wherein n
      comprises at least one gc dinucleotide and bases at positions
      (4)...(8) can not be absent

<400> SEQUENCE: 126
tgcnnnnnnn nnnnnnnnnn nnnnnnnnnn nnnnnnnnnn nnnnnnnnnn nnn           53

<210> SEQ ID NO 127
<211> LENGTH: 54
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)...(53)
<223> OTHER INFORMATION: n = absent or any nucleotide wherein n
      comprises at least one gc dinucleotide and bases at positions
      (4)...(8) can not be absent

<400> SEQUENCE: 127
tgcnnnnnnn nnnnnnnnnn nnnnnnnnnn nnnnnnnnnn nnnnnnnnnn nnna          54

<210> SEQ ID NO 128
<211> LENGTH: 55
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)...(53)
<223> OTHER INFORMATION: n = absent or any nucleotide wherein n
      comprises at least one gc dinucleotide and bases at positions
      (4)...(8) can not be absent

<400> SEQUENCE: 128
```

```
tgcnnnnnnn nnnnnnnnnn nnnnnnnnnn nnnnnnnnnn nnnnnnnnnn nnnca         55
```

<210> SEQ ID NO 129
<211> LENGTH: 56
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)...(53)
<223> OTHER INFORMATION: n = absent or any nucleotide wherein n
    comprises at least one gc dinucleotide and bases at positions
    (4)...(8) can not be absent

<400> SEQUENCE: 129

```
tgcnnnnnnn nnnnnnnnnn nnnnnnnnnn nnnnnnnnnn nnnnnnnnnn nnngca         56
```

<210> SEQ ID NO 130
<211> LENGTH: 1003
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U or T
<220> FEATURE:
<221> NAME/KEY: misc_feature
<222> LOCATION: 4-1003
<223> OTHER INFORMATION: n = absent or any nucleotide
<220> FEATURE:
<221> NAME/KEY: misc_feature
<222> LOCATION: 1-3
<223> OTHER INFORMATION: nucleotides at positons 1-3 comprise a
    modification

<400> SEQUENCE: 130

```
ncgnnnnnnn nnnnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnn                     1003
```

```
<210> SEQ ID NO 131
<211> LENGTH: 1004
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4
<223> OTHER INFORMATION: n= any modified nucleotide
<220> FEATURE:
<221> NAME/KEY: misc_feature
<222> LOCATION: 5-1004
<223> OTHER INFORMATION: n = Absent or any nucleotide comprising a
      modification

<400> SEQUENCE: 131
gggnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnn                    1004

<210> SEQ ID NO 132
<211> LENGTH: 2207
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U or T
<220> FEATURE:
<221> NAME/KEY: misc_feature
<222> LOCATION: (1)...(3)
<223> OTHER INFORMATION: nucleotides at position 1-3 comprise a
      modification
<220> FEATURE:
<221> NAME/KEY: misc_feature
<222> LOCATION: 4
<223> OTHER INFORMATION: n = any nucleotide
<220> FEATURE:
<221> NAME/KEY: misc_feature
<222> LOCATION: (5)...(1003)
<223> OTHER INFORMATION: n = any nucleotide or absent
<220> FEATURE:
<221> NAME/KEY: misc_feature
<222> LOCATION: 1004
```

```
<223> OTHER INFORMATION: n = an unmodified nucleotide
<220> FEATURE:
<221> NAME/KEY: misc_feature
<222> LOCATION: (1005)...(1103)
<223> OTHER INFORMATION: n = an unmodified nucleotide or absent
<220> FEATURE:
<221> NAME/KEY: misc_feature
<222> LOCATION: (1108)...(1108)
<223> OTHER INFORMATION: n = an unmodified nucleotide
<220> FEATURE:
<221> NAME/KEY: misc_feature
<222> LOCATION: (1109)...(1207)
<223> OTHER INFORMATION: n= an unmodified nucleotide or absent
<220> FEATURE:
<221> NAME/KEY: misc_feature
<222> LOCATION: (1208)...(1208)
<223> OTHER INFORMATION: n = a modified nucleotide
<220> FEATURE:
<221> NAME/KEY: misc_feature
<222> LOCATION: (1209)...(2207)
<223> OTHER INFORMATION: n = a  modified nucleotide or absent

<400> SEQUENCE: 132
ngcnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnggggnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
```

-continued

| | |
|---|---|
| nnnnnnnnnn nnnnnnnnnn nnnnnnnnnn nnnnnnnnnn nnnnnnnnnn nnnnnnnnnn | 1740 |
| nnnnnnnnnn nnnnnnnnnn nnnnnnnnnn nnnnnnnnnn nnnnnnnnnn nnnnnnnnnn | 1800 |
| nnnnnnnnnn nnnnnnnnnn nnnnnnnnnn nnnnnnnnnn nnnnnnnnnn nnnnnnnnnn | 1860 |
| nnnnnnnnnn nnnnnnnnnn nnnnnnnnnn nnnnnnnnnn nnnnnnnnnn nnnnnnnnnn | 1920 |
| nnnnnnnnnn nnnnnnnnnn nnnnnnnnnn nnnnnnnnnn nnnnnnnnnn nnnnnnnnnn | 1980 |
| nnnnnnnnnn nnnnnnnnnn nnnnnnnnnn nnnnnnnnnn nnnnnnnnnn nnnnnnnnnn | 2040 |
| nnnnnnnnnn nnnnnnnnnn nnnnnnnnnn nnnnnnnnnn nnnnnnnnnn nnnnnnnnnn | 2100 |
| nnnnnnnnnn nnnnnnnnnn nnnnnnnnnn nnnnnnnnnn nnnnnnnnnn nnnnnnnnnn | 2160 |
| nnnnnnnnnn nnnnnnnnnn nnnnnnnnnn nnnnnnnnnn nnnnnnn | 2207 |

<210> SEQ ID NO 133
<211> LENGTH: 1104
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: n =  an unmodified nucleotide
<220> FEATURE:
<221> NAME/KEY: misc_feature
<222> LOCATION: (6)...(104)
<223> OTHER INFORMATION: n = an unmodified nucleotide or absent
<220> FEATURE:
<221> NAME/KEY: misc_feature
<222> LOCATION: 105
<223> OTHER INFORMATION: n = modified nucleotide
<220> FEATURE:
<221> NAME/KEY: misc_feature
<222> LOCATION: (106)...(1104)
<223> OTHER INFORMATION: n = modified nucleotide or absent

<400> SEQUENCE: 133

| | |
|---|---|
| ggggnnnnnn nnnnnnnnnn nnnnnnnnnn nnnnnnnnnn nnnnnnnnnn nnnnnnnnnn | 60 |
| nnnnnnnnnn nnnnnnnnnn nnnnnnnnnn nnnnnnnnnn nnnnnnnnnn nnnnnnnnnn | 120 |
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nnnnnnnnnn nnnnnnnnnn nnnnnnnnnn nnnnnnnnnn | 300 |
| nnnnnnnnnn nnnnnnnnnn nnnnnnnnnn nnnnnnnnnn nnnnnnnnnn nnnnnnnnnn | 360 |
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nnnnnnnnnn nnnnnnnnnn nnnnnnnnnn nnnnnnnnnn | 480 |
| nnnnnnnnnn nnnnnnnnnn nnnnnnnnnn nnnnnnnnnn nnnnnnnnnn nnnnnnnnnn | 540 |
| nnnnnnnnnn nnnnnnnnnn nnnnnnnnnn nnnnnnnnnn nnnnnnnnnn nnnnnnnnnn | 600 |
| nnnnnnnnnn nnnnnnnnnn nnnnnnnnnn nnnnnnnnnn nnnnnnnnnn nnnnnnnnnn | 660 |
| nnnnnnnnnn nnnnnnnnnn nnnnnnnnnn nnnnnnnnnn nnnnnnnnnn nnnnnnnnnn | 720 |
| nnnnnnnnnn nnnnnnnnnn nnnnnnnnnn nnnnnnnnnn nnnnnnnnnn nnnnnnnnnn | 780 |
| nnnnnnnnnn nnnnnnnnnn nnnnnnnnnn nnnnnnnnnn nnnnnnnnnn nnnnnnnnnn | 840 |
| nnnnnnnnnn nnnnnnnnnn nnnnnnnnnn nnnnnnnnnn nnnnnnnnnn nnnnnnnnnn | 900 |
| nnnnnnnnnn nnnnnnnnnn nnnnnnnnnn nnnnnnnnnn nnnnnnnnnn nnnnnnnnnn | 960 |
| nnnnnnnnnn nnnnnnnnnn nnnnnnnnnn nnnnnnnnnn nnnnnnnnnn nnnnnnnnnn | 1020 | nnnnnnnnnn nnnnnnnnnn nnnnnnnnnn nnnnnnnnnn nnnnnnnnnn nnnnnnnnnn       1080 nnnnnnnnnn nnnnnnnnnn nnnn       1104

<210> SEQ ID NO 134
<211> LENGTH: 1104
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = any nucleotide
<220> FEATURE:
<221> NAME/KEY: misc_feature
<222> LOCATION: (2)...(1000)
<223> OTHER INFORMATION: n = any nucleotide or absent
<220> FEATURE:
<221> NAME/KEY: misc_feature
<222> LOCATION: 1001
<223> OTHER INFORMATION: n = an unmodified nucleotide
<220> FEATURE:
<221> NAME/KEY: misc_feature
<222> LOCATION: (1002)...(1100)
<223> OTHER INFORMATION: n = an unmodified nucleotide or absent

<400> SEQUENCE: 134
nnnnnnnnnn nnnnnnnnnn nnnnnnnnnn nnnnnnnnnn nnnnnnnnnn nnnnnnnnnn         60
nnnnnnnnnn nnnnnnnnnn nnnnnnnnnn nnnnnnnnnn nnnnnnnnnn nnnnnnnnnn        120
nnnnnnnnnn nnnnnnnnnn nnnnnnnnnn nnnnnnnnnn nnnnnnnnnn nnnnnnnnnn        180
nnnnnnnnnn nnnnnnnnnn nnnnnnnnnn nnnnnnnnnn nnnnnnnnnn nnnnnnnnnn        240
nnnnnnnnnn nnnnnnnnnn nnnnnnnnnn nnnnnnnnnn nnnnnnnnnn nnnnnnnnnn        300
nnnnnnnnnn nnnnnnnnnn nnnnnnnnnn nnnnnnnnnn nnnnnnnnnn nnnnnnnnnn        360
nnnnnnnnnn nnnnnnnnnn nnnnnnnnnn nnnnnnnnnn nnnnnnnnnn nnnnnnnnnn        420
nnnnnnnnnn nnnnnnnnnn nnnnnnnnnn nnnnnnnnnn nnnnnnnnnn nnnnnnnnnn        480
nnnnnnnnnn nnnnnnnnnn nnnnnnnnnn nnnnnnnnnn nnnnnnnnnn nnnnnnnnnn        540
nnnnnnnnnn nnnnnnnnnn nnnnnnnnnn nnnnnnnnnn nnnnnnnnnn nnnnnnnnnn        600
nnnnnnnnnn nnnnnnnnnn nnnnnnnnnn nnnnnnnnnn nnnnnnnnnn nnnnnnnnnn        660
nnnnnnnnnn nnnnnnnnnn nnnnnnnnnn nnnnnnnnnn nnnnnnnnnn nnnnnnnnnn        720
nnnnnnnnnn nnnnnnnnnn nnnnnnnnnn nnnnnnnnnn nnnnnnnnnn nnnnnnnnnn        780
nnnnnnnnnn nnnnnnnnnn nnnnnnnnnn nnnnnnnnnn nnnnnnnnnn nnnnnnnnnn        840
nnnnnnnnnn nnnnnnnnnn nnnnnnnnnn nnnnnnnnnn nnnnnnnnnn nnnnnnnnnn        900
nnnnnnnnnn nnnnnnnnnn nnnnnnnnnn nnnnnnnnnn nnnnnnnnnn nnnnnnnnnn        960
nnnnnnnnnn nnnnnnnnnn nnnnnnnnnn nnnnnnnnnn nnnnnnnnnn nnnnnnnnnn       1020
nnnnnnnnnn nnnnnnnnnn nnnnnnnnnn nnnnnnnnnn nnnnnnnnnn nnnnnnnnnn       1080
nnnnnnnnnn nnnnnnnnnn gggg       1104

<210> SEQ ID NO 135
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-18
<223> OTHER INFORMATION: all nucleotides are modified with a 2'-O-Me

```
        sugar modification

<400> SEQUENCE: 135
ugcuccugga gggguugu                                                 18

<210> SEQ ID NO 136
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-18
<223> OTHER INFORMATION: all nucleotides are modified with
        phosphoramidate modification, a phosphate modification

<400> SEQUENCE: 136
ugcuccugga gggguugu                                                 18

<210> SEQ ID NO 137
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5, 6
<223> OTHER INFORMATION: nuclotides are modified with a 5-methyl dC (M)
        modification, a base modification

<400> SEQUENCE: 137
ugcuccugga gggguugu                                                 18

<210> SEQ ID NO 138
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
        modification

<400> SEQUENCE: 138
ugctcctgga ggggttgt                                                 18

<210> SEQ ID NO 139
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15-18
<223> OTHER INFORMATION: nucleotides are modified with a 2'-O-Me sugar
        modification

<400> SEQUENCE: 139
tgctcctgga gggguugu                                                 18

<210> SEQ ID NO 140
<211> LENGTH: 18
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: 1-3, 15-18
<223> OTHER INFORMATION: nucleotides are modified with a 2'-O-Me sugar
      modification

<400> SEQUENCE: 140
ugctcctgga gggguugu                                                      18

<210> SEQ ID NO 141
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11-14
<223> OTHER INFORMATION: nucleotides are modified with a 2'-O-Me sugar
      modification

<400> SEQUENCE: 141
tgctcctgga ggggttgt                                                      18

<210> SEQ ID NO 142
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification

<400> SEQUENCE: 142
ugcttgtcct ggaggggttg t                                                  21

<210> SEQ ID NO 143
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 19-22
<223> OTHER INFORMATION: nucleotides are modified with a 2'-O-Me sugar
      modification

<400> SEQUENCE: 143
tgctcctgga ggggaagtuu gu                                                 22

<210> SEQ ID NO 144
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 18-21
<223> OTHER INFORMATION: nucleotides are modified with a 2'-O-Me sugar
      modification

<400> SEQUENCE: 144
ugcttgtcct ggaggggguug u                                                 21
```

<210> SEQ ID NO 145
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 22-25
<223> OTHER INFORMATION: nucleotides are modified with a 2'-O-Me sugar
      modification

<400> SEQUENCE: 145
ugcttgtcct ggagggaaag tuugu                                              25

<210> SEQ ID NO 146
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 21-24
<223> OTHER INFORMATION: nucleotides are modified with a 2'-O-Me sugar
      modification

<400> SEQUENCE: 146
ugctgtcctg gaggggaagt uugu                                               24

<210> SEQ ID NO 147
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 20-23
<223> OTHER INFORMATION: nucleotides are modified with a 2'-O-Me sugar
      modification

<400> SEQUENCE: 147
ugcgtcctgg aggggaagtu ugu                                                23

<210> SEQ ID NO 148
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 20-23
<223> OTHER INFORMATION: nucleotides are modified with a 2'-O-Me sugar
      modification

<400> SEQUENCE: 148
ugcttgtcct ggaggggtgu ugu                                                23

<210> SEQ ID NO 149
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 19-22

-continued

<223> OTHER INFORMATION: nucleotides are modified with a 2'-O-Me sugar
     modification

<400> SEQUENCE: 149
ugctgtcctg gaggggtguu gu                                              22

<210> SEQ ID NO 150
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 18-21
<223> OTHER INFORMATION: nucleotides are modified with a 2'-O-Me sugar
     modification

<400> SEQUENCE: 150
ugcgtcctgg aggggtguug u                                               21

<210> SEQ ID NO 151
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 19-21
<223> OTHER INFORMATION: nucleotides are modified with a 2'-O-Me sugar
     modification

<400> SEQUENCE: 151
ugcttgtcct ggaggggtug u                                               21

<210> SEQ ID NO 152
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 18-20
<223> OTHER INFORMATION: nucleotides are modified with a 2'-O-Me sugar
     modification

<400> SEQUENCE: 152
ugctgtcctg gagggtugu                                                  20

<210> SEQ ID NO 153
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 17-19
<223> OTHER INFORMATION: nucleotides are modified with a 2'-O-Me sugar
     modification

<400> SEQUENCE: 153
ugcgtcctgg aggggtugu                                                  19

<210> SEQ ID NO 154
<211> LENGTH: 25
<212> TYPE: DNA

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 22-25
<223> OTHER INFORMATION: nucleotides are modified with a 2'-O-Me sugar
      modification

<400> SEQUENCE: 154
ugcttgtcct ggaggggttg tuugu                                              25

<210> SEQ ID NO 155
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 20-25
<223> OTHER INFORMATION: nucleotides are modified with a 2'-O-Me sugar
      modification

<400> SEQUENCE: 155
ugcttgtcct ggaggggttg uuugu                                              25

<210> SEQ ID NO 156
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 22-25
<223> OTHER INFORMATION: nucleotides are modified with a 2'-O-Me sugar
      modification

<400> SEQUENCE: 156
ugctgctcct ggaggggttg tuugu                                              25

<210> SEQ ID NO 157
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 22-25
<223> OTHER INFORMATION: nucleotides are modified with a 2'-O-Me sugar
      modification

<400> SEQUENCE: 157
ugctgctcct tgaggggttg tuugu                                              25

<210> SEQ ID NO 158
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 20-23
<223> OTHER INFORMATION: nucleotides are modified with a 2'-O-Me sugar
      modification

<400> SEQUENCE: 158
```

```
ugctgctcct tgaggggtgu ugu                                          23

<210> SEQ ID NO 159
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 20-24
<223> OTHER INFORMATION: nucleotides are modified with a 2'-O-Me sugar
      modification

<400> SEQUENCE: 159
ugctgctcct tgagggttg uuug                                          24

<210> SEQ ID NO 160
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-21
<223> OTHER INFORMATION: nucleotides are modified with a 2'-O-Me sugar
      modification

<400> SEQUENCE: 160
ugcugcuccu ugagagguug u                                            21

<210> SEQ ID NO 161
<211> LENGTH: 18
<212> TYPE: DNA
<213> ORGANISM: Artificial Sequence
<220> FEATURE:
<223> OTHER INFORMATION: Synthetic Construct

<400> SEQUENCE: 161
tgctcctgga ggggttgt                                                18

<210> SEQ ID NO 162

<400> SEQUENCE: 162

000

<210> SEQ ID NO 163
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3, 20-25
<223> OTHER INFORMATION: nucleotides are modified with a 2'-O-Me sugar
      modification

<400> SEQUENCE: 163
ugctgctcct ggaggggttg uuugu                                        25

<210> SEQ ID NO 164
<211> LENGTH: 25
<212> TYPE: DNA
<213> ORGANISM: Artificial Sequence
<220> FEATURE:
<223> OTHER INFORMATION: Synthetic Construct
```

```
<400> SEQUENCE: 164
tgctgctcct ggaggggttg tttgt                                    25

<210> SEQ ID NO 165
<211> LENGTH: 25
<212> TYPE: DNA
<213> ORGANISM: Artificial Sequence
<220> FEATURE:
<223> OTHER INFORMATION: Synthetic Construct

<400> SEQUENCE: 165
tgctgctcct tgaggggttg tttgt                                    25

<210> SEQ ID NO 166
<211> LENGTH: 21
<212> TYPE: DNA
<213> ORGANISM: Artificial Sequence
<220> FEATURE:
<223> OTHER INFORMATION: Synthetic Construct

<400> SEQUENCE: 166
tgctgctcct tgaggggttg t                                        21

<210> SEQ ID NO 167
<211> LENGTH: 21
<212> TYPE: DNA
<213> ORGANISM: Artificial Sequence
<220> FEATURE:
<223> OTHER INFORMATION: Synthetic Construct

<400> SEQUENCE: 167
tgctgctcct ggaggggttg t                                        21

<210> SEQ ID NO 168
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = 7-deaza-dG

<400> SEQUENCE: 168
tgctgctcct tgagnggttg tttgt                                    25

<210> SEQ ID NO 169
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n= deoxy-inosine

<400> SEQUENCE: 169
tgctgctcct tgagnggttg tttgt                                    25

<210> SEQ ID NO 170
<211> LENGTH: 25
<212> TYPE: DNA
<213> ORGANISM: Artificial Sequence
<220> FEATURE:
```

```
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification

<400> SEQUENCE: 170
ugctgctcct tgagggttg tttgt                                                25

<210> SEQ ID NO 171
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification

<400> SEQUENCE: 171
ugctgctcct ggaggggttg tttgt                                               25

<210> SEQ ID NO 172
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12
<223> OTHER INFORMATION: n =  deoxy-inosine

<400> SEQUENCE: 172
tgctccttga gnggttgttt gt                                                  22

<210> SEQ ID NO 173
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 173
ugctgctcct tgagnggttg tttgt                                               25

<210> SEQ ID NO 174
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification
<220> FEATURE:
<221> NAME/KEY: misc_feature
```

```
<222> LOCATION: 15
<223> OTHER INFORMATION: n = 7-deaza-dG

<400> SEQUENCE: 174
ugctgctcct tgagnggttg tttgt                                          25

<210> SEQ ID NO 175
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 175
ugctgctcct tgagnggttg tttg                                           24

<210> SEQ ID NO 176
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 176
ugctgctcct tgagnggttg ttt                                            23

<210> SEQ ID NO 177
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 177
ugctgctcct tgagnggttg tt                                             22

<210> SEQ ID NO 178
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

```
<222> LOCATION: 1-3
<223> OTHER INFORMATION: nucleotides are modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 178
ugctgctcct tgagnggttg t                                              21

<210> SEQ ID NO 179
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 179
ugctgctcct tgagnggtt                                                 19

<210> SEQ ID NO 180
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 180
ugctgctcct tgagnggt                                                  18

<210> SEQ ID NO 181
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification
<220> FEATURE:
<221> NAME/KEY: misc_difference
<222> LOCATION: 15
<223> OTHER INFORMATION: n = deoxy-inosine

<400> SEQUENCE: 181
ugctgctcct tgagngg                                                   17

<210> SEQ ID NO 182
<211> LENGTH: 16
<212> TYPE: DNA
```

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 182
ugctgctcct tgagng                                                       16

<210> SEQ ID NO 183
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 183
ugctgctcct tgagn                                                        15

<210> SEQ ID NO 184
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1,2
<223> OTHER INFORMATION: nucleotides are modified with a 2'-O-Me sugar
      modification
<220> FEATURE:
<221> NAME/KEY: misc_feature
<222> LOCATION: 14
<223> OTHER INFORMATION: n = deoxy-inosine

<400> SEQUENCE: 184
gctgctcctt gagnggttgt ttgt                                              24

<210> SEQ ID NO 185
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: nucleotide is modified with a 2'-O-Me sugar
      modification
<220> FEATURE:
<221> NAME/KEY: misc_feature
<222> LOCATION: 13
<223> OTHER INFORMATION: n = deoxy-inosine

<400> SEQUENCE: 185
ctgctccttg agnggttgtt tgt                                               23
```

<210> SEQ ID NO 186
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: nucleotides are modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 186
ugctgctcct tgagnggttg                                               20

<210> SEQ ID NO 187
<211> LENGTH: 1104
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2
<223> OTHER INFORMATION: n = G or a molecule that is capable of
      preventing G-tetrad formation and/or preventing Hoogsteen
      base pairing such as I or 7-deaza-dG
<220> FEATURE:
<221> NAME/KEY: misc_feature
<222> LOCATION: 5
<223> OTHER INFORMATION: n = an unmodified nucleotide
<220> FEATURE:
<221> NAME/KEY: misc_feature
<222> LOCATION: (6)...(104)
<223> OTHER INFORMATION: n = an unmodified nucleotide or absent
<220> FEATURE:
<221> NAME/KEY: misc_feature
<222> LOCATION: 105
<223> OTHER INFORMATION: n = a modified nucleotide
<220> FEATURE:
<221> NAME/KEY: misc_feature
<222> LOCATION: (106)...(1104)
<223> OTHER INFORMATION: n = a modified nucleotide or absent

<400> SEQUENCE: 187
gnggnnnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnnnnnnn nnnnnnnnnn   240
nnnnnnnnnn nnnnnnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnnnnnnnnn nnnnnnnnnn nnnnnnnnnn nnnnnnnnnn   540
nnnnnnnnnn nnnnnnnnnn nnnnnnnnnn nnnnnnnnnn nnnnnnnnnn nnnnnnnnnn   600
nnnnnnnnnn nnnnnnnnnn nnnnnnnnnn nnnnnnnnnn nnnnnnnnnn nnnnnnnnnn   660
nnnnnnnnnn nnnnnnnnnn nnnnnnnnnn nnnnnnnnnn nnnnnnnnnn nnnnnnnnnn   720
nnnnnnnnnn nnnnnnnnnn nnnnnnnnnn nnnnnnnnnn nnnnnnnnnn nnnnnnnnnn   780

```
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnn                                           1104

<210> SEQ ID NO 188
<211> LENGTH: 2207
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U or T
<220> FEATURE:
<221> NAME/KEY: misc_feature
<222> LOCATION: 4
<223> OTHER INFORMATION: n = any nucleotide
<220> FEATURE:
<221> NAME/KEY: misc_feature
<222> LOCATION: (5)...(1003)
<223> OTHER INFORMATION: n = any nucleotide or absent
<220> FEATURE:
<221> NAME/KEY: misc_feature
<222> LOCATION: 1004
<223> OTHER INFORMATION: n = unmodified nucleotide
<220> FEATURE:
<221> NAME/KEY: misc_feature
<222> LOCATION: (1005)...(1103)
<223> OTHER INFORMATION: n = unmodified nucleotide or absent
<220> FEATURE:
<221> NAME/KEY: misc_feature
<222> LOCATION: (1105)...(1105)
<223> OTHER INFORMATION: n = G or a molecule that is capable of
      preventing G-tetrad formation and/or preventing Hoogsteen
      base such as I or 7-deaza-dGpairing
<220> FEATURE:
<221> NAME/KEY: misc_feature
<222> LOCATION: (1108)...(1108)
<223> OTHER INFORMATION: n =  unmodified nucleotide
<220> FEATURE:
<221> NAME/KEY: misc_feature
<222> LOCATION: (1109)...(1207)
<223> OTHER INFORMATION: n = unmodified nucleotide or absent
<220> FEATURE:
<221> NAME/KEY: misc_feature
<222> LOCATION: (1208)...(1208)
<223> OTHER INFORMATION: n = modified nucleotide
<220> FEATURE:
<221> NAME/KEY: misc_feature
<222> LOCATION: (1209)...(2207)
<223> OTHER INFORMATION: n = modified nucleotide or absent

<400> SEQUENCE: 188
ngcnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
```

| | | |
|---|---|---|
| nnnnnnnnnn nnnnnnnnnn nnnnnnnnnn nnnnnnnnnn nnnnnnnnnn nnnnnnnnnn | 480 | |
| nnnnnnnnnn nnnnnnnnnn nnnnnnnnnn nnnnnnnnnn nnnnnnnnnn nnnnnnnnnn | 540 | |
| nnnnnnnnnn nnnnnnnnnn nnnnnnnnnn nnnnnnnnnn nnnnnnnnnn nnnnnnnnnn | 600 | |
| nnnnnnnnnn nnnnnnnnnn nnnnnnnnnn nnnnnnnnnn nnnnnnnnnn nnnnnnnnnn | 660 | |
| nnnnnnnnnn nnnnnnnnnn nnnnnnnnnn nnnnnnnnnn nnnnnnnnnn nnnnnnnnnn | 720 | |
| nnnnnnnnnn nnnnnnnnnn nnnnnnnnnn nnnnnnnnnn nnnnnnnnnn nnnnnnnnnn | 780 | |
| nnnnnnnnnn nnnnnnnnnn nnnnnnnnnn nnnnnnnnnn nnnnnnnnnn nnnnnnnnnn | 840 | |
| nnnnnnnnnn nnnnnnnnnn nnnnnnnnnn nnnnnnnnnn nnnnnnnnnn nnnnnnnnnn | 900 | |
| nnnnnnnnnn nnnnnnnnnn nnnnnnnnnn nnnnnnnnnn nnnnnnnnnn nnnnnnnnnn | 960 | |
| nnnnnnnnnn nnnnnnnnnn nnnnnnnnnn nnnnnnnnnn nnnnnnnnnn nnnnnnnnnn | 1020 | |
| nnnnnnnnnn nnnnnnnnnn nnnnnnnnnn nnnnnnnnnn nnnnnnnnnn nnnnnnnnnn | 1080 | |
| nnnnnnnnnn nnnnnnnnnn nnngnggnnn nnnnnnnnnn nnnnnnnnnn nnnnnnnnnn | 1140 | |
| nnnnnnnnnn nnnnnnnnnn nnnnnnnnnn nnnnnnnnnn nnnnnnnnnn nnnnnnnnnn | 1200 | |
| nnnnnnnnnn nnnnnnnnnn nnnnnnnnnn nnnnnnnnnn nnnnnnnnnn nnnnnnnnnn | 1260 | |
| nnnnnnnnnn nnnnnnnnnn nnnnnnnnnn nnnnnnnnnn nnnnnnnnnn nnnnnnnnnn | 1320 | |
| nnnnnnnnnn nnnnnnnnnn nnnnnnnnnn nnnnnnnnnn nnnnnnnnnn nnnnnnnnnn | 1380 | |
| nnnnnnnnnn nnnnnnnnnn nnnnnnnnnn nnnnnnnnnn nnnnnnnnnn nnnnnnnnnn | 1440 | |
| nnnnnnnnnn nnnnnnnnnn nnnnnnnnnn nnnnnnnnnn nnnnnnnnnn nnnnnnnnnn | 1500 | |
| nnnnnnnnnn nnnnnnnnnn nnnnnnnnnn nnnnnnnnnn nnnnnnnnnn nnnnnnnnnn | 1560 | |
| nnnnnnnnnn nnnnnnnnnn nnnnnnnnnn nnnnnnnnnn nnnnnnnnnn nnnnnnnnnn | 1620 | |
| nnnnnnnnnn nnnnnnnnnn nnnnnnnnnn nnnnnnnnnn nnnnnnnnnn nnnnnnnnnn | 1680 | |
| nnnnnnnnnn nnnnnnnnnn nnnnnnnnnn nnnnnnnnnn nnnnnnnnnn nnnnnnnnnn | 1740 | |
| nnnnnnnnnn nnnnnnnnnn nnnnnnnnnn nnnnnnnnnn nnnnnnnnnn nnnnnnnnnn | 1800 | |
| nnnnnnnnnn nnnnnnnnnn nnnnnnnnnn nnnnnnnnnn nnnnnnnnnn nnnnnnnnnn | 1860 | |
| nnnnnnnnnn nnnnnnnnnn nnnnnnnnnn nnnnnnnnnn nnnnnnnnnn nnnnnnnnnn | 1920 | |
| nnnnnnnnnn nnnnnnnnnn nnnnnnnnnn nnnnnnnnnn nnnnnnnnnn nnnnnnnnnn | 1980 | |
| nnnnnnnnnn nnnnnnnnnn nnnnnnnnnn nnnnnnnnnn nnnnnnnnnn nnnnnnnnnn | 2040 | |
| nnnnnnnnnn nnnnnnnnnn nnnnnnnnnn nnnnnnnnnn nnnnnnnnnn nnnnnnnnnn | 2100 | |
| nnnnnnnnnn nnnnnnnnnn nnnnnnnnnn nnnnnnnnnn nnnnnnnnnn nnnnnnnnnn | 2160 | |
| nnnnnnnnnn nnnnnnnnnn nnnnnnnnnn nnnnnnnnnn nnnnnnn | 2207 | |

<210> SEQ ID NO 189
<211> LENGTH: 6
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U or T
<220> FEATURE:
<221> NAME/KEY: misc_feature
<222> LOCATION: 1-3
<223> OTHER INFORMATION: nucleotides comprise a modification

<400> SEQUENCE: 189 ngctgc                                                           6

```
<210> SEQ ID NO 190
<211> LENGTH: 154
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(4)
<223> OTHER INFORMATION: n = G, I (deoxy-inosine), or 7-deaza-dG
<220> FEATURE:
<221> NAME/KEY: misc_feature
<222> LOCATION: 5
<223> OTHER INFORMATION: n  = any nucleotide
<220> FEATURE:
<221> NAME/KEY: misc_feature
<222> LOCATION: (6)...(104)
<223> OTHER INFORMATION: n = any nucleotide or absent
<220> FEATURE:
<221> NAME/KEY: misc_feature
<222> LOCATION: 105
<223> OTHER INFORMATION: n = a modified nucleotide
<220> FEATURE:
<221> NAME/KEY: misc_feature
<222> LOCATION: (106)...(154)
<223> OTHER INFORMATION: n = a modified nucleotide or absent

<400> SEQUENCE: 190
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnn                                 154

<210> SEQ ID NO 191
<211> LENGTH: 2207
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U or T
<220> FEATURE:
<221> NAME/KEY: misc_feature
<222> LOCATION: (1)...(3)
<223> OTHER INFORMATION: nucleotides 1-3 comprise a modification
<220> FEATURE:
<221> NAME/KEY: misc_feature
<222> LOCATION: 4
<223> OTHER INFORMATION: n = any nucleotide
<220> FEATURE:
<221> NAME/KEY: misc_feature
<222> LOCATION: (5)...(1003)
<223> OTHER INFORMATION: n = any nucleotide or absent
<220> FEATURE:
<221> NAME/KEY: misc_feature
<222> LOCATION: 1004
<223> OTHER INFORMATION: n = an unmodified nucleotide
<220> FEATURE:
<221> NAME/KEY: misc_feature
<222> LOCATION: (1005)...(1103)
<223> OTHER INFORMATION: n = an unmodified nucleotide or absent
<220> FEATURE:
<221> NAME/KEY: misc_feature
<222> LOCATION: (1104)...(1107)
<223> OTHER INFORMATION: n = G or a molecule that is capable of
      preventing G-tetrad formation and/or preventing Hoogsteen
      base pairing
<220> FEATURE:
<221> NAME/KEY: misc_feature
<222> LOCATION: (1108)...(1108)
<223> OTHER INFORMATION: n = an unmodified nucleotide
<220> FEATURE:
```

```
<221> NAME/KEY: misc_feature
<222> LOCATION: (1109)...(1207)
<223> OTHER INFORMATION: n = an unmodified nucleotide or absent
<220> FEATURE:
<221> NAME/KEY: misc_feature
<222> LOCATION: (1208)...(1208)
<223> OTHER INFORMATION: n = a modified nucleotide
<220> FEATURE:
<221> NAME/KEY: misc_feature
<222> LOCATION: (1209)...(2207)
<223> OTHER INFORMATION: n = a modified nucleotide or absent

<400> SEQUENCE: 191
ngcnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
```

```
nnnnnnnnnn nnnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnnnnnnn nnnnnnnnnn    2160
nnnnnnnnnn nnnnnnnnnn nnnnnnnnnn nnnnnnnnnn nnnnnn                   2207

<210> SEQ ID NO 192
<211> LENGTH: 1104
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(4)
<223> OTHER INFORMATION: n = G or a molecule that is capable of
      preventing G-tetrad formation and/or preventing Hoogsteen
      base pairing
<220> FEATURE:
<221> NAME/KEY: misc_feature
<222> LOCATION: 5
<223> OTHER INFORMATION: n = an unmodified nucleotide
<220> FEATURE:
<221> NAME/KEY: misc_feature
<222> LOCATION: (6)...(104)
<223> OTHER INFORMATION: n = an unmodified nucleotide or absent
<220> FEATURE:
<221> NAME/KEY: misc_feature
<222> LOCATION: 105
<223> OTHER INFORMATION: n = a modified nucleotide
<220> FEATURE:
<221> NAME/KEY: misc_feature
<222> LOCATION: (106)...(1104)
<223> OTHER INFORMATION: n = a modified nucleotide or absent

<400> SEQUENCE: 192
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnn                                           1104
```

```
<210> SEQ ID NO 193
<211> LENGTH: 1104
<212> TYPE: DNA
<213> ORGANISM: Artificial Sequence
<220> FEATURE:
<223> OTHER INFORMATION: Synthetic Construct
<220> FEATURE:
<221> NAME/KEY: misc_difference
<222> LOCATION: 2
<223> OTHER INFORMATION: n = G or a molecule that is capable of
      preventing G-tetrad formation and/or preventing Hoogsteen
      base pairing such as I or 7-deaza-dG
<220> FEATURE:
<221> NAME/KEY: misc_feature
<222> LOCATION: 5
<223> OTHER INFORMATION: n = an unmodified nucleotide
<220> FEATURE:
<221> NAME/KEY: misc_feature
<222> LOCATION: (6)...(104)
<223> OTHER INFORMATION: n = an unmodified nucleotide or absent
<220> FEATURE:
<221> NAME/KEY: misc_feature
<222> LOCATION: 105
<223> OTHER INFORMATION: n = a modified nucleotide
<220> FEATURE:
<221> NAME/KEY: misc_feature
<222> LOCATION: (106)...(1104)
<223> OTHER INFORMATION: n = a modified nucleotide or absent

<400> SEQUENCE: 193
gnggnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnn                                           1104

<210> SEQ ID NO 194
<211> LENGTH: 53
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

```
<222> LOCATION: 4-53
<223> OTHER INFORMATION: n = absent or any nucleotide and bases at
      positions 4-8 can not be absent

<400> SEQUENCE: 194
tgcnnnnnnn nnnnnnnnnn nnnnnnnnnn nnnnnnnnnn nnnnnnnnnn nnn            53

<210> SEQ ID NO 195
<211> LENGTH: 1104
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = any nucleotide
<220> FEATURE:
<221> NAME/KEY: misc_feature
<222> LOCATION: (2)...(1000)
<223> OTHER INFORMATION: n = any nucleotide or absent
<220> FEATURE:
<221> NAME/KEY: misc_feature
<222> LOCATION: 1001
<223> OTHER INFORMATION: n = an unmodified nucleotide
<220> FEATURE:
<221> NAME/KEY: misc_feature
<222> LOCATION: (1002)...(1100)
<223> OTHER INFORMATION: n = an unmodified nucleotide or absent
<220> FEATURE:
<221> NAME/KEY: misc_feature
<222> LOCATION: (1101)...(1104)
<223> OTHER INFORMATION: n = G or a molecule that is capable of
      preventing G-tetrad formation and/or preventing Hoogsteen
      base pairing

<400> SEQUENCE: 195
nnnnnnnnnn nnnnnnnnnn nnnnnnnnnn nnnnnnnnnn nnnnnnnnnn nnnnnnnnnn       60
nnnnnnnnnn nnnnnnnnnn nnnnnnnnnn nnnnnnnnnn nnnnnnnnnn nnnnnnnnnn      120
nnnnnnnnnn nnnnnnnnnn nnnnnnnnnn nnnnnnnnnn nnnnnnnnnn nnnnnnnnnn      180
nnnnnnnnnn nnnnnnnnnn nnnnnnnnnn nnnnnnnnnn nnnnnnnnnn nnnnnnnnnn      240
nnnnnnnnnn nnnnnnnnnn nnnnnnnnnn nnnnnnnnnn nnnnnnnnnn nnnnnnnnnn      300
nnnnnnnnnn nnnnnnnnnn nnnnnnnnnn nnnnnnnnnn nnnnnnnnnn nnnnnnnnnn      360
nnnnnnnnnn nnnnnnnnnn nnnnnnnnnn nnnnnnnnnn nnnnnnnnnn nnnnnnnnnn      420
nnnnnnnnnn nnnnnnnnnn nnnnnnnnnn nnnnnnnnnn nnnnnnnnnn nnnnnnnnnn      480
nnnnnnnnnn nnnnnnnnnn nnnnnnnnnn nnnnnnnnnn nnnnnnnnnn nnnnnnnnnn      540
nnnnnnnnnn nnnnnnnnnn nnnnnnnnnn nnnnnnnnnn nnnnnnnnnn nnnnnnnnnn      600
nnnnnnnnnn nnnnnnnnnn nnnnnnnnnn nnnnnnnnnn nnnnnnnnnn nnnnnnnnnn      660
nnnnnnnnnn nnnnnnnnnn nnnnnnnnnn nnnnnnnnnn nnnnnnnnnn nnnnnnnnnn      720
nnnnnnnnnn nnnnnnnnnn nnnnnnnnnn nnnnnnnnnn nnnnnnnnnn nnnnnnnnnn      780
nnnnnnnnnn nnnnnnnnnn nnnnnnnnnn nnnnnnnnnn nnnnnnnnnn nnnnnnnnnn      840
nnnnnnnnnn nnnnnnnnnn nnnnnnnnnn nnnnnnnnnn nnnnnnnnnn nnnnnnnnnn      900
nnnnnnnnnn nnnnnnnnnn nnnnnnnnnn nnnnnnnnnn nnnnnnnnnn nnnnnnnnnn      960
nnnnnnnnnn nnnnnnnnnn nnnnnnnnnn nnnnnnnnnn nnnnnnnnnn nnnnnnnnnn     1020
nnnnnnnnnn nnnnnnnnnn nnnnnnnnnn nnnnnnnnnn nnnnnnnnnn nnnnnnnnnn     1080
nnnnnnnnnn nnnnnnnnnn nnnn                                            1104
```

-continued

```
<210> SEQ ID NO 196
<211> LENGTH: 1104
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = any nucleotide
<220> FEATURE:
<221> NAME/KEY: misc_feature
<222> LOCATION: (2)...(1000)
<223> OTHER INFORMATION: n = any nucleotide or absent
<220> FEATURE:
<221> NAME/KEY: misc_feature
<222> LOCATION: 1001
<223> OTHER INFORMATION: n = an unmodified nucleotide
<220> FEATURE:
<221> NAME/KEY: misc_feature
<222> LOCATION: (1002)...(1100)
<223> OTHER INFORMATION: n = an unmodified nucleotide or absent
<220> FEATURE:
<221> NAME/KEY: misc_feature
<222> LOCATION: 1102
<223> OTHER INFORMATION: n = G or a molecule that is capable of
      preventing G-tetrad formation and/or preventing Hoogsteen
      base pairing such as I or 7-deaza-dG

<400> SEQUENCE: 196
nnnnnnnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnnnnnnn nnnnnnnnnn   240
nnnnnnnnnn nnnnnnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnnnnnnnnn nnnnnnnnnn nnnnnnnnnn nnnnnnnnnn   540
nnnnnnnnnn nnnnnnnnnn nnnnnnnnnn nnnnnnnnnn nnnnnnnnnn nnnnnnnnnn   600
nnnnnnnnnn nnnnnnnnnn nnnnnnnnnn nnnnnnnnnn nnnnnnnnnn nnnnnnnnnn   660
nnnnnnnnnn nnnnnnnnnn nnnnnnnnnn nnnnnnnnnn nnnnnnnnnn nnnnnnnnnn   720
nnnnnnnnnn nnnnnnnnnn nnnnnnnnnn nnnnnnnnnn nnnnnnnnnn nnnnnnnnnn   780
nnnnnnnnnn nnnnnnnnnn nnnnnnnnnn nnnnnnnnnn nnnnnnnnnn nnnnnnnnnn   840
nnnnnnnnnn nnnnnnnnnn nnnnnnnnnn nnnnnnnnnn nnnnnnnnnn nnnnnnnnnn   900
nnnnnnnnnn nnnnnnnnnn nnnnnnnnnn nnnnnnnnnn nnnnnnnnnn nnnnnnnnnn   960
nnnnnnnnnn nnnnnnnnnn nnnnnnnnnn nnnnnnnnnn nnnnnnnnnn nnnnnnnnnn  1020
nnnnnnnnnn nnnnnnnnnn nnnnnnnnnn nnnnnnnnnn nnnnnnnnnn nnnnnnnnnn  1080
nnnnnnnnnn nnnnnnnnnn gngg                                         1104

<210> SEQ ID NO 197
<211> LENGTH: 15
<212> TYPE: DNA
<213> ORGANISM: Artificial Sequence
<220> FEATURE:
<223> OTHER INFORMATION: Synthetic Construct

<400> SEQUENCE: 197
```

-continued

```
tcctgcaggt taagt                                                   15

<210> SEQ ID NO 198
<211> LENGTH: 1013
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-10
<223> OTHER INFORMATION: n = Absent or any nucleotide comprising a
      modification
<220> FEATURE:
<221> NAME/KEY: misc_feature
<222> LOCATION: 14-1013
<223> OTHER INFORMATION: n = Absent or any nucleotide

<400> SEQUENCE: 198
nnnnnnnnnn tgcnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnn          1013
```